US011590221B2

(12) United States Patent
Wallace

(10) Patent No.: US 11,590,221 B2
(45) Date of Patent: *Feb. 28, 2023

(54) DENGUE VACCINE UNIT DOSE AND ADMINISTRATION THEREOF

(71) Applicant: Takeda Vaccines, Inc., Cambridge, MA (US)

(72) Inventor: Derek Wallace, Brookline, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/561,953

(22) Filed: Sep. 5, 2019

(65) Prior Publication Data

US 2020/0230230 A1 Jul. 23, 2020

(30) Foreign Application Priority Data

| | | |
|---|---|---|
| Sep. 5, 2018 | (EP) | 18192701 |
| Sep. 5, 2018 | (EP) | 18192711 |
| Sep. 5, 2018 | (EP) | 18192717 |
| Sep. 5, 2018 | (EP) | 18192776 |
| Sep. 5, 2018 | (EP) | 18192787 |
| Sep. 5, 2018 | (EP) | 18192793 |
| Sep. 5, 2018 | (EP) | 18192800 |
| Sep. 5, 2018 | (EP) | 18192814 |
| Jan. 29, 2019 | (EP) | 19154334 |
| Mar. 7, 2019 | (EP) | 19161184 |

(51) Int. Cl.

| | |
|---|---|
| ***A61K 39/295*** | (2006.01) |
| ***A61P 31/14*** | (2006.01) |
| ***A61K 35/76*** | (2015.01) |
| *A61K 39/00* | (2006.01) |

(52) U.S. Cl.

CPC ............ *A61K 39/295* (2013.01); *A61K 35/76* (2013.01); *A61K 2039/545* (2013.01); *A61P 31/14* (2018.01)

(58) Field of Classification Search

None

See application file for complete search history.

(56) References Cited

U.S. PATENT DOCUMENTS

| | | | |
|---|---|---|---|
| 4,810,092 | A | 3/1989 | Auth |
| 5,021,347 | A | 6/1991 | Yasui et al. |
| 5,229,293 | A | 7/1993 | Matsuura et al. |
| 5,494,671 | A | 2/1996 | Lai et al. |
| 5,514,375 | A | 5/1996 | Paoletti et al. |
| 6,165,477 | A | 12/2000 | Ivy et al. |
| 6,184,024 | B1 | 2/2001 | Lai et al. |
| 6,660,273 | B2 | 12/2003 | Pletnev et al. |
| 7,094,411 | B2 | 8/2006 | Kinney et al. |
| 8,673,316 | B2 | 3/2014 | Kinney et al. |
| 2006/0062803 | A1 | 3/2006 | Kinney et al. |
| 2010/0303860 | A1 | 12/2010 | Stinchcomb et al. |
| 2011/0311579 | A1 | 12/2011 | Mason et al. |
| 2014/0302088 | A1 | 10/2014 | Stinchcomb et al. |
| 2015/0150961 | A1 | 6/2015 | Stinchcomb et al. |
| 2015/0265695 | A1 | 9/2015 | Yao et al. |
| 2017/0304426 | A1 | 10/2017 | Tornieporth et al. |
| 2019/0381163 | A1* | 12/2019 | Wallace .................. A61P 37/04 |
| 2020/0069751 | A1* | 3/2020 | Wallace ............... A61K 39/295 |

FOREIGN PATENT DOCUMENTS

| | | | |
|---|---|---|---|
| EP | 2353609 | A1 | 8/2011 |
| JP | H05276941 | A | 10/1993 |
| JP | 2003-523189 | A | 8/2003 |
| JP | 2016-513970 | A | 5/2016 |
| KR | 20080018271 | A | 2/2008 |
| TW | I726312 | B | 3/2014 |
| WO | 1990001946 | A1 | 3/1990 |
| WO | 1992003545 | A1 | 3/1992 |
| WO | 1993006214 | A1 | 4/1993 |
| WO | 1996040933 | A1 | 12/1996 |
| WO | 1998037911 | A1 | 9/1998 |
| WO | 1999063095 | A1 | 12/1999 |
| WO | 2001060847 | A2 | 8/2001 |
| WO | 2001060847 | A3 | 4/2002 |
| WO | 2002072036 | A2 | 9/2002 |
| WO | 2002072036 | A3 | 5/2003 |
| WO | 2006134443 | A1 | 12/2006 |
| WO | 2009048658 | A9 | 6/2009 |
| WO | 2009139725 | A1 | 11/2009 |
| WO | 2010/141386 | A1 | 12/2010 |
| WO | 2011038473 | A1 | 4/2011 |
| WO | 2013/188315 | A1 | 12/2013 |
| WO | 2014016360 | A1 | 1/2014 |
| WO | 2014016362 | A1 | 1/2014 |
| WO | 2014074912 | A1 | 5/2014 |
| WO | 2014093182 | A1 | 6/2014 |
| WO | 2014150939 | A2 | 9/2014 |
| WO | 2016034629 | A1 | 3/2016 |
| WO | 2017005652 | A1 | 1/2017 |
| WO | 2017005654 | A1 | 1/2017 |
| WO | 2017041156 | A1 | 3/2017 |
| WO | 2017179017 | A1 | 10/2017 |
| WO | 2018052375 | A1 | 3/2018 |

OTHER PUBLICATIONS

ALAPE 2018. Takeda vacuna contra el dengue. McIntosh Sep. 5, 2018.

Haiyan Chu, et al., "CD8+ T-cell Responses in Flavivirus-Naïve Individuals Following Immunization with a Live-Attenuated Tetravalent Dengue Vaccine Candidate"—Major Article JID 2015:212 (Nov. 15).

(Continued)

*Primary Examiner* — Benjamin P Blumel

(74) *Attorney, Agent, or Firm* — Honigman LLP; Fernando Alberdi; Jonathan P. O'Brien

(57) ABSTRACT

The invention relates to a unit dose of a dengue vaccine composition and methods and uses for preventing dengue disease and methods for stimulating an immune response to all four dengue virus serotypes in a subject or subject population. The unit dose of a dengue vaccine composition includes constructs of each dengue serotype, such as TDV-1, TDV-2, TDV-3 and TDV-4, at various concentrations in order to improve protection from dengue infection.

17 Claims, 13 Drawing Sheets

Specification includes a Sequence Listing.

(56) References Cited

OTHER PUBLICATIONS

Lisa A. Jackson, et al., "A phase 1 study of safety and immunogenicity following intradermal administration of a tetravalent dengue vaccine candidate"—Vaccine 36 (2018) p. 3976-3983—May 19, 2018.
Medical Director Clinical Science Study Director Takeda: "Safety and Immunogenicity With Two Different Serotype 2 Potencies of Takeda's Tetravalent Dengue Vaccine Candidate (TDV) in Adults in Singapore"—Clinical Trials Jul. 16, 2019—DEN 205.
Jorge Osorio et al: "Efficacy of a Tetravalent Chimeric Dengue Vaccine (DENVax) in Cynomolgus Macaques", Am. J. Trop. Med. Hyg., 84(6), 2011, pp. 978-987—The American Society of Tropical Medicine and Hygiene.
Presentation Biswal Asia Dengue Summit (2016) DEN-204.
Presentation Lorenzato Medtrop (2018) DEN-204.
Presentation Wallace(2016) DEN-204 (p. 86).
Press Release: "Takeda's Dengue Vaccine Candidate Meets Primary Endpoint in Pivotal Phase 3 Efficacy Trial"—Jan. 29, 2019.
Takeda Press Release: "Takeda Completes Enrollment of More Than 20,000 Children and Adolescents in Global Phase 3 Trial of Dengue Vaccine Candidate"—Apr. 5, 2017—DEN-301.
Derek Wallace: "Persistence of neutralizing antibodies one year after two doses of a candidate recombinant tetravalent dengue vaccine in subjects aged from 1.5 to 45 years"—ASTMH Oct. 27, 2015 DEN-203.
European Search Report dated Feb. 12, 2019 for corresponding EP application 18192701.3.
European Search Report dated Nov. 13, 2018 for corresponding EP application 18192701.3.
European Search Report dated May 3, 2019 for corresponding EP application 19161184.7.
European Search Report dated Nov. 13, 2018 for corresponding EP application 18192711.2.
European Search Report dated Nov. 13, 2018 for corresponding EP application 18192717.9.
European Search Report dated Nov. 29, 2018 for corresponding EP application 18192776.5.
European Search Report dated Nov. 13, 2018 for corresponding EP application 18192800.3.
European Search Report dated Nov. 13, 2018 for corresponding EP application 18192793.0.
European Search Report dated Nov. 13, 2018 for corresponding EP application 18192787.2.
European Search Report dated Nov. 13, 2018 for corresponding EP application 18192814.4.
Saez-Llorens, X. et al., "Immunogenicity and safety of one versus two doses of tetravalent dengue vaccine in healthy children aged 2-17 years in Asia and Latin America: 18-month interim data from a phase 2, randomised, placebo-controlled study", The Lancet Infectious Diseases, Feb. 2018, pp. 162-170, vol. 18.
World Health Organization, "Guidelines for plaque reduction neutralization testing of human antibodies to dengue viruses", Jul. 2007.
Takeda Vaccines, "Immunogenicity and Safety of Tetravalent Dengue Vaccine (TDV) Co-administered With an Hepatitis A Virus Vaccine", ClinicalTrials.gov, May 15, 2018.
World Health Organization, "Table 3: Recommendations for Interrupted or Delayed Routine Immunization—Summary of WHO position papers", Aug. 2018.
Brewoo, J. N. et al., "Immunogenicity and efficacy of chimeric dengue vaccine (DENVax) formulations in interferon-deficient AG129 mice", Vaccine, 2012, pp. 1513-1520, vol. 30(8).
Chokephaibulkit, K., "Combination Vaccines", Journal of the Medical Association of Thailand, Aug. 2002, pp. 694-699, vol. 85 suppl. 2.
Crevat, D., et al. "First Experience of Concomitant Vaccination Against Dengue and MMR in Toddlers", The Pediatric Infectious Disease Journal, Aug. 2015, pp. 884-892, vol. 34, No. 8.
Putnak, J.R. et al., "Comparative Evaluation of Three Assays for Measurement of Dengue Virus Neutralizing Antibodies", The American Journal of Tropical Medicine and Hygiene, 2008, pp. 115-122, vol. 79(1).
Dubey, A.P. et al., "Immunogenicity and safety of a tetravalent dengue vaccine in healthy adults in India: A randomized, observer-blind, placebo-controlled phase II trial", Human Vaccines & Immunotherapeutics, Feb. 2016, pp. 512-518, vol. 12 No. 2.
George, S. L. et al., "Safety and Immunogenicity of a Live Attenuated Tetravalent Dengue Vaccine Candidate in Flavivirus-Naive Adults: A Randomized, Double-Blinded Phase 1 Clinical Trial", The Journal of Infectious Diseases, Oct. 1, 2015, pp. 1032-1041, vol. 212(7).
Huang, L. et al., "Concomitant administration of live attenuated Japanese encephalitis chimeric virus vaccine (JE-CV) and measles, mumps, rubella (MMR) vaccine: Randomized study in toddlers in Taiwan", Vaccine, 2014, pp. 5363-5369, vol. 32(41).
King, G.E., et al., "Simultaneous administration of childhood vaccines: an important public health policy that is safe and efficacious", The Pediatric Infectious Disease Journal, May 1994, pp. 394-407, vol. 13 No. 5.
Lopez, P. et al., "Immunogenicity and Safety of Yellor Fever Vaccine (Stamaril) When Administered Concomitantly With a Tetravalent Dengue Vaccine Candidate in Healthy Toddlers at 12-13 Months of Age in Colombia and Peru", The Pediatric Infectious Disease Journal, Oct. 2016, pp. 1140-1147, vol. 35 No. 10.
Osorio, J. E. et al., "A recombinant, chimeric tetravalent dengue vaccine candidate based on a dengue virus serotype 2 backbone", Expert Review of Vaccines, 2016, pp. 497-508, vol. 15, No. 4.
Osorio, J. E. et al., "Development of DENVax: A chimeric dengue-2 PDK-53-based tetravalent vaccine for protection against dengue fever", Vaccine, 2011, pp. 7251-7260, vol. 29(42).
Osorio, J. E. et al., "Safety and immunogenicity of a recombinant live attenuated tetravalent dengue vaccine (DENVax) in flavivirus-naive healthy adults in Colombia: a randomised, placebo-controlled, phase 1 study", The Lancet Infectious Diseases, Sep. 2014, pp. 830-838, vol. 14(9).
Roehrig, J. T. et al., "Guidelines for Plaque-Reduction Neutralization Testing of Human Antibodies to Dengue Viruses", Viral Immunology, 2008, pp. 123-132, vol. 21 No 2.
Rupp, R. et al., "Safety and immunogenicity of different doses and schedules of a live attenuated tetravalent dengue vaccine (TDV) in healthy adults: A Phase 1b randomized study", Vaccine, 2015, pp. 6351-6359, vol. 33.
Saez-Llorens, X. et al., "Safety and immunogenicity of one versus two doses of Takeda's tetravalent dengue vaccine in children in Asia and Latin America: interim results from a phase 2, randomised, placebo-controlled study", The Lancet Infectious Diseases, Jun. 2017, pp. 615-625, vol. 17(6).
Rinderknecht, S. et al., "Immunogenicity and Safety of an Inactivated Hepatitis A Vaccine When Coadministered with Measles-mumps-rubella and Varicella Vaccines in Children Less Than 2 years of Age", The Pediatric Infectious Disease Journal, Oct. 2011, pp. e179-e185, vol. 30, No. 10.
Sirivichayakul, C. et al., "Safety and Immunogenicity of a Tetravalent Dengue Vaccine Candidate in Healthy Children and Adults in Dengue-Endemic Regions: A Randomized, Placebo-Controlled Phase 2 Study", The Journal of Infectious Diseases, May 15, 2016, pp. 1562-1572, vol. 213(10).
Timiryasova, T. M. et al., "Optimization and Validation of a Plaque Reduction Neutralization Test for the Detection of Neutralizing Antibodies to Four Serotypes of Dengue Virus Used in Support of Dengue Vaccine Development", The American Journal of Tropical Medicine and Hygiene, 2013, pp. 962-970, vol. 88(5).
Wichmann, O. et al., "Live-attenuated tetravalent dengue vaccines: The needs and challenges of post-licensure evaluation of vaccine safety and effectiveness", Vaccine, 2017, pp. 5535-5542, vol. 35(42).
Wilder-Smith, A. et al., "Age specific differences in efficacy and safety for the CYD-tetravalent dengue vaccine", Expert Review of Vaccines, 2016, pp. 437-441, vol. 15 No. 4.

(56) References Cited

OTHER PUBLICATIONS

Vesikari, T. et al., "Safety and Immunogenicity of a Booster Dose of the 10-Valent Pneumococcal Nontypeable Haemophilus influenzae Protein D Conjugate Vaccine Coadministered With Measles-Mumps-Rubella-Varicella Vaccine in Children Aged 12 to 16 Months", The Pediatric Infectious Disease Journal, Jun. 2010, pp. e47-e56, vol. 29, No. 6.

Rodriguez Melo, F. I. et al., "Immunogenicity and Safety of a Booster Injection of DTap-IPV//Hib (Pentaxim) Administered Concomitantly With Tetravalent Dengue Vaccine in Healthy Toddlers 15-18 Months of Age in Mexico: A Randomized Trial", The Pediatric Infectious Disease Journal, Jun. 2017, pp. 602-608, vol. 36, No. 6.

Schilling, A. et al., "Coadministration of a 9-Valent Human Papillomavirus Vaccine with Meningococcal and Tdap Vaccines", Pediatrics, Sep. 2015, pp. e563-e572, vol. 136, No. 3.

Update: "West Nile Virus Activity—Northeastern United States, 2000," Morb. Mortal. Wkly. Rep., Sep. 15, 2000, vol. 49, No. 36, pp. 820-822.

Van Der Most et al., "Chimeric yellow fever/dengue virus as a candidate dengue vaccine: quantification of the dengue virus-specific CD8 T-cell response," Journal of Virology, Sep. 1, 2000 2(Sep. 1, 2000), vol. 74. No. 17, pp. 8094-8101.

Vaughn et al., "Testing of dengue 2 live-attenuated vaccine (strain 16681 PDK 53) in ten American volunteers," Vaccine 1996, vol. 14 No. 4, pp. 329-336.

Venugopal et al., "Immunity to St. Louis encephalitis virus by sequential immunization with recombinant vaccinia and baculovirus derived PrM/E proteins," Vaccine, 1995, vol. 13, No. 11, pp. 1000-1005.

Villar et al., "Safety and immunogenicity of a recombinant tetravalent dengue vaccine in 9-16 year olds: a randomized, controlled, phase II trial in Latin America," Pediatr Infect Dis J, Oct. 2013, vol. 32, No. 10, pp. 1102-1109.

Wallace Presentation Session: Vaccines (Developpers),"Takeda's dengue vaccine candidate in children: one or two dos-es?," Apr. 20-23, 2016, p. 86.

Wang et al., "Immune Response to Neonatal Genetic Immunization," Virology, 1997, vol. 228, pp. 278-284.

Wolff et al., "Long-term persistence of plasmid DNA and foreign gene expression in mouse muscle," Hum. Mol. Genet., 1992, vol. 1, No. 6, pp. 363-369.

World Health Organization, "Dengue vaccine research: Immunization, Vaccines and Biologicals" www.who.int/immunization/research/development/dengue_vaccines/en/, Sep. 12, 2018, 3 pages.

World Health Organization, Dengue Vaccine Research, website page at www.who.int/immunuzation/research/development/dengue_vaccines/en, last updated Dec. 5, 2017, 3 pages . . . .

World Health Organization, Recommendations for all immunization programmes, Aug. 1, 2018, Retrieved from the Internet, 10 pages.

World Health Organization, Updated Questions and Answers related to the dengue vaccine Dengvaxia and its use, website page at www.who.int/immunization/diseases/dengue/q_and_a_dengue_vaccine_dengvaxia_use/en/ published Dec. 22, 2017, 7 pages.

World Health Organization, Wkly Epidemiol Rec, "Dengue vaccine: WHO position paper—Sep. 2018," Sep. 7, 2018, vol. 93, pp. 457-476.

Xie et al., "Membrane Topology and Function of Dengue Virus NS2A Protein," Journal of Virology, Apr. 2013, vol. 87, No. 8, pp. 4609-4622.

Yamshchikov et al., "Processing of the Intracellular Form of the West Nile Virus Capsid Protein by the Viral NS2B-NS3 Protease: an In Vitro Study," Journal of Virology, LNKDPUBMED:8057458, Sep. 1994, vol. 68, No. 9, pp. 5765-5771.

Yang et al., "A p300/CBP-associated factor that competes with the adenoviral oncoprotein E1A," Nature, Jul. 25, 1996, vol. 382.

Yoksan et al., "Dengue Virus Vaccine Development: Study on Biological Markers of Uncloned Dengue 1-4 Viruses Serially Passaged in Primary Kidney Cells," Arbovirus Research in Australia—Proceedings 4th Symposium, T. D. St. George, B.H. Kay, and J. Blok (eds.), CSIRO/QIMR, Brisbane 1986, pp. 35-38.

Zhang et al., "Immunization of Mice with Dengue Structural Proteins and Nonstructural Protein NS1 Expressed by Baculovirus Recombinant Induces Resistance to Dengue Virus Encephalitis," J. Viro., Aug. 1988, vol. 62, No. 8, pp. 3027-3031.

Zhang et al., "Passive Protection of Mice, Goats, and Monkeys Against Japanese Encephalitis With Monoclonal Antibodies," 1989, J. Med. Virol., vol. 29, pp. 133-138.

Zhao et al., "Cloning Full-Length Dengue Type 4 Viral DNA Sequences: Analysis of Genes Coding for Structural Proteins," Virology, 1986, vol. 155, pp. 77-88.

Zhao et al., "Expression of Dengue Virus Structural Proteins and Nonstructural Protein NS1 by a Recombinant Vaccinia Virus," Journal of Virology, Dec. 1987, vol. 61, No. 12, pp. 4019-4022.

Aberle et al., "A DNA Immunization Model Study with Constructs Expressing the Tick-Borne Encephalitis Virus Envelope Protein E in Different Physical Forms," Journal of Immunology, 199, vol. 163, pp. 6756-6761.

*AK Steel Corporation* v. *Sollac and Ugine*; United States Court of Appeals for the Federal Circuit; http://laws.lp.findlaw.com/fed/031074.html (Sep. 24, 2003), 8 pages.

Allison et al., "Synthesis and Secretion of Recombinant Tick-Borne Encephalitis Virus Protein E in Soluble and Particulate Form," Journal of Virology, Sep. 1995, vol. 69, No. 9, pp. 5816-5820.

Alvarez et al., "A Phase I Study of Recombinant Adenovirus Vector-Mediated Delivery of an Anti-erbB-2 Single-Chain (sFv) Antibody Gene for Previously Treated Ovarian and Extraovarian Cancer Patients," Mary Ann Liebert, Inc., Human Gene Therapy, Jan. 20, 1997, vol. 8, pp. 229-242.

Anderson et al., "Isolation of West Nile Virus from Mosquitoes, Crows, and a Cooper's Hawk in Connecticut", Ovid: Anderson: Science, vol. Dec. 17, 1999, vol. 286(5448), pp. 2331-2333.

Anonymous, "Guidelines for plaque reduction neutralization testing of human antibodies to dengue viruses," Sep. 21, 2007 (Sep. 21, 2007), p. 1-36,; Retrieved from the Internet:; URL:http://apps.who.int/iris/bitstream/handle/10665/69687/who_ivb_07.07_eng.pdf;jsessionid=E54172674C933124415AFC5BB972E6B9?sequence=1; XP055519586.

Arnon Ruth "Synthetic Vaccines vol. I" CRC Press, Inc. Boca Raton, Florida pp. 83-92.

Arroyo et al., Molecular Basis for Attenuation of Neurovirulence of a Yellow Fever Virus/Japanese Encephalitis Virus Chimera Vaccine (ChimeriVax-JE), Journal of Virology, Jan. 2001, vol. 75, No. 2, pp. 934-942.

Asnis et al., "The West Nile Virus Outbreak of 1999 in New York: The Flushing Hospital Experience," Clinical Infectious Diseases, 2000, vol. 30, pp. 413-418.

Azevedo et al., "Main features of DNA-based immunization vectors," Brazilian Journal of Medical and Biological Research 1999, vol. 32, No. 2, pp. 147-153.

Beatty et al., "Dengue virus NS1 triggers endothelial permeability and vascular leak that is prevented by NS1 vaccination," Sci. Transl. Med. Sep. 9, 2015, vol. 7, No. 304, pp. 1-13.

Benjamin, Sarah, "Optimization and analysis of live attenuated denvax-4 constructs," Masters Thesis: Colorado State University, Summer 2013, 97 pages.

Bhamarapravati et al., "Immunization with a live attenuated dengue-2-virus candidate vaccine (?16681-PDK 53 : clinical, immunological and biological responses in adult volunteers," Bulletin of the World Health Organization, 1987, vol. 65, No. 2, pp. 189-195.

Bhamarapravati et al., "Live attenuated tetravalent dengue vaccine," Cab International, Wallingford, OX, UK, 1997, Dengue and Dengue Hamorrhagic Fever, D.J. Gubler and G. Kuno (ed), Chapter 17, pp. 367-377.

Bhamarapravati et al., "Live attenuated tetravalent dengue vaccine," Vaccine, 2000, vol. 18, pp. 44-47.

Bhatt et al., "Growth characteristics of the chimeric Japanese encephalitis virus vaccine candidate, chimeriVax-je (YF/JE SA14-14-2), in culex tritaeniorhynchus, aedes albopictus, and aedes aegypti mosquitoes," Am. J. Trop. Med. Hyg., 2000, vol. 62, No. 4, pp. 480-484.

Bhatt et al., "The global distribution and burden of dengue," Nature, Apr. 25, 2013, vol. 496 (7446), pp. 504-507.

(56) References Cited

OTHER PUBLICATIONS

Biswal et al., "Efficacy of a Tetravalent Dengue Vaccine in Healthy Children Aged 4-16 years: a randomised, placebo-controlled, phase 3 trial," Lancet, Mar. 17, 2020, vol. 395, pp. 1423-1433.
Biswal et al., "Efficacy of a Tetravalent Dengue Vaccine in Healthy Children and Adolescents," New England Journal of Medicine, Nov. 21, 2019, vol. 381, No. 21, pp. 2009-2019.
Blok et al., "Comparison of a Dengue-2 Virus and Its Candidate Vaccine Derivative: Sequence Relationships with the Flaviviruses and Other Viruses," Virology, 1992, vol. 187, pp. 573-590.
Bray et al., "Construction of intertypic chimeric dengue viruses by substitution of structural protein genes," Proc. Nat. Acad. Sci. USA, Medical Sciences, Nov. 1991, vol. 88, pp. 10342-10346.
Bray et al., "Mice Immunized with Recombinant Vaccinia Virus Expressing Dengue 4 Virus Structural Proteins with or without Nonstructural Protein NS1 are Protected against Fatal Dengue Virus Encephalitis," Journal of Virology, Jun. 1989, vol. 63, No. 6, pp. 2853-2856.
Bray et al., "Monkeys Immunized with Intertypic Chimeric Dengue Viruses Are Protected against Wild-Type Virus Challenge," Journal of Virology, Jun. 1998, vol. 70, No. 6, pp. 4162-4166.
Butrapet et al., "Attenuation markers of a candidate dengue type 2 vaccine virus, strain 16681 (PDK-53), are defined by mutations in the 5' noncoding region and nonstructural proteins 1 and 3," J. Virol., Apr. 2000, vol. 74, No. 7, pp. 3111-3119.
Butrapet et al., "Chimeric Dengue Type 2/Type 1 Viruses Induce Immune Responses in Cynomolgus Monkeys," Southeast Asian J. Trap. Med. Public Health, Sep. 2002, vol. 33, No. 3, pp. 589-599.
Butrapet et al., "Determining genetic stabilities of chimeric dengue vaccine candidates based on dengue 2 PDK-53 virus by sequencing and quantitative TaqMAMA," Journal of Virological Methods, 2006, vol. 131, No. 1, pp. 1-9.
Cahour et al., "Growth-Restricted Dengue Virus Mutants Containing Deletions in the 5' Noncoding Region of the RNA Genome," Virology, 1995, vol. 207, pp. 68-76.
Calvert et al., "Non-structural proteins of dengue 2 virus offer limited protection to interferon-deficient mice after dengue 2 virus challenge,", Journal of General Virology, vol. 87, 2006, pp. 339-346.
Capeding et al., "Clinical efficacy and safety of a novel tetravalent dengue vaccine in healthy children in Asia: a phase 3, randomised, observer-masked, placebo-controlled trial," Lancet, 2014, vol. 384, pp. 1358-1365.
Caufour et al., "Construction, characterization and immunogenicity of recombinant yellow fever 17D-dengue type 2 viruses," Virus Research, 2011, vol. 79, pp. 1-14.
Chambers et al., "Flavivirus Genome Organization, Expression, and Replication," Annu. Rev. Microbiol. 1990, vol. 44, pp. 649-688.
Chambers et al., "Yellow Fever Virus/Dengue-2 Virus and Yellow Fever Virus/Dengue-4 Virus Chimeras: Biological Characterization, Immunogenicity, and Protection against Dengue Encephalitis in the Mouse Model," Journal of Virology, Mar. 2003. vol. 77, No. 6, pp. 3655-3668.
Chambers et al., "Yellow Fever/Japanese Encephalitis Chimeric Viruses: Construction and Biological Properties," Journal of Virology, Apr. 1999, vol. 73, No. 4, pp. 3095-3101.
Chang et al., "A Single Intramuscular Injection of Recombinant Plasmid DNA Induces Protective Immunity and Prevents Japanese Encephalitis in Mice," Journal of Virology, May 2020, vol. 74, No. 9, pp. 4244-4252.
Chen et al., "Construction of Intertypic Chimeric Dengue Viruses Exhibiting Type 3 Antigenicity and Neurovirulence for Mice," Journal of Virology, Aug. 1995, vol. 69, No. 8, pp. 5186-5190.
Clarke et al., "Techniques for Hemagglutination and Hemagglutination-Inhibition with Arthropod-Borne Viruses," The Rockefeller Foundation Virus Laboratories, New York, N.Y., Am. J. Trop. Med. Hyg., 1958, p. 561-573.
Cooper et al., "Update: Surveillance for West Nile Virus in Overwintering Mosquitoes—New York, 2000," 3 pages.
Database UniProt Accession No. Q9WLZ7, XP-002731515, http://ibis/exam/dbfetch.jsp?id=UNIPROT%3AQ9WLZ7, 2 pages.
Database UniProt accession No. D2KQW7 Database UniProt SubName: Full=Polyprotein (ECO:0000313 EMBL: ADA00411.1); XP002731516, retrieved from EBI accession No. UNIPROT:D2KQW7, http://ibis/exam/dbfetch.jsp?id=UNIPROT:D2KQW7 Feb. 9, 2010, 2 pages.
Database UniProt Accession No. P29991 "RecName: Full=Genome polyprotein; Contains: RecName: Full=Capsid protein C; AltName: Full=Core protein; Contains: RecName: Full=prM; Contains," XP002731514, retrieved from EBI accession No. UNIPROT: P29991; Apr. 1, 1993 http://ibis/exam/dbfetch.jsp?id=UNIPROT%3AP29991 .6 pages.
Davis et al., "West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, May 2001, vol. 75, No. 9, pp. 4040-4047.
DeLaBarrera et al., "Comparative Evaluation of Three Assays for Measurement of Dengue Virus Neutralizing Antibodies," Dengue Virus NS1 Disrupts the Endothelial Glycocalyx, Leading to Hyperpermeability, Jul. 1, 2008, vol. 79, No. 1, pp. 115-122.
Deubel et al., "Nucleotide Sequence and Deduced Amino Acid Sequence of the Nonstructural Proteins of Dengue Type 2 Virus, Jamaica Genotype: Comparative Analysis of the Full-Length Genome" Virology, 1988, vol. 165, pp. 234-244.
Deubel et al., "Nucleotide Sequence and Deduced Amino Acid Sequence of the Structural Proteins of Dengue Type 2 Virus, Jamaica Genotype," Virology, 1986, vol. 155, pp. 365-377.
Dharakul et al., "Dengue Virus-Specific Memory T Cell Responses in Human Volunteers Receiving a Live Attenuated Dengue Virus Type 2 Candidate Vaccine," JID Jul. 1994, vol. 170, pp. 27-33.
Dmitriev et al., "Immunization with recombinant vaccinia viruses expressing structural and part of the nonstructural region of tick-borne encephalitis virus eDNA protect mice against lethal encephalitis," Journal of Biotechnology, 1996, vol. 44, pp. 97-103.
Duarte Dos Santos et al., "Complete nucleotide sequence of yellow fever virus vaccine strains 17DD and 17D-213," Virus Research 1995, vol. 35, pp. 35-41.
Durbin et al., "Attenuation and Immunogenicity in Humans of a Live Dengue Virus Type-4 Vaccine Candidate with a 30 Nucleotide Deletion in its 3'-Untranslated Region," Am. J. Trop. Med. Hyg. 2001, vol. 65(5), pp. 405-413.
Endy, "Dengue Human Infection Model Performance Parameters," Journal Infectious Diseases, 2014, vol. 209 (Suppl. 2), pp. S56-S60.
Falgout et al., "Immunization of Mice with Recombinant Vaccinia Virus Expressing Authentic Dengue Virus Nonstructural Protein NS1 Protects against Lethal Dengue Virus Encephalitis," Journal of Virology, Sep. 1990, vol. 64, No. 9, pp. 4356-4363.
Lai et al., "Immunization of Monkeys with Baculovirus Recombinant-expressed Dengue Envelope and NS1 Glycoproteins Induces Partial Resistance to Challenge with Homotypic Dengue Virus," Vaccines 90: Modern approaches to New Vaccines including Prevention of AIDS, Cold Spring Harbor, NY, 1990, pp. 119-124.
Lanciotti R. et al., "Origin of the West Nile Virus Responsible for an Outbreak of Encephalitis in the Northeastern United States," Science, Dec. 17, 1999, vol. 286, pp. 2333-2337.
Liljeström et al., "In Vitro Mutagenesis of a Full-Length eDNA Clone of Semliki Forest Virus: the Small 6,000-Molecular-Weight Membrane Protein Modulates Virus Release," Journal of Virology, Aug. 1991, vol. 65, No. 8, pp. 4107-4113.
Lin et al., "DNA Immunization with Japanese Encephalitis Virus Nonstructural Protein NS1 Elicits Protective Immunity in Mice," Journal of Virology, Jan. 1998, vol. 72, No. 1, pp. 191-200.
López-Medina et al., ""Effcacy of a Dengue Vaccine Candidate (TAK-003) in Healthy Children and Adolescents 2 Years after Vaccination,"" The Journal of Infectious Diseases, 2021, pp. 1-12.
Mackow et al., "The Nucleotide Sequence of Dengue Type 4 Virus: Analysis of Genes Coding for Nonstructural Proteins," Virology, 1987, vol. 159, pp. 217-228.
Mandl et al., "Complete Genomic Sequence of Powassan Virus: Evaluation of Genetic Elements in Tick-Borne versus Mosquito-Borne Flaviviruses," Virology, 1993, vol. 194, pp. 173-184.

(56) References Cited

OTHER PUBLICATIONS

Martin et al., "Standardization of Immunoglobulin M Capture Enzyme-Linked Immunosorbent Assays for Routine Diagnosis of Arboviral Infections," Journal of Clinical Microbiology, May 2000, vol. 38, No. 5, pp. 1823-1826.
Mason et al., "Japanese Encephalitis Virus-Vaccinia Recombinants Produce Particulate Forms of the Structural Membrane Proteins and Induce High Levels of Protection against Lethal JEV infection," Virology, 1991, vol. 180, pp. 294-305.
Mason et al., "Sequence of the Dengue-1 Virus Genome in the Region Encoding the Three Structural Proteins and the Major Nonstructural Protein NS1," Virology,1987, vol. 161, pp. 262-267.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," Journal of Virology, Jun. 1996, vol. 70, No. 6, pp. 3930-3937.
Mir et al., "High-efficiency gene transfer into skeletal muscle mediated by electric pulses," Applied Biological Sciences, Proc. Natl. Acad. Sci. USA, Apr. 1999, vol. 96, pp. 4262-4267.
Monath et al., "Recombinant, chimeric live, attenuated vaccine (ChimeriVax) incorporating the envelope genes of Japanese encephalitis (SA14-14-2) virus and the capsid and nonstructural genes of yellow fever (17D) virus is safe, immunogenic and protective in non-human primates," Vaccine, 1999, vol. 17pp. 1869-1882.
Mullard, "Sanofi's dengue vaccine rounds final corner," Nature Reviews Drug Discovery, Nov. 2014, vol. 13, pp. 801-802.
NCT02993757 "Immunogenic;ty and Safety of a Tetravalent Dengue Vaccine Administered Concomitantly or Sequentially With Gardasil," ClinicalIrials.gov, Apr. 5, 2018, Retrieved from the Internet Oct. 25, 2018, 10 pages.
Nitayaphan et al., "Nucleotide Sequence of the Virulent SA-14 Strain of Japanese Encephalitis Virus and Its Attenuated Vaccine Derivative, SA-14-14-2," Virology, 1990, vol. 177, pp. 541-552.
Novello et al., "Update: West Nile Virus Activity—Northeastern United States, 2000," http://www.cdc.gov/mmwr/preview/mmwrhtml/mm4936a4.htm MMWR Weekly Sep. 15, 2000 / vol. 49, No. 36, pp. 820-822.
Nowak et al., "Analysis of the Terminal 4 Sequences of West Nile Virus Structural Proteins and of the in Vitro Translation of these Proteins Allow the Proposal of a Complete Scheme of the Proteolytic Cleavages Involved in Their Synthesis," Virology, Academic Press. Orlando, Apr. 1, 1989, vol. 169, No. 2, pp. 365-376.
Osatomi et al., "Complete Nucleotide Sequence of Dengue Type 3 Virus Genome RNA," Virology, 1990, vol. 176, pp. 643-647.
Osatomi et al., "Nucleotide Sequence of Dengue Type 3 Virus Genomic RNA Encoding Viral Structural Proteins," Virus Genes, Oct. 1988, vol. 2, No. 1, pp. 99-108. Abstract Only.
Phillpotts et al., "Immunisation with DNA polynucleotides protects mice against lethal challenge with St. Louis encephalitis virus." Arch Virol., 1996, vol. 141, pp. 743-749.
Pinheiro-Michelsen et al., "Anti-dengue Vaccines: From Development to Clinical Trials," Frontiers in Immunology, Jun. 18, 2020, vol. 11, Art. 1252, pp. 1-18.
Pletnev et al., "Construction and characterization of chimeric tick-borne encephalitis/ dengue type 4 viruses." Proc. Nat. Acad. Sci. USA, Medical Sciences, Nov. 1992, vol. 89: pp. 10532-10536.
Pletnev, et al., "Chimeric Tick-Borne Encephalitis and Dengue Type 4 Viruses: Effects of Mutations on Neurovirulence in Mice." J. Virol., Aug. 1993, vol. 67, No. 8, pp. 4956-4963.
Press Release: "Potential Impact of Takeda's Dengue Vaccine Candidate Reinforced by Long-Term Safety and Efficacy Results," May 22, 2021, 5 pages.
Press Release: "Takeda Begins Regulatory Submissions for Dengue Vaccine Candidate in EU and Dengue-Endemic Countries," Mar. 25, 2021, 4 pages.
Press Release: "Takeda's Pipeline Has Potential to Contribute Signi?cantly to Revenue Growth Over Next Decade," Dec. 9, 2020, 4 pages.
Puerta-Guardo et al., "Dengue Virus NS1 Disrupts the Endothelial Glycocalyx, Leading to Hyperpermeability," PloS Pathog, Jul. 14, 2016, vol. 12, No. 7, pp. 1-29.
Puri et al., "Molecular analysis of dengue virus attenuation after serial passage in primary in dog kidney cells." J. Gen Virol., 1997, vol. 78, pp. 2287-2291.
Rice et al., "Nucleotide Sequence of Yellow Fever Virus: Implications for Flavivirus Gene Expression and Evolution," Science, 1985, vol. 229, pp. 726-733.
Rice et al., "Transcription of Infectious Yellow Fever RNA From Full-Length eDNA Templates Produced by In Vitro Ligation," The New Biologist, Dec. 1989, vol. 1, No. 3, pp. 285-296.
Roehrig et al., "Identification of Epitopes on the E Glycoprotein of Saint Louis Encephalitis Virus Using Monoclonal Antibodies." Virology, 1986, vol. 128, pp. 118-126.
Roehrig et al., "Synthetic Peptides Derived from the Deduced Amino Acid Sequence of the E-Glycoprotein of Murray Valley Encephalitis Virus Elicit Antiviral Antibody," Virology, 1989, vol. 171, pp. 49-60.
Sabchareon et al., "Safety and Immunogenictiy of Tetra Live-Attenuated Dengue Vaccines in Thai Adult Volunteers: Role of Serotype Concentration, Ratio, and Multiple Doses," Am. J. Trop. Med. Hyg., 2002, vol. 66, No. 3, pp. 264-272.
Sabchareon, et al., "Protective efficacy of the recombinant, live-attenuated, CYD tetravalent dengue vaccine in Thai schoolchildren: a randomised, controlled phase 2b trial," The Lancet, Nov. 3, 2021, vol. 380, pp. 1559-1567.
Sato et al., "Immunostimulatory DNA Sequences Necessary for Effective Intradermal Gene Immunization," Science, Jul. 19, 1996, vol. 273, No. 5273, pp. 352-354.
Seeger et al., "The cloned genome of ground squirrel hepatitis virus is infectious in the animal," Proc. Nat. Acad. Sci. USA, Medical Sciences, Sep. 1984, vol. 81, pp. 5849-5852.
Sela, Michael, "The Choice of Carrier." In Synthetic Vaccines vol. I, R. Amon, (ed) CRC Press Inc., Boca Raton, FL. Chapter 6, 1987, pp. 83-92.
Smithburn et al., "A Neurotropic Virus Isolated From the Blood of a Native of Uganda," Am. J. Trop. Med. Hyg., 1940, vol. 20, pp. 471-492.
Sridhar et al., "Effect of Dengue Serostatus on Dengue Vaccine Safety and Efficacy," New England Journal of Medicine, Jul. 26, 2018, vol. 379, No. 4, pp. 327-340.
Stanaway et al., "The global burden of dengue: an analysis from the Global Burden of Disease Study 2013," Lancet Infect Dis., Jun. 16, 2016, vol. 16, No. 6, pp. 712-723.
Stocks et al: "Signal Peptidase Cleavage at the Flavivirus C-prM Junction: Dependence on the Viral NS2B-3 Protease for Efficient Processing Requires Determinants in C, the Signal Peptide, and prM," Journal of Virology, LNKDPUBMED: 9499070, Mar. 1998, Mar. 1998 (Mar. 1998), vol. 72, No. 3, pp. 2141-2149.
Sumiyoshi et al., "Complete Nucleotide Sequence of Japanese Encephalitis Virus Genome RNA," Virology, 1987, vol. 161, pp. 497-510.
Tardei et al., "Evaluation of Immunoglobulin M (IgM) and IgG Enzyme Immunoassays in Serologic Diagnosis of West Nile Virus Infection," J Clin. Microbiol. Jun. 2000, vol. 38, No. 6, pp. 2232-2239.
Trent Dennis W. et al., "Partial Nucleotide Sequence of St. Louis Encephalitis Virus RNA: Structural Proteins, NS1, ns2a, and ns2b," Virology, 1987, vol. 156, pp. 293-304.
Trent Dennis W. et al., "Recombinant dengue virus vaccines." In: Dengue and Dengue Hemorrhagic Fever. D.J. Gubler and G. Kuno (eds.). CAB International, New York, NY Chapter 18, 1997, pp. 379-403.
Troyer et al., "A Live Attenuated Recombinant Dengue-4 Virus Vaccine Candidate With Restricted Capacity for Dissemination in Mosquitoes and Lack of Transmission From Vaccinees to Mosquitoes," Am. J. Trop. Med. Hyg., 2001, vol. 65, No. 5, pp. 414-419.
Tsai et al "Japanese Encephalitis Vaccines," In Vaccines, (3rd edition) Plotkin and Orenstein (eds), W.B. Saunders Company, Philadelphia, PA. Chapter 27, 199, pp. 672-710.

(56) References Cited

OTHER PUBLICATIONS

Tsai et al., "Japanese Encephalitis Vaccines," In Vaccines, (2nd edition), Plotkin and Mortimer (eds.), W.B. Saunders Co., Philadelphia, PA. Chapter 24, 1994, pp. 671-713.
Update: "Surveillance for Weste Nile Virus in Overwintering Mosquitoes—New York, 2000," Morb. Mortal. Wkly. Rep., Mar. 10, 2000, vol. 49, No. 09, pp. 178-179.
Falgout et al., "Proper Processing of Dengue Virus Nonstructural Glycoprotein NS1 Requires the N-Terminal Hydrophobic Signal Sequence and the Downstream Nonstructural Protein NS2a," Journal of Virology, May 1989, vol. 63, No. 5, pp. 1852-1860.
Garmendia et al., "Recovery and Identification of West Nile Virus from a Hawk in Winter," Journal of Clinical Microbiology, Aug. 2000, vol. 38, No. 8, pp. 3110-3111.
Gentry et al., "Identification of distinct antigenic determinants on dengue-2 virus using monoclonal antibodies," May 1982, Am. J. Trop. Med. Hyg., vol. 31, No. 3, Pt. 1, pp. 548-555.
Glasner et al., "Dengue virus NS1 cytokine-independent vascular leak is dependent on endothelial glycocalyx components," PloS Pathog., Nov. 9, 2017, vol. 13, No. 11, pp. 1-22.
Gruenberg et al., "Partial Nucleotide Sequence and Deduced Amino Acid Sequence of the Structural Proteins of Dengue Virus Type 2, New Guinea C and PUO-218 Strains" J. gen. Virol., 1988, vol. 69, pp. 1391-198.
Guirakhoo et al., "Construction, Safety, and Immunogenicity in Nonhuman Primates of a Chimeric Yellow Fever-Dengue Virus Tetravalent Vaccine" Journal of Virology, Aug. 2001, vol. 75, No. 16, pp. 7290-7304.
Guirakhoo et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate against Japanese Encephalitis," Virology, 1999, vol. 257, pp. 363-372.
Guirakhoo et al., "Recombinant Chimeric Yellow Fever-Dengue Type 2 Virus Is Immunogenic and Protective in Nonhuman Primates" Journal of Virology, The American Society for Microbiology, Jun. 1, 2000, vol. 74, No. 12, pp. 5477-5485.
Guirakhoo et al., "Viremia and Immunogenicity in Nonhuman Primates of a Tetravalent Yellow Fever-Dengue Chimeric Vaccine: Genetic Reconstructions, Dose Adjustment, and Antibody Responses against Wild-type Dengue Virus Isolates" Virology, 2002, vol. 298, pp. 146-159.
Hadinegoro et al., "Efficacy and Long-Term Safety of a Dengue Vaccine in Regions of Endemic Disease," New England Journal of Medicine, Sep. 24, 2015, vol. 373, No. 13, p. 1195-1206.
Hahn et al., "Nucleotide Sequence of Dengue 2 RNA and Comparison of the Encoded Proteins with Those of Other Flaviviruses," Virology, 1988, vol. 162, pp. 167-180.
Halstead et al., Observations related to the pathogenesis of dengue hemorrhagic fever. II. Antigenic and Biologic Properties of Dengue Viruses and their Association with disease in the host; Yale Journal of Biology and Medicine, Apr. 1970, vol. 42, pp. 276-292.
Hashimoto et al., "Molecular Cloning and Complete Nucleotide Sequence of the Genome of Japanese Encephalitis Virus Beijing-1 Strain," Virus Genes, 1988, vol. 1, No. 3, pp. 305-317.
Heinz et al., "Flaviviruses" Immunochemistry of viruses II, The basis for serodiagnosis and vaccines, (edited by von Regenmortel and Neurath), Elsevier Science Publishers B.V., Chapter 14, 1990 pp. 289-305.
Henchal et al., "Dengue virus-specific and flavivirus group determinants identified with monoclonal antibodies by indirect immunofluorescence," Jul. 13, 1982, Am. J. Trop. Med. Hyg., vol. 31, No. 4, pp. 830-836.
Henchal et al., "Dengue Virus-Specific and Flavivirus Group Determinants Identified with Monoclonal Antibodies by Indirect Immunofluorescence," Flavivirus-Specific and Group Determinants, Am. J. Trop Med. Hyg., 1982, vol. 31, No. 4, pp. 830-836.
Henchal et al., "Epitopic Analysis of Antigenic Determinants on the Surface of Dengue-2 Virions Using Monoclonal Antibod-ies," Am. J. Trop. Med. Hyg., 1985, vol. 34, No. 1, pp. 162-169.
Hennessy et al., "Effectiv ness of live-attenuated Japanese encephalitis vaccine (SA14-14-2): a case-control study" The Lancet, vol. 347, Jun. 8, 1996, pp. 1583-1586.
Ho et al., "DNA vaccination induces a long-term antibody response and protective immunity against pseudorabies virus in mice" Archives of Virology, 1998, vol. 143, pp. 115-125.
Hsiang-Chi et al., "Dengue Type 4 Live-Attenuated Vaccine Viruses Passaged in Vero Cells Affect Genetic Stability and Dengue-Induced Hemorrhaging in Mice," PLOS One, Oct. 28, 2011 (Oct. 28, 2011), vol. 6, No. 10, p. e25800.
Huang et al "Chimeric Dengue Type 2 (Vaccine Strain PDK-53)/ Dengue Type 1 Virus as a Potential Candidate Dengue Type 1 Virus Vaccine" Journal of Virology, Apr. 2000, vol. 74, No. 7, pp. 3020-3028.
Huang et al., "Dengue 2 PDK-53 virus as a chimeric carrier for tetravalent dengue vaccine development," J. Virology, Nov. 2003, vol. 77, No. 21, pp. 11436-11447.
Huang et al., "Genetic and Phenotypic Characterization of Manufacturing Seeds for a Tetravalent Dengue Vaccine (DEN-Vax)," PLOS Neglected Dis, May 2013, vol. 7, No. 5, e2243, 11 pages.
Hubálek et al., "West Nile Fever—a Reemerging Mosquito-Borne Viral Disease in Europe". Emerg. Infect. Dis., Oct. 1988, vol. 5, No. 5, pp. 643-650.
Hunt et al., "Relationships of Bunyamwera Group Viruses by Neutralization" Am. J. Trop. Med. Hyg. 1979, vol. 28, No. 4, pp. 740-749.
Jia et al., "Genetic analysis of West Nile New York 1999 encephalitis virus" The Lancet, Dec. 4, 1999, vol. 354, pp. 1971-1972.
Jirakanjanakit et al., "Dynamics of Susceptibility and Transmissibility of the Live Attenuated, Candidate Vaccines Dengue-1 PDK-13, Dengue-3 PGMK30F3, and Dengue-4 PDK-48 after Oral Infection in Aedes Aegypti," Am. J. Trop. Med. Hyg. 1999, vol. 61, No. 4, pp. 672-676.
Johnson et al., "Detection of Anti-Arboviral Immunoglobulin G by Using a Monoclonal Antibody-Based Capture Enzyme-Linked Immunosorbent Assay," Journal of Clinical Microbiology, May 2000, vol. 38, No. 5, pp. 1827-1831.
Johnson et al., "Growth Characteristics of ChimeriVax-DEN2 Vaccine Virus in *Aedes aegypti* and *Aedes albopictus* Mosquitoes," Am. J. Trop Med. Hyg., 2002, vol. 67, No. 3, pp. 260-265.
Kanesa-Thasan et al., "Safety and immunogenicity of attenuated dengue virus vaccines (Aventis Pasteur) in human volunteers," Vaccine, 2001 vol. 19 pp. 3179-3188.
Kawano et al., "Genetic Determinants of Dengue Type 4 Virus Neurovirulence for Mice," Journal of Virology, Nov. 1993, vol. 67, No. 11, pp. 6567-6575.
Kelly et al., "Evolution of attenuating mutations in dengue-2 strain S16803 PDK50 vaccine and comparison of growth kinetics with parent virus," Virus Genes, 2011, vol. 43, pp. 18-26.
Khin et al., "Infection, Dissemination, Transmission, and Biological Attributes of Dengue-2 PDK53 Candidate Vaccine Virus after Oral Infection in Aedes Aegypti," Am. J. Trop. Med. Hyg., 1994, vol. 51, No. 6, pp. 864-869.
Kimura-Kuroda et al., "Antigenic Comparison of Envelope Protein E between Japanese Encephalitis Virus and Some Other Flaviviruses Using Monoclonal Antibodies," J. Gen. Virol., 1986, vol. 67, pp. 2663-1672.
Kimura-Kuroda et al., "Topographical Analysis of Antigenic Determinants on Envelope Glycoprotein V3 (E) of Japanese Encephalitis Virus, Using Monoclonal Antibodies" Journal of Virology, Jan. 1983, vol. 45, No. 1, pp. 124-132.
Kinney et al. "Construction of Infectious cDNA Clones for Dengue 2 Virus: Strain 16681 and Its Attenuated Vaccine Deriva-tive, Strain PDK-531" Virology, 1997, vol. 230, No. 2, pp. 300-308.
Kinney et al., "Development of New Vaccines against Dengue Fever and Japanese Encephalitis," Intervirology, 2001, vol. 44, pp. 176-197.
Klinman et al., "CpG motifs as immune adjuvants," Vaccine, 1999, vol. 17, pp. 19-25.
Kochel Tadeusz et al., "Inoculation of plasmids expressing the dengue-2 envelope gene elicit neutralizing antibodies in mice," Vaccine. 1997, vol. 15, No. 5, pp. 547-552.

(56) References Cited

OTHER PUBLICATIONS

Kohler et al., "Continuous cultures of fused cells secreting antibody of predefined specificity," Nature, Aug. 7, 1975, vol. 256, pp. 495-497.
Konishi et al., "Avipox virus-vectored Japanese encephalitis virus vaccines: use as vaccine candidates in combination with purified subunit immunogens," Vaccine, 1994, vol. 12, No. 7, pp. 633-638.
Konishi et al., "Comparison of Protective Immunity Elicited by Recombinant Vaccinia Viruses That Synthesize E or NS1 of Japanese Encephalitis Virus," Virology, 1991, vol. 185, pp. 401-410.
Konishi et al., "Generation and Characterization of a Mammalian Cell Line Continuously Expressing Japanese Encephalitis Virus Subviral Particles," Journal of Virology, Mar. 2001, vol. 75, No. 5, pp. 2204-2212.
Konishi et al., "Induction of Protective Immunity against Japanese Encephalitis in Mice by Immunization with a Plasmid Encoding Japanese Encephalitis Virus Premembrane and Envelope Genes," Journal of Virology, Jun. 1998, vol. 72, No. 6, pp. 4925-4930.
Konishi et al., "Mice Immunized with a Subviral Particle Containing the Japanese Encephalitis Virus prM/M and E Proteins Are Protected from Lethal JEV Infection," Virology, 1992, vol. 188, pp. 714-720.
Kozak "Circumstances and Mechanisms of Inhibition of Translation by Secondary Structure in Eucaryotic mRNAs," Molecular and Cellular Biology, Nov. 1989, vol. 9, No. 11, pp. 5134-5142.
Kuno et al., "Phylogeny of the Genus Flavivirus," Journal of Virology, Jan. 1998, vol. 72, No. 1, pp. 73-83.
Laemmli U.K. "Cleavage of Structural Proteins during the Assembly of the Head of Bacteriophage T4," Nature, Aug. 15, 1970, vol. 227, pp. 680-685.
Lai et al., "Evaluation of molecular strategies to develop a live dengue vaccine," Clinical and Diagnostic Virology, 1998, vol. 10, pp. 173-179.
Bray, M. et al., "Monkeys Immunized with Intertypic Chimeric Dengue Viruses Are Protected against Wild-Type Virus Challenge," Journal of Virology, Jun. 1996, vol. 70, No. 6, pp. 4162-4166.
Caufour, P. S. et al., "Construction, characterization and immunogenicity of recombinant yellow fever 17D-dengue type 2 viruses," Virus Research, 2001, vol. 79, pp. 1-14.
Chang, G. et al., "A Single Intramuscular Injection of Recombinant Plasmid DNA Induces Protective Immunity and Prevents Japanese Encephalitis in Mice," Journal of Virology, May 2000, vol. 74, No. 9, pp. 4244-4252.
Huang, C. et al., "Chimeric Dengue 2 PDK-53/West Nile NY99 Viruses Retain the Phenotypic Attenuation Markers of the Candidate PDK-53 Vaccine Virus and Protect Mice against Lethal Challenge with West Nile Virus" Journal of Virology, vol. 79, No. 12, Jun. 2005, pp. 7300-7310.
Hubálek et al., "West Nile Fever—a Reemerging Mosquito-Borne Viral Disease in Europe" Emerging Infectious Diseases, Sep.-Oct. 1999, vol. 5, No. 5, pp. 643-650.
JP 19920043682 19920228 "Non-infective structure particle prepn., useful as vaccine—by infecting preliminarily flavivirus infected cell with cDNA integrated recombinant vaccinia virus, and then sepg. non-infective structure particles contg. E-protein of flavivirus" XP-00211903; Abtract Only.
Köhler, G. et al., "Continuous cultures of fused cells secreting antibody of predefined specificity," Nature, Aug. 7, 1975, vol. 256, pp. 495-497.
Roehrig, J. T. et al., "Identification of Epitopes on the E Glycoprotein of Saint Louis Encephalitis Virus Using Monoclonal Antibodies." Virology, 1983, vol. 128, pp. 118-126.
Villar, L. et al., "Efficacy of a Tetravalent Dengue Vaccine in Children in Latin America," New England Journal of Medicine, Jan. 8, 2015, vol. 372, No. 2, pp. 113-123.
Midgley, C. M. et al. "Structural analysis of a dengue cross-reactive antibody complexed with envelope domain III reveals the molecular basis of cross-reactivity", J. Immunol. (2012) vol. 188(10): 4971-4979.

* cited by examiner

| | Month 0 | Month 3.0 | Month 14.5 | Month 15.9 | Month 18.0 |
|---|---|---|---|---|---|
| Placebo - Seronegative | n=1,832 | n=1,817 | n=1,744 | n=94 | n=7 |
| Placebo - Seropositive | n=4,852 | n=4,805 | n=4,607 | n=218 | n=6 |
| TDV - Seronegative | n=3,714 | n=3,690 | n=3,615 | n=157 | n=10 |
| TDV - Seropositive | n=9,661 | n=9,591 | n=9,391 | n=417 | n=10 |

| | Month 0 | Month 3.0 | Month 14.5 | Month 15.9 | Month 18.0 |
|---|---|---|---|---|---|
| Placebo - Seronegative | n=1,832 | n=1,827 | n=1,776 | n=94 | n=7 |
| Placebo - Seropositive | n=4,852 | n=4,823 | n=4,700 | n=220 | n=6 |
| TDV - Seronegative | n=3,714 | n=3,693 | n=3,635 | n=157 | n=10 |
| TDV - Seropositive | n=9,661 | n=9,599 | n=9,435 | n=417 | n=10 |

DENGUE VACCINE UNIT DOSE AND ADMINISTRATION THEREOF

FIELD OF THE INVENTION

The present invention relates to a safe and effective method of inoculation against dengue disease and a corresponding safe and effective dengue vaccine. In particular the present invention relates to a safe and effective method of inoculation against dengue disease irrespective of serostatus and a corresponding safe and effective dengue vaccine. The present invention relates also to unit doses of a dengue vaccine composition and methods for administering a unit dose of a dengue vaccine composition to a subject or a subject population in a broad age group. The present invention is also related to particular concomitant administration regimes, wherein the unit does/vaccine composition is administered concomitantly with one or more of: a yellow fever (YF) vaccine, a hepatitis A vaccine, a human papillomavirus (HPV) vaccine, a combined measles, mumps and rubella (MMR) vaccine, a combined tetanus, diphtheria, and pertussis (whooping cough) (Tdap) vaccine, and/or a combined vaccine for diphtheria, tetanus, pertussis, poliomyelitis and *Haemophilus influenzae* type b (DTap/IPV/Hib), or any combination of the concomitant administration regimes mentioned above. The unit dose according to this invention provides immune responses against all serotypes of dengue virus, i.e. DENV-1, DENV-2, DENV-3 and DENV-4.

The Sequence Listing submitted in text format (.txt) filed on Sep. 5, 2019, named "T08269US2_ST25.txt", (created on Sep. 5, 2019, 345 KB), is incorporated herein by reference.

BACKGROUND OF THE INVENTION

Vaccines for protection against viral infections have been effectively used to reduce the incidence of human disease. One of the most successful technologies for viral vaccines is to immunize animals or humans with a weakened or attenuated virus strain (a "live attenuated virus"). Due to limited replication after immunization, the attenuated virus strain does not cause disease. However, the limited viral replication is sufficient to express the full repertoire of viral antigens and can generate potent and long-lasting immune responses to the virus. Thus, upon subsequent exposure to a pathogenic virus strain, the immunized individual is protected from the disease. These live attenuated viral vaccines are among the most successful vaccines used in public health.

Dengue disease is a mosquito-borne disease caused by infection with a dengue virus. Dengue virus infections can lead to debilitating and painful symptoms, including a sudden high fever, headaches, joint and muscle pain, nausea, vomiting and skin rashes. To date, four serotypes of dengue virus have been identified: dengue-1 (DENV-I), dengue-2 (DENV-2), dengue-3 (DENV-3) and dengue-4 (DENV-4). Dengue virus serotypes 1-4 can also cause dengue hemorrhagic fever (DHF) and dengue shock syndrome (DSS). In the most severe cases, DHF and DSS can be life threatening. Dengue viruses cause 50-100 million cases of debilitating dengue fever, 500,000 cases of DHF/DSS, and more than 20,000 deaths each year, a large portion of which are children. All four dengue virus serotypes are endemic throughout the tropical regions of the world and constitute the most significant mosquito-borne viral threat to humans there. Dengue viruses are transmitted to humans primarily by *Aedes aegypti* mosquitoes, but also by *Aedes albopictus* mosquitoes. Infection with one dengue virus serotype results in life-long protection from re-infection by that serotype, but does not prevent secondary infection by one of the other three dengue virus serotypes. In fact, previous infection with one dengue virus serotype may lead to an increased risk of severe disease (DHF/DSS) upon secondary infection with a different serotype.

To date, only one vaccine, a tetravalent dengue vaccine based on a yellow fever backbone, CYD-TDV (Dengvaxia®, Sanofi Pasteur, Lyon, France), has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). However, clinical trials have shown that Dengvaxia® can enhance, rather than reduce, the risk of severe disease due to dengue infection in individuals who had not been previously infected by a dengue virus (seronegative populations). Therefore, Dengvaxia® is only recommended for use in individuals who had been previously infected with at least one dengue virus serotype (seropositive populations). More specifically, according to the European Medicine Agencys European Public Assessment report (EPAR) for the product, Dengvaxia® is only for use in people from 9 to 45 years of age who have been infected with dengue virus before and who live in areas where this infection is endemic. Endemic areas are areas where the disease occurs regularly throughout the year. See also Sridhar S et al. Effect of Dengue Serostatus on Dengue Vaccine Safety and Efficacy. N Engl J Med 2018, 379:327-40; and World Health Organization. Dengue vaccine: WHO position paper—September 2018. Wkly. Epidemiol. Rec. 2018, 93:457-476. S. R. Hadinegoro et al. report in the New England Journal of Medicine, Vol. 373, page 1195, in "Efficacy and Long-Term Safety of a Dengue Vaccine in Regions of Endemic Disease" a pooled risk of hospitalization for virologically-confirmed dengue disease among those under the age of 9 years of 1.58 indicating an increased risk for the vaccinated group with respect to severe dengue. This leaves a substantial unmet need for an effective vaccine with a good safety profile in both dengue-naïve and seropositive individuals, including those dengue-naïve populations living in endemic areas, younger individuals who may not have developed any seropositive response to dengue or been exposed to dengue, and travelers and individuals from non-endemic regions. There is also a need for outbreak control or travel vaccination, offering a reduction in the risk of dengue after only one dose.

One further disadvantage of the only currently approved dengue vaccine, Dengvaxia®, is that it must only be given to people who have had a positive test result showing a previous infection with dengue virus (EPAR), i.e. individuals with known serostatus for dengue. Thus, individuals with unknown serostatus for dengue cannot be vaccinated with Dengvaxia®.

There is hence a need for a dengue vaccine and corresponding method of inoculation that stimulates an immune response to all dengue serotypes, preferably a balanced immune response to all serotypes, and protects against dengue disease of any severity (including DSS, DHF), both in seronegative and seropositive populations, which is safe for a larger group of ages, in particular also for subjects of 9 years and younger. The development of a safe and effective vaccine capable of protecting all populations, including both seronegative and seropositive populations, and in particular children and young adults and elderly subjects in endemic settings and for the purpose of traveling, represents an important approach to the prevention and control of this global disease.

There is thus a medical need for a dengue vaccine and corresponding method of inoculation which, as well as being safe and efficacious irrespective of serostatus and in a broad age group. There is a need for a dengue vaccine and corresponding method of inoculation that avoids costly and time consuming serostatus tests or seroprevalence considerations. There is a need for a dengue vaccine and corresponding method of inoculation that can be used in an outbreak situation. Furthermore there is a medical need for a dengue vaccine which as well as being safe and effective can also be administered to individuals with unknown dengue serostatus, children under 9 years and seronegative individuals.

There is also a need for a vaccine that is administered in fewer doses than the current Dengvaxia® dosing schedule of 3 doses, 6 months apart, such as a vaccine that can be administered in only two doses or one dose to be efficacious.

The above objects are commensurate with the research priorities provided by the WHO in the Dengue Vaccine: WHO position paper—September 2018 (Wkly. Epidemiol. Rec. 2018, 93:457-476).

Yellow fever (YF) is an acute viral hemorrhagic disease transmitted by infected mosquitoes of the *Aedes aegypti* specie. Symptoms of yellow fever take 3 to 6 days to develop and include fever, headache, jaundice, muscle pain, nausea, vomiting and fatigue. A small proportion of patients (about 15% of people) who contract the virus develop a severe disease that can lead to bleeding, shock, organ failure, and sometimes death. The virus is endemic in tropical areas of Africa and Central and South America.

Dengue fever and yellow fever (YF) viruses belong to the same family of flaviviridae and share antigenic determinants, which may result in cross-reacting antibodies. They are both transmitted between humans by mosquitoes (primarily *Aedes aegypti*), and are both endemic in tropical areas of Africa and Latin America with a high public health impact.

Today there exists a yellow fever vaccine (YF-17D vaccine) which is based on a live, attenuated viral strain, and is the only commercially available YF vaccine administered as a single subcutaneous injection. The YF-17D vaccine is highly effective (approaching 100%) and generally safe with the exception of very rare cases of vaccine-associated neurotropic and viscerotropic disease. Vaccination against YF is also required for travelers to certain countries in accordance with the International Health Regulations, and is also recommended by the WHO for all subjects travelling to areas where there is evidence of persistent or periodic YF virus transmission. A YF-17D vaccine is available under the product name YF-VAX® from Sanofi.

A yellow fever vaccine is recommended for people from nine months of age and older who are living in or traveling to endemic areas, persons travelling to or through countries requiring. A single dose of yellow fever vaccine administered subcutaneously is usually sufficient to confer sustained lifelong protective immunity against yellow fever. However, for people who remain at risk, a booster dose is recommended every 10 years.

Hence, there is a need for a safe and effective method of simultaneously preventing dengue disease and yellow fever.

Hepatitis A is a liver disease caused by the hepatitis A virus (HAV). The virus is primarily spread when an uninfected (and unvaccinated) person ingests food or water that is contaminated with the feces of an infected person. The disease is closely associated with unsafe water or food, inadequate sanitation and poor personal hygiene. The virus can also be transmitted through close physical contact with an infectious person. Unlike hepatitis B and C, hepatitis A infection does not cause chronic liver disease and is rarely fatal, but it can cause debilitating symptoms and fulminant hepatitis (acute liver failure), which is often fatal. Hepatitis A occurs sporadically and in epidemics worldwide, with a tendency for cyclic recurrences.

The hepatitis A virus is one of the most frequent causes of foodborne infection. Epidemics related to contaminated food or water can erupt explosively, such as the epidemic in Shanghai in 1988 that affected about 300,000 people. Hepatitis A viruses persist in the environment and can withstand food-production processes routinely used to inactivate and/or control bacterial pathogens. The disease can lead to significant economic and social consequences in communities. It can take weeks or months for people recovering from the illness to return to work, school, or daily life. The impact on food establishments identified with the virus, and local productivity in general, can be substantial. In developing countries with poor sanitary conditions and hygienic practices, most children (90%) have been infected with the hepatitis A virus before the age of 10 years.

The number of people traveling internationally has grown substantially in recent decades. According to the United Nations World Tourism Organization (UNWTO), over 1.1 billion tourists travelled abroad in 2014. The risk of becoming ill during international travel depends on many factors, such as the region of the world visited, the length of the trip, and the diversity of planned activities. Vaccine recommendations are a prominent part of health preparations before international travel. Vaccination against hepatitis A virus is commonly recommended for travelers to at-risk areas around the world including Asia, Africa, and Latin America.

For routine hepatitis A vaccination, a two-dose schedule is recommended, particularly in travelers at substantial risk of contracting hepatitis A and in immunocompromised individuals. However, in healthy individuals, comparable effectiveness has been achieved with a single dose. The vaccination schedule for children/adolescents (12 months through 18 years of age) as well as for adults (≥19 years of age) consists of a primary dose administered intramuscularly, and a further booster dose administered intramuscularly 6 to 18 months later.

Available hepatitis A vaccines include HAVRIX® and VAQTA®.

Hence, there is a need for a safe and effective method of simultaneously preventing dengue disease and hepatitis A.

Human papillomavirus (HPV) is a common virus that is passed from one person to another through direct skin-to-skin contact during sexual activity. Most sexually active people will be infected with HPV at some time in their lives and the infection is most common in people in their late teens and early 20s. There are about 40 types of HPV that can infect the genital areas of men and women. While most HPV types cause no symptoms and are cleared by the body's immune system, some HPV types are persistent and can cause cervical cancer in women and other less common cancers—like cancers of the anus, penis, vagina, vulva and oropharynx or warts in the genital areas of men and women, called genital warts.

HPV vaccination prevents HPV-associated cervical cancers as well as HPV-associated cancers of the anus, vulva, vagina, and oropharynx. The vaccination can also prevent HPV-associated genital warts. HPV vaccination is recommended in particular for 11 and 12 year-old girls. It is also recommended for girls and women age 13 through 26 years of age who have not yet been vaccinated or completed the vaccine series. HPV vaccine can also be given to girls beginning at age 9 years. The CDC recommends 11 to 12 year olds girls get two doses of HPV vaccine to protect against cancers caused by HPV. More recently, vaccination of boys in the same age ranges has also been recommended.

The routine HPV vaccination schedule for adolescents who start the vaccination series before the 15th birthday includes two doses of a HPV vaccine. The two doses are usually separated by 6 to 12 months. The minimum interval between doses is five calendar months. A three dose schedule is recommended for subjects who start the series on or after the 15th birthday and for subjects with certain immunocompromising conditions (such as cancer, HIV infection, or taking immunosuppressive drugs). The second dose is usually given 1 to 2 months after the first dose and the third dose 6 months after the first dose. The minimum interval between the first and second doses of vaccine is usually 4 weeks. The minimum interval between the second and third doses of vaccine is usually 12 weeks. The minimum interval between the first and third doses is usually 5 calendar months. If the vaccination series is interrupted, the series does not need to be restarted.

Available HPV vaccines include Gardasil® 9, which is a recombinant 9-valent HPV (9vHPV) vaccine for preventing HPV serotypes 6, 11, 16, 18, 31, 33, 45, 52, and 58. The HPV vaccine does not include any live or inactivated HPV, but the L1 proteins of the respective HPV serotypes.

Hence, there is a need for a safe and effective method of simultaneously preventing dengue disease and HPV-associated cancers or genital warts.

Measles is a highly contagious infectious disease caused by the measles virus, a single-stranded, negative-sense, enveloped (non-segmented) RNA virus of the genus *Morbillivirus* within the family Paramyxoviridae. Complications occur in about 30% of cases and may include diarrhea, blindness, inflammation of the brain, and pneumonia, among others. Encephalitis occurs in approximately one of every 2000 reported cases; survivors often have permanent brain damage and mental retardation. Death, predominantly from respiratory and neurological causes, occurs in one of every 3000 reported measles cases. The risk of death is greater for infants and adults than for children and adolescents. Contracting measles during pregnancy increases fetal risk. Most commonly, this risk involves premature labor and moderately increases rates of spontaneous abortion and of low birth weight. Subacute sclerosing panencephalitis, a slow virus infection of the central nervous system, is associated with measles virus. Measles is an airborne disease which spreads easily through the coughs and sneezes of infected people and may also be spread through contact with saliva or nasal secretions.

Mumps is an acute disease of children and young adults, caused by the mumps virus, a single-stranded, negative-sense RNA virus of the genus *Rubulavirus* within the family Paramyxoviridae. Mumps virus produces no symptoms in about one-third of infected people. In those with a clinical response, glandular and nerve tissue are most often affected and the most common symptoms include fever and swelling of the parotid glands. Complications may include meningitis (15%), pancreatitis (4%), inflammation of the heart, or permanent deafness. Frequent viruria and abnormal renal function suggest that mumps virus may infect the kidneys. Mumps is highly contagious and spreads rapidly among people living closely together by respiratory droplets or direct contact with an infected person.

Rubella (German measles) is an infection caused by the rubella virus, a single-stranded, positive-sense RNA virus of the genus *Rubivirus* within the family Togaviridae. The virus usually results in a mild illness, accompanied by few constitutional symptoms, and occurs most commonly in childhood. If the infection occurs in a woman in early pregnancy however, the virus may cross the placenta to reach the fetus, in which the infection can induce birth defects. These defects may be serious and permanent and include congenital heart disease, cataract formation, deafness and mental retardation. Rubella is usually spread through the air via coughs of people who are infected.

Combined vaccine for measles, mumps and rubella (MMR) is used widely for the immunization of children in certain regions of the world, because of its advantages over the individual vaccines. Combined vaccine provokes an adequate immune response in children simultaneously for the three infections.

MMR vaccines are indicated for simultaneous vaccination against measles, mumps, and rubella in individuals 12 months of age or older. Individuals first vaccinated at 12 months of age or older should be revaccinated prior to elementary school entry. Revaccination is intended to seroconvert those who do not respond to the first dose. The Advisory Committee on Immunization Practices (ACIP) recommends administration of the first dose at 12 to 15 months of age and administration of the second dose at 4 to 6 years of age.

Hence, there is a need for a safe and effective method of simultaneously preventing dengue disease and measles, mumps and rubella.

Tetanus is caused by an infection with the bacterium *Costridium tetani* which is commonly found in soil, saliva, dust, and manure. The bacteria generally enter the body through a break in the skin such as a cut or puncture wound by a contaminated object. The bacteria produce toxins that interfere with muscle contractions, resulting in the typical signs of muscle spasms. It affects the brain and nervous system and causes extremely painful muscle spasms, usually all over the body. Spasms of the jaw can make it impossible to open the mouth, a condition called "lockjaw." Tetanus kills one out of ten people infected with the disease.

Diphtheria is an infection caused by the bacterium *Corynebacterium diphtheriae* which primarily infects the throat and upper airways, and produces a toxin affecting other organs. Diphtheria has an acute onset and the main characteristics are sore throat, low fever and swollen glands in the neck. The toxin may, in severe cases, cause myocarditis or peripheral neuropathy. The diphtheria toxin causes a membrane of dead tissue to build up over the throat and tonsils, making breathing and swallowing difficult. Diphtheria is a very contagious infection and the bacteria usually spread between people by direct contact or through the air, but it may also be spread by contaminated objects.

Pertussis, or whooping cough, caused by the bacterium *Bordetella pertussis* is an airborne disease that results in an extremely contagious respiratory infection that can lead to severe breathing problems, especially in infants. Pertussis first appears like an ordinary cold, but then causes intense, uncontrollable coughing spells which can cause difficulty breathing, vomiting, and disturbed sleep. A person may cough so hard that they vomit, break ribs, or become very tired from the effort. Children less than one year old may have little or no cough and instead have periods where they do not breathe. A high-pitched "whoop" noise is heard when the person tries to take a breath after coughing. Complications include pneumonia or death. Pertussis can affect people of all ages, but can be very serious and even deadly, for babies less than a year old.

Tdap is a combination vaccine that protects against the three potentially life-threatening bacterial diseases tetanus, diphtheria, and pertussis (whooping cough). Tdap stands for tetanus and diphtheria toxoids with acellular pertussis. Tdap is an inactive vaccine produced by using dead bacteria. It is recommended that vaccination against tetanus, diphtheria and pertussis carried out in infancy (in children of less than 7 years of age) is done by using a particular diphtheria toxoid, tetanus toxoid and acellular pertussis absorbed vaccine, such as INFANRIX® from GlaxoSmithKline. A further booster Tdap vaccine is recommended for children of greater than 10 years to ensure that immunity against tetanus, diphtheria and pertussis is maintained into adulthood. A booster Tdap vaccine based on combined tetanus toxoid, reduced diphtheria toxoid and acellular pertussis (adsorbed) is available under the brand name BOOSTRIX® from GlaxoSmithKline. Tdap vaccination is administered intramuscularly as a single dose.

Hence, there is a need for a safe and effective method of simultaneously preventing dengue disease and tetanus, diphtheria, and pertussis.

In addition to diphtheria, tetanus and pertussis, poliomyelitis, often called polio or infantile paralysis, is a highly infectious viral disease caused by the poliovirus. It invades the nervous system, and can cause total paralysis in a matter of hours. The virus is transmitted by person-to-person spread mainly through the fecal-oral route or, less frequently, by a common vehicle (for example, contaminated water or food) and multiplies in the intestine. Initial symptoms are fever, fatigue, headache, vomiting, stiffness of the neck and pain in the limbs. 1 in 200 infections leads to irreversible paralysis (usually in the legs). Among those paralyzed, 5% to 10% die when their breathing muscles become immobilized. Polio mainly affects children under 5 years of age. There is no cure for polio, it can only be prevented.

*Haemophilus influenzae* type b (Hib) is a bacteria responsible for severe pneumonia, meningitis and other invasive diseases almost exclusively in children aged less than 5 years. It is transmitted through the respiratory tract from infected to susceptible individuals. Hib also causes potentially severe inflammatory infections of the face, mouth, blood, epiglottis, joints, heart, bones, peritoneum, and trachea. Although this problem occurs worldwide the burden of Hib disease was considerably higher in resource-poor countries, prior to the introduction of the vaccine into their national immunization programs. In 2000, Hib was estimated to have caused two to three million cases of serious disease, notably pneumonia and meningitis, and 386,000 deaths in young children. Hib disease is observed in all parts of the world but is difficult to confirm because it requires prompt laboratory investigation in patients that have not received prior antibiotic treatment.

Commercially available combined DTaP/IPV/Hib vaccines include Pentacel®, which is based on combined diphtheria toxoid, tetanus toxoid, acellular pertussis (adsorbed), and inactivated poliovirus in combination with a Hib conjugate vaccine.

Hence, there is a need for a safe and effective method of simultaneously preventing dengue disease and diphtheria, tetanus, pertussis, poliomyelitis and diseases caused by *Haemophilus influenzae* type b.

Furthermore, it has been reported that elderly subjects infected with dengue virus often present atypically, wherein fever may be the only symptom and are less likely to present with typical symptoms and signs of dengue fever which may be defined as fever plus at least one of the following symptoms: bone pain, myalgia, arthralgia, retro-orbital pain, headache and maculopapular rash (Lee et al. (2013) Am. J. Emerg. Med. 31(5): 783-787). Yet, elderly adults are at increased risk of developing severe dengue and DHF/DSS compared to younger subjects (Liu et al. (2008) Am. J. Infect. Dis. 4(1): 10-17; Lin et al. (2012) Emerg. Infect. Dis. 18(10): 2003-1009; Rowe et al. (2014) PloS Negl. Trop. Dis. 8(4)). Several reasons which may contribute to severe disease in the elderly have been discussed, such as impaired physiological and immune functions, an increased probability of acquiring secondary dengue and an increased prevalence of chronic diseases and other comorbidities in the elderly, i.e. above 60 (see the discussion in Lin et al. (2017) Expert Review of Anti-infective Therapy 15(8): 729-735).

OBJECTS AND SUMMARY

It is an object of the present invention to provide a safe and effective vaccine and corresponding method of inoculation against all serotypes of dengue virus for dengue-endemic and dengue non-endemic populations and for a broad range of ages, in particular for subjects between 2 months and 60 years of age, and independent of previous exposure to dengue virus and corresponding seropositive or seronegative status before vaccination.

It is an object of the present invention to minimize the risk of DHF and DSS caused by infection with DENV-1, DENV-2, DENV-3 or DENV-4, in particular following vaccination in children of young age and individuals of any age who have never been previously exposed to dengue, or who are seronegative to dengue before vaccination.

It is an object of the invention to provide a vaccine and corresponding method of inoculating for controlling a dengue outbreak situation.

It is an object of the invention to provide a vaccine and corresponding method of inoculating which is useful in settings less familiar with clinical management of dengue or in those with fewer resources.

It is an object of the invention to provide a vaccine and corresponding method of inoculating which avoids testing for individual serostatus before individual inoculation or analysis of seroprevalence rates in areas to be mass vaccinated.

It is an object of the invention to provide a vaccine and corresponding method of inoculating which reduces and/or avoids the risk for later antibody dependent enhancement.

It is an object of the invention to provide a vaccine and corresponding method which reduces and/or avoids dengue NS1 toxicosis.

It is an object of the invention to provide a vaccine and corresponding method of inoculating which induces cross reactive multitypic antibody and/or cell mediated immunity.

It is one object of the present invention to provide a safe and effective protection against dengue disease and yellow fever.

It is another object of the present invention to provide a safe and effective protection against dengue disease and hepatitis A.

It is a further object of the present invention to provide a safe and effective protection against dengue disease and HPV-associated cancers or genital warts.

It is a certain object of the present invention to provide a safe and effective protection against dengue disease and measles, mumps and rubella.

It is another object of the present invention to provide safe and effective protection against dengue disease and tetanus, diphtheria, and pertussis.

It is another object of the present invention to provide a safe and effective protection against dengue disease and diphtheria, tetanus, pertussis, poliomyelitis and diseases caused by *Haemophilus influenzae* type b.

It is another object of the present invention to provide safe and effective protection against any combination of the above mentioned diseases.

It is another object of the present invention to provide a vaccine which stimulates a balanced immune response to all four dengue serotypes in a subject, in particular in an elderly subject (i.e. more than 60 years of age).

The present invention is therefore directed in part to a dengue vaccine for a method of mass vaccination without individual testing for serostatus or prior evaluation of seroprevalence rates. This mass vaccination includes endemic regions including outbreak situations as well as in non-endemic regions for travelers.

The present invention is therefore directed to a tetravalent dengue virus composition including four live attenuated dengue virus strains representing serotype 1, serotype 2, serotype 3 and serotype 4, wherein preferably the tetravalent dengue virus composition includes a chimeric dengue serotype 2/1 strain and a dengue serotype 2 strain and a chimeric dengue serotype 2/3 strain and a chimeric dengue serotype 2/4 strain, wherein preferably the dengue serotype 2 strain is derived from the wild type virus strain DEN-2 16681 (represented by SEQ ID NO 11) and differs in at least three nucleotides from the wild type as follows:

a) 5'-noncoding region (NCR)-57 (nt-57 C-to-T)

b) NS1-53 Gly-to-Asp (nt-2579 G-to-A)

c) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

The present invention is in particular directed to a composition or lyophilized unit dose which upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is also in particular directed to such a composition or unit dose which upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or preferably at least 10%, or at least 12%, or at least 14%, or at least 16%, or at least 18%.

The present invention is also in particular directed to such method and use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

The present invention is therefore directed to a method including and corresponding use of a tetravalent dengue virus composition including four live attenuated dengue virus strains representing serotype 1, serotype 2, serotype 3 and serotype 4, the method being directed to inoculating a subject against virologically confirmable dengue disease, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (represented by SEQ ID NO 11) and differs in at least three nucleotides from the wild type as follows:

d) 5'-noncoding region (NCR)-57 (nt-57 C-to-T)

e) NS1-53 Gly-to-Asp (nt-2579 G-to-A)

f) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

The present invention is in particular directed to such method and use wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is also in particular directed to such method and use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, and wherein the subject is preferably 2 to 17 years of age or 4 to 16 years of age.

The present invention is also in particular directed to such method and use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%, wherein the subject is 18 to 60 years of age.

The present invention is therefore directed to a method and corresponding use, the method comprising a primary vaccination with only two administrations of the unit dose comprising the steps of:

(A) administering a first unit dose of the tetravalent dengue virus composition to the subject, and (B) administering a second unit does of the tetravalent dengue virus composition to the subject within 3 months of administration of the first unit dose, wherein preferably the method and use do not include a step of determination whether there was a previous dengue infection in the subject before administration of the unit dose or wherein the serostatus of the subject is unknown before administration of the unit dose or wherein the method and use do not include a step of determination of a previous dengue infection in the subjects preferably at any time before, during or after the steps of administration or wherein the serostatus of the subject is unknown preferably at any time before, during or after the steps of administration.

According to one embodiment such a method and use do not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method and use do not include vaccine immunogenicity analysis including GMTs for dengue neutralizing antibodies.

According to one embodiment such a method and use do not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

The method according to the invention does not require the testing of the serostatus before vaccination and thus allows immediate treatment and outbreak control. According to certain embodiments the invention is directed to a method and use wherein the subject is exposed to a dengue outbreak. In certain such embodiments the outbreak is due to a dengue serotype 2, and/or due to a serotype 1.

According to certain embodiments the method of inoculation against the virologically confirmable dengue disease is due to a dengue serotype 2, and/or due to a dengue serotype 1.

According to one embodiment the method comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method further optionally comprises at least 1 years after the administration of the second unit dose a booster dose of the unit dose.

According to one embodiment the method and use is directed to a method of inoculating a subject against virologically confirmable dengue disease with a tetravalent dengue virus composition including four live attenuated dengue virus strains representing serotype 1, serotype 2, serotype 3 and serotype 4, the dengue serotype 2 strain being derived from the wild type virus strain DEN-2 16681 (represented by SEQ ID NO 11) and differing in at least three nucleotides from the wild type as follows:

a) 5'-noncoding region (NCR)-57 (nt-57 C-to-T)

b) NS1-53 Gly-to-Asp (nt-2579 G-to-A)

c) NS3-250 Glu-to-Val (nt-5270 A-to-T); and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera, the method comprises a primary vaccination consisting of the steps of:

(A) selecting a subject for administration of the unit doses of the tetravalent dengue virus composition in need for protection against dengue infection without determination whether there was a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method further optionally comprises at least 1 years after the administration of the second unit dose a booster dose of the unit dose.

According to the invention the method and use is applicable to subjects of all kinds of ages. The present invention is in particular directed to such a method and use wherein the subject is under 9 years of age, or 4 to 5 years of age, or 6 to 11 years of age, or 12 to 16 years, or 6 to 16 years of age, or 4 to 16 years of age, or 2 to 17 years of age, or 9 years of age, or over 9 years of age, or 9 to 17 years of age, or 18 to 60 years of age, or 18 to 45 years of age, or 46 to 60 years of age, or over 60 years of age.

In particular the present invention is directed to such use wherein the method is safe.

In particular the present invention is directed to such use wherein the method provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

In particular the present invention is directed to such use wherein the method is effective.

In particular the present invention is directed to such use wherein the method provides a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the last administration of the administration schedule.

The present invention is also directed in part to a reconstituted dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent (i) dengue serotype 1 has a concentration of at least 3.3 log 10 pfu/0.5 mL and optionally to 5.0 log 10 pfu/0.5 mL, (ii) dengue serotype 2 has a concentration of at least 2.7 log 10 pfu/0.5 mL and optionally to 4.9 log 10 pfu/0.5 mL, (iii) dengue serotype 3 has a concentration of at least 4.0 log 10 pfu/0.5 mL and optionally to 5.7 log 10 pfu/0.5 mL, and (iv) dengue serotype 4 has a concentration of at least 4.5 log 10 pfu/0.5 mL and optionally to 6.2 log 10 pfu/0.5 mL.

The present invention is therefore directed in part to a dengue vaccine composition for use in a method of preventing virologically confirmable dengue disease (VCD) in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4, wherein the attenuated dengue virus strains comprise chimeric dengue viruses and preferably at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL, in particular wherein the dengue serotype 3 is at least about 10% of the total concentration in pfu/0.5 mL and in particular wherein the dengue serotype 4 is at least about 70% of the total concentration in pfu/0.5 mL.

The present invention is therefore directed in part to a unit dose of a dengue vaccine composition and use thereof, the unit dose comprising:

a tetravalent dengue virus composition including four live attenuated dengue serotypes (e.g. virus strains):

(i) a dengue serotype 1 (e.g. chimeric dengue serotype 2/1 strain), (ii) a dengue serotype 2 (e.g. dengue serotype 2 strain), (iii) a dengue serotype 3 (e.g. chimeric dengue serotype 2/3 strain), (iv) a dengue serotype 4 (e.g. chimeric dengue serotype 2/4 strain), and one or more pharmaceutically acceptable excipients thereof.

The present invention is further directed in part to a unit dose of a dengue vaccine composition and use thereof, the unit dose comprising:

a tetravalent virus composition including four live attenuated dengue virus strains:

(i) a dengue serotype 1 (e.g. chimeric dengue serotype 2/1 strain) in a concentration of at least 3.3 log 10 pfu/0.5 ml, (ii) a dengue serotype 2 (e.g. dengue serotype 2 strain) in a concentration of at least 2.7 log 10 pfu/0.5 ml, (iii) a dengue serotype 3 (e.g. chimeric dengue serotype 2/3 strain) in a concentration of at least 4.0 log 10 pfu/0.5 ml, and (iv) a dengue serotype 4 (e.g. chimeric dengue serotype 2/4 strain) in a concentration of at least 4.5 log 10 pfu/0.5 ml, and one or more pharmaceutically acceptable excipients.

The present invention is further directed in part to a unit dose of a dengue vaccine composition and use thereof, the unit dose comprising:

a tetravalent virus composition including four live attenuated dengue virus strains, wherein the unit dose is lyophilized and upon reconstitution with 0.5 mL of a pharmaceutically acceptable diluent comprises:

(i) a dengue serotype 1 (e.g. chimeric dengue serotype 2/1 strain) in a concentration of at least 3.3 log 10 pfu/0.5 ml, (ii) a dengue serotype 2 (e.g. dengue serotype 2 strain) in a concentration of at least 2.7 log 10 pfu/0.5 ml, (iii) a dengue serotype 3 (e.g. chimeric dengue serotype 2/3 strain) in a concentration of at least 4.0 log 10 pfu/0.5 ml, and (iv) a dengue serotype 4 (e.g. chimeric dengue serotype 2/4 strain) in a concentration of at least 4.5 log 10 pfu/0.5 ml.

The present invention is further directed in part to a unit dose of a dengue vaccine composition and use thereof, wherein said unit dose is lyophilized and obtained by lyophilizing 0.5 mL of a solution comprising:

a tetravalent virus composition including four live attenuated dengue virus strains:

(i) a dengue serotype 1 (e.g. chimeric dengue serotype 2/1 strain) in a concentration of at least 3.3 log 10 pfu/0.5 ml, (ii) a dengue serotype 2 (e.g. dengue serotype 2 strain) in a concentration of at least 2.7 log 10 pfu/0.5 ml, (iii) a dengue serotype 3 (e.g. chimeric dengue serotype 2/3 strain) in a concentration of at least 4.0 log 10 pfu/0.5 ml, and (iv) a dengue serotype 4 (e.g. chimeric dengue serotype 2/4 strain) in a concentration of at least 4.5 log 10 pfu/0.5 ml, and one or more pharmaceutically acceptable excipients.

The present invention is in particular directed to such unit dose or composition wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, in particular wherein the concentration of (iii) in pfu/0.5 mL is at least 10%.

The present invention is in particular directed to such unit dose or composition, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

The present invention is further directed in part to a kit for preparing a reconstituted unit dose and use thereof, the kit comprising the following components:

a) a lyophilized unit dose of the present invention as described herein, and b) a pharmaceutically acceptable diluent for reconstitution.

The present invention is further directed in part to a container, such as a vial, comprising one to ten unit doses of the present invention as described herein.

The present invention is further directed to a method of preventing dengue disease in a subject comprising administering to the subject a reconstituted unit dose of a dengue vaccine composition as described herein, for example by subcutaneous injection.

The present invention is further directed to the use of the reconstituted unit dose of a dengue vaccine composition as described herein for the manufacture of a medicament for preventing dengue disease in a subject, for example by subcutaneous injection.

The present invention is further directed to the reconstituted unit dose of a dengue vaccine composition as described herein for use in a method of preventing dengue disease in a subject, for example by subcutaneous injection.

The present invention is further directed to a method of preventing dengue disease in a subject population, comprising administering to the subject population a reconstituted unit dose of a vaccine composition as described herein, wherein the subject population is seronegative to all dengue serotypes. In said method the geometric mean neutralizing antibody titers (GMTs) when tested in at least 40, or at least 50, or at least 60 subjects at day 180 or day 365 after at least a first administration of said unit dose, and optionally a second administration of said unit dose 90 days after said first administration, may provide a ratio of not more than 50, or not more than 40, or nor more than 30, or not more than 20 for the GMT of dengue serotype 2 to the GMT of dengue serotype 4 (GMT DENV-2:GMT DENV-4), and optionally a ratio of not more than 20 for the GMT of dengue serotype 2 to the GMT of dengue serotype 1 (GMT DENV-2:GMT DENV-1), and optionally a ratio of not more than 20 for the GMT of dengue serotype 2 to the GMT of dengue serotype 3 (GMT DENV-2:GMT DENV-3).

The present invention is further directed to a method of preventing dengue disease in a subject, comprising administering to the subject a reconstituted unit dose of a vaccine composition as described herein, wherein the subject is seronegative to all dengue serotypes. In said method the neutralizing antibody titers when tested in the subject at day 180 or day 365 after at least a first administration of said unit dose, and optionally a second administration of said unit dose 90 days after said first administration, may provide a ratio of not more than 50, or not more than 40, or nor more than 30, or not more than 20 for the neutralizing antibody titer of dengue serotype 2 to the neutralizing antibody titer of dengue serotype 4, and optionally a ratio of not more than 20 for the neutralizing antibody titer of dengue serotype 2 to the neutralizing antibody titer of dengue serotype 1, and optionally a ratio of not more than 20 for the neutralizing antibody titer of dengue serotype 2 to the neutralizing antibody titer of dengue serotype 3.

In one preferred embodiment, the methods of preventing dengue disease of the present invention are not associated with an increased likelihood of solicited systemic adverse events, such as in children under 9 or seronegative individuals.

The present invention is therefore directed in part to a method of preventing dengue disease as well as yellow fever.

The present invention is therefore directed in part to a method of preventing dengue disease as well as hepatitis A.

The present invention is therefore directed in part to a method of preventing dengue disease as well as HPV-associated cancers or genital warts.

The present invention is therefore directed in part to a method of preventing dengue disease as well as measles, mumps and rubella.

The present invention is therefore directed in part to a method of preventing dengue disease as well as tetanus, diphtheria, and pertussis.

The present invention is therefore directed in part to a method of preventing dengue disease as well as diphtheria, tetanus, pertussis, poliomyelitis and diseases caused by *Haemophilus influenzae* type b.

The present invention is therefore also directed in part to a method of prevention any combination of the above mentioned diseases.

The present invention is further directed in part to the use of the reconstituted unit dose of a dengue vaccine composition/tetravalent dengue virus composition as described herein for the manufacture of a medicament for preventing dengue disease in a subject, for example by subcutaneous injection.

The present invention is further directed in part to the reconstituted unit dose of a dengue vaccine composition/tetravalent dengue virus composition as described herein for use in a method of preventing dengue disease in a subject, as described herein.

Definitions

In describing the present invention, the following terms are to be used as indicated below. As used herein, the singular forms "a," "an," and "the" include plural references unless the context clearly indicates otherwise.

As used herein, the terms "unit dose of a dengue vaccine composition", "unit dose" and "unit dose of the invention as described herein" refer to the amount of a dengue vaccine which is administered to a subject in a single dose. In one embodiment, one unit dose is present in a vial and this unit dose is administered to a subject, e.g. optionally after reconstitution. In one embodiment, more than one unit dose of the dengue vaccine composition may be present in a vial so that with the content of one vial more than one subject can be vaccinated.

A "lyophilized unit dose" or "unit dose in lyophilized form" refers to the unit dose that is obtained by subjecting a given volume of the liquid dengue vaccine composition, such as 0.5 mL, to lyophilization. Thus, the aqueous formulations of the dengue vaccine composition being produced by combining the pharmaceutically acceptable excipients and the dengue virus composition comprising the four dengue virus strains, preferably TDV-1 to TDV-4, is subjected to lyophilization to obtain the lyophilized unit dose.

A "reconstituted unit dose" or "unit dose in reconstituted form" is obtained from the lyophilized dose by reconstitution with a pharmaceutically acceptable diluent. The diluent does not contain dengue virus. The reconstituted unit dose is a liquid which can be administered to a subject, for example by injection, such as subcutaneous injection.

As used herein, the term "upon reconstitution with 0.5 mL" is not limiting the reconstitution to be performed using 0.5 mL of the diluent, but refers to the concentration of the dengue viruses that will be present in the reconstituted unit dose when 0.5 mL diluent are used for reconstitution. While using a different volume for reconstitution (e.g. 0.8 mL) will result in a different concentration of dengue viruses in the reconstituted unit dose, the administration of the total volume of the unit dose (e.g. 0.8 mL) will result in the same total amount of dengue virus being administered.

As used herein, a "concentration of at least X log 10 pfu/0.5 mL" refers to the concentration of a dengue serotype in 0.5 mL, but is not limiting the unit dose to be 0.5 mL. If the unit dose has a volume different than 0.5 mL, or is lyophilized from a volume different than 0.5 mL, or is reconstituted with a volume different than 0.5 mL, said concentration will differ from the "concentration of at least X log 10 pfu/0.5 mL". However, if the unit dose has a volume of 0.5 mL, or is lyophilized from a volume of 0.5 mL, or is reconstituted with a volume of 0.5 mL, said concentration will be the "concentration of at least X log 10 pfu/0.5 mL". Thus, while the concentration may differ, the total amount of virus in the unit dose remains the same.

As used herein, the term "dengue serotype" refers to a species of dengue virus which is defined by its cell surface antigens and therefore can be distinguished by serological methods known in the art. At present, four serotypes of dengue virus are known, i.e. dengue serotype 1 (DENV-1), dengue serotype 2 (DENV-2), dengue serotype 3 (DENV-3) and dengue serotype 4 (DENV-4).

As used herein, the term "tetravalent dengue virus composition" refers to a dengue virus composition comprising four different immunogenic components from the four different dengue serotypes DENV-1, DENV-2, DENV-3 and DENV-4, preferably comprising four different live, attenuated dengue viruses, each representing one dengue serotype, and which aims to stimulate immune responses to all four dengue serotypes.

As used herein, the term "live attenuated dengue virus" refers to a viable dengue virus which is mutated to provide reduced virulence. The live attenuated dengue virus can be a dengue virus in which all components are derived from the same dengue serotype or it can be a chimeric dengue virus having parts from two or more dengue serotypes.

A "virus strain" and in particular a "dengue virus strain" is a genetic subtype of a virus, in particular of a dengue virus, which is characterized by a specific nucleic acid sequence. A dengue serotype may comprise different strains with different nucleic acid sequences which have the same cell surface antigens. A dengue virus strain can be a dengue virus in which all components are derived from the same dengue serotype or it can be a chimeric dengue virus having parts from two or more dengue serotypes.

As used herein, "TDV-2" refers to a molecularly characterized and cloned dengue serotype 2 strain derived from the live attenuated DEN-2 PDK-53 virus strain. The PDK-53 strain is described for example in Bhamarapravati et al. (1987) Bulletin of the World Health Organization 65(2): 189-195. In one embodiment, the TDV-2 strain served as a backbone for the chimeric TDV-1, TDV-3 and TDV-4 strains into which parts from the TDV-1, TDV-3 and TDV-4 strains were introduced.

A "non-chimeric dengue virus" or "non-chimeric dengue serotype strain" or "non-chimeric dengue strain" comprises only parts from one dengue serotype. In particular, a non-chimeric dengue virus does not include parts from a different flavivirus such as yellow fever virus, Zika virus, West Nile virus, Japanese encephalitis virus, St. Louis encephalitis virus, tick-borne encephalitis virus. TDV-2 is an example of a non-chimeric dengue virus.

A "chimeric dengue virus" or "chimeric dengue serotype strain" or "chimeric dengue strain" comprises parts from at least two different dengue serotypes. As used herein, the chimeric dengue virus does not include parts from a different flavivirus such as yellow fever virus, Zika virus, West Nile virus, Japanese encephalitis virus, St. Louis encephalitis virus, tick-borne encephalitis virus. In particular, the chimeric dengue virus described herein does not include parts from the yellow fever virus. As used herein, a "chimeric dengue serotype 2/1 strain" or "DENV-2/1 chimera" or "TDV-1" refers to a dengue virus chimeric construct which comprises parts from both DENV-2 and DENV-1. In particular, in the chimeric dengue serotype 2/1 strain the prM and E proteins from DENV-1 replace the prM and E proteins from DENV-2 as detailed below. As used herein, a "chimeric dengue serotype 2/3 strain" or "DENV-2/3 chimera" or "TDV-3" refers to a dengue virus chimeric construct which comprises parts from both DENV-2 and DENV-3. In particular, in the chimeric dengue serotype 2/3 strain the prM and E proteins from DENV-3 replace the prM and E proteins from DENV-2 as detailed below. As used herein, a "chimeric dengue serotype 2/4 strain" or "DENV-2/4 chimera" or "TDV-4" refers to a dengue virus chimeric construct which comprises parts from both DENV-2 and DENV-4. In particular, in the chimeric dengue serotype 2/4 strain the prM and E proteins from DENV-4 replace the prM and E proteins from DENV-2 as detailed below.

As used herein, "TDV" refers to a tetravalent live attenuated dengue vaccine that comprises a mixture of the four live attenuated dengue virus strains TDV-1, TDV-2, TDV-3 and TDV-4 expressing surface antigens from the four dengue serotypes DENV-1, DENV-2, DENV-3 and DENV-4, respectively. In one embodiment (e.g. also in the examples), TDV-1 has the nucleotide sequence according to SEQ ID No. 1 and/or the amino acid sequence according to SEQ ID No. 2. In one embodiment, TDV-2 has the nucleotide sequence according to SEQ ID No. 3 and/or the amino acid sequence according to SEQ ID No. 4. In one embodiment, TDV-3 has the nucleotide sequence according to SEQ ID No. 5 and/or the amino acid sequence according to SEQ ID No. 6. In one embodiment, TDV-4 has the nucleotide sequence according to SEQ ID No. 7 and/or the amino acid sequence according to SEQ ID No. 8.

As used herein, the term "dengue disease" refers to the disease which is caused by infection with dengue virus. Symptoms of dengue disease include sudden high fever, headaches, joint and muscle pain, nausea, vomiting and skin rashes. The term dengue disease also includes the more severe forms of dengue hemorrhagic fever (DHF) and dengue shock syndrome (DSS). Symptoms of DHF include increased vascular permeability, hypovolemia and abnormal blood clotting mechanisms. Subjects with DHF may present with severe manifestations of plasma leakage and hemorrhage. When a subject with DHF experiences shock he or she will be categorized as having DSS. Symptoms of DSS include bleeding that may appear as tiny spots of blood on the skin and larger patches of blood under the skin. Prolonged shock is the main factor associated with complications including massive gastrointestinal hemorrhage that can lead to death. As used herein, DHF cases are defined as VCD cases meeting WHO 1997 DHF criteria. In the context of preventing dengue disease in elderly subjects, the term "preventing dengue disease" preferably includes preventing DHF and/or DSS. In the context of preventing dengue disease in elderly subjects, the term "preventing dengue disease" preferably includes preventing severe end-organ manifestations of dengue such as hepatomegaly and acute renal failure.

As used herein, "preventing dengue disease" refers to preventing a subject from developing one or more symptoms of dengue disease because of an infection with a dengue virus. In particular, preventing dengue disease is achieved by vaccinating or inoculating a subject with a dengue vaccine composition, such as the reconstituted unit dose described herein. As used herein, the term "prophylactically treating dengue disease" is equivalent to "preventing dengue disease". In a particular embodiment, preventing dengue disease includes preventing DHS and/or DSS.

As used herein, the terms "virologically-confirmed dengue disease", "VCD case", or "VCD fever" refer to febrile illness or illness clinically suspected to be dengue disease with a positive serotype-specific reverse transcriptase polymerase chain reaction (RT-PCR). The term "virologically confirmable dengue" disease refers to a subject having febrile illness or illness clinically suspected to be dengue disease, wherein testing the subject, e.g. using RT-PCR, would confirm the presence of at least one dengue serotype. Severe forms of VCD fever will be identified as follows: Dengue Hemorrhagic Fever (DHF) was defined according to the WHO 1997 criteria. Severe dengue was defined through an assessment of an independent Dengue Case Adjudication Committee which will assess all hospitalized VCD cases (severe/non-severe) based on criteria redefined in a charter. All non-hospitalized cases are considered non-severe.

As used herein, the term "febrile illness" is defined as temperature ≥38° C. on any 2 of 3 consecutive days.

As used herein, the terms "virologically-confirmed dengue disease with hospitalization", is considered to be a surrogate for severe dengue and the "incidence of virologically-confirmed dengue disease with hospitalization" is used as a safety parameter. As used herein, the "relative risk with respect to virologically-confirmed dengue disease with hospitalization" means the number of events of virologically confirmed dengue disease with hospitalization divided by the number of subjects treated with the unit dose as disclosed herein over the number of events of virologically confirmed dengue disease with hospitalization divided by the number of subjects treated with placebo. If the "relative risk with respect to virologically-confirmed dengue disease with hospitalization" is 1 or lower the vaccine provides for the same or less risk for virologically-confirmed dengue disease with hospitalization as placebo and is considered "safe". In this context the risk of virologically-confirmed dengue disease with hospitalization may be also 0.9 or less, 0.8 or less, 0.7 or less, 0.6 or less, 0.5 or less, 0.4 or less, 0.3 or less, 0.2 or less, or 0.1 or less, in particular when determined from 30 days after a second administration until 12 months after a second administration, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects.

As used herein, alternatively a vaccine is considered "safe" when the vaccine efficacy (VE) with respect to virologically-confirmed dengue disease with hospitalization is 0% or higher. This means that the vaccine provides for the same likelihood or less for virologically-confirmed dengue disease with hospitalization as placebo. In particular considered "safe" is the combined vaccine efficacy against virologically-confirmed dengue with hospitalization against all four serotypes with a 2-sided 95% confidence interval, wherein the lower bound is more than 25%, in particular when measured against placebo in a subject population of at least 1,500 or at least 2,000 healthy subjects (in particular when measured in age groups selected in particular from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects) being seronegative against all serotypes at baseline or being seropositive against at least one serotype at baseline, in particular when said unit dose or said placebo is administered at least twice within less than 6 months, such as within 3 months, about from first administration or from 30 days after the second or last administration of the administration schedule until at least 12 months, until 12 to 18 months, until 12 months, or until 18 months after the second or last administration of the administration schedule. In particular, the lower bound may be more than 30%, more than 40%, more than 50%, more than 60%, more than 65%, more than 66%, more than 67%, more than 68% more than 70%, or more than 75%. In particular, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. In a particular embodiment "safe" means providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

If one of the criteria as defined above for the term "safe" is fulfilled, the vaccine is considered safe within the meaning of this invention. In this context, safe in particular refers to a vaccine that is safe for all subjects irrespective of their serostatus at baseline. This means that the vaccine can be administered without the need to determine the occurrence of a previous dengue infection in the subject before administration. Preferably, the vaccine is safe as defined above with respect to all age groups starting from 4 years of age and preferably irrespective of the serostatus, in particular from 4 years of age to 60 years of age, or 4 years of age to 16 years of age. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. For further definitions of VE against virologically-confirmed dengue disease with hospitalization reference is made to the disclosure below with respect to certain methods of treatment.

As used herein, "vaccine efficacy" or "VE" measure the proportionate reduction in cases among vaccinated persons. Vaccine efficacy (VE) is measured by calculating the risk of disease among vaccinated and unvaccinated persons and determining the percentage reduction in risk of disease among vaccinated persons relative to unvaccinated persons. The greater the percentage reduction of illness in the vaccinated group, the greater the vaccine efficacy. For example, a VE of 90% indicates a 90% reduction in disease occurrence among the vaccinated group, or a 90% reduction from the number of cases you would expect if they have not been vaccinated. The vaccine efficiency is calculated by the formula: 100*(1−HR), wherein HR is the Hazard Ratio which is defined as the Hazard rate of vaccine (λv) divided by the Hazard rate of placebo (λc), i.e. HR=λv/λc. λv denote the hazard rate for the subjects vaccinated with a tetravalent dengue vaccine composition as disclosed herein and λc denote the hazard rate for unvaccinated subjects, i.e. subjects receiving placebo. The hazard rate ratio HR is estimated from a Cox proportional hazard model with study vaccine as a factor, adjusted for age, and stratified by region. As used herein the term "combined vaccine efficacy against all four serotypes" is defined as the vaccine efficacy in relation to the risk of dengue disease irrespective of the serotype being responsible for the virologically-confirmed dengue disease and the subject baseline serostatus. A vaccine is considered "effective" in case the combined vaccine efficacy is above 30%. In this context the combined vaccine efficacy may be also 40% or more, 50% or more, 60% or more, 70% or more, 72% or more, or 80% or more, in particular when determined from 30 days after a second administration until 12 months after a second administration or 18 months after a second vaccination, in particular when determined in age groups selected from the age group of 4 to 16 year old subjects, the age group of 4 to under 9 year old subjects, the age group of 2 to under 9 year old subjects, the age group of 4 to 5 year old subjects, the age group of 6 to 11 year old subjects, and the age group of 12 to 16 year old subjects. In this context, effective in particular refers to a vaccine that is effective for all subjects irrespective of their serostatus at baseline. Preferably, the vaccine is effective with respect to all age groups starting from 4 years of age and preferably irrespective of the serostatus, in particular from 4 years of age to 60 years of age or from 4 years of age to 16 years of age and irrespective of the serostatus. Relevant subgroups in this context are under 9 years of age, from 2 years of age to under 9 years of age, from 4 years of age to under 9 years of age, 4 to 5 years of age, 6 to 11 years of age and 12 to 16 years of age or any age group within 4 to 16 years of age. In certain embodiments "effective" means providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 4 to 16 years of age, from the first administration of the administration schedule until 18 months after the last administration of the administration schedule. Further specific efficacies can be defined. As used herein, "combined vaccine efficacy against all four serotypes in seronegative subjects" refers to the efficacy measured in subjects which are seronegative at baseline. As used herein, "vaccine efficacy against a specific serotype, e.g. serotype 1" refers to the efficacy in relation to a specific serotype being responsible for the virologically-confirmed dengue disease. As used herein, "combined vaccine efficacy against all four serotypes against virologically-confirmed dengue with hospitalization" refers to the efficacy wherein only virologically-confirmed dengue cases with hospitalization are considered. Such vaccine efficacies can be determined with respect to subjects being seronegative or seropositive at baseline and for different age groups.

As used herein, the "relative risk" means the number of events of virologically confirmed dengue disease divided by the number of subjects treated with the unit dose as disclosed herein over the number of events of virologically confirmed dengue disease divided by the number of subjects treated with placebo. As used herein the term"combined relative risk against all four serotypes" is defined as the relative risk in relation to the risk of dengue disease irrespective of the serotype being responsible for the virologically-confirmed dengue disease and the subject baseline serostatus.

As used herein, "vaccinating" or "inoculating" refers to the administration of a vaccine to a subject, with the aim to prevent the subject, from developing one or more symptoms of a disease. As used herein, "vaccinating against dengue disease" or "inoculating against dengue disease" refers to the administration of a dengue vaccine composition to a subject, with the aim to prevent the subject, from developing one or more symptoms of dengue disease. In principle the method comprises a primary vaccination and optionally one or more booster vaccinations. The primary vaccination is defined as the primary administration schedule for administering the composition or unit dose as disclosed herein to establish a protective immune response and e.g. consists of two administrations e.g. within three months. Whenever an administration is mentioned within this disclosure such administration refers to the primary vaccination unless it is specified as booster vaccination. The booster vaccination refers to an administration or administration schedule which takes place after the primary vaccination e.g. at least 1 year or even 5 or 10 years after the last administration, e.g. the second administration, of the primary vaccination schedule. The booster administration attempts at enhancing or reestablishing the immune response of the primary vaccination.

As used herein, the terms "subject" or "subjects" are limited to human subjects (e.g. infants, children or adults). The terms "elderly subject" or "elderly subjects" refer to subjects with an age of more than 60 years, such as 61 years to 100 years, 61 years to 90 years, 61 years to 80 years, 61 years to 75 years, or 61 years to 70 years.

As used herein, "subject population" refers to a group of subjects. The subject population may refer to least 40 subjects, at least 50 subjects, at least 60 subjects, at least 100 subjects or at least 1000 subjects and is defined by certain parameters. The parameters that may be used to define a subject population include, but are not limited to, the age of the subjects, whether the subjects are from a dengue endemic region or from a dengue non-endemic region and the serostatus of the subjects.

As used herein, "endemic region" refers to a region where a disease or infectious agent is constantly present and/or usually prevalent in a population within this region. As used herein, "non-endemic region" refers to a region from which the disease is absent or in which it is usually not prevalent. Accordingly, a "dengue endemic region" refers to geographic areas in which an infection with dengue virus is constantly maintained at a baseline level. A "dengue non-endemic region" is a geographic area in which an infection with dengue virus is not constantly maintained at a baseline level. Accordingly, subject populations or subjects "from a dengue endemic region" or "from a dengue non-endemic region" refer to subject populations or subjects living in geographic areas as defined above. Whether a geographic area or a subject population is dengue-endemic or not can be determined by different calculatory methods such as the ones described in Bhatt et al. (2013) Nature 496 (7446): 504-507 and supplementary material and in Stanaway et al. (2016) Lancet Infect Dis. 16(6): 712-723 and supplementary material. Overviews of dengue endemic regions and dengue epidemiology are regularly published, for example, by the WHO or CDC. Typical dengue-endemic regions are in Latin America, Southeast Asia and the Pacific islands and dengue endemic countries include, but are not limited to, Australia, Brazil, Bangladesh, Colombia, China, Dominican Republic, Indonesia, India, Mexico, Malaysia, Nicaragua, Nigeria, Pakistan, Panama, Philippines, Puerto Rico, Singapore, Sri Lanka, Thailand and Vietnam. The area's force of infection is measured by seroprevalence surveys provided as seroprevalence rate. Areas with very high force of infection are considered to have a seroprevalence rate of more than 80%. As used herein the term "region" when it concerns seroprevalence rates refers to a geographic area where the seroprevalence rate could be determined or is known, e.g. a village, a town, a city, a region, a county, a state, a province or parts of the foregoing or a whole country.

As used herein, "serostatus" refers to the amount of antibodies a subject has with respect to a certain infectious agent, in particular dengue virus. As used herein, "seronegative" or"seronaïve" means that the subject does not have neutralizing antibodies against any one of dengue serotypes DENV-1, DENV-2, DENV-3 and DENV-4 in the serum. A seronegative or seronaïve subject or subject population is defined by a neutralizing antibody titer of less than 10 for each one of the four dengue serotypes. A subject or subject population having a neutralizing antibody titer of equal to or more than 10 for at least one dengue serotype is defined as being "seropositive" with respect to said dengue serotype. Serostatus at baseline refers to the serostatus before the administration of a dengue vaccine composition as described herein.

As used herein, a "neutralizing antibody titer" refers to the amount of antibodies in the serum of a subject that neutralize the respective dengue serotype. The neutralizing antibody titer against DENV-1, DENV-2, DENV-3 and DENV-4 is determined in a serum sample of the subject using known methods such as the plaque reduction neutralization test (PRNT) as described in the WHO Guidelines (World Health Organization Department of Immunization Vaccines Biologicals (2007) Guidelines for plaque reduction neutralization testing of human antibodies to dengue viruses, WHO/IVB/07.07) or a microneutralization (MNT50) assay as described herein. As used herein, the "ratio of not more than 20 for the neutralizing antibody titer of dengue serotype 2 to the neutralizing antibody titer of dengue serotype 4" means that the neutralizing antibody titer of dengue serotype 2 is divided by the neutralizing antibody titer of dengue serotype 4 and that the ratio obtained hereby is no more than 20. In other words, the neutralizing antibody titer of dengue serotype 2 is not more than 20-times higher than the neutralizing antibody titer of dengue serotype 4 in the subject.

As used herein, the terms "geometric mean neutralizing antibody titer" and "GMT" refer to the geometric mean value of the titer of neutralizing antibodies against the corresponding dengue serotype in the serum of subjects in a subject population. The geometric mean value is calculated by a well-known formula. As used herein, the "ratio of not more than 20 for the GMT of dengue serotype 2 to the GMT of dengue serotype 4" means that the geometric mean neutralizing antibody titer of dengue serotype 2 (GMT DENV-2) is divided by the geometric mean neutralizing antibody titer of dengue serotype 4 (GMT DENV-4) and that the ratio obtained hereby is no more than 20. In other words, the geometric mean neutralizing antibody titer of dengue serotype 2 is not more than 20-times higher than the geometric mean neutralizing antibody titer of dengue serotype 4 in the subject population.

As used herein, an "immune response" refers to a subject's response to the administration of the dengue vaccine. In particular, the immune response includes the formation of neutralizing antibodies to one or more dengue serotypes. It may also include the stimulation of a cell-mediated response or the formation of antibodies to non-structural proteins such as NS1. An immune response is stimulated by the administration of a unit dose of the invention as described herein, if the titer of neutralizing antibodies against at least one dengue virus serotype and preferably against all four dengue virus serotypes is increased after said administration of said unit dose. An immune response is stimulated by the administration of a unit dose of the invention as described herein, if the secretion of interferon gamma by peripheral blood mononuclear cells stimulated with peptides from dengue virus proteins is increased after said administration of said unit dose. An immune response is stimulated by the administration of a unit dose of the invention as described herein, if the titer of antibodies to non-structural proteins such as NS1 is increased after said administration of said unit dose. In a particular embodiment, the administration of a reconstituted unit dose of the present invention as described herein stimulates the formation of neutralizing antibodies to one or more dengue serotypes, a cell-mediated response and the formation of antibodies to non-structural proteins such as NS1.

As used herein, a "balanced immune response" means that the immune response to the four dengue serotypes is sufficient to provide protection against infection by all four dengue serotypes and preferably the immune response to the four dengue serotypes has a similar strength. In particular, the neutralizing antibody titer against the four dengue serotypes at day 180 or day 365 after administration of a first reconstituted unit dose of the invention as described herein is similar, i.e. it differs by less than factor 30, by less than factor 25 or by less than factor 20.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 log 10 pfu/0.5 ml, a dengue serotype 2 concentration of 4.00 log 10 pfu/0.5 ml, a dengue serotype 3 concentration of 4.60 log 10 pfu/0.5 ml and a dengue serotype 4 concentration of 5.11 log 10 pfu/0.5 ml. Primarily, the logarithmic values of the concentrations are converted into numerical values. The results of this conversion are $4\times10^3$ pfu/0.5 ml for serotype 1, $1\times10^4$ pfu/0.5 ml for serotype 2, $4\times10^4$ pfu/0.5 ml for serotype 3 and $1.3\times10^5$ pfu/0.5 ml for serotype 4. The total concentration in pfu/0.5 ml is the sum of the preceding numerical values resulting in $1.84\times10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.:

$$\text{Percentage concentration of serotype 1}=(4\times10^3\ \text{pfu/0.5 ml}\div1.84\times10^5\ \text{pfu/0.5 ml})\times100=2\%$$

$$\text{Percentage concentration of serotype 2}=(1\times10^4\ \text{pfu/0.5 ml}\div1.84\times10^5\ \text{pfu/0.5 ml})\times100=5\%$$

$$\text{Percentage concentration of serotype 3}=(4\times10^4\ \text{pfu/0.5 ml}\div1.84\times10^5\ \text{pfu/0.5 ml})\times100=22\%$$

$$\text{Percentage concentration of serotype 4}=(1.3\times10^5\ \text{pfu/0.5 ml}\div1.84\times10^5\ \text{pfu/0.5 ml})\times100=71\%.$$

The percentage concentrations are rounded to whole numbers.

As used herein the "concomitant" administration of vaccines refers to a combined administration of two or more vaccines. In the context of parts of the invention, the combined administration of two or more vaccines refers to combining the administration schedule of a dengue vaccine, such as the unit dose of the invention, with the administration schedule of a fellow fever vaccine, such as YF-17D, and/or of a hepatitis A vaccine, such as HAVRIX® or VAQTA®, and/or of a HPV vaccine, such as a 9vHPV vaccine, and/or of a combined measles, mumps and rubella (MMR) vaccine, and/or of a combined Tdap vaccine, such as a combined tetanus toxoid, reduced diphtheria toxoid and acellular pertussis (adsorbed) vaccine, such as BOOSTRIX®, and/or of a DTaP/IPV/HIB vaccine, in particular a combined DTaP/IPV/Hib vaccine, such as Pentacel®.

As used herein "simultaneous" administration means an administration of at least two different vaccines, such as a dengue vaccine and a fellow fever vaccine, or a dengue vaccine and a hepatitis A vaccine, or a dengue vaccine and a HPV vaccine, or a dengue vaccine and a MMR vaccine, or a dengue vaccine and a Tdap vaccine, or a dengue vaccine and a DTaP/IPV/Hib vaccine on the same day. The simultaneous administration may be administered by the same medical practitioner, such as during the same medical appointment.

As used herein "sequential" administration means an administration of at least two different vaccines, such as a dengue vaccine and a fellow fever vaccine, or a dengue vaccine and a hepatitis A vaccine, or a dengue vaccine and a HPV vaccine, or a dengue vaccine and a MMR vaccine, or a dengue vaccine and a Tdap vaccine, or a dengue vaccine and a DTaP/IPV/Hib vaccine on subsequent days, such as within 90 days, but in a combined administration schedule including the administration of the dengue vaccine and the fellow fever vaccine.

As used herein "HPV-associated cancers or genital warts" refers to cancers and genital wards caused by an HPV infection, respectively. The HPV serotypes 16, 18, 45, 31, 33, 52, 58, also referred to as "high-risk" HPV serotypes, are the types most common in cervical cancers, wherein the two HPV serotypes 16 and 18 cause about 70% of cervical cancers worldwide. The HPV serotypes 6 and 11, also referred to as "low-risk" HPV serotypes, cause genital warts.

As used herein a "9vHPV vaccine" refers to a 9-valent HPV vaccine that provides protection against the HPV serotypes 6, 11, 16, 18, 31, 33, 45, 52, and 58. In particular, the 9vHPV vaccine is used to prevent cervical, vulvar, vaginal, and anal cancers, precancerous or dysplastic lesions, and genital warts caused by one or more of these HPV serotypes.

As used herein, a "MMR vaccine" refers to a combined vaccine for measles, mumps and rubella. Several MMR vaccine are known in the prior art and include M-M-R® II, Priorix®, Tresivac®, and Trimovax®.

As used herein, a "Tdap vaccine" refers to a combined vaccine for tetanus, diphtheria and pertussis. Tdap vaccines known in the prior art include INFANRIX® (for vaccination of children from 6 weeks to 7 years of age), and BOOSTRIX® from GlaxoSmithKline and Adacel from Sanofi Pasteur (both for use in individuals of 10 years of age or older).

As used herein, "DTaP" refers to diphtheria, tetanus and acellular pertussis.

As used herein, "IPV" refers to inactivated poliovirus.

As used herein, "Hib" refers to *Haemophilus influenzae* type b.

As used herein, a "DTaP/IPV/Hib vaccine" refers to a combined vaccine for diphtheria, tetanus, pertussis, poliomyelitis and *Haemophilus influenzae* type b. A DTaP/IPV/Hib vaccine known in the prior art includes Pentacel® from Sanofi Pasteur.

As used herein, the term "chronic disease or condition" includes those diseases and conditions which persist in an elderly subject for three months or more. In particular, it includes diabetes, hypertension, allergies, previous strokes, ischemic heart disease, chronic renal impairment and chronic obstructive pulmonary disease.

As used herein, the term "impaired immune system" means that at least one function of at least one component of the immune system is weaker than in younger subjects, i.e. in subjects with an age of less than 60 years. These functions include a lower antioxidant response of monocytes against oxidative stress induced by dengue virus and lower T cell responses and cytokine production in response to dengue virus infection.

As used herein, "solicited systemic adverse events" in children under 6 years are defined as fever, irritability/fussiness, drowsiness and loss of appetite that occurred within 14 days after each vaccination, and in children of 6 years or more are defined as fever, headache, asthenia, malaise and myalgia that occurred within 14 days after each vaccination.

As used herein, "solicited local adverse events" are injection site pain, injection site erythema and injection site swelling that occurred within 7 days after each vaccination.

As used herein, "unsolicited adverse events" are any adverse events (AEs) that are not solicited local or systemic AEs, as defined above.

As used herein, a "serious adverse event" or "SAE" is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.

The relationship of each AE, including solicited systemic AEs (solicited local AEs are considered as related) to trial vaccine(s) will be assessed using the following categories: As used herein, "IP-Related AE" or "vaccine related AE" means that there is suspicion that there is a relationship between the vaccine and the AE (without determining the extent of probability); there is a reasonable possibility that the vaccine contributed to the AE. As used herein, "Non-IP Related" or "non-vaccine related" means that there is no suspicion that there is a relationship between the vaccine and the AE; there are other more likely causes and administration of the vaccine is not suspected to have contributed to the AE.

As used herein, a subject or subject population being "2 to 17 years of age" refers to a subject or subject population being 2 to 17 years of age on the first day of the administration of the dengue vaccine composition as described herein.

As used herein "%-points" refers to the difference of two %-values in a %-value. For example two values in % which are within 5%-points refers to e.g. one value at 1% and a second value at 6%.

As used herein, the term "determination of the previous dengue infection in the subject before administration" means that a previous dengue infection has to be assessed before vaccination in that there is a laboratory confirmed history of dengue or through an appropriately validated serological test e.g. by the method as disclosed herein such as the MNT50 test described in Example 2 or any serotesting with adequate performance in terms of specificity and cross reactivity based on the locale disease epidemiology.

As used herein % w/v refers to % mg/ml wherein e.g. 150 mg/ml are 15% w/v.

DETAILED DESCRIPTION

Dengue Virus Strains

Figure 1:
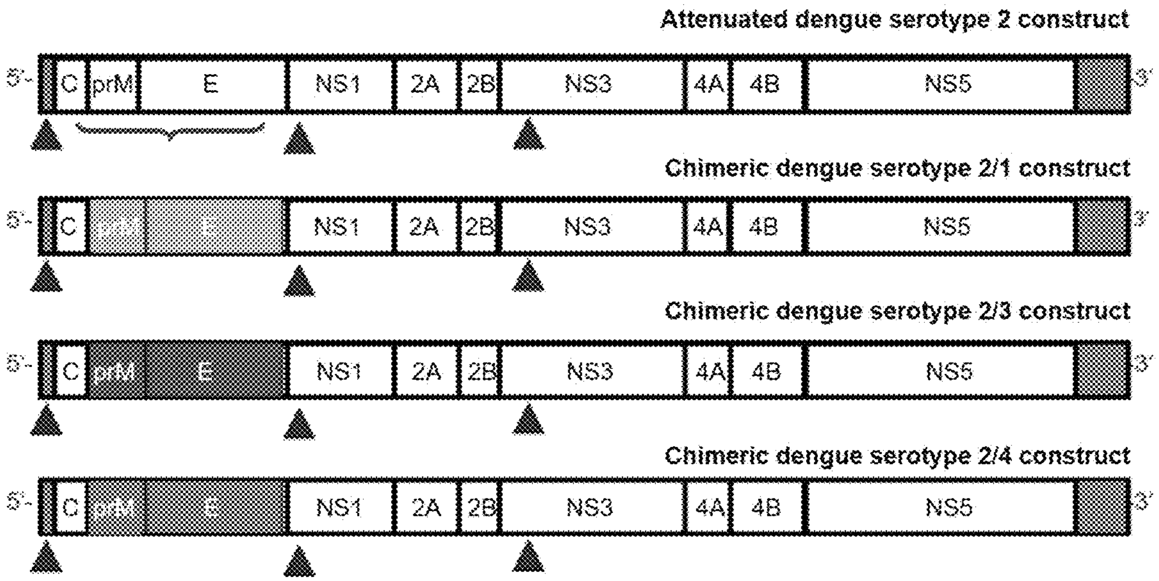
FIG. 1: Genetic structure of the four dengue strains contained in TDV. The solid red triangles indicate the three attenuating mutations present in the 5'NCR, NS1 and NS3 proteins. The TDV-1, TDV-3 and TDV-4 strains are chimeric viruses where the prM and E genes from dengue serotype 1, 3 and 4, respectively, are inserted into the TDV-2 backbone.

The dengue virus is a single stranded, positive sense RNA virus of the family flaviviridae. The taxonomy is outlined in Table 1. The family flaviviridae includes three genera, flavivirus, hepacivirus and pestivirus. The genus flavivirus contains highly pathogenic and potentially hemorrhagic fever viruses, such as yellow fever virus and dengue virus, encephalitic viruses, such as Japanese encephalitis virus, Murray Valley encephalitis virus and West Nile virus, and a number of less pathogenic viruses.

TABLE 1

Dengue Virus Taxonomy of the GMO Parental Strain

| Family | Flaviviridae |
|---|---|
| Genus | Flavivirus |
| Species | Dengue virus |
| Strains | Dengue Serotype 2 (Strain 16681), Strain DEN-2 PDK-53 |
| GMO parent | TDV-2 |

The flavivirus genome comprises in 5' to 3' direction (see FIG. 1):

a 5'-noncoding region (5'-NCR), a capsid protein (C) encoding region, a pre-membrane protein (prM) encoding region, an envelope protein (E) encoding region, a region encoding nonstructural proteins (NSI, NS2A, NS2B, NS3, NS4A, NS4B, NS5) and a 3' noncoding region (3'-NCR).

The viral structural proteins are C, prM and E, and the nonstructural proteins are NSI to NS5. The structural and nonstructural proteins are translated as a single polyprotein and processed by cellular and viral proteases.

The unit dose of the invention as described herein comprises a dengue virus composition that comprises four live attenuated dengue virus strains (tetravalent dengue virus composition) representing dengue serotype 1, dengue serotype 2, dengue serotype 3 and dengue serotype 4. Preferably the composition comprises chimeric dengue viruses and optionally at least one non-chimeric dengue virus, in particular a molecularly characterized and cloned dengue serotype 2 strain derived from the live attenuated DEN-2 PDK-53 virus strain (TDV-2), and three chimeric dengue strains derived from the TDV-2 strain by replacing the structural proteins prM and E from TDV-2 with the corresponding structural proteins from the other dengue serotypes, resulting in the following chimeric dengue strains:

a DENV-2/1 chimera (TDV-1),
a DENV-2/3 chimera (TDV-3) and
a DENV-2/4 chimera (TDV-4).

The genetically modified tetravalent dengue vaccine TDV is based on a molecularly characterized and cloned dengue-2 virus strain (TDV-2). This attenuated TDV-2 strain was generated by cDNA cloning of the attenuated laboratory-derived DEN-2 PDK-53 virus strain that was originally isolated at Mahidol University, Bangkok, Thailand (Kinney et al. (1997) Virology 230(2): 300-308). DEN-2 PDK-53 was generated by 53 serial passages in primary dog kidney (PDK) cells at 32° C. (Bhamarapravati et al. (1987) Bull. World Health Organ. 65(2): 189-195).

The attenuated DEN-2 PDK-53 strain (the precursor of TDV-2) was derived from the wild type virus strain DEN-2 16681 (SEQ ID NO 11) and differs in nine nucleotides from the wild type as follows (Kinney et al. (1997) Virology 230(2): 300-308):

(i) 5'-noncoding region (NCR)-57 (nt-57 C-to-T): major attenuation locus
(ii) prM-29 Asp-to-Val (nt-524 A-to-T)
(iii) nt-2055 C-to-T (E gene) silent mutation
(iv) NS1-53 Gly-to-Asp (nt-2579 G-to-A): major attenuation locus
(v) NS2A-181 Leu-to-Phe (nt-4018 C-to-T)
(vi) NS3-250 Glu-to-Val (nt-5270 A-to-T): major attenuation locus
(vii) nt-5547 (NS3 gene) T-to-C silent mutation
(viii) NS4A-75 Gly-to-Ala (nt-6599 G-to-C)
* nt-8571 C-to-T (NS5 gene) silent mutation The three nucleotide changes located in the 5' noncoding region (NCR) (nucleotide 57) (mutation (i)), the NS-1 (amino acid 828 of SEQ ID NO. 4) (mutation (iv)) and NS-3 genes (amino acid 1725 of SEQ ID NO. 4) (mutation (vi)) form the basis for the attenuation phenotype of the DEN-2 PDK-53 strain (Butrapet et al. (2000) J. Virol. 74(7): 3111-3119) (Table 2). These three mutations are referred to herein as the "attenuating mutations" and are comprised in TDV-1, TDV-2, TDV-3 and TDV-4.

TABLE 2

Attenuating mutations in the common genetic backbone of all TDV strains

| Location of Mutation | Nucleotide Change in TDV-2 | Amino Acid Change in TDV-2 |
|---|---|---|
| 5' Noncoding Region (5'NCR) | 57 C to T | Not applicable (silent) |
| Nonstructural Protein 1 (NS1) | 2579 G to A | 828 Gly to Asp |
| Nonstructural Protein 3 (NS3) | 5270 A to T | 1725 Glu to Val |

In one embodiment, TDV-2 comprises in addition to the three attenuating mutations one or more mutations selected from:

a) a mutation in the prM gene at nucleotide 524 from adenine to thymine resulting in an amino acid change at position 143 from asparagine to valine, and/or b) a silent mutation in the E gene at nucleotide 2055 from cytosine to thymine, and/or c) a mutation in the NS2A gene at nucleotide 4018 from cytosine to thymine resulting in an amino acid change at position 1308 from leucine to phenylalanine, and/or d) a silent mutation in the NS3 gene at nucleotide 5547 from thymine to cytosine, and/or e) a mutation in the NS4A gene at nucleotide 6599 from guanine to cytosine resulting in an amino acid change at position 2168 from glycine to alanine, and/or f) a silent mutation in the prM gene at nucleotide 900 from thymine to cytosine.

The silent mutation in the NS5 gene at nucleotide 8571 from cytosine to thymine of DEN-2 PDK-53 is not present in the TDV-2 strain.

In another embodiment, TDV-2 comprises in addition to the three attenuating mutations one or more mutations selected from:

g) a mutation in the prM gene at nucleotide 592 from adenine to guanine resulting in an amino acid change at position 166 from lysine to glutamic acid, and/or h) a mutation in the NS5 gene at nucleotide 8803 from adenine to guanine resulting in an amino acid change at position 2903 from isoleucine to valine.

In another embodiment, TDV-2 comprises in addition to the three attenuating mutations the mutations a) and g), preferably the mutations a), g), c), e) and h), more preferably the mutations a), g), c), e), h) and b), even more preferably the mutations a), g), c), e), h), b) and d), and most preferably the mutations a) to h). The nucleotide positions and amino acids positions of TDV-2 refer to the nucleotide sequence as shown in SEQ ID NO. 3 and amino acid sequence as shown in SEQ ID NO. 4.

The dengue virus structural envelope (E) protein and pre-membrane (prM) protein have been identified as the primary antigens that elicit a neutralizing protective antibody response (Plotkin 2001). For creation of the tetravalent dengue vaccine (TDV), TDV-2 was modified by replacing the nucleic acid sequence encoding the DENV-2 prM and E glycoproteins with the nucleic acid sequence encoding the corresponding wild type prM and E glycoproteins from the DENV-1, DENV-3, and DENV-4 wild type strains DENV-1 16007, DENV-3 16562 or DENV-4 1036 virus, respectively, (see Table 3) using standard molecular genetic engineering methods (Huang et al. (2003) J. Virol. 77(21): 11436-11447).

TABLE 3

Viral origin of prM/E gene regions of the TDV virus strains

| Virus | Strain | Origin | Source | Reference | Nucleotide sequence | Amino acid sequence |
|---|---|---|---|---|---|---|
| DENV-1 | 16007 | Thailand, 1964 | DHF/DSS patient | Halstead and Simasthien, 1970 | SEQ ID NO. 9 | SEQ ID NO. 10 |
| DENV-2 | 16681 | Thailand, 1964 | DHF/DSS patient | Halstead and Simasthien, 1970 | SEQ ID NO. 11 | SEQ ID NO. 12 |

TABLE 3-continued

| Viral origin of prM/E gene regions of the TDV virus strains | | | | | | |
|---|---|---|---|---|---|---|
| Virus | Strain | Origin | Source | Reference | Nucleotide sequence | Amino acid sequence |
| DENV-3 | 16562 | Philippines, 196 | DHF patient | Halstead and Simasthien, 1970 | SEQ ID NO. 13 | SEQ ID NO. 14 |
| DENV-4 | 1036 | Indonesia, 1976 | DF patient | Gubler et al., 1979 | SEQ ID NO. 15 | SEQ ID NO. 16 |

A diagram of the four TDV strains comprised in the dengue vaccine composition is shown in FIG. 1.

The chimeric dengue strains TDV-1, TDV-3 and TDV-4 express the surface antigens prM and E of the DENV-1, DENV-3 or DENV-4 viruses, as depicted in Table 3 respectively, and retain the genetic alterations responsible for the attenuation of TDV-2. Thus, each of the TDV-1, TDV-3 and TDV-4 strains comprises the attenuating mutations described in Table 2.

In one embodiment, TDV-1 comprises in addition to the three attenuating mutations one or more mutations selected from:

c) a mutation in the NS2A gene at nucleotide 4018 from cytosine to thymine resulting in an amino acid change at position 1308 from leucine to phenylalanine, and/or d) a silent mutation in the NS3 gene at nucleotide 5547 from thymine to cytosine, and/or e) a mutation in the NS4A gene at nucleotide 6599 from guanine to cytosine resulting in an amino acid change at position 2168 from glycine to alanine, and/or i) a silent mutation in the E gene at nucleotide 1575 from thymine to cytosine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymine-guanine to cytosine-cytosine resulting in an amino acid change at position 762 from valine to alanine.

In another embodiment, TDV-1 comprises in addition to the three attenuating mutations one or more mutations selected from:

l) a mutation in the NS2A gene at nucleotide 3823 from adenine to cytosine resulting in an amino acid change at position 1243 from isoleucine to leucine, and/or m) a mutation in the NS2B gene at nucleotide 4407 from adenine to thymine resulting in an amino acid change at position 1437 from glutaminc acid to aspartic acid, and/or n) a silent mutation in the NS4B gene at nucleotide 7311 from adenine to guanine.

In another embodiment, the TDV-1 strain comprises in addition to the three attenuating mutations the mutations l) and m), preferably the mutations l), m), c) and e), even more preferably the mutations l), m), c), e), d) and n), and most preferably the mutations l), m), c), e), d), n), i), j) and k). The nucleotide positions and amino acids positions of TDV-1 refer to the nucleotide sequence as shown in SEQ ID NO. 1 and amino acid sequence as shown in SEQ ID NO. 2.

In one embodiment, TDV-3 comprises in addition to the three attenuating mutations one or more mutations selected from:

c) a mutation in the NS2A gene at nucleotide 4012 from cytosine to thymine resulting in an amino acid change at position 1306 from leucine to phenylalanine, and/or d) a silent mutation in the NS3 gene at nucleotide 5541 from thymine to cytosine, and/or e) a mutation in the NS4A gene at nucleotide 6593 from guanine to cytosine resulting in an amino acid change at position 2166 from glycine to alanine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2375/2376 from thymine-guanine to cytosine-cytosine resulting in an amino acid change at position 760 from valine to alanine, and/or o) a silent mutation in the prM gene at nucleotide 552 from cytosine to thymine, and/or p) a mutation in the E gene at nucleotide 1970 from adenine to thymine resulting in an amino acid change at position 625 from histidine to leucine.

In another embodiment, TDV-3 comprises in addition to the three attenuating mutations one or more mutations selected from:

q) a mutation in the E gene at nucleotide 1603 from adenine to thymine resulting in an amino acid change at position 503 from threonine to serine, and/or r) a silent mutation in the NS5 gene at nucleotide 7620 from adenine to guanine.

In another embodiment, TDV-3 comprises in addition to the three attenuating mutations the mutations p) and q), preferably the mutations p), q), c) and e), even more preferably the mutations p), q), c), e), d) and r), and most preferably the mutations p), q), c), e), d), r), j), k) and o). The nucleotide positions and amino acids positions of TDV-3 refer to the nucleotide sequence as shown in SEQ ID NO. 5 and amino acid sequence as shown in SEQ ID NO. 6.

In one embodiment, TDV-4 comprises in addition to the three attenuating mutations one or more mutations selected from:

c) a mutation in the NS2A gene at nucleotide 4018 from cytosine to thymine resulting in an amino acid change at position 1308 from leucine to phenylalanine, and/or d) a silent mutation in the NS3 gene at nucleotide 5547 from thymine to cytosine, and/or e) a mutation in the NS4A gene at nucleotide 6599 from guanine to cytosine resulting in an amino acid change at position 2168 from glycine to alanine, and/or j) a silent mutation in the junction site between the prM-E gene and the DEN-2 PDK-53 backbone at nucleotide 453 from adenine to guanine, and/or k) a mutation in the junction site between the prM-E gene and the DEN-2 PDK-53 backbone at nucleotides 2381/2382 from thymine-guanine to cytosine-cytosine resulting in an amino acid change at position 762 from valine to alanine, and/or s) a mutation in the C gene at nucleotide 396 from adenine to cytosine resulting in an amino acid change at position 100 from arginine to serine, and/or t) a silent mutation in the E gene at nucleotide 1401 from adenine to guanine, and/or u) a mutation in the E gene at nucleotide 2027 from cytosine to thymine resulting in an amino acid change at position 644 from alanine to valine, and/or v) a mutation in the E gene at nucleotide 2275 from adenine to cytosine resulting in an amino acid change at position 727 from methionine to leucine.

In another embodiment, TDV-4 comprises in addition to the three attenuating mutations one or more mutations selected from:

w) a silent mutation in the C gene at nucleotide 225 from adenine to thymine, and/or x) a mutation in the NS2A gene at nucleotide 3674 from adenine to guanine resulting in an amino acid change at position 1193 from aspartic acid to glycine, and/or y) a mutation in the NS2A gene at nucleotide 3773 from adenine to an adenine/guanine mix resulting in an amino acid change at position 1226 from lysine to a lysine/arginine mix, and/or z) a silent mutation in the NS3 gene at nucleotide 5391 from cytosine to thymine, and/or aa) a mutation in the NS4A gene at nucleotide 6437 from cytosine to thymine resulting in an amino acid change at position 2114 from alanine to valine, and/or bb) a silent mutation in the NS4B gene at nucleotide 7026 from thymine to a thymine/cytosine mix, and/or cc) a silent mutation in the NS5 gene at nucleotide 9750 from adenine to cytosine.

In another embodiments, TDV-4 comprises in addition to the three attenuating mutations the mutation s), u) and v), preferably the mutations s), u), v), c), e), x), y) and aa), even more preferably the mutations s), u), v), c), e), x), y), aa) and w), even more preferably the mutations s), u), v), c), e), x), y), aa), w), d), z), bb) and cc), and most preferably the mutations s), u), v), c), e), x), y), aa), w), d), z), bb), cc), j), k) and t). The nucleotide positions and amino acids positions of TDV-4 refer to the nucleotide sequence as shown in SEQ ID NO. 7 and amino acid sequence as shown in SEQ ID NO. 8.

In a preferred embodiment, TDV-1 has the nucleotide sequence of SEQ ID NO. 1, TDV-2 has the nucleotide sequence of SEQ ID NO. 3, TDV-3 has the nucleotide sequence of SEQ ID NO. 5, and/or TDV-4 has the nucleotide sequence of SEQ ID NO. 7. In a further preferred embodiment, TDV-1 has the amino acid sequence of SEQ ID NO. 2, TDV-2 has the amino acid sequence of SEQ ID NO. 4, TDV-3 has the amino acid sequence of SEQ ID NO. 6, and TDV-4 has the amino acid sequence of SEQ ID NO. 8. In a further preferred embodiment, TDV-1 has a nucleotide sequence encoding the amino acid sequence of SEQ ID NO. 2, TDV-2 has a nucleotide sequence encoding the amino acid sequence of SEQ ID NO. 4, TDV-3 has a nucleotide sequence encoding the amino acid sequence of SEQ ID NO. 6, and TDV-4 has a nucleotide sequence encoding the amino acid sequence of SEQ ID NO. 8.

TABLE 4

Sequences of the TDV virus strains

| SEQ ID NO. | dengue virus strain | sequence type |
|---|---|---|
| SEQ ID NO. 1 | TDV-1 | nucleotide sequence |
| SEQ ID NO. 2 | TDV-1 | amino acid sequence |
| SEQ ID NO. 3 | TDV-2 | nucleotide sequence |
| SEQ ID NO. 4 | TDV-2 | amino acid sequence |
| SEQ ID NO. 5 | TDV-3 | nucleotide sequence |
| SEQ ID NO. 6 | TDV-3 | amino acid sequence |
| SEQ ID NO. 7 | TDV-4 | nucleotide sequence |
| SEQ ID NO. 8 | TDV-4 | amino acid sequence |

Thus, in a particularly preferred embodiment, the unit dose of the invention as described herein comprises the live attenuated dengue virus strains TDV-1, TDV-2, TDV-3 and TDV-4, wherein TDV-1, TDV-3 and TDV-4 are based on TDV-2 and comprise the prM and E regions of DENV-1, -3 and -4, respectively. In another particularly preferred embodiment, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The E protein of DENV-3 has two fewer amino acids than the E protein of DENV-2. Therefore, the nucleotides and encoded amino acid backbone of TDV-2 starting after the E region of DENV-3 at nucleotide 2374 of SEQ ID NO. 5 and amino acid 760 of SEQ ID NO. 6 are 6 nucleotides less and 2 amino acids less than the original TDV-2 nucleotide and amino acid positions, respectively.

Dengue Vaccine Composition

The present invention is in part directed to a unit dose of a dengue vaccine composition as described. The dengue vaccine composition comprises a tetravalent dengue virus composition, also referred to as dengue virus composition, and pharmaceutically acceptable excipients.

Dengue Virus Composition, Virus Concentrations and %-Concentrations

The present invention is in part directed to a unit dose of a dengue vaccine composition, wherein the dengue vaccine composition comprises a tetravalent dengue virus composition including four live attenuated dengue virus strains:

(i) a dengue serotype 1 preferably in a concentration of at least 3.3 log 10 pfu/0.5 mL, (ii) a dengue serotype 2 preferably in a concentration of at least 2.7 log 10 pfu/0.5 mL, (iii) a dengue serotype 3 preferably in a concentration of at least 4.0 log 10 pfu/0.5 mL, and (iv) a dengue serotype 4 preferably strain in a concentration of at least 4.5 log 10 pfu/0.5 mL.

In one embodiment, the dengue vaccine composition comprises a tetravalent dengue virus composition including four live attenuated dengue virus strains:

(i) a dengue serotype 1 preferably in a concentration of at least 3.3 log 10 pfu/0.5 mL to 3.8 log 10 pfu/0.5 mL, (ii) a dengue serotype 2 preferably in a concentration of at least 2.7 log 10 pfu/0.5 mL, (iii) a dengue serotype 3 preferably in a concentration of at least 4.0 log 10 pfu/0.5 mL, and (iv) a dengue serotype 4 preferably strain in a concentration of at least 4.5 log 10 pfu/0.5 ml or 4.6 log 10 pfu/0.5 mL, optionally to 6.2 log 10 pfu/0.5 ml.

The present invention is further in part directed to a unit dose of a dengue vaccine composition, wherein the dengue vaccine composition comprises a tetravalent dengue virus composition including four live attenuated dengue virus strains:

(i) a chimeric dengue serotype 2/1 strain in a concentration of at least 3.3 log 10 pfu/0.5 mL, (ii) a dengue serotype 2 strain in a concentration of at least 2.7 log 10 pfu/0.5 mL, (iii) a chimeric dengue serotype 2/3 strain in a concentration of at least 4.0 log 10 pfu/0.5 mL, and (iv) a chimeric dengue serotype 2/4 strain in a concentration of at least 4.5 log 10 pfu/0.5 mL.

In one embodiment, the dengue vaccine composition comprises a tetravalent dengue virus composition including four live attenuated dengue virus strains:

(i) a chimeric dengue serotype 2/1 strain in a concentration of at least 3.3 log 10 pfu/0.5 mL to 3.8 log 10 pfu/0.5 ml, (ii) a dengue serotype 2 strain in a concentration of at least 2.7 log 10 pfu/0.5 mL, (iii) a chimeric dengue serotype 2/3 strain in a concentration of at least 4.0 log 10 pfu/0.5 mL, and (iv) a chimeric dengue serotype 2/4 strain in a concentration of at least 4.5 log 10 pfu/0.5 mL or at least 4.6 log 10 pfu/0.5 mL to optionally 6.2 log 10 pfu/0.5 ml.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/0.5 mL to 5.3 log 10 pfu/0.5 mL, (ii) the dengue serotype 2 (e.g. dengue serotype 2 strain) has a concentration of 2.7 log 10 pfu/0.5 mL to 5.0 log 10 pfu/0.5 mL, (iii) the dengue serotype 3 (e.g. chimeric dengue serotype 2/3 strain) has a concentration of 4.0 log 10 pfu/0.5 mL to 6.0 log 10 pfu/0.5 mL, and (iv) the dengue serotype 4 (e.g. chimeric dengue serotype 2/4 strain) has a concentration of 4.5 log 10 pfu/0.5 mL to 6.5 log 10 pfu/0.5 mL.

In one such embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/0.5 mL to 5.0 log 10 pfu/0.5 mL, (ii) the dengue serotype 2 (e.g. dengue serotype 2 strain) has a concentration of 2.7 log 10 pfu/0.5 mL to 4.9 log 10 pfu/0.5 mL, (iii) the dengue serotype 3 (e.g. chimeric dengue serotype 2/3 strain) has a concentration of 4.0 log 10 pfu/0.5 mL to 5.7 log 10 pfu/0.5 mL, and (iv) the dengue serotype 4 (e.g. chimeric dengue serotype 2/4 strain) has a concentration of 4.5 log 10 pfu/0.5 mL to 6.2 log 10 pfu/0.5 mL.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 5.0 log 10 pfu/dose, (ii) a dengue serotype 2 (e.g. dengue serotype 2 strain) has a concentration of 2.7 log 10 pfu/dose to 4.9 log 10 pfu/dose, (iii) a dengue serotype 3 (e.g. chimeric dengue serotype 2/3 strain) has a concentration of 4.0 log 10 pfu/dose to 5.7 log 10 pfu/dose, and (iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 4.1 log 10 pfu/dose, (ii) a dengue serotype 2 (e.g. dengue serotype 2 strain) has a concentration of 2.7 log 10 pfu/dose to 3.6 log 10 pfu/dose, (iii) a dengue serotype 3 (e.g. chimeric dengue serotype 2/3 strain) has a concentration of 4.0 log 10 pfu/dose to 4.7 log 10 pfu/dose, and (iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/0.5 mL to 3.6 log 10 pfu/0.5 mL, (ii) a dengue serotype 2 (e.g. dengue serotype 2 strain) has a concentration of 2.7 log 10 pfu/0.5 mL to 4.0 log 10 pfu/0.5 mL, (iii) a dengue serotype 3 (e.g. chimeric dengue serotype 2/3 strain) has a concentration of 4.0 log 10 pfu/0.5 mL to 4.6 log 10 pfu/0.5 mL, and (iv) a dengue serotype 4 (e.g. chimeric dengue serotype 2/4 strain) has a concentration of 4.5 log 10 pfu/0.5 ml or 4.6 log 10 pfu/0.5 mL to 5.1 log 10 pfu/0.5 mL.

In another embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.3 log 10 pfu/0.5 mL to 4.4 log 10 pfu/0.5 mL, (ii) the dengue serotype 2 (e.g. dengue serotype 2 strain) has a concentration of 3.7 log 10 pfu/0.5 mL to 3.8 log 10 pfu/0.5 mL, (iii) the dengue serotype 3 (e.g. chimeric dengue serotype 2/3 strain) has a concentration of 4.5 log 10 pfu/0.5 mL to 5.0 log 10 pfu/0.5 mL, and (iv) the dengue serotype 4 (e.g. chimeric dengue serotype 2/4 strain) has a concentration of 5.5 log 10 pfu/0.5 mL to 5.6 log 10 pfu/0.5 mL.

In a particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.4 log 10 pfu/0.5 mL, (ii) the dengue serotype 2 (e.g. dengue serotype 2 strain) has a concentration of 3.8 log 10 pfu/0.5 mL, (iii) the dengue serotype 3 (e.g. chimeric dengue serotype 2/3 strain) has a concentration of 4.5 log 10 pfu/0.5 mL, and (iv) the dengue serotype 4 (e.g. chimeric dengue serotype 2/4 strain) has a concentration of 5.6 log 10 pfu/0.5 mL.

In another particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.6 log 10 pfu/0.5 mL, (ii) the dengue serotype 2 (e.g. dengue serotype 2 strain) has a concentration of 4.0 log 10 pfu/0.5 mL, (iii) the dengue serotype 3 (e.g. chimeric dengue serotype 2/3 strain) has a concentration of 4.6 log 10 pfu/0.5 mL, and (iv) the dengue serotype 4 (e.g. chimeric dengue serotype 2/4 strain) has a concentration of 5.1 log 10 pfu/0.5 mL.

In another preferred embodiment, the dengue vaccine composition comprises a tetravalent dengue virus composition including four live attenuated dengue virus strains wherein the arithmetic sum of all four serotypes is less than 6.7 log 10 pfu/0.5 mL, preferably less than 5.5 log 10 pfu/0.5 mL. In certain such embodiments, the arithmetic sum of all four serotypes is at least 4.6 log 10 pfu/0.5 mL. In a preferred embodiment, the dengue vaccine composition comprises a tetravalent dengue virus composition including four live attenuated dengue virus strains wherein the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The present invention is in part directed to a unit dose of a dengue vaccine composition, wherein the dengue vaccine composition comprises a tetravalent dengue virus composition including four live attenuated dengue virus strains:

(i) a dengue serotype 1 (e.g. chimeric dengue serotype 2/1 strain) in a concentration of at least 3.3 log 10 pfu/dose, (ii) a dengue serotype 2 (e.g. dengue serotype 2 strain) in a concentration of at least 2.7 log 10 pfu/dose, (iii) a dengue serotype 3 (e.g. chimeric dengue serotype 2/3 strain) in a concentration of at least 4.0 log 10 pfu/dose, and (iv) a dengue serotype 4 (e.g. chimeric dengue serotype 2/4 strain) in a concentration of at least 4.5 log 10 pfu/dose.

In one embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/dose to 5.3 log 10 pfu/dose, (ii) the dengue serotype 2 (e.g. dengue serotype 2 strain) has a concentration of 2.7 log 10 pfu/dose to 5.0 log 10 pfu/dose, (iii) the dengue serotype 3 (e.g. chimeric dengue serotype 2/3 strain) has a concentration of 4.0 log 10 pfu/dose to 6.0 log 10 pfu/dose, and (iv) the dengue serotype 4 (e.g. chimeric dengue serotype 2/4 strain) has a concentration of 4.5 log 10 pfu/dose to 6.5 log 10 pfu/dose.

In one such embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.3 log 10 pfu/dose to 5.0 log 10 pfu/dose, (ii) the dengue serotype 2 (e.g. dengue serotype 2 strain) has a concentration of 2.7 log 10 pfu/dose to 4.9 log 10 pfu/dose, (iii) the dengue serotype 3 (e.g. chimeric dengue serotype 2/3 strain) has a concentration of 4.0 log 10 pfu/dose to 5.7 log 10 pfu/dose, and (iv) the dengue serotype 4 (e.g. chimeric dengue serotype 2/4 strain) has a concentration of 4.5 log 10 pfu/dose to 6.2 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 5.0 log 10 pfu/dose, (ii) a dengue serotype 2 (e.g. dengue serotype 2 strain) has a concentration of 2.7 log 10 pfu/dose to 4.9 log 10 pfu/dose, (iii) a dengue serotype 3 (e.g. chimeric dengue serotype 2/3 strain) has a concentration of 4.0 log 10 pfu/dose to 5.7 log 10 pfu/dose, and (iv) a dengue serotype 4 (e.g. chimeric dengue serotype 2/4 strain) has a concentration of 4.5 log 10 pfu/dose to 5.5 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 4.1 log 10 pfu/dose, (ii) a dengue serotype 2 (e.g. dengue serotype 2 strain) has a concentration of 2.7 log 10 pfu/dose to 3.6 log 10 pfu/dose, (iii) a dengue serotype 3 (e.g. chimeric dengue serotype 2/3 strain) has a concentration of 4.0 log 10 pfu/dose to 4.7 log 10 pfu/dose, and (iv) a dengue serotype 4 (e.g. chimeric dengue serotype 2/4 strain) has a concentration of 4.5 log 10 pfu/dose to 5.3 log 10 pfu/dose.

In a further such embodiment, the dengue vaccine composition comprises a tetravalent dengue virus composition including four live attenuated dengue virus strains wherein:

(i) a dengue serotype 1 (e.g. chimeric dengue serotype 2/1 strain) has a concentration of 3.3 log 10 pfu/dose to 3.6 log 10 pfu/dose, (ii) a dengue serotype 2 (e.g. dengue serotype 2 strain) has a concentration of 2.7 log 10 pfu/dose to 4.0 log 10 pfu/dose, (iii) a dengue serotype 3 (e.g. chimeric dengue serotype 2/3 strain) has a concentration of 4.0 log 10 pfu/dose to 4.6 log 10 pfu/dose, and (iv) a dengue serotype 4 (e.g. chimeric dengue serotype 2/4 strain) has a concentration of 4.5 log 10 pfu/dose 4.6 log 10 pfu/dose to 5.1 log 10 pfu/dose.

In another embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.3 log 10 pfu/dose to 4.4 log 10 pfu/dose, (ii) the dengue serotype 2 (e.g. dengue serotype 2 strain) has a concentration of 3.7 log 10 pfu/dose to 3.8 log 10 pfu/dose, (iii) the dengue serotype 3 (e.g. chimeric dengue serotype 2/3 strain) has a concentration of 4.5 log 10 pfu/dose to 5.0 log 10 pfu/dose, and (iv) the dengue serotype 4 (e.g. chimeric dengue serotype 2/4 strain) has a concentration of 5.5 log 10 pfu/dose to 5.6 log 10 pfu/dose.

In a particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 4.4 log 10 pfu/dose, (ii) the dengue serotype 2 (e.g. dengue serotype 2 strain) has a concentration of 3.8 log 10 pfu/dose, (iii) the dengue serotype 3 (e.g. chimeric dengue serotype 2/3 strain) has a concentration of 4.5 log 10 pfu/dose, and (iv) the dengue serotype 4 (e.g. chimeric dengue serotype 2/4 strain) has a concentration of 5.6 log 10 pfu/dose.

In another particularly preferred embodiment, the dengue vaccine composition comprises a tetravalent dengue virus composition including four live attenuated dengue virus strains wherein:

(i) the dengue serotype 1 (e.g. chimeric dengue serotype 2/1 strain) has a concentration of 3.6 log 10 pfu/dose, (ii) the dengue serotype 2 (e.g. dengue serotype 2 strain) has a concentration of 4.0 log 10 pfu/dose, (iii) the dengue serotype 3 (e.g. chimeric dengue serotype 2/3 strain) has a concentration of 4.6 log 10 pfu/dose, and (iv) the dengue serotype 4 (e.g. chimeric dengue serotype 2/4 strain) has a concentration of 5.1 log 10 pfu/dose.

In another preferred embodiment, the dengue vaccine composition comprises a tetravalent dengue virus composition including four live attenuated dengue virus strains wherein the arithmetic sum of all four serotypes is less than 6.7 log 10 pfu/dose, preferably less than 5.5 log 10 pfu/dose. In certain such embodiments, the arithmetic sum of all four serotypes is at least 4.6 log 10 pfu/dose. in a preferred embodiment, the dengue vaccine composition comprises a tetravalent dengue virus composition including four live attenuated dengue virus strains wherein the arithmetic sum of all four serotypes is in the range of 4.6 log 10 pfu/dose to 6.7 log 10 pfu/dose, preferably in the range of 4.6 log 10 pfu/dose to 5.5 log 10 pfu/dose.

In one embodiment in the composition (i), (ii), (iii), and (iv) provide a total concentration of pfu/0.5 mL and based on said concentration, the concentration of (iii) at least 10% of the total concentration in pfu/0.5 mL.

In one embodiment in the composition (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment in the composition (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

The concentration of the different dengue viruses is preferably determined by an immuno-focus assay known in the art. For example, the concentration may be determined by an immuno-focus assay wherein serial dilutions of dengue virus are applied to monolayers of adherent cells, such as Vero cells. After a period of time which allows infectious viruses to bind to the cells and to be taken up by the cells, an overlay containing thickening agents, such as agarose or carboxymethylcellulose, is added to prevent diffusion of viruses so that progeny viruses can only infect cells adjacent to the original infected cells. After a period of incubation to allow viral replication, cells are fixed and stained using serotype-specific anti-dengue monoclonal antibodies and a secondary antibody such as an antibody labeled with alkaline phosphatase. The foci are stained by adding a suitable substrate for the enzyme attached to the secondary antibody, such as 5-bromo-4-chloro-3-indolyl-phosphate/nitro blue tetrazolium phosphatase substrate. The number of plaques on the plate corresponds to the plaque forming units of the virus in the solutions applied to the cells. For example, a concentration of 1,000 pfu/μl indicates that 1 μl of the solution applied to the cells contains enough viruses to produce 1,000 plaques in a cell monolayer.

The dengue vaccine composition comprises a tetravalent dengue virus composition including four live attenuated dengue virus strains, wherein a chimeric dengue serotype 2/1 strain, a dengue serotype 2 strain, a chimeric dengue serotype 2/3 strain, and a chimeric dengue serotype 2/4 strain provide a total concentration in pfu/0.5 mL. The term "total concentration in pfu/0.5 mL" or "total concentration in pfu/dose" is the sum of the concentrations of the dengue serotype 1 (e.g. chimeric dengue serotype 2/1 strain), dengue serotype 2 (e.g. the dengue serotype 2 strain), the dengue serotype 3 (e.g. chimeric dengue serotype 2/3 strain) and the dengue serotype 4 (e.g. chimeric dengue serotype 2/4 strain), preferably the sum of the concentrations of TDV-1, TDV-2, TDV-3 and TDV-4, and is defined as 100% of the dengue virus concentration as determined by pfu (plaque forming units) in 0.5 mL or in a dose.

In one embodiment, the dengue vaccine composition comprises a tetravalent dengue virus composition including four live attenuated dengue virus strains, wherein a dengue serotype 1 (e.g. chimeric dengue serotype 2/1 strain), a dengue serotype 2 (e.g. dengue serotype 2 strain), a dengue serotype 3 (e.g. chimeric dengue serotype 2/3 strain), and a dengue serotype 4 (e.g. chimeric dengue serotype 2/4 strain) provide a total concentration in pfu/0.5 mL, wherein based on said total concentration the concentration of a dengue serotype 2 (e.g. dengue serotype 2 strain) measured in pfu/0.5 mL is less than 10% of the total concentration, or less than 8%, or less than 6% of the total concentration, and wherein the concentration of a dengue serotype 4 (e.g. chimeric dengue serotype 2/4 strain) measured in pfu/0.5 mL is at least 50% or at least 60% or at least 65% of the total concentration. In one embodiment, based on said total concentration the concentration of a dengue serotype 2 (e.g. dengue serotype 2 strain) measured in pfu/0.5 mL is 0.3 to 10% or 0.5 to 8% of the total concentration and the concentration of a dengue serotype 4 (e.g. chimeric dengue serotype 2/4 strain) measured in pfu/0.5 mL is 50% to 90% or 60% to 88% of the total concentration. This means that the concentration of the dengue serotype 2 (e.g. dengue serotype 2 strain) is lower than the concentration of the dengue serotype 4 (e.g. chimeric dengue serotype 2/4 strain).

In one such embodiment, the concentration of a dengue serotype 1 (e.g. chimeric dengue serotype 2/1 strain) measured in pfu/0.5 mL is at least 1% of the total concentration, and/or the concentration of a dengue serotype 3 (e.g. chimeric dengue serotype 2/3 strain) measured in pfu/0.5 mL is at least 6% of the total concentration, or at least 7% or 8%, 10%, 12%, 14%, 16% or 18% of the total concentration. In one such embodiment, the concentration of a dengue serotype 2 (e.g. chimeric dengue serotype 2/1 strain) measured in pfu/0.5 mL is 1% to 7% or 2% to 6% or 2.0% to 5.0% of the total concentration, and/or the concentration of a dengue serotype 3 (e.g. chimeric dengue serotype 2/3 strain) measured in pfu/0.5 mL is 6% to 25% or 7% to 25% or 10% to 25% or 18% to 25% of the total concentration. This means that the concentration of the dengue serotype 1 (e.g. chimeric dengue serotype 2/1 strain) is lower than the concentration of the dengue serotype 3 (e.g. chimeric dengue serotype 2/3 strain).

In a preferred embodiment, the concentration of a dengue serotype 2 strain, such as TDV-2, measured in pfu/0.5 mL is less than 10% of the total concentration, preferably less than 6% or less than 2%, the concentration of a dengue serotype 4 (e.g. chimeric dengue serotype 2/4 strain), such as TDV-4, measured in pfu/0.5 mL is at least 50% of the total concentration, preferably at least 65%, the concentration of a dengue serotype 1 (e.g. chimeric dengue serotype 2/1 strain), such as TDV-1, measured in pfu/0.5 mL is at least 1% of the total concentration, preferably between 1% and 7% or 2.0% to 5.0%, and the concentration of a dengue serotype 3 (e.g. chimeric dengue serotype 2/3 strain), such as TDV-3, measured in pfu/0.5 mL is at least 6% of the total concentration, preferably between 6% and 25% or 10% to 25% or 18% to 25%.

In a further preferred embodiment, a dengue virus composition comprising a dengue serotype 1 (e.g. chimeric dengue serotype 2/1 strain), a dengue serotype 2 (e.g. dengue serotype 2 strain), a dengue serotype 1 (e.g. chimeric dengue serotype 2/3 strain), and a dengue serotype 4 (e.g. chimeric dengue serotype 2/4 strain), such as TDV-1, TDV-2, TDV-3 and TDV-4, is provided, wherein the concentration of the dengue serotype 1 (e.g. chimeric dengue serotype 2/1 strain) measured in pfu/0.5 mL is at least 1% of the total concentration, preferably between 1% and 7% or 2.0% and 5.0%, the concentration of the dengue serotype 2 (e.g. dengue serotype 2 strain) measured in pfu/0.5 mL is less than 10% of the total concentration, preferably less than 6% or less than 2% and the concentration of the dengue serotype 3 (e.g. chimeric dengue serotype 2/3 strain) measured in pfu/0.5 mL is at least 6% of the total concentration, preferably between 6% and 25% or 10% to 25% or 18% to 25%. It is particularly preferred that the dengue serotype 4 (e.g. chimeric dengue serotype 2/4 strain) has the highest concentration of all four dengue serotypes.

In a further preferred embodiment, the dengue vaccine composition comprises a tetravalent dengue virus composition including four live attenuated dengue virus strains, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, in said embodiments the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

According to a further embodiment, the chimeric dengue serotype 2/4 strain, preferably TDV-4, has the highest concentration in the dengue vaccine composition, followed by the chimeric dengue serotype 2/3 strain, preferably TDV-3, followed by the chimeric dengue serotype 2/1 strain, preferably TDV-1, followed by the dengue serotype 2 strain, preferably TDV-2. It is particularly preferred that the dengue serotype 2 strain has the lowest concentration of the four strains present in the dengue vaccine composition.

Whenever reference is made to a concentration/0.5 ml, this does not limit the volume of the unit dose described herein to 0.5 ml. 0.5 ml is the reference volume for the determination of the concentrations of the virus strains in the composition in pfu/ml. The volume and/or amount per unit dose is described in the respective chapter.

Pharmaceutically Acceptable Excipients

The present invention is in part directed to a unit dose of a dengue vaccine composition, wherein the dengue vaccine composition comprises one or more pharmaceutically acceptable excipients. In one embodiment, the dengue vaccine composition comprises a non-reducing sugar, a surfactant, a protein and an inorganic salt. Preferably, the non-reducing sugar is trehalose, the surfactant is poloxamer 407, the protein is human serum albumin and the inorganic salt is sodium chloride.

In one embodiment, the unit dose of a dengue vaccine composition comprises the following pharmaceutically acceptable excipients:

- from about 10% w/v to about 20% w/v α,α-trehalose dihydrate or an equimolar amount of other forms of α,α-trehalose,
- from about 0.5% w/v to about 1.5% w/v poloxamer 407,
- from about 0.05% w/v to about 2% w/v human serum albumin, and
- from about 70 mM to 140 mM sodium chloride.

In one embodiment, the unit dose of a dengue vaccine composition comprises the following pharmaceutically acceptable excipients when measured in 0.5 ml:

- from about 10% w/v to about 20% w/v α,α-trehalose or an equimolar amount of other forms of α,α-trehalose,
- from about 0.5% w/v to about 1.5% w/v poloxamer 407,
- from about 0.05% w/v to about 2% w/v human serum albumin, and
- from about 70 mM to 140 mM sodium chloride, and preferably
- has a pH of 7 to 8.5.

In one embodiment, the unit dose of a dengue vaccine composition comprises the following pharmaceutically acceptable excipients when measured in 0.5 ml:

- from about 143 mg/ml to about 185 mg/ml α,α-trehalose dihydrate or an equimolar amount of other forms of α,α-trehalose,
- from about 9.1 mg/ml to about 12.4 mg/ml poloxamer 407,
- from about 0.88% mg/ml to about 1.32 mg/ml human serum albumin, and
- from about 70 mM to 140 mM sodium chloride, and preferably
- has a pH of 7 to 8.5.

In a preferred embodiment, the lyophilized unit dose of the invention as described herein comprises the following pharmaceutically acceptable excipients:

- about 15% w/v α,α-trehalose dihydrate,
- about 1% w/v poloxamer 407,
- about 0.1% w/v human serum albumin, and
- about 100 mM sodium chloride.

In a preferred embodiment, the lyophilized unit dose of the invention as described herein comprises the following pharmaceutically acceptable excipients when measured in 0.5 ml:

- about 15% w/v α,α-trehalose,
- about 1% w/v poloxamer 407,
- about 0.1% w/v human serum albumin, and
- about 100 mM sodium chloride.

In a preferred embodiment, the lyophilized unit dose of the invention as described herein comprises the following pharmaceutically acceptable excipients:

- about 82.9 mg α,α-trehalose dihydrate,
- about 5 mg poloxamer 407,
- about 0.5 mg human serum albumin, and
- about 50 μmoles sodium chloride.

In a preferred embodiment, the reconstituted unit dose of the invention as described herein comprises the following pharmaceutically acceptable excipients:

- about 15% w/v α,α-trehalose dihydrate,
- about 1% w/v poloxamer 407,
- about 0.1% w/v human serum albumin, and
- about 137 mM sodium chloride, and preferably
- has a pH of 7 to 8.5

In a preferred embodiment, the reconstituted unit dose of the invention as described herein comprises the following pharmaceutically acceptable excipients when measured in 0.5 ml:

- about 15% w/v α,α-trehalose,
- about 1% w/v poloxamer 407,
- about 0.1% w/v human serum albumin, and preferably
- about 137 mM sodium chloride and preferably
- has a pH of 7 to 8.5.

In a preferred embodiment, the reconstituted unit dose of the invention as described herein comprises the following pharmaceutically acceptable excipients:

- about 82.9 mg α,α-trehalose dihydrate,
- about 5 mg poloxamer 407,
- about 0.5 mg human serum albumin, and preferably
- about 68.5 μmoles sodium chloride, and preferably
- has a pH of 7 to 8.5.

The human serum albumin may be a native or recombinant human serum albumin (rHSA). The poloxamer 407 may be e.g. Pluronic F127.

In one embodiment, the unit dose further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of 7.0 to 8.5 at 25° C.

Unit Dose

The present invention is directed in part to a unit dose of a dengue vaccine composition comprising a tetravalent dengue virus composition as described herein and pharmaceutically acceptable excipients as described herein.

The present invention is directed in part to a unit dose of a dengue vaccine composition as described above e.g. of (i) a dengue serotype 1 (e.g. chimeric dengue serotype 2/1 strain) with a concentration of at least 3.3 log 10 pfu/0.5 mL, (ii) a dengue serotype 2 (e.g. dengue serotype 2 strain) with a concentration of at least 2.7 log 10 pfu/0.5 mL, (iii) a dengue serotype 3 (e.g. chimeric dengue serotype 2/3 strain) with a concentration of at least 4.0 log 10 pfu/0.5 mL, and (iv) a dengue serotype 4 (e.g. chimeric dengue serotype 2/4 strain) with a concentration of at least 4.5 log 10 pfu/0.5 mL.

Preferably, the chimeric dengue serotype 2/1 strain is TDV-1, the dengue serotype 2 strain is TDV-2, the chimeric dengue serotype 2/3 strain is TDV-3, and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one embodiment, the unit dose is lyophilized. In one such embodiment, the lyophilized unit dose is obtained by subjecting a volume of 0.5 mL of the aqueous dengue vaccine composition produced by combining pharmaceutically acceptable excipients as described herein and the dengue vaccine composition as described herein comprising the four dengue virus strains, in particular TDV-1 to TDV-4, to lyophilization. In a preferred embodiment the residual moisture content as determined by Karl Fischer Determination is equal to or less than 5.0%, preferably equal to or less than 3%.

In another embodiment, the unit dose is reconstituted. The reconstituted unit dose is obtained by subjecting the lyophilized unit dose to reconstitution with a pharmaceutically acceptable diluent, preferably before administration of the dengue vaccine. In one such embodiment, reconstitution will be accomplished by adding a pharmaceutically acceptable diluent, such as water for injection, phosphate buffered saline or an aqueous sodium chloride solution, to the lyophilized unit dose. In one embodiment, an aqueous sodium chloride solution, such as a 37 mM aqueous sodium chloride solution, is added to the lyophilized unit dose for reconstitution. In one such embodiment, the lyophilized unit dose will be reconstituted with 0.3 to 0.8 mL, or 0.4 to 0.7 mL, or 0.5 mL of diluent. In a preferred embodiment, the lyophilized unit dose is reconstituted with 0.3 to 0.8 mL, 0.4 to 0.7 mL or 0.5 mL of 37 mM aqueous sodium chloride solution. In a more preferred embodiment, the lyophilized unit dose is reconstituted with 0.5 mL of 37 mM aqueous sodium chloride solution. The reconstituted unit dose can subsequently be administered subcutaneously.

It is preferred that the unit dose in lyophilized form is the final product after manufacture of the unit dose and the storage form of the unit dose, wherein the unit dose in reconstituted form is prepared before administration of the unit dose to a subject.

The present invention is, moreover, directed in part to a unit dose of a dengue vaccine composition comprising:

a tetravalent virus composition including four live attenuated dengue virus strains, wherein the unit dose is lyophilized and upon reconstitution with 0.5 mL of a pharmaceutically acceptable diluent comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (iv) a dengue serotype 4, such as a chimeric dengue serotype 2/4 strain, in a concentration of at least 4.5 log 10 pfu/0.5 ml.

In one embodiment, the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said concentration, the concentration of (iii) at least 10% of the total concentration in pfu/0.5 mL.

In another embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%.

It is preferred that the concentration in the reconstituted unit dose of (iii) in pfu/0.5 mL is at least 10%.

In one embodiment the reconstituted unit dose has a volume of e.g. 0.5 mL, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%.

In one embodiment, the present invention is directed to a lyophilized unit dose of a dengue vaccine composition comprising upon reconstitution with 0.5 mL of a pharmaceutically acceptable diluent a dengue serotype 1 (e.g. chimeric dengue serotype 2/1 strain) with a concentration of at least 3.3 log 10 pfu/0.5 mL, a dengue serotype 2 (e.g. dengue serotype 2 strain) with a concentration of at least 2.7 log 10 pfu/0.5 mL, a dengue serotype 3 (e.g. chimeric dengue serotype 2/3 strain) with a concentration of at least 4.0 log 10 pfu/0.5 mL, and a dengue serotype 4 (e.g. chimeric dengue serotype 2/4 strain) with a concentration of at least 4.5 log 10 pfu/0.5 mL and pharmaceutically acceptable excipients as described herein, wherein the unit dose is preferably formulated in 0.5 mL before lyophilization. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/dose to 5.0 log 10 pfu/0.5 mL, a dengue serotype 2 (e.g. dengue serotype 2 strain) in a concentration of 2.7 log 10 pfu/dose to 4.9 log 10 pfu/0.5 mL, a dengue serotype 3 (e.g. chimeric dengue serotype 2/3 strain) in a concentration of 4.0 log 10 pfu/dose to 5.7 log 10 pfu/0.5 mL, and a dengue serotype 4 (e.g. chimeric dengue serotype 2/4 strain) in a concentration of 4.5 log 10 pfu/dose to 5.5 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In one such embodiment, the lyophilized unit dose is obtained by lyophilizing 0.5 mL of a dengue vaccine composition comprising a dengue serotype 1 (e.g. chimeric dengue serotype 2/1 strain) in a concentration of 3.3 log 10 pfu/0.5 mL to 3.6 log 10 pfu/0.5 mL, a dengue serotype 2 (e.g. dengue serotype 2 strain) in a concentration of 2.7 log 10 pfu/0.5 mL to 4.0 log 10 pfu/0.5 mL, a dengue serotype 3 (e.g. chimeric dengue serotype 2/3 strain) in a concentration of 4.0 log 10 pfu/0.5 mL to 4.6 log 10 pfu/0.5 mL, and a dengue serotype 4 (e.g. chimeric dengue serotype 2/4 strain) in a concentration of 4.5 log 10 pfu/0.5 mL or 4.6 log 10 pfu/0.5 mL to 5.1 log 10 pfu/0.5 mL and pharmaceutically acceptable excipients as described herein. Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4.

In certain embodiments, the lyophilized unit dose refers to 0.5 mL before lyophilization, wherein TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In certain embodiments, the reconstituted unit dose has a volume of 0.5 mL and TDV-2 and TDV-4 are present in certain relative amounts, based on the total concentration of TDV-1, TDV-2, TDV-3 and TDV-4 in pfu/0.5 mL, and the concentration of TDV-2 measured in pfu/0.5 mL is less than 10% or less than 8% or less than 6%, and the concentration of TDV-4 measured in pfu/0.5 mL is at least 50% or at least 65%. In some of these embodiments, the concentration of TDV-1 measured in pfu/0.5 mL is at least 1% and/or the concentration of TDV-3 measured in pfu/0.5 mL is at least 6%, 7%, 8%, 10%, 12%, 14%, 16% or at least 18%.

In a further preferred embodiment, the reconstituted unit dose has a volume of 0.5 mL and comprises a tetravalent dengue virus composition including four live attenuated dengue virus strains, wherein the concentration of the dengue serotype 1 (e.g. dengue serotype 2/1 strain) measured in pfu/0.5 mL is 1% to 7% of the total concentration, the concentration of the dengue serotype 2 (e.g dengue serotype 2 strain) measured in pfu/0.5 mL is less than 8% of the total concentration, such as in the range of 1% to 8% of the total concentration, the concentration of the dengue serotype 3 (e.g. dengue serotype 2/3 strain) measured in pfu/0.5 mL is at least 10% of the total concentration, and the concentration of the dengue serotype 4 (e.g. dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL.

In a further preferred embodiment, the reconstituted unit dose has a volume of 0.5 mL and comprises a tetravalent dengue virus composition including four live attenuated dengue virus strains, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

The lyophilized unit dose reconstituted in 0.5 mL will provide the above concentrations for the four dengue serotypes. While the unit dose of a dengue vaccine composition as described herein refers to the concentrations of the dengue serotypes in 0.5 mL, the lyophilized unit dose can be reconstituted with other volumes of a pharmaceutically acceptable diluent, such as an aqueous sodium chloride solution, without changing the absolute virus amount administered or the ratios of the viruses to one another.

In certain embodiments, the lyophilized unit dose of the invention is prepared from a solution comprising a non-reducing sugar, a surfactant, a protein and an inorganic salt.

In certain embodiments, the lyophilized unit dose of the invention is prepared from a solution comprising trehalose, poloxamer 407, human serum albumin and sodium chloride.

In certain embodiments, the lyophilized unit dose of the invention is prepared from a solution comprising about 10% w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and about 70 mM to about 120 mM sodium chloride.

In preferred embodiments, the lyophilized unit dose of the invention as described herein is prepared from a solution comprising about 15% w/v α,α-trehalose dihydrate, about 1% w/v poloxamer 407, about 0.1% w/v human serum albumin and about 100 mM sodium chloride.

In one embodiment, the solution from which the lyophilized unit dose is prepared further comprises a buffer. The buffer may be phosphate buffered saline (PBS). The buffer may include at least one of sodium chloride (NaCl), monosodium dihydrogen phosphate ($NaH_2PO_4$), disodium hydrogen phosphate ($Na_2HPO_4$), potassium chloride (KCl), and potassium dihydrogen phosphate ($KH_2PO_4$). In a preferred embodiment, the buffer may include disodium hydrogen phosphate ($Na_2HPO_4$), potassium chloride (KCl), and potassium dihydrogen phosphate ($KH_2PO_4$). The buffer may have a pH in the range of about 7.0 to about 8.5 at 25° C. or a pH of about 6.8 to about 7.6 at 25° C., preferably a pH of about 7.2 at 25° C.

In preferred embodiments, the reconstituted unit dose of the invention as described herein comprising about 15% w/v α,α-trehalose dihydrate, about 1% w/v poloxamer 407, about 0.1% w/v human serum albumin and about 137 mM sodium chloride. The reconstituted unit dose may have a pH of about 7.0 to about 8.5 at 25° C., preferably a pH of about 7.2 at 25° C.

The unit dose of the invention as described herein activates multiple arms of the immune system—neutralizing antibodies, cellular immunity and anti-NS1 antibodies—in both seronegative and seropositive subject populations or in both seronegative and seropositive subjects. Thus, the unit dose of the invention as described herein protects both dengue seronegative and dengue seropositive subject populations or subjects against dengue disease.

In one embodiment, one unit dose is present in a container, preferably a vial, and said unit dose is administered to a subject after reconstitution. In one embodiment, more than one unit dose of the dengue vaccine composition may be present in a container, preferably a vial, so that with the content of one container, preferably a vial, more than one subject can be vaccinated. In one embodiment, the container comprising more than one unit doses of the invention as described herein is used for providing the reconstituted unit dose to be used in the methods of the invention as described herein.

The certain embodiments, the container comprising the unit dose of the invention is part of a kit. Thus, the invention is directed in part to a kit for preparing a reconstituted unit dose comprising a lyophilized unit dose of the present invention as described herein, and a pharmaceutically acceptable diluent for reconstitution.

In certain embodiments, the diluent for reconstitution provided in a container, preferably a vial, or a pre-filled syringe. In some embodiments, the diluent for reconstitution is selected from water for injection, phosphate buffered saline or an aqueous sodium chloride solution. In a preferred embodiment, the diluent for reconstitution is 30 to 40 mM sodium chloride, such as 37 mM sodium chloride.

In certain embodiments, the kit may further comprise a yellow fever vaccine, in particular YF-17D. In some embodiments, the yellow fever vaccine may be in a separate container, such as a vial. In another embodiment, the yellow fever vaccine and the unit dose of the invention may be in the same container. Thus, the invention is directed in part to a combined dengue/yellow fever vaccine, wherein the unit dose of the invention as described herein is combined with a yellow fever vaccine. Such a combined dengue/yellow fever vaccine comprises the unit dose of the invention as described herein and a yellow fever vaccine, in particular YF-17D, in the same formulation. In certain embodiments, the invention is directed to a kit comprising such a combined dengue/yellow fever vaccine and a unit dose of the invention as described herein.

In certain embodiments, the kit may further comprise a hepatitis A vaccine, such as HAVRIX® or VAQTA®. In some embodiments, the hepatitis A vaccine may be in a separate container, such as a vial. In another embodiment, the hepatitis A vaccine and the unit dose of the invention may be in the same container. Thus, the invention is directed in part to a combined dengue/hepatitis A vaccine, wherein the unit dose of the invention as described herein is combined with a hepatitis A vaccine. Such a combined dengue/hepatitis A vaccine comprises the unit dose of the invention as described herein and a hepatitis A vaccine, such as HAVRIX® or VAQTA®, in the same formulation. In certain embodiments, the invention is directed to a kit comprising such a combined dengue/hepatitis A vaccine and a unit dose of the invention as described herein.

In certain embodiments, the kit may further comprise a HPV vaccine, in particular a 9vHPV vaccine, such as GARDASIL® 9. In some embodiments, the HPV vaccine may be in a separate container, such as a vial. In another embodiment, the HPV vaccine and the unit dose of the invention may be in the same container. Thus, the invention is directed in part to a combined dengue/HPV vaccine, wherein the unit dose of the invention as described herein is combined with a HPV vaccine. Such a combined dengue/HPV vaccine comprises the unit dose of the invention as described herein and a HPV vaccine, in particular a 9vHPV vaccine, such as GARDASIL® 9, in the same formulation. In certain embodiments, the invention is directed to a kit comprising such a combined dengue/HPV vaccine and a unit dose of the invention as described herein.

In certain embodiments, the kit may further comprise a MMR vaccine, such as M-M-R® II. In some embodiments, the MMR vaccine may be in a separate container, such as a vial. In another embodiment, the MMR vaccine and the unit dose of the invention may be in the same container. Thus, the invention is directed in part to a combined dengue/MMR vaccine, wherein the unit dose of the invention as described herein is combined with a MMR vaccine. Such a combined dengue/MMR vaccine comprises the unit dose of the invention as described herein and a MMR vaccine, such as M-M-R® II, in the same formulation. In certain embodiments, the invention is directed to a kit comprising such a combined dengue/MMR vaccine and a unit dose of the invention as described herein.

In certain embodiments, the kit may further comprise a Tdap vaccine, in particular a combined tetanus toxoid, reduced diphtheria toxoid and acellular pertussis (adsorbed) vaccine, such as BOOSTRIX®. In some embodiments, the Tdap vaccine may be in a separate container, such as a vial. In another embodiment, the Tdap vaccine and the unit dose of the invention may be in the same container. Thus, the invention is directed in part to a combined dengue/Tdap vaccine, wherein the unit dose of the invention as described herein is combined with a Tdap vaccine. Such a combined dengue/Tdap vaccine comprises the unit dose of the invention as described herein and a Tdap vaccine, in particular a combined tetanus toxoid, reduced diphtheria toxoid and acellular pertussis (adsorbed) vaccine, such as BOOSTRIX®, in the same formulation. In certain embodiments, the invention is directed to a kit comprising such a combined dengue/Tdap vaccine and a unit dose of the invention as described herein.

In certain embodiments, the kit may further comprise a DTaP/IPV/Hib vaccine, in particular a combined DTaP/IPV/Hib vaccine, such as Pentacel®. In some embodiments, the DTaP/IPV/Hib vaccine may be in a separate container, such as a vial. In another embodiment, the DTaP/IPV/Hib vaccine and the unit dose of the invention may be in the same container. Thus, the invention is directed in part to a combined dengue/DTaP/IPV/Hib vaccine, wherein the unit dose of the invention as described herein is combined with a DTaP/IPV/Hib vaccine. Such a combined dengue/DTaP/IPV/Hib vaccine comprises the unit dose of the invention as described herein and a DTaP/IPV/Hib vaccine, in particular a combined DTaP/IPV/Hib vaccine, such as Pentacel®, in the same formulation. In certain embodiments, the invention is directed to a kit comprising such a combined dengue/DTaP/IPV/Hib vaccine and a unit dose of the invention as described herein.

Yellow Fever Vaccine

YF-VAX®, a yellow fever vaccine from Sanofi, for subcutaneous use, is prepared by culturing the YF-17D strain of yellow fever virus in living avian leukosis virus-free (ALV-free) chicken embryos. The vaccine contains sorbitol and gelatin as a stabilizer and is lyophilized. No preservative is added. YF-VAX is formulated to contain not less than 4.74 $\log_{10}$ pfu per 0.5 mL dose throughout the life of the product.

Hepatitis a Vaccine

HAVRIX®, a hepatitis A vaccine from GlaxoSmithKline, is a sterile suspension of inactivated virus for intramuscular administration. The virus (strain HM175) is propagated in MRC-5 human diploid cells. After removal of the cell culture medium, the cells are lysed to form a suspension. This suspension is purified through ultrafiltration and gel permeation chromatography procedures. Treatment of this lysate with formalin ensures viral inactivation. Viral antigen activity is referenced to a standard using an enzyme linked immunosorbent assay (ELISA), and is therefore expressed in terms of ELISA Units (EL.U.). Each 1-mL dose for adults (≥18 years of age) of vaccine contains 1440 EL.U. of viral antigen, adsorbed on 0.5 mg of aluminum as aluminum hydroxide. Each 0.5-mL dose for children and adolescents (12 months through 18 years of age) of vaccine contains 720 EL.U. of viral antigen, adsorbed onto 0.25 mg of aluminum as aluminum hydroxide. HAVRIX® contains the following excipients: Amino acid supplement (0.3% w/v) in a phosphate-buffered saline solution and polysorbate 20 (0.05 mg/mL). From the manufacturing process, HAVRIX® also contains residual MRC-5 cellular proteins (not more than 5 µg/mL), formalin (not more than 0.1 mg/mL), and neomycin sulfate (not more than 40 ng/mL), an aminoglycoside antibiotic included in the cell growth media. HAVRIX® is formulated without preservatives.

VAQTA®, a hepatitis A vaccine from Merck Sharp & Dohme Corp., is an inactivated whole virus vaccine derived from hepatitis A virus grown in cell culture in human MRC-5 diploid fibroblasts. It contains inactivated virus of a strain, which was originally derived by further serial passage of a proven attenuated strain. The virus is grown, harvested, purified by a combination of physical and high performance liquid chromatographic techniques developed at the Merck Research Laboratories, formalin inactivated, and then adsorbed onto amorphous aluminum hydroxyphosphate sulfate. VAQTA® is a sterile suspension for intramuscular injection. One milliliter of the vaccine contains approximately 50 U of hepatitis A virus antigen, which is purified and formulated without a preservative. Within the limits of current assay variability, the 50 U dose of VAQTA® contains less than 0.1 µg of non-viral protein, less than $4\times10^{-}$µg of DNA, less than $10^{-}$µg of bovine albumin, and less than 0.8 µg of formaldehyde. Other process chemical residuals are less than 10 parts per billion (ppb), including neomycin. Each 0.5-mL pediatric dose contains 25 U of hepatitis A virus antigen and adsorbed onto approximately 0.225 mg of aluminum provided as amorphous aluminum hydroxyphosphate sulfate, and 35 µg of sodium borate as a pH stabilizer, in 0.9% sodium chloride. Each 1-mL adult dose contains 50 U of hepatitis A virus antigen and adsorbed onto approximately 0.45 mg of aluminum provided as amorphous aluminum hydroxyphosphate sulfate, and 70 µg of sodium borate as a pH stabilizer, in 0.9% sodium chloride.

HPV Vaccine

GARDASIL® 9, a HPV vaccine from Merck, is a non-infectious recombinant 9-valent vaccine prepared from the purified virus-like particles (VLPs) of the major capsid (L1) protein of HPV serotypes 6, 11, 16, 18, 31, 33, 45, 52, and 58. The L1 proteins are produced by separate fermentations using recombinant *Saccharomyces cerevisiae* and self-assembled into VLPs. The fermentation process involves growth of *S. cerevisiae* on chemically-defined fermentation media which include vitamins, amino acids, mineral salts, and carbohydrates. The VLPs are released from the yeast cells by cell disruption and purified by a series of chemical and physical methods. The purified VLPs are adsorbed on preformed aluminum-containing adjuvant (amorphous aluminum hydroxyphosphate sulfate or AAHS). The 9-valent HPV VLP vaccine is a sterile liquid suspension that is prepared by combining the adsorbed VLPs of each HPV serotype and additional amounts of the aluminum-containing adjuvant and the final purification buffer. GARDASIL 9 is a sterile suspension for intramuscular administration. Each 0.5-mL dose contains approximately 30 µg of HPV serotype 6 L1 protein, 40 µg of HPV serotype 11 L1 protein, 60 µg of HPV serotype 16 L1 protein, 40 µg of HPV serotype 18 L1 protein, 20 µg of HPV serotype 31 L1 protein, 20 µg of HPV serotype 33 L1 protein, 20 µg of HPV serotype 45 L1 protein, 20 µg of HPV serotype 52 L1 protein, and 20 µg of HPV serotype 58 L1 protein. Each 0.5-mL dose of the vaccine also contains approximately 500 µg of aluminum (provided as AAHS), 9.56 mg of sodium chloride, 0.78 mg of L-histidine, 50 µg of polysorbate 80, 35 µg of sodium borate.

MMR Vaccine

Several MMR vaccines are known in the prior art and include M-M-R® II, Priorix®, Tresivac®, and Trimovax®.

M-M-R® II, a MMR vaccine from Merck Sharp & Dohme Corp., is a live virus vaccine for vaccination against measles, mumps and rubella. M-M-R® II is a sterile lyophilized preparation of (1) ATTENUVAX® (measles virus vaccine live), a more attenuated line of measles virus, derived from Enders' attenuated Edmonston strain and propagated in chick embryo cell culture, (2) MUMPSVAX® (mumps virus vaccine live), the Jeryl Lynn™ (B level) strain of mumps virus propagated in chick embryo cell culture, and (3) MERUVAX® II (rubella virus vaccine live), the Wistar RA 27/3 strain of live attenuated rubella virus propagated in WI-38 human diploid lung fibroblasts. The growth medium for measles and mumps is Medium 199 (a buffered salt solution containing vitamins and amino acids and supplemented with fetal bovine serum) containing SPGA (sucrose, phosphate, glutamate, and recombinant human albumin) as stabilizer and neomycin. The growth medium for rubella is Minimum Essential Medium (MEM) (a buffered salt solution containing vitamins and amino acids and supplemented with fetal bovine serum) containing recombinant human albumin and neomycin. Sorbitol and hydrolyzed gelatin stabilizer are added to the individual virus harvests. The cells, virus pools, and fetal bovine serum are all screened for the absence of adventitious agents. The reconstituted vaccine is for subcutaneous administration. Each 0.5 mL dose contains not less than 1,000 $TCID_{50}$ (tissue culture infectious doses) of measles virus, 12,500 $TCID_{50}$ of mumps virus, and 1,000 $TCID_{50}$ of rubella virus. Each dose of the vaccine is calculated to contain sorbitol (14.5 mg), sodium phosphate, sucrose (1.9 mg), sodium chloride, hydrolyzed gelatin (14.5 mg), recombinant human albumin (50.3 mg), fetal bovine serum (<1 ppm), other buffer and media ingredients and approximately 25 μg of neomycin. The product contains no preservative. The lyophilized vaccine is reconstituted before administration.

Combined Tetanus, Diphtheria, and Oertussis (Tdap) Vaccine

BOOSTRIX®, a combined tetanus toxoid, reduced diphtheria toxoid and acellular pertussis (adsorbed) (Tdap) vaccine, is a non-infectious, sterile vaccine for intramuscular administration. It contains tetanus toxoid, diphtheria toxoid, and pertussis antigens (inactivated pertussis toxin (iPT) and formaldehyde-treated filamentous hemagglutinin (FHA) and pertactin (PRN)). The antigens are the same as those in INFANRIX®, but BOOSTRIX® is formulated with reduced quantities of these antigens.

BOOSTRIX® is supplied as a 0.5 mL suspension for injection. Each 0.5 mL dose of BOOSTRIX® is formulated to contain 5 Limits of flocculation (Lf) of tetanus toxoid, 2.5 Lf of diphtheria toxoid, 8 μg of iPT, 8 μg of formaldehyde treated FHA, and 2.5 μg of PRN (69 kiloDalton outer membrane protein), aluminum hydroxide as adjuvant (not more than 0.39 mg aluminum by assay), 4.5 mg of sodium chloride, ≤100 μg of residual formaldehyde, and ≤100 μg of polysorbate 80 (Tween 80).

Tetanus toxin is produced by growing *Clostridium tetani* in a modified Latham medium derived from bovine casein. The diphtheria toxin is produced by growing *Corynebacterium diphtheriae* in Fenton medium containing a bovine extract. Both toxins are detoxified with formaldehyde, concentrated by ultrafiltration, and purified by precipitation, dialysis, and sterile filtration. Tetanus and diphtheria toxoid potency is determined by measuring the amount of neutralizing antitoxin in previously immunized guinea pigs.

The acellular pertussis antigens (iPT, FHA, and PRN) are isolated from *Bordetella pertussis* culture grown in modified Stainer-Scholte liquid medium. iPT and FHA are isolated from the fermentation broth, PRN is extracted from the cells by heat treatment and flocculation. The antigens are purified in successive chromatographic and precipitation steps. iPT is detoxified using glutaraldehyde and formaldehyde. FHA and PRN are treated with formaldehyde. Each antigen is individually adsorbed onto aluminum hydroxide. The potency of the acellular pertussis components (inactivated iPT and formaldehyde-treated FHA and PRN) is determined by enzyme-linked immunosorbent assay (ELISA) on sera from previously immunized mice.

Combined Diphtheria, Tetanus, Pertussis, Poliomyelitis and *Haemophilus influenzae* Type b (DTaP/IPV/Hib) Vaccine Pentacel®, a combined DTaP/IPV/Hib vaccine, consists of a diphtheria and tetanus toxoids and acellular pertussis adsorbed and inactivated poliovirus (DTaP-IPV) component and an ActHIB® component combined through reconstitution for intramuscular injection. ActHIB® (*Haemophilus* b Conjugate Vaccine (Tetanus Toxoid Conjugate)), consists of *Haemophilius influenzae* type b capsular polysaccharide (polyribosyl-ribitol-phosphate (PRP)) covalently bound to tetanus toxoid (PRP-T). The DTaP-IPV component is supplied as a sterile liquid used to reconstitute the lyophilized ActHIB® component to form Pentacel®.

Each 0.5 mL dose contains 15 Limits of flocculation (Lf) diphtheria toxoid, 5 Lf tetanus toxoid, acellular pertussis antigens (20 μg detoxified pertussis toxin (PT), 20 μg filamentous hemagglutinin (FHA), 3 μg pertactin (PRN), 5 μg fimbriae types 2 and 3 (FIM)), inactivated polioviruses (40 D-antigen units (DU) Type 1 (Mahoney), 8 DU Type 2 (MEF-1), 32 DU Type 3 (Saukett)) and 10 μg PRP of *Haemophilius influenzae* type b covalently bound to 24 μg of tetanus toxoid (PRP-T).

Other ingredients per 0.5 mL dose include 1.5 mg aluminum phosphate (0.33 mg aluminum) as the adjuvant, polysorbate 80 (approximately 10 ppm by calculation), 42.5 mg sucrose, ≤5 μg residual formaldehyde, <50 ng residual glutaraldehyde, 550 ng residual bovine serum albumin, 3.3 mg (0.6% v/v) 2-phenoxyethanol (not as a preservative), <4 μg of neomycin and <4 μg polymyxin B sulfate.

*Corynebacterium diphtheriae* is grown in modified Mueller's growth medium. After purification by ammonium sulfate fractionation, the diphtheria toxin is detoxified with formaldehyde and diafiltered.

*Clostridium tetani* is grown in modified Mueller-Miller casamino acid medium without beef heart infusion. Tetanus toxin is detoxified with formaldehyde and purified by ammonium sulfate fractionation and diafiltration. Diphtheria and tetanus toxoids are individually adsorbed onto aluminum phosphate.

The acellular pertussis vaccine antigens are produced from *Bordetella pertussis* cultures grown in Stainer-Scholte medium modified by the addition of casamino acids and dimethyl-beta-cyclodextrin. PT, FHA and PRN are isolated separately from the supernatant culture medium. FIM are extracted and co-purified from the bacterial cells. The pertussis antigens are purified by sequential filtration, salt-precipitation, ultrafiltration and chromatography. PT is detoxified with glutaraldehyde. FHA is treated with formaldehyde and the residual aldehydes are removed by ultrafiltration. The individual antigens are adsorbed separately onto aluminum phosphate.

Poliovirus Type 1, Type 2 and Type 3 are each grown in separate cultures of MRC-5 cells, a line of normal human diploid cells, by the microcarrier method. The cells are grown in CMRL (Connaught Medical Research Laboratories) 1969 medium, supplemented with calf serum. For viral growth, the culture medium is replaced by Medium 199, without calf serum. After clarification and filtration, the viral suspensions are concentrated by ultrafiltration, and purified by liquid chromatography steps. The monovalent viral suspensions are inactivated with formaldehyde. Monovalent concentrates of each inactivated poliovirus are combined to produce a trivalent poliovirus concentrate.

The adsorbed diphtheria, tetanus and acellular pertussis antigens are combined with aluminum phosphate (as adjuvant), 2-phenoxyethanol (not as a preservative) and water for injection, into an intermediate concentrate. The trivalent poliovirus concentrate is added and the DTaP-IPV component is diluted to its final concentration. The DTaP-IPV component does not contain a preservative.

Both diphtheria and tetanus toxoids induce at least 2 neutralizing units per mL in the guinea pig potency test. The potency of the acellular pertussis antigens is evaluated by the antibody response of immunized mice to detoxified PT, FHA, PRN and FIM as measured by enzyme-linked immunosorbent assay (ELISA). The potency of inactivated poliovirus antigens is determined by measuring antibody-mediated neutralization of poliovirus in sera from immunized rats.

PRP, a high molecular weight polymer, is prepared from the *Haemophilus influenzae* type b strain 1482 grown in a semi-synthetic medium. The tetanus toxoid for conjugation to PRP is prepared by ammonium sulfate purification, and formalin inactivation of the toxin from cultures of *Clostridium tetani* (Harvard strain) grown in a modified Mueller and Miller medium. The toxoid is filter sterilized prior to the conjugation process. The ActHIB® component does not contain a preservative. Potency of the ActHIB® component is specified on each lot by limits on the content of PRP polysaccharide and protein per dose and the proportion of polysaccharide and protein that is characterized as high molecular weight conjugate.

Method of Preventing and Uses, Method of Inoculating and Uses

Method of Preventing, Method of Inoculating

The present invention is directed in part to a method of preventing dengue disease (in particular virologically confirmable dengue, VCD) in a subject. Thus, in certain embodiments the invention is directed to a method of preventing dengue disease in a subject, comprising administering to the subject, a unit dose/tetravalent dengue virus composition, in particular a reconstituted unit dose of the invention as described herein.

The present invention is directed in part to a method of preventing dengue hemorrhagic fever (DHF) and dengue shock syndrome (DSS). Thus, in certain embodiments the invention is directed to a method of preventing dengue hemorrhagic fever (DHF) and dengue shock syndrome (DSS), comprising administering to the subject a reconstituted unit dose/tetravalent dengue virus composition of the invention as described herein.

The present invention is therefore directed to a method of inoculating a subject against virologically confirmable dengue disease with a tetravalent dengue virus composition including four live attenuated dengue virus strains representing serotype 1, serotype 2, serotype 3 and serotype 4, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (SEQ ID NO 11) and differs in at least three nucleotides from the wild type as follows:

a) 5'-noncoding region (NCR)-57 (nt-57 C-to-T): major attenuation locus b) NS1-53 Gly-to-Asp (nt-2579 G-to-A): major attenuation locus c) NS3-250 Glu-to-Val (nt-5270 A-to-T): major attenuation locus; and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera,
a DENV-2/3 chimera and
a DENV-2/4 chimera.

Further information regarding the serotypes of the tetravalent composition can be derived from section "Dengue virus strains" above.

The tetravalent dengue virus composition for such a method may be in the form of a unit dose comprising:

(i) a dengue serotype 1 in a concentration of at least 3.3 log 10 pfu/0.5 ml,
(ii) a dengue serotype 2, in a concentration of at least 2.7 log 10 pfu/0.5 ml,
(iii) a dengue serotype 3, in a concentration of at least 4.0 log 10 pfu/0.5 ml, and
(iv) a dengue serotype 4, in a concentration of at least 4.5 log 10 pfu/0.5 ml.

The present invention is in particular directed to such a method wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml,
(ii) a dengue serotype 2, in a concentration of at least 2.7 log 10 pfu/0.5 ml,
(iii) a dengue serotype 3, in a concentration of at least 4.0 log 10 pfu/0.5 ml, and
(iv) a dengue serotype 4, in a concentration of at least 4.5 log 10 pfu/0.5 ml.

The present invention is also in particular directed to such a method wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, and wherein preferably the subject is 2 to 17 years of age or 4 to 16 years of age.

The present invention is also in particular directed to such a method wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6%, wherein preferably the subject is 18 to 60 years of age.

Further information regarding the tetravalent composition or the unit dose can be derived from section "Dengue vaccine composition" and "Unit dose" above.

The present invention is therefore directed to a method and corresponding use, the method comprising a primary vaccination with only two administrations of the unit dose comprising the steps of:

(A) administering a first unit dose of the tetravalent dengue virus composition to the subject, and
(B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail below in this the section.

In certain embodiments the unit dose is reconstituted and administered by subcutaneous injection. According to some of these embodiments, the subcutaneous injection is administered to the arm, preferably to the deltoid region of the arm.

According to one embodiment such a method does not include a step of determination whether there was a previous dengue infection in the subject before administration of the unit dose or wherein the serostatus of the subject is unknown before administration of the unit dose.

According to one embodiment such a method does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above the method according to one embodiment comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

In particular the present invention is directed to such a method wherein the method which is safe.

In particular the present invention is directed to such a method providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

In particular the present invention is directed to such a method wherein the method which is effective. In particular the present invention is directed to such a method providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the last administration of the administration schedule.

In certain embodiments, the invention is directed to said methods, wherein the subject is seronegative to all dengue serotypes.

The present invention is directed in part to a method of preventing dengue disease (in particular virologically confirmable dengue, VCD) in a subject population. Thus, in certain embodiments the invention is directed to a method of preventing dengue disease in a subject population, comprising administering to the subject population a unit dose, in particular a reconstituted unit dose of the invention as described herein.

The present invention is in part directed to said method for preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2. Without wishing to be bound to any theory, it is presently understood that a method inducing a more balanced immune response due to the administration of the reconstituted unit dose of the invention as described herein, in terms of less differences between the geometric mean neutralizing antibody titers (GMTs) against the four dengue serotypes or the neutralizing antibody titers against the four dengue serotypes, is beneficial to the subject or subject population to be vaccinated. In particular, it is understood that a much greater response to any one of the four serotypes, such as to DENV-2 in comparison to the other serotypes, is less beneficial.

The present invention is in part directed to said method for preventing dengue disease (in particular virologically confirmable dengue, VCD) in a subject or subject population wherein the method provides a seropositivity rate in a subject population of at least 50 subjects including the administration of two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85%, or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

The present invention is in part directed to said method for preventing dengue disease (in particular virologically confirmable dengue, VCD) in a subject or subject population wherein the method provides a seropositivity rate in a subject population of at least 100 subjects including administration of two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to a method of preventing virologically confirmable dengue disease in a subject or subject population comprising administering to the subject or subject population a reconstituted unit dose of a tetravalent dengue virus composition including four live, attenuated dengue serotypes, in particular the virus strains as described herein.

The present invention is in part directed to a method of preventing virologically confirmable dengue disease with hospitalization in a subject or subject population comprising administering to the subject or subject population a reconstituted unit dose of a tetravalent dengue virus composition including four live, attenuated dengue serotypes, in particular the virus strains as described herein.

In certain embodiments, the method includes a reconstituted unit dose/tetravalent dengue virus composition of a dengue vaccine composition administered for preventing dengue disease in a subject or a subject population, the reconstituted unit dose comprising: a tetravalent virus composition including four live attenuated dengue virus strains, wherein a unit dose is lyophilized and upon reconstitution with 0.5 mL of a pharmaceutically acceptable diluent the reconstituted unit dose is obtained which comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the reconstituted unit dose/tetravalent dengue virus composition is used in the method of preventing dengue disease of the present invention, wherein upon reconstitution of the unit dose with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the reconstituted unit dose/tetravalent dengue virus composition is used in the method of preventing dengue disease of the present invention, wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

In certain embodiments, the invention is directed to said methods, wherein said unit dose comprises a tetravalent dengue virus composition including four live attenuated dengue serotypes, in particular the virus strains described herein wherein the serotypes have certain concentrations as described herein with respect to the virus composition and unit dose such as:

(i) a dengue serotype 1 (e.g. chimeric dengue serotype 2/1 strain) has a concentration of 3.3 log 10 pfu/dose to 5.0 log 10 pfu/dose, or 3.3 log 10 pfu/0.5 mL to 5.0 log 10 pfu/0.5 mL (ii) a dengue serotype 2 (e.g. dengue serotype 2 strain) has a concentration of 2.7 log 10 pfu/dose to 4.9 log 10 pfu/0.5 dose, or 2.7 log 10 pfu/0.5 ml to 4.9 log 10 pfu/0.5 ml (iii) a dengue serotype 3 (e.g. chimeric dengue serotype 2/3 strain) has a concentration of 4.0 log 10 pfu/dose to 5.7 log 10 pfu/0.5 dose, or 4.0 log 10 pfu/0.5 mL to 5.7 log 10 pfu/0.5 mL and (iv) a dengue serotype 4 (e.g. chimeric dengue serotype 2/4 strain) has a concentration of 4.5 log 10 pfu/dose to 5.5 log 10 pfu/0.5 dose, or 4.5 log 10 pfu/0.5 mL to 5.5 log 10 pfu/0.5 mL. In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein said unit dose upon reconstitution with 0.5 mL of a pharmaceutically acceptable diluent has a concentration of 3.3 log 10 pfu/0.5 mL to 3.6 log 10 pfu/0.5 mL for dengue serotype 1 (e.g. chimeric dengue serotype 2/1 strain), has a concentration of 2.7 log 10 pfu/0.5 mL to 4.0 log 10 pfu/0.5 mL for dengue serotype 2 (e.g. dengue serotype 2 strain), has a concentration of 4.0 log 10 pfu/0.5 mL to 4.6 log 10 pfu/0.5 mL for dengue serotype 3 (e.g. chimeric dengue serotype 2/3 strain) and has a concentration of 4.5 log 10 pfu/0.5 mL or 4.6 log 10 pfu/0.5 mL to 5.1 log 10 pfu/0.5 mL for dengue serotype 4 (e.g. chimeric dengue serotype 2/4 strain). In preferred such embodiments, the subject or subject population is of 2 to 17 years of age, such as 4 to 16 years of age, and preferably less than 9 years of age. In other preferred embodiments, the subject or subject population is 4-5 years of age, 6-11 years of age or 12-16 years of age.

In certain embodiments, the invention is directed to said methods, wherein the concentration of the dengue serotype 1 (e.g. chimeric dengue serotype 2/1 strain) measured in pfu/0.5 mL is 1% to 7% of the total concentration, the concentration of the dengue serotype 2 (e.g. dengue serotype 2 strain) measured in pfu/0.5 mL is less than 8% of the total concentration, such as in the range of 1% to 8% of the total concentration, the concentration of the dengue serotype 3 (e.g. chimeric dengue serotype 2/3 strain) measured in pfu/0.5 mL is at least 10% of the total concentration, and the concentration of the dengue serotype 4 (e.g. chimeric dengue serotype 2/4 strain) measured in pfu/0.5 mL is at least 65% of the total concentration, such as in the range of 65% to 80%. In certain such embodiments, the arithmetic sum of all four serotypes is in the range of 4.6 log 10 pfu/0.5 mL to 6.7 log 10 pfu/0.5 mL, preferably in the range of 4.6 log 10 pfu/0.5 mL to 5.5 log 10 pfu/0.5 mL Preferably, in said embodiments the subject or subject population is of 2 to 17 years of age, such as 4 to 16 years of age, and even more preferably less than 9 years of age. In other preferred embodiments, the subject or subject population is 4-5 years of age, 6-11 years of age or 12-16 years of age.

In a further preferred embodiment, the invention is directed to said methods, wherein the dengue serotype 1 (e.g. chimeric dengue serotype 2/1 strain) such as TDV-1 and the dengue serotype 2 (e.g. dengue serotype 2 strain) such as TDV-2 are present each in a concentration based on the total concentration in pfu/0.5 mL which is within 5%-points of each other and/or are together less than about 10% of the total concentration in pfu/0.5 mL. In certain such embodiments the dengue serotype 3 (e.g. chimeric dengue serotype 2/3 strain) such as TDV-3 is preferably at least about 10% of the total concentration in pfu/0.5 mL and more preferably the dengue serotype 4 (e.g. chimeric dengue serotype 2/4 strain) such as TDV-4 is at least about 70% of the total concentration in pfu/0.5 mL. In certain such embodiments the dengue serotype 4 (e.g. chimeric dengue serotype 2/4 strain) such as TDV-4 represents the highest concentration in the composition of all four serotypes, preferably with at least about 70% of the total concentration in pfu/0.5 mL, dengue serotype 3 (e.g. chimeric dengue serotype 2/3 strain) such as TDV-3 represents the second highest concentration in the composition of all four serotypes, preferably with at least about 10% of the total concentration in pfu/0.5 mL, and dengue serotype 1 (e.g. chimeric dengue serotype 2/1 strain) such as TDV-1 and dengue serotype 2 (e.g. dengue serotype 2 strain) such as TDV-2 each represent lower concentrations than the concentration of serotype 3 (e.g. chimeric dengue serotype 2/3 strain) such as TDV-3, and optionally together represent less than about 10% of the total concentration in pfu/0.5 mL.

Preferably, the chimeric dengue serotype 2/1 strain is TDV-1, the dengue serotype 2 strain is TDV-2, the chimeric dengue serotype 2/3 strain is TDV-3 and the chimeric dengue serotype 2/4 strain is TDV-4. More preferably, TDV-1 is characterized by the nucleotide sequence according to SEQ ID No. 1 and the amino acid sequence according to SEQ ID No. 2, TDV-2 is characterized by the nucleotide sequence according to SEQ ID No. 3 and the amino acid sequence according to SEQ ID No. 4, TDV-3 is characterized by the nucleotide sequence according to SEQ ID No. 5 and the amino acid sequence according to SEQ ID No. 6 and TDV-4 is characterized by the nucleotide sequence according to SEQ ID No. 7 and the amino acid sequence according to SEQ ID No. 8.

In certain embodiments, the invention is directed to said methods, wherein the reconstituted unit dose of the invention as described herein is administered by subcutaneous injection. According to some of these embodiments, the subcutaneous injection is administered to the arm, preferably to the deltoid region of the arm.

In certain embodiments, the invention is directed to said methods, wherein the reconstituted unit dose is administered to a subject of unknown serostatus and/or wherein no test has been carried out to determine whether the subject is seropositive or seronegative (before) the unit dose as described herein is administered. In certain embodiments, the invention is directed to said methods which do not include a step of determination of a previous dengue infection in the subject or subjects. In certain embodiments, the invention is directed to said methods which do not include the analysis of the seroprevalence rate in the region or is conducted in a region with a seroprevalence of below 80%, below 70% or below 60%. In certain embodiments the invention is directed to a method wherein the serostatus of the subject is unknown. In such embodiments the serostatus is not determined at any time before and after administration in relation to this method. In certain embodiments of the invention the method is used in an outbreak situation. In certain embodiments, the invention is directed to said methods being conducted outside a clinical trial In certain embodiments, the invention is directed to said methods, wherein the subject, or subject population is seronegative to all dengue serotypes.

In certain embodiments, the invention is directed to said methods, wherein two unit doses of the invention as described herein are administered. In some embodiments the two unit doses are administered within 12 months or more, or within six months, or within three months, and optionally at least 4 weeks apart such as at day 0 and day 90 or at day 1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the method of the invention comprises or consists of a single unit dose of the invention being administered.

In certain embodiments, the invention is directed to said methods, wherein the reconstituted unit dose of the invention as described herein is administered subcutaneously to a subject or subject population that is seronegative with respect to all dengue serotypes. In other embodiments, the subject or subject population is seropositive with respect to at least one dengue serotype.

In certain embodiments, the invention is directed to said methods, wherein the unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In a preferred embodiment, the subject or subject population is from Asia Pacific or from Latin America. In some other of these embodiments, the subject or subject population is from Thailand, Sri Lanka, Philippines, Panama, Nicaragua, Dominican Republic, Colombia or Brazil. In other embodiments, the subject, or subject population is from a dengue non-endemic region. Such a subject population or such a subject may be vaccinated according to the present invention in the context of traveling to a dengue endemic region. In certain embodiments, the reconstituted unit dose of the invention as described herein is administered subcutaneously to a subject, or subject population that is from a dengue endemic region or a dengue non-endemic region.

In certain embodiments, the invention is directed to said methods, wherein the reconstituted unit dose of the invention as described herein is administered subcutaneously to a subject or subject population of 2 to 60 years of age. In some embodiments, the subjects or subject population are adults of more than 17 years, or more than 18 years, or 18 to 60 years. In further specific embodiments, the subjects or subject population are adults of more than 21 years, or 21 to 60 years, or 21 to 45 years of age.

In certain embodiments, the invention is directed to said methods, wherein the reconstituted unit dose of the invention as described herein is administered subcutaneously to children and adolescents of 2 to 17 years of age. In some embodiments, the subjects or subject population are less than 9 years of age, or less than 4 years of age. In some embodiments, the subjects or subject population are from 2 to 9 years of age, or from 2 to 5 years of age, or from 4 to 9 years of age or from 6 to 9 years of age. In other embodiment, the subject or subject population is 4 to 16 years of age. In some such embodiments, the subject or subject population is 4-5 years of age, 6-11 years of age or 12-16 years of age. Optionally, the subject or subject population is seronegative with respect to all dengue serotypes.

In certain embodiments, the invention is directed to said methods, wherein the unit dose of the invention as described herein is administered to a pediatric subject or pediatric subject population of less than 2 years of age, preferably of 2 months to 2 years or 2 months to 1.5 years or 2 months to 1 year. According to some of these embodiments, the pediatric subject or pediatric subject population is seronegative and from a dengue endemic region.

In certain embodiments, the invention is directed to said methods, wherein the reconstituted unit dose of the invention as described herein is administered to a pediatric subject or pediatric subject population of less than 2 years of age, preferably of 2 months to 2 years or 2 months to 1.5 years or 2 months to 1 year, preferably by subcutaneous injection. According to some of these embodiments, the pediatric subject or pediatric subject population is seronegative and from a dengue endemic region.

In a certain embodiments, the invention is directed to said methods, wherein the subject or subject population is 4-5 years of age and from Asia Pacific, 6-11 years of age and from Asia Pacific, or 12-16 years of age and from Asia Pacific. In other embodiments, the subject or subject population is 4-5 years of age and from Latin America, 6-11 years of age and from Latin America, or 12-16 years of age and from Latin America.

In a certain embodiments, the invention is directed to said methods, wherein the subject or subject population is 4-5 years of age and seropositive for at least 1 dengue serotype, 6-11 years of age and seropositive for at least 1 dengue serotype, or 12-16 years of age and seropositive for at least 1 dengue serotype. In other embodiments, the subject or subject population is 4-5 years of age and seronegative for all dengue serotypes, 6-11 years of age and seronegative for all dengue serotypes, or 12-16 years of age and seronegative for all dengue serotypes.

In a certain embodiments, the invention is directed to said methods, wherein the subject or subject population is from Asia Pacific or Latin America and seropositive for at least one dengue serotype at baseline. In other embodiments, the subject or subject population is from Asia Pacific or Latin America and seronegative for at all dengue serotype at baseline.

In certain embodiments, the invention is directed to said methods, wherein the subject or subject population is from Asia Pacific, seropositive for at least one dengue serotype at baseline and 4-5 years of age, 6-11 years of age, or 12-16 years of age. In other embodiments, the subject or subject population is from Asia Pacific, seronegative for all dengue serotypes at baseline and 4-5 years of age, 6-11 years of age, or 12-16 years of age. In yet other embodiments, the subject or subject population is from Latin America, seropositive for at least one dengue serotype at baseline and 4-5 years of age, 6-11 years of age, or 12-16 years of age. In other embodiments, the subject or subject population is from America, seronegative for all dengue serotypes at baseline and 4-5 years of age, 6-11 years of age, or 12-16 years of age.

In certain embodiments, the invention is directed to said methods, wherein the subject or subject population had prior vaccination against Yellow Fever. In other embodiments, the subject or subject population had prior vaccination against Japanese Encephalitis. In yet other embodiments, the subject or subject population had no prior vaccination against Yellow Fever. In other embodiments, the subject or subject population had no prior vaccination against Japanese Encephalitis. Prior vaccination indicates a vaccination prior to 30 days after a second administration, such as within 4 months after the first administration, with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination. In certain embodiments, the subject or subject population received Dengvaxia® within the administration regimen as described herein or within 4.5 years after administration of the first dose.

Particularly unbalanced titers of neutralizing antibodies against the four dengue serotypes are observed in seronegative populations or subjects after administration of the commercially available dengue vaccine. The present invention shows that in particular seronegative subjects show a more balanced immune response to the four dengue serotypes after administration of the reconstituted unit dose of the invention as described herein. It is therefore contemplated that the unit dose of the invention as described herein and methods of the present invention as described herein may provide a more robust immune response in a subject population including both seropositive and seronegative subjects. This balanced response and balanced efficacy and safety is required to allow inoculation without prior serostatus analysis which is a major advantage in vaccination programs and in particular in outbreak situations.

The present invention is directed in part to a method of preventing virologically confirmable dengue disease in a subject comprising administering to the subject a tetravalent dengue virus composition including four dengue virus strains representing serotype 1, serotype 2, serotype 3 and serotype 4, wherein the virus strains are optionally live, attenuated dengue virus strains.

The present invention is directed in part to a method of preventing virologically confirmable dengue disease in a subject consisting of administering to the subject a tetravalent dengue virus composition including four dengue virus strains representing serotype 1, serotype 2, serotype 3 and serotype 4, wherein the virus strains are optionally live, attenuated dengue virus strains.

In certain embodiments, the invention is directed to said methods, wherein there is no step of determining the serostatus of the subject at baseline, in other words, said methods do not comprise a determination of a previous dengue infection of the subject at baseline before the administration of the tetravalent dengue virus composition. In particular, such methods are safe and effective. Thus, in certain such embodiments, the subject has not been tested for the presence a previous dengue infection.

In certain embodiments, the invention is directed to said methods, wherein the vaccine administration is safe irrespective of whether there is a determination that the subject had a previous dengue infection before the administration of the tetravalent dengue virus composition. In particular, such methods are also effective.

In certain embodiments, the invention is directed to said methods, wherein the method is safe and/or effective.

In certain embodiments, the invention is directed to said methods, wherein the composition includes at least one chimeric dengue virus. In certain such embodiments, the invention is directed to said methods, wherein the composition includes at least one non-chimeric dengue virus and at least one chimeric dengue virus, in particular a chimeric dengue serotype 2/1 strain and a dengue serotype 2 strain and a chimeric dengue serotype 2/3 strain and a chimeric dengue serotype 2/4 strain. The details of the composition are described above.

Therefore, in certain embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose/tetravalent dengue virus composition as described herein or placebo is administered e.g. at least twice within less than 6 months, such as within 3 months, after first administration or 30 days after the second/last administration until at least 12 to 18 months (e.g. at 12 or at 18 months) after the second/last administration. In embodiments, the invention is directed to said methods having a vaccine efficacy, preferably a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 to 21 months (e.g. 15 or 21 months) after the first administration of the administration schedule. In certain such embodiments, the lower bound is more than 30%, more than 40%, more than 50%, more than 55%, more than 60%, more than 65%, more than 70% or more than 72%. Preferably said reconstituted unit dose or placebo is administered subcutaneously within about 3 months, such as on days 0 and 90.

Therefore, in certain embodiments, the invention is directed to said methods having a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the lower bound is e.g. more than 62%, more than 64%, more than 66%, more than 68%, or more than 69%.

In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline and e.g. 14 to 16 years of age, wherein a reconstituted unit dose or tetravalent dengue virus composition as described herein or placebo is administered at least twice within less than 6 months, such as within 3 months, after first administration or 30 days after the second administration/last administration until at least 12 months or until 12 to 18 months (e.g. at 12 or at 18 months) after the second administration/last administration. In certain embodiments, the invention is directed to said methods having a vaccine efficacy, preferably a combined vaccine efficacy against all four serotypes, in preventing virologically confirmable dengue disease of more than 30%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least once, until 15 months after the first administration of the administration schedule. In certain such embodiments, the vaccine efficacy is more than 40%, more than 50%, more than 55%, more than 60%, more than 65%, more than 70%, more than 75%, more than 78%, more than 79% or about 80%. Preferably said reconstituted unit dose or placebo is administered subcutaneously within about 3 month, such as on days 0 and 90.

Therefore, in certain embodiments, the invention is directed to said methods having a combined vaccine efficacy against all four serotypes, in preventing virologically confirmable dengue disease of more than 66%, when measured against placebo in a subject population of at least 5,000 healthy subjects (or at least 10,000, or at least 15,000 healthy subjects) irrespective of serostatus at baseline and 14 to 16 years of age, wherein a reconstituted unit dose/tetravalent dengue virus composition as described herein or placebo is administered e.g. at least twice within less than 6 months, such as within 3 months, after the first administration until 18 months after the last administration. In these embodiments, the vaccine efficacy is e.g. more than 68%, more than 70%, more than 72%, or more than 74%.

In certain embodiments, the invention is directed to said methods having a vaccine efficacy, preferably a combined vaccine efficacy against all four serotypes, in preventing virologically confirmable dengue disease with hospitalization with a 2-sided 95% confidence interval, wherein the lower bound is more than 0%, when measured against placebo in a subject population of at least 5,000 healthy subjects (or at least 10,000, or at least 15,000 healthy subjects) irrespective of serostatus at baseline, wherein a reconstituted unit dose or tetravalent dengue virus composition as described herein or placebo is administered at least twice within less than 6 months, such as within 3 months, 30 days after the second administration until at least 18 months after the second administration. In certain such embodiments, the lower bound is more than 10%, is more than 20%, is more than 30%, is more than 40%, is more than 50%, is more than 55%, is more than 60%, is more than 65%, is more than 70% or is more than 80%, or more than 90%.

In certain embodiments, the invention is directed to said methods having a combined vaccine efficacy against all four dengue serotypes in seronegative subjects with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, or is more than 55%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 30%, is more than 35%, is more than 40%, or is more than 45%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 40%, is more than 45%, is more than 50%, is more than 60%, or is more than 65%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four dengue serotypes in seronegative subjects of more than 30%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes in seronegative subjects is more than 40%, is more than 50%, is more than 60%, is more than 65%, or is more than 70%.

In certain embodiments, the invention is directed to said methods having a combined vaccine efficacy against all four serotypes, in preventing virologically confirmable dengue disease, when measured against placebo in a subject population of at least 1,500 or at least 2,000 or at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 30%, is more than 40%, is more than 50%, is more than 55%, is more than 60%, or is more than 65%.

In certain embodiments, the invention is directed to said methods having a combined vaccine efficacy against all four serotypes, in preventing virologically confirmable dengue disease, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments the said vaccine efficacy is more than 40%, is more than 50%, is more than 60%, is more than 65%, is more than 70%, or is more than 75%.

In certain embodiments, the invention is directed to said methods having a combined vaccine efficacy against all four serotypes, in preventing virologically confirmable dengue disease with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points, or is no more than 10%-points.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 45%.

In certain embodiments, the invention is directed to said methods having a combined vaccine efficacy against all four dengue serotypes of more than 30%, when measured against placebo in a subject population of at least 1,000 healthy subjects 4 to 5 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 65%, or is more than 70%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, or is more than 70%.

In certain embodiments, the invention is directed to said methods having a combined vaccine efficacy against all four dengue serotypes of more than 30%, when measured against placebo in a subject population of at least 1,000 healthy subjects 6 to 11 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a combined vaccine efficacy against all four dengue serotypes with a 2-sided 95% confidence interval, wherein the lower bound is more than 25%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 65%, or is more than 68%.

In certain embodiments, the invention is directed to said methods having a combined vaccine efficacy against all four dengue serotypes of more than 30%, when measured against placebo in a subject population of at least 1,000 healthy subjects 12 to 16 years of age at the time of randomization and irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against all four dengue serotypes is more than 40%, is more than 50%, is more than 60%, is more than 70%, is more than 75%, or is more than 80%.

In certain embodiments, the invention is directed to said methods having a vaccine efficacy against dengue serotype 1 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, or is more than 50%.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against dengue serotype 1 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 1 is more than 40%, is more than 50%, is more than 60%, is more than 65%, or is more than 70%.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against dengue serotype 2 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50, is more than 60, is more than 70, is more than 80, or is more than 90%.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/ tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against dengue serotype 2 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the vaccine efficacy against dengue serotype 2 is more than 40%, is more than 50%, is more than 60%, is more than 70%, is more than 80, or is more than 90%.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 or at 18 months) after the last administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

In certain embodiments, the invention is directed to said methods having a vaccine efficacy against dengue serotype 3 with a 2-sided 95% confidence interval, wherein the lower bound is more than 25%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, about 30 days after the second administration of the administration schedule until at least 12 months after the second administration of the administration schedule. In certain such embodiments, the lower bound is more than 30%, is more than 40%.

In certain embodiments, the invention is directed to said methods having a vaccine efficacy against dengue serotype 3 of more than 30%, when measured against placebo in a subject population of at least 5,000 healthy subjects, or at least 10,000 healthy subjects, or at least 15,000 healthy subjects irrespective of serostatus at baseline, wherein said unit dose/tetravalent dengue virus composition or said placebo is administered at least twice within less than 6 months, such as within 3 months, 30 days after the second administration until at least 12 months after the second administration. In certain such embodiments, the vaccine efficacy against dengue serotype 3 is more than 40%, is more than 50%, is more than 55%, or is more than 60%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the lower bound is more than 10%, is more than 20%, is more than 30%, is more than 40%, is more than 50%, is more than 55%, is more than 60%, is more than 65%, is more than 66%, is more than 67%, is more than 70%, is more than 75%, is more than 77%, or is more than 80%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) irrespective of serostatus at baseline and 4 to 16 years of age, wherein a reconstituted unit dose/tetravalent dengue virus composition as described herein or placebo is e.g. administered at least twice within less than 6 months, such as within 3 months, from first administration until 12 to 18 months (e.g. at 12 months or at 18 months) after the last administration, or from 30 days post last administration until 12 to 18 months (e.g. at 12 or at 18 months) after the last administration. In certain such embodiments, the vaccine efficacy is more than is more than 70%, is more than 75%, is more than 80%, or is more than 82%, or is more than 85%, more than 88%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seronegative against all serotypes at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 75%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 66%, is more than 67%, is more than 70%, is more than 75%, is more than 77% or is more than 80%.

In certain embodiments, the invention is directed to said methods having a combined vaccine efficacy against virologically-confirmed dengue with hospitalization against all four serotypes of more than 30%, when measured against placebo in a subject population of at least 1,500 or at least 2,000 healthy subjects, healthy subjects being seronegative against all serotypes at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the said vaccine efficacy is more than 60%, is more than 65%, is more than 66%, is more than 67%, is more than 70%, is more than 75%, is more than 77%, is more than 80, or is more than 85%.

In certain embodiments, the invention is directed to said methods having a combined vaccine efficacy against virologically-confirmed dengue with hospitalization against all four serotypes with a 2-sided 95% confidence interval, wherein the lower bound is more than 25%, when measured against placebo in a subject population of at least 1,500 or at least 2,000 healthy subjects being seropositive at baseline, wherein said unit dose/tetravalent dengue virus composition or said placebo is administered at least twice within less than 6 months, such as within 3 months, about 30 days after the second administration of the administration schedule until at least 12 months or until 12 to 18 months (e.g. at 12 or at 18 months) after the second administration of the administration schedule. In certain such embodiments, the lower bound is more than 30%, is more than 40%, is more than 50%, is more than 60%, is more than 70%, or is more than 80%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the lower bound is more than 60%, is more than 65%, is more than 70%, is more than 75%, or is more than 80%.

In certain embodiments, the invention is directed to said methods having a combined vaccine efficacy against virologically-confirmed dengue with hospitalization against all four serotypes of more than 30%, when measured against placebo in a subject population at least 1,500 or of at least 2,000 healthy subjects, healthy subjects being seropositive at baseline, wherein said unit dose/tetravalent dengue virus composition or said placebo is administered at least twice within less than 6 months, such as within 3 months, 30 days after the second administration until at least 12 months or until 12 to 18 months (e.g. at 12 or at 18 months) after the second administration. In certain such embodiments, the combined vaccine efficacy against virologically-confirmed dengue with hospitalization against all four serotypes is more than 40%, is more than 50%, is more than 60%, is more than 70%, is more than 80%, or is more than 90%.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the vaccine efficacy is more than 75%, is more than 70%, is more than 80%, is more than 85%, or is more than 90%.

In certain embodiments, the invention is directed to said methods having a combined vaccine efficacy against all four serotypes, in preventing virologically confirmable dengue disease with hospitalization with a 2-sided 95% confidence interval, wherein the lower bound is more than 25%, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the lower bound provided by the seropositive subjects at baseline and the subjects seronegative against all serotypes at baseline is no more than 15%-points.

In certain embodiments, the invention is directed to said methods having a combined vaccine efficacy against all four serotypes, in preventing virologically confirmable dengue disease with hospitalization, when measured against placebo in a subject population of at least 5,000 healthy subjects (or at least 10,000, or at least 15,000 healthy subjects) being seropositive at baseline being or seronegative against all serotypes at baseline and 4 to 16 years of age, wherein a reconstituted unit dose/tetravalent dengue virus composition as described herein or placebo is e.g. administered at least twice within less than 6 months, such as within 3 months, from 30 days post last administration until 12 to 18 months (e.g. at 12 months or at 18 months) after the last administration. In certain such embodiments, the difference between the vaccine efficacy provided by the seropositive subjects at baseline and the subjects seronegative against all serotypes at baseline is no more than 10%-points or no more than 5%-points.

In certain embodiments, the invention is directed to said methods having a relative risk, preferably a combined relative risk against all four serotypes, with a 2-sided 95% confidence interval, wherein the upper bound is less than 0.75, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the upper bound is less than 0.70, less than 0.65, less than 0.60, less than 0.55, less than 0.50, less than 0.45, less than 0.40, less than 0.35, less than 0.30 or less than 0.28. Preferably said reconstituted unit dose or placebo is administered subcutaneously within about 3 month, such as on days 0 and 90.

In certain embodiments, the invention is directed to said methods having a relative risk, preferably a combined relative risk against all four serotypes, of less than 0.70, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months after the second administration. In certain such embodiments, the relative risk is less than 0.65, less than 0.60, less than 0.55, less than 0.50, less than 0.45, less than 0.40, less than 0.35, less than 0.30, less than 0.25 or less than 0.23. Preferably said reconstituted unit dose or placebo is administered subcutaneously within about 3 month, such as on days 0 and 90.

In certain embodiments, the invention is directed to said methods, wherein virologically confirmable dengue disease occurs in less than 2.5% of the subjects, when measured against placebo in a subject population of at least 5,000 healthy subjects (or at least 10,000, or at least 15,000 healthy subjects) irrespective of serostatus at baseline, wherein a reconstituted unit dose/tetravalent dengue virus composition as described herein or placebo is administered at least twice within less than 6 months, such as within 3 months, 30 days after the second administration until at least 12 months or at least 18 months after the second administration. In certain such embodiments, virologically confirmable dengue disease occurs in less than 2.0% of the subjects, less than 1.5% of the subjects, less than 1.0% of the subjects, less than 0.8% of the subjects, or less than 0.6% of the subjects. Preferably said reconstituted unit dose or placebo is administered subcutaneously within about 3 month, such as on days 0 and 90.

In certain embodiments, the invention is directed to said methods having a combined vaccine efficacy against all four serotypes with a 2-sided 95% confidence interval, wherein the lower bound is more than 61.0%, or more than 65.0 or more than 70.0% or more than 72.0% when measured against placebo in a subject population of at least 5,000 healthy subjects (or at least 10,000, or at least 15,000 healthy subjects) from endemic irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 or 13 months after the last administration of the administration schedule.

In certain embodiments, the invention is directed to said methods having a combined vaccine efficacy against all four serotypes of more than 66%, or of more than 70%, or of more than 75%, or of more than 77%, or of more than 80.0%, when measured against placebo in a subject population of at least 5,000 healthy subjects (or at least 10,000, or at least 15,000 healthy subjects) from endemic areas irrespective of serostatus at baseline and being selected from the group consisting of 4 to 16 year old subjects at the time of randomization, wherein said unit dose/tetravalent dengue virus composition or said placebo is administered at least twice within 6 months or less, about 30 days after the last administration of the administration schedule until at least 12 months or 13 month after the last administration of the administration schedule.

In certain embodiments, the invention is directed to said methods, wherein the combined vaccine efficacy against all four serotypes is measured about 30 days after the last administration of the administration schedule until 12 or 13 months after the last administration of the administration schedule.

In certain embodiments, the invention is directed to said methods, wherein said unit dose or said placebo is administered at least twice within three months, in particular at about day 1 and about day 90, and wherein the combined vaccine efficacy against all four serotypes is measured 30 days after the second administration until 12 or 13 months after the second administration of the administration schedule.

In certain embodiments, the invention is directed to said methods, wherein said methods are effective and safe. In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein said methods having a relative risk for virologically confirmed dengue with hospitalization of 1 or less, or 0.8 or less, or 0.6 or less, when measured against placebo in a subject population of at least 5,000 healthy subjects (or at least 10,000, or at least 15,000 healthy subjects). In some of these embodiments, the subject or subject population is under 9 years of age, under 4 years of age, or under 2 years of age or from 2 to 9 years of age, or from 2 to 5 years of age, or from 4 to 9 years of age or from 6 to 9 years of age. Optionally the subject is seronegative with respect to all dengue serotypes.

In certain embodiments, the invention is directed to said methods, wherein the healthy subjects of the subject population are 4 to 16 years of age. In some of such embodiments, the healthy subjects of the subject population are 4 to 5 years of age, 6 to 11 years of age, or 12 to 16 years of age.

In certain embodiments, the invention is directed to said methods, wherein the healthy subjects of the subject population are defined as being healthy in view of the exclusion criteria specified in Example 6.

In certain embodiments, the invention is directed to said methods, wherein the healthy subjects of the subject population are from Asia Pacific or Latin America.

In certain embodiments, the invention is directed to said methods, wherein the healthy subjects of the subject population are seropositive with respect to at least one serotype. In other embodiments, the healthy subjects of the subject population are seronegative with respect to all serotypes.

In certain embodiments, the invention is directed to said methods, wherein the healthy subjects of the subject population are 4-5 years of age and from Asia Pacific, 6-11 years of age and from Asia Pacific, or 12-16 years of age and from Asia Pacific. In other embodiments, the healthy subjects of the subject population are 4-5 years of age and from Latin America, 6-11 years of age and from Latin America, or 12-16 years of age and from Latin America.

In certain embodiments, the invention is directed to said methods, wherein the healthy subjects of the subject population are 4-5 years of age and seropositive for at least 1 dengue serotype, 6-11 years of age and seropositive for at least 1 dengue serotype, or 12-16 years of age and seropositive for at least 1 dengue serotype. In other embodiments, the healthy subjects of the subject population are 4-5 years of age and seronegative for all dengue serotypes, 6-11 years of age and seronegative for all dengue serotypes, or 12-16 years of age and seronegative for all dengue serotypes.

In certain embodiments, the invention is directed to said methods, wherein the healthy subjects of the subject population are from Asia Pacific or Latin America and seropositive for at least one dengue serotype at baseline. In other embodiments, the healthy subjects of the subject population are from Asia Pacific or Latin America and seronegative for at all dengue serotype at baseline.

In certain embodiments, the invention is directed to said methods, wherein the healthy subjects of the subject population are from Asia Pacific, seropositive for at least one dengue serotype at baseline and 4-5 years of age, 6-11 years of age, or 12-16 years of age. In other embodiments, the healthy subjects of the subject population are from Asia Pacific, seronegative for all dengue serotypes at baseline and 4-5 years of age, 6-11 years of age, or 12-16 years of age. In yet other embodiments, the healthy subjects of the subject population are from Latin America, seropositive for at least one dengue serotype at baseline and 4-5 years of age, 6-11 years of age, or 12-16 years of age. In other embodiments, the healthy subjects of the subject population are from America, seronegative for all dengue serotypes at baseline and 4-5 years of age, 6-11 years of age, or 12-16 years of age.

In certain embodiments, the invention is directed to said methods, wherein the healthy subjects of the subject population had prior vaccination against Yellow Fever. In other embodiments, the healthy subjects of the subject population had no prior vaccination against Yellow Fever. Prior vaccination indicates a vaccination prior to the first vaccination with the reconstituted unit dose as described herein. For example for vaccine efficacy (VE) as determined in Example 6 from 30 days post-second vaccination, a prior vaccination of Yellow Fever is defined as a Yellow Fever vaccination occurring before 30 days post-second vaccination.

In certain embodiments, the invention is directed to said methods, wherein the healthy subjects of the subject population had prior vaccination against Japanese Encephalitis. In other embodiments, the healthy subjects of the subject population had no prior vaccination against Japanese Encephalitis.

In certain embodiments, the invention is directed to said methods, wherein the healthy subjects of the subject population received Dengvaxia® within the administration regimen as described herein or within 4.5 years after administration of the first dose. In certain embodiments, the invention is directed to said methods, wherein the occurrence of vaccine related serious adverse events is less than 0.1%.

In certain embodiments, the invention is directed to said methods, wherein the occurrence of vaccine related unsolicited adverse events occurring within 4 weeks of administration is less than 2%.

In certain embodiments, the invention is directed to said methods, wherein the occurrence of vaccine related solicited adverse events occurring within 2 weeks of administration is less than 35%.

In certain embodiments, the invention is directed to said methods, wherein the occurrence of vaccine related solicited local reactions occurring within 1 weeks of administration is less than 40%.

In certain embodiments, the invention is directed to said methods, wherein the method does not increase the risk of virologically-confirmed dengue with hospitalization in the individual, such as in a seronegative individual.

In one embodiment, the unit dose is co-administered with a vaccine selected from the group of a DTaP/IPV/Hib vaccine, in particular a combined DTaP/IPV/Hib vaccine, an MMR vaccine, a yellow fever vaccine, in particular YF-17D, an HPV vaccine, in particular a 9vHPV vaccine, a tetanus, diphtheria, and pertussis (Tdap) vaccine, in particular a combined tetanus toxoid, reduced diphtheria toxoid and acellular pertussis (adsorbed) vaccine, and a hepatitis A vaccine as described in more detail below.

Unit Dose for Use in a Method of Preventing Dengue Disease

The present invention is directed in part to the composition or unit dose of the invention as described herein for use in a method of preventing dengue disease (in particular virologically-confirmable dengue, VCD) in a subject.

The present invention is directed in part to the composition or unit dose of the invention as described herein for use in a method of preventing dengue disease (in particular virologically-confirmable dengue, VCD) in a subject population.

Inoculating against dengue disease, vaccinating against dengue disease and preventing dengue disease have the same meaning. The present invention is directed in part to a method of preventing dengue hemorrhagic fever (DHF) and dengue shock syndrome (DSS).

Any method described herein above under the heading "Method of preventing, method of inoculating" is to be understood to be also disclosed as unit dose for use in such a method of preventing dengue disease in a subject or subject population irrespective of being expressly stated below.

According to a certain aspect the composition or unit dose of the invention is a tetravalent dengue virus composition including a chimeric dengue serotype 2/1 strain and a dengue serotype 2 strain and a chimeric dengue serotype 2/3 strain and a chimeric dengue serotype 2/4 strain. According to certain such aspects the dengue serotype 2 strain is derived from the wild type virus strain DEN-2 16681 (represented by SEQ ID NO 11) and differs in at least three nucleotides from the wild type as follows:

a) 5'-noncoding region (NCR)-57 (nt-57 C-to-T)

b) NS1-53 Gly-to-Asp (nt-2579 G-to-A)

c) NS3-250 Glu-to-Val (nt-5270 A-to-T); and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

Further information regarding the serotypes of the tetravalent composition can be derived from section "Dengue virus strains" above.

The tetravalent dengue virus composition for such use may be in the form of a unit dose comprising:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The tetravalent dengue virus composition for such use may also be in the form of a lyophilized unit dose which upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

In the tetravalent dengue virus composition for such use according to one embodiment upon reconstitution with a pharmaceutically acceptable diluent (i), (ii), (iii), and (iv) provide a total concentration of pfu/0.5 mL and based on said total concentration the concentration of (ii) in pfu/0.5 mL is preferably less than 10%, and the concentration of (iv) in pfu/0.5 mL is preferably at least 50%, and the concentration of (i) in pfu/0.5 mL is preferably at least 1%, and the concentration of (iii) in pfu/0.5 mL is preferably at least 8%, or more preferred at least 10%, or at least 12%, or at least 14%, or at least 16%, or at least 18% and wherein the subject is preferably 2 to 17 years of age or 4 to 16 years of age.

In the tetravalent dengue virus composition for such use according to one embodiment upon reconstitution with a pharmaceutically acceptable diluent (i), (ii), (iii), and (iv) provide a total concentration of pfu/0.5 mL and based on said total concentration the concentration of (ii) in pfu/0.5 mL is preferably less than 2%, the concentration of (iv) in pfu/0.5 mL is preferably at least 50%, the concentration of (i) in pfu/0.5 mL is at preferably least 1%, and the concentration of (iii) in pfu/0.5 mL is preferably at least 6% and wherein the subject preferably is 18 to 60 years of age.

Further information regarding the tetravalent composition or the unit dose can be derived from section "Dengue vaccine composition" and "Unit dose" above.

According to one embodiment the unit dose for such use is directed to a method comprising a primary vaccination with only two administrations of the unit dose comprising the steps of:

(A) administering a first unit dose of the tetravalent dengue virus composition to the subject, and (B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the use is for a method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to said methods having a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said methods having a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said methods having a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said methods having a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail in the section "method of preventing, method of inoculating".

In certain embodiments the unit dose is reconstituted and administered by subcutaneous injection. According to some of these embodiments, the subcutaneous injection is administered to the arm, preferably to the deltoid region of the arm.

According to one embodiment such a method does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above the method according to one embodiment comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method however further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 10%, and the concentration of (iv) in pfu/0.5 mL is preferably at least 50%, and the concentration of (i) in pfu/0.5 mL is preferably at least 1%, and the concentration of (iii) in pfu/0.5 mL is preferably at least 8%, or more preferred at least 10%, or at least 12%, or at least 14%, or at least 16%, or at least 18% and the subject is 2 to 17 years of age or 4 to 16 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 2%, the concentration of (iv) in pfu/0.5 mL is preferably at least 50%, the concentration of (i) in pfu/0.5 mL is at preferably least 1%, and the concentration of (iii) in pfu/0.5 mL is preferably at least 6% and the subject is 18 to 60 years of age.

Further specific embodiments are described below.

The present invention is directed in part to a reconstituted unit dose of a dengue vaccine composition as described herein for use in a method of preventing virologically confirmable dengue disease in a subject comprising administering at least a first unit dose of the dengue vaccine composition to the subject, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated dengue virus strains and/or comprise chimeric dengue viruses and/or at least one non-chimeric dengue virus, and wherein upon reconstitution with 0.5 mL of a pharmaceutically acceptable diluent (i) dengue serotype 1 has a concentration of at least 3.3 log 10 pfu/0.5 mL and optionally to 5.0 log 10 pfu/0.5 mL, (ii) dengue serotype 2 has a concentration of at least 2.7 log 10 pfu/0.5 mL and optionally to 4.9 log 10 pfu/0.5 mL, (iii) dengue serotype 3 has a concentration of at least 4.0 log 10 pfu/0.5 mL and optionally to 5.7 log 10 pfu/0.5 mL, and (iv) dengue serotype 4 has a concentration of at least 4.5 log 10 pfu/0.5 mL and optionally to 6.2 log 10 pfu/0.5 mL.

The present invention is directed in part to a reconstituted unit dose of a dengue vaccine composition as described herein for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, and wherein upon reconstitution with 0.5 mL of a pharmaceutically acceptable diluent (v) dengue serotype 1 has a concentration of at least 3.3 log 10 pfu/0.5 mL and optionally to 5.0 log 10 pfu/0.5 mL, (vi) dengue serotype 2 has a concentration of at least 2.7 log 10 pfu/0.5 mL and optionally to 4.9 log 10 pfu/0.5 mL, (vii) dengue serotype 3 has a concentration of at least 4.0 log 10 pfu/0.5 mL and optionally to 5.7 log 10 pfu/0.5 mL, and (viii) dengue serotype 4 has a concentration of at least 4.5 log 10 pfu/0.5 mL and optionally to 6.2 log 10 pfu/0.5 mL.

In certain embodiments, the invention is directed to a reconstituted unit dose of a dengue vaccine composition for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, wherein the dengue vaccine composition is a tetravalent dengue virus composition including four dengue virus strains representing dengue serotype 1, dengue serotype 2, dengue serotype 3 and dengue serotype 4, optionally wherein the dengue virus strains are live, attenuated, wherein the subject is under 9 years of age and/or when the serostatus of the subject is unknown or seronegative and wherein upon reconstitution with 0.5 mL of a pharmaceutically acceptable diluent (i) dengue serotype 1 has a concentration of at least 3.3 log 10 pfu/0.5 mL and optionally to 5.0 log 10 pfu/0.5 mL, (ii) dengue serotype 2 has a concentration of at least 2.7 log 10 pfu/0.5 mL and optionally to 4.9 log 10 pfu/0.5 mL, (iii) dengue serotype 3 has a concentration of at least 4.0 log 10 pfu/0.5 mL and optionally to 5.7 log 10 pfu/0.5 mL, and (iv) dengue serotype 4 has a concentration of at least 4.5 log 10 pfu/0.5 mL and optionally to 6.2 log 10 pfu/0.5 mL.

In certain embodiments, the reconstituted unit dose is administered to a subject of unknown serostatus and/or wherein no test has been carried out to determine whether the subject is seropositive or seronegative before the unit dose as described herein is administered.

In certain embodiments, the subject is under 9 years of age and/or the serostatus of the subject is unknown or seronegative. In certain such embodiments, the subject is under 9 years of age and the serostatus of the subject is unknown or seronegative, preferably seronegative.

In certain embodiments, the method is safe. In certain such embodiments, the subject is under 9 years of age or from 4 years of age and/or the serostatus of the subject is unknown or seronegative. In certain such embodiments, the subject is from 4 years of age and the serostatus of the subject is unknown or seronegative, preferably seronegative.

In certain embodiments, the method is effective. In certain such embodiments, the subject is under 9 years of age and/or the serostatus of the subject is unknown or seronegative. In certain such embodiments, the subject is under 9 years of age and the serostatus of the subject is unknown or seronegative, preferably seronegative.

In certain embodiments, the dengue serotype 1 and the dengue serotype 2 are present each in a concentration based on the total concentration in pfu/0.5 mL which is within 5%-points of each other and/or are together less than about 10% of the total concentration in pfu/0.5 mL. In certain such embodiments, the dengue serotype 3 is at least about 10% of the total concentration in pfu/0.5 mL and/or the dengue serotype 4 is at least about 70% of the total concentration in pfu/0.5 mL.

In certain embodiments, the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

In certain embodiments, the composition includes at least one chimeric dengue virus. In certain such embodiments, the composition includes at least one non-chimeric dengue virus and at least one chimeric dengue virus.

In certain embodiments, the subject is seronegative to all dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In other embodiments, the subject is seropositive to at least one dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age.

In certain embodiments, the method does not comprise a determination of a previous dengue infection in the subject before the administration of the first unit dose of the tetravalent dengue virus composition. Thus, in certain embodiments, the subject has not been tested for the presence a previous dengue infection.

In certain embodiments, the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain and the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

In certain embodiments, the unit dose further comprises from about 10% w/v to about 20% w/v α,α-trehalose dihydrate or an equimolar amount of other forms of α,α-trehalose, from about 0.5% w/v to about 1.5% w/v poloxamer 407, from about 0.05% w/v to about 2% w/v human serum albumin, and from about 70 mM to 140 mM sodium chloride when measured in 0.5 mL. In certain such embodiments, the unit dose comprises about 15% (w/v) α,α-trehalose dihydrate, about 1% (w/v) poloxamer 407, about 0.1% (w/v) human serum albumin, and about 100 mM sodium chloride when measured in 0.5 mL.

In certain embodiments, the method is for preventing dengue hemorrhagic fever (DHF) or dengue shock syndrome (DSS).

In certain embodiments, the subject is from a dengue endemic region. In other embodiments, the subject is from a dengue non-endemic region.

In certain embodiments, the subject is from Asia Pacific or Latin America.

In certain embodiments, the reconstituted unit dose provides a seropositivity rate when it is administered to a subject population of at least 50 subjects in two unit doses subcutaneously at day 1 and at day 90, wherein the subjects of the subject population are seronegative to all dengue serotypes at baseline. In certain such embodiments, at least 80% of the subject population are seropositive for all four dengue serotypes at least one month after administration of the first unit dose, such as at day 30, and/or at least 80% of the subject population are seropositive for all four dengue serotypes before or at the time of the administration of the second unit dose, such as at day 90, and/or at least 80%, or at least 85% or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270. In certain such embodiments, at least 80% of the subject population are seropositive for all four dengue serotypes at least one month after administration of the first unit dose, such as at day 30, and before or at the time of the administration of the second unit dose, such as at day 90, and after the administration of the second unit dose, such as at day 120 and at day 270.

In certain embodiments, the reconstituted unit dose provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

In certain particular embodiments, the invention is directed to a dengue vaccine composition as described herein for use in a method of preventing virologically confirmable dengue disease in a subject comprising consecutively administering at least a first and a second unit dose of the dengue vaccine composition to the subject, wherein said first and second unit dose are administered subcutaneously within 3 months and at least 4 weeks apart, optionally at about day 1 and at about day 90, and wherein the dengue vaccine composition is a tetravalent dengue virus composition including four live, attenuated dengue virus strains representing dengue serotype 1, dengue serotype 2, dengue serotype 3 and dengue serotype 4, wherein the attenuated dengue virus strains comprise chimeric dengue viruses and at least one non-chimeric dengue virus, and wherein the dengue serotype 1 and the dengue serotype 2 are present each in a concentration based on the total concentration in pfu/0.5 mL which is within 5%-points of each other and/or are together less than about 10% of the total concentration in pfu/0.5 mL.

In certain embodiments, the method does not comprise a determination of a previous dengue infection of the subject before the administration of the first unit dose of the tetravalent dengue virus composition and wherein the method is safe and effective. Thus, in certain embodiments, the subject has not been tested for the presence a previous dengue infection.

In certain embodiments, the dengue serotype 3 is at least about 10% of the total concentration in pfu/0.5 mL and/or the dengue serotype 4 is at least about 70% of the total concentration in pfu/0.5 mL.

In certain embodiments, the dengue serotype 4 represents the highest concentration in the composition of all four serotypes, preferably with at least about 70% of the total concentration in pfu/0.5 mL, dengue serotype 3 represents the second highest concentration in the composition of all four serotypes, preferably with at least about 10% of the total concentration in pfu/0.5 mL, and dengue serotype 1 and dengue serotype 2 each represent lower concentrations than the concentration of serotype 3, and optionally together represent less than about 10% of the total concentration in pfu/0.5 mL.

In certain embodiments, the dengue serotype 1 is a chimeric dengue serotype 2/1 strain, the dengue serotype 2 is a non-chimeric dengue serotype 2 strain, the dengue serotype 3 is a chimeric dengue serotype 2/3 strain and the dengue serotype 4 is a chimeric dengue serotype 2/4 strain and the dengue serotype 1 has the amino acid sequence of SEQ ID NO. 2, the dengue serotype 2 has the amino acid sequence of SEQ ID NO. 4, the dengue serotype 3 has the amino acid sequence of SEQ ID NO. 6, and the dengue serotype 4 has the amino acid sequence of SEQ ID NO. 8.

In certain embodiments, in the unit dose upon reconstitution with 0.5 mL of a pharmaceutically acceptable diluent (i) dengue serotype 1 has a concentration of 3.3 log 10 pfu/0.5 mL to 5.0 log 10 pfu/0.5 mL, (ii) dengue serotype 2 has a concentration of 2.7 log 10 pfu/0.5 mL to 4.9 log 10 pfu/0.5 mL, (iii) dengue serotype 3 has a concentration of 4.0 log 10 pfu/0.5 mL to 5.7 log 10 pfu/0.5 mL, and (iv) dengue serotype 4 has a concentration of 4.5 log 10 pfu/0.5 mL to 6.2 log 10 pfu/0.5 mL, and optionally the composition further comprises about 15% (w/v) α,α-trehalose dihydrate, about 1% (w/v) poloxamer 407, about 0.1% (w/v) human serum albumin, and about 100 mM sodium chloride when measured in 0.5 mL.

In certain embodiments, the unit doses are administered to the deltoid region of the arm.

In certain embodiments, the composition is administered without determining the serostatus of the subject at baseline and wherein the administration is safe and effective regardless of the serostatus at base line.

In certain embodiments, the subject is seronegative to all dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In particular the subject may be under 9 years of age and seronegative to all four dengue serotypes at baseline. In other embodiments, the subject is seropositive to at least one dengue serotypes at baseline and/or is from 4 years of age, optionally to 60 years of age. In certain such embodiments, the subject is 4 to 16 years of age, under 9 years of age, from 2 years of age to under 9 years of age, from 4 years of age to under 9 years of age, 4 to 5 years of age, 6 to 11 years of age, or 12 to 16 years of age. In particular the subject may be under 9 years of age and seropositive to at least one dengue serotypes at baseline. In certain preferred embodiments, the subject is 4 to 5 years of age, 6 to 11 years of age or 12 to 16 years of age.

In certain embodiments, the method is for preventing dengue hemorrhagic fever (DHF) or dengue shock syndrome (DSS).

In certain embodiments, the subject is from a dengue endemic region or from a dengue non-endemic region.

In certain embodiments, the subject is from Asia Pacific or Latin America.

In certain embodiments, the composition provides a seropositivity rate when it is administered to a subject population of at least 50 subjects in two unit doses subcutaneously at day 1 and at day 90, wherein the subjects of the subject population are seronegative to all dengue serotypes at baseline, in particular wherein at least one month after administration of the first unit dose, such as at day 30, at least 80% of the subject population are seropositive for all four dengue serotypes, and/or at least 80% of the subject population are seropositive for all four dengue serotypes before or at the time of the administration of the second unit dose, such as at day 90, and/or at least 80%, or at least 85% or at least 90%, or at least 95% of the subject population are seropositive for all four dengue serotypes after the administration of the second unit dose, such as at day 120, and/or at least 80%, or at least 85%, or at least 90% of the subject population are seropositive for all four dengue serotypes after the administration of the second unit dose, such as at day 270.

In certain embodiments, the composition provides a seropositivity rate, when it is administered to a subject population of at least 100 subjects in two unit doses subcutaneously at day 1 and at day 90, wherein the subjects of the subject population comprises from 20% to 40% subjects who are seronegative to all dengue serotypes and from 60% to 80% subjects who are seropositive to at least one dengue serotype at base line, wherein at day 120 and/or day 270 the seropositivity rate for all four dengue serotypes in the seronegative part of the subject population and the seropositivity rate for all four dengue serotypes in the seropositive part of the subject population do not deviate more than 10%-points and/or wherein at day 120 the seropositivity rate for all four dengue serotypes in the seronegative part of the subject population and the seropositivity rate for all four dengue serotypes in the seropositive part of the subject population do not deviate more than 5%-points.

The present invention is in part directed to the unit dose of the invention as described herein for use in a method of preventing dengue disease (in particular virologically confirmable dengue, VCD) in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of the invention as described herein for use in a method of preventing dengue disease (in particular virologically confirmable dengue, VCD) in a subject comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

The geometric mean neutralizing antibody titers (GMTs) of a subject population or the neutralizing antibody titers of a subject are determined in accordance with the microneutralization test disclosed herein, for example according to the method described in Example 2.

In certain embodiments the invention is directed to the reconstituted unit dose of the invention as described herein for said uses, wherein said unit dose is administered by subcutaneous injection. According to some of these embodiments the subcutaneous injection is administered to the arm, preferably to the deltoid region of the arm.

In certain embodiments the invention is directed to a reconstituted unit dose of the invention as described herein for said uses, wherein the subject or subject population is seronegative to all dengue serotypes.

In certain embodiments the invention is directed to a reconstituted unit dose of the invention as described herein for said uses, wherein a single unit dose of the invention as described herein is administered.

In certain embodiments the invention is directed to a reconstituted unit dose of the invention as described herein for said uses, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to a reconstituted unit dose of the invention as described herein for said uses, wherein the reconstituted unit dose of the invention as described herein is administered at most in two doses or in one dose.

In certain embodiments of the invention the subject is seronegative with respect to all dengue serotypes. In certain embodiments of the invention the subject is seronegative with respect to all dengue serotypes and the reconstituted unit dose is administered to the seronegative subject by subcutaneous injection.

In certain other embodiments of the invention the subject is seropositive with respect to at least one dengue serotype.

In certain embodiments the invention is directed to the reconstituted unit dose of the invention as described herein for said uses, wherein the reconstituted unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In other embodiments, the subject or subject population is from a dengue non-endemic region. Such a subject population or such a subject may be vaccinated according to the invention in the context of traveling to a dengue-endemic region. In certain embodiments, the reconstituted unit dose of the invention as described herein is administered subcutaneously to a subject or subject population from a dengue endemic region or from a dengue non-endemic region.

In some embodiments the invention is directed to the unit dose of the invention as described herein for said uses, wherein the subject or subject population is of 2 to 60 years of age, or more than 17 years, or more than 18 years, or 18 to 60 years of age. In certain embodiments, the subject or subject population is of 1 to 17 years of age, or less than 9 years of age, or less than 4 years of age or less than 2 years of age. In further specific embodiments, the subjects or subject population are adults of more than 21 years, or 21 to 60 years, or 21 to 45 years of age. According to some of these embodiments the subject or subject population is seronegative and from a dengue-endemic region.

In certain embodiments, the invention is directed to the reconstituted unit dose of the invention as described herein for said uses, wherein the unit dose of the invention as described herein is administered to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

In certain embodiments, the invention is directed to the reconstituted unit dose of the invention as described herein for said uses, wherein the reconstituted unit dose is administered subcutaneously to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

The unit dose for use in the methods described above may be any unit dose of a dengue vaccine composition as described above under the headings “Unit dose” or “Dengue vaccine composition” and comprise any dengue virus strain as described above under the heading “Dengue virus strain”.

The present invention is directed in part to the unit dose of the invention as described herein for use in a method of preventing dengue hemorrhagic fever (DHF) and dengue shock syndrome (DSS) in an elderly subject.

In certain embodiments the invention is directed to a reconstituted unit dose of the invention as described herein for said uses, wherein the elderly subject is seronegative to all dengue serotypes.

In certain embodiments the invention is directed to a reconstituted unit dose of the invention as described herein for said uses, wherein the elderly subject is seronegative to all dengue serotypes.

In certain embodiments the invention is directed to a reconstituted unit dose of the invention as described herein for said uses, wherein two reconstituted unit doses of the invention as described herein are administered. In some embodiments, the two reconstituted unit doses are administered within 12 months or more, or within six months, or within three months, such as at day 0/1 and day 90. According to some of these embodiments, a third reconstituted unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments of the invention the elderly subject is seronegative with respect to all dengue serotypes. In certain embodiments of the invention the elderly subject is seronegative with respect to all dengue serotypes and the reconstituted unit dose is administered to the seronegative subject by subcutaneous injection.

In certain other embodiments of the invention the elderly subject is seropositive with respect to at least one dengue serotype.

In certain embodiments the invention is directed to the reconstituted unit dose of the invention as described herein for said uses, wherein the reconstituted unit dose of the invention as described herein is administered to an elderly subject from a dengue endemic region. In some of these embodiments, the elderly subject is from Singapore, Dominican Republic, Panama, Philippines, Colombia, Puerto Rico or Thailand, in particular from Singapore, Dominican Republic, Panama, or Philippines. In other embodiments, the elderly subject is from a dengue non-endemic region. Such an elderly subject may be vaccinated according to the invention in the context of traveling to a dengue-endemic region. In certain embodiments, the reconstituted unit dose of the invention as described herein is administered subcutaneously to an elderly subject from a dengue endemic region or from a dengue non-endemic region.

In certain embodiments, the invention is directed to the reconstituted unit dose of the invention as described herein for said uses, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to the reconstituted unit dose of the invention as described herein for said uses, wherein the elderly subject has an impaired immune system.

Use for the Manufacture of a Medicament for Preventing Dengue Disease

The present invention is directed in part to the use of a unit dose of the invention as described herein for the manufacture of a medicament for preventing dengue disease (in particular virologically confirmable dengue, VCD) in a subject.

The present invention is directed in part to the use of a unit dose of the invention as described herein for the manufacture of a medicament for preventing dengue disease (in particular virologically confirmable dengue, VCD) in a subject population.

The present invention is therefore directed to the use of a tetravalent dengue virus composition including four live attenuated dengue virus strains representing serotype 1, serotype 2, serotype 3 and serotype 4 in the manufacture of a medicament for the method of inoculating a subject against virologically confirmable dengue disease, wherein in particular the tetravalent dengue virus composition includes a chimeric dengue serotype 2/1 strain and a dengue serotype 2 strain and a chimeric dengue serotype 2/3 strain and a chimeric dengue serotype 2/4 strain, wherein in particular the dengue serotype 2 strain is derived from the wild type virus strain DEN-2 16681 (SEQ ID NO 11) and differs in at least three nucleotides from the wild type as follows:

d) 5'-noncoding region (NCR)-57 (nt-57 C-to-T): major attenuation locus e) NS1-53 Gly-to-Asp (nt-2579 G-to-A): major attenuation locus f) NS3-250 Glu-to-Val (nt-5270 A-to-T): major attenuation locus; and wherein the three chimeric dengue strains are derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera.

Further information regarding the serotypes of the tetravalent composition can be derived from section "Dengue virus strains" above.

The present invention is in particular directed to such use wherein the tetravalent dengue virus composition is in the form of a unit dose comprising:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is in particular directed to such use wherein the unit dose is lyophilized and upon reconstitution with 0.5 mL of a pharmaceutically acceptable diluent comprises:

(i) a dengue serotype 1 in a concentration of at least 3.3 log 10 pfu/0.5 ml, (ii) a dengue serotype 2, in a concentration of at least 2.7 log 10 pfu/0.5 ml, (iii) a dengue serotype 3, in a concentration of at least 4.0 log 10 pfu/0.5 ml, and (iv) a dengue serotype 4, in a concentration of at least 4.5 log 10 pfu/0.5 ml.

The present invention is also in particular directed to such use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8%, or at least 10%, or at least 12%, or at least 14%, or at least 16%, or at least 18%, and wherein the subject is preferably 2 to 17 years of age or 4 to 16 years of age.

The present invention is also in particular directed to such use wherein upon reconstitution with a pharmaceutically acceptable diluent (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject preferably is 18 to 60 years of age.

Further information regarding the tetravalent composition or the unit dose can be derived from section "Dengue vaccine composition" and "Unit dose" above.

According to one embodiment the use is directed to a method comprising a primary vaccination with only two administrations of the unit dose comprising the steps of:

(A) administering a first unit dose of the tetravalent dengue virus composition to the subject, and (B) administering a second unit does of the tetravalent dengue virus composition to the subject within 3 months of administration of the first unit dose.

According to this embodiment the administration of only two doses within 3 months is sufficient to provide effective protection against a subsequent dengue infection.

Such method preferably provides a combined vaccine efficacy against all four serotypes in preventing virologically confirmable dengue disease with a 2-sided 95% confidence interval, wherein the lower bound is more than 60%, when measured against placebo in a subject population of at least 5,000 healthy subjects irrespective of serostatus at baseline and 14 to 16 years of age, from the first administration of the administration schedule until 18 months after the second administration of the administration schedule.

Such method also preferably provides a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 14 to 16 years of age, from 30 days after the second administration of the administration schedule until 18 months after the second administration of the administration schedule.

According to certain embodiments the use is for a method of inoculation against the virologically confirmable dengue disease is due to a dengue serotype 2, and/or due to a dengue serotype 1. The method has very high efficacy against dengue serotype 2 and dengue serotype 1 and the highest efficacy against dengue serotype 2.

In certain embodiments, the invention is directed to the use wherein said methods have a vaccine efficacy against serotype 1, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 30%, is more than 35% is more than 40%, is more than 45%, is more than 50%, or is more than 54%. In certain such embodiments the subject population of at least 1,500 is seronegative against all serotypes at base line and the lower bound is more than 35%. In certain such embodiments the seronegative and seropositive population each provide a vaccine efficacy against serotype 1 with a 2-sided 95% confidence interval, wherein the lower bounds are within 10%-points.

In certain embodiments, the invention is directed to said use wherein said methods have a vaccine efficacy against serotype 1, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 40%, is more than 50%, is more than 60%, or is more than 65%. In certain such embodiments the subject population of at least 1,500 is seronegative against all serotypes at base line. In certain such embodiments the seronegative and seropositive population each provide a vaccine efficacy against serotype 1 which are within 5%-points.

In certain embodiments, the invention is directed to said use wherein said methods have a vaccine efficacy against serotype 2, in preventing virologically confirmable dengue disease with a 2-sided 95% confidence interval, wherein the lower bound is more than 25%, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the lower bound is more than 50%, is more than 60%, is more than 70%, is more than 80%, or is more than 85%. In certain such embodiments the subject population of at least 1,500, is seronegative against all serotypes. In certain such embodiments the seronegative and seropositive population each provide a vaccine efficacy against serotype 2 with a 2-sided 95% confidence interval, wherein the lower bounds are within 5%-points.

In certain embodiments, the invention is directed to said use wherein said methods have a vaccine efficacy against serotype 2, in preventing virologically confirmable dengue disease, when measured against placebo in a subject population of at least 1,500, or at least 2,000, or at least 5,000 healthy subjects (or at least 10,000, or at least 15,000 healthy subjects) irrespective of serostatus at baseline and 4 to 16 years of age from 30 days post second administration until 12 to 18 months (e.g. at 12 or at 18 months) after the second administration. In certain such embodiments, the vaccine efficacy is more than 60%, is more than 70%, is more than 80%, or is more than 90%. In certain such embodiments the subject population of at least 1,500 is seronegative against all serotypes at base line. In certain such embodiments the seronegative and seropositive population each provide a vaccine efficacy against serotype 2 which are within 5%-points.

The efficacy of the method is further described in more detail in the section "method of preventing, method of inoculating".

In certain embodiments the unit dose is reconstituted and administered by subcutaneous injection. According to some of these embodiments, the subcutaneous injection is administered to the arm, preferably to the deltoid region of the arm.

According to one embodiment such use is directed to a method which does not include a step of determination of a previous dengue infection in the subjects preferably at any time before, during or after the steps of administration or wherein the serostatus of the subject is unknown preferably at any time before, during or after the steps of administration.

The method according to the invention does not require the testing of the serostatus before vaccination and thus allows immediate treatment and outbreak control. According to certain embodiments the use is for a method wherein the subject is exposed to a dengue outbreak. In certain such embodiments the outbreak is due to a dengue serotype 2, and/or due to a serotype 1.

According to one embodiment such a method the subject is from a region wherein the seroprevalence rate is unknown and/or wherein the seroprevalence rate is below 80%, or below 70%, or below 60%.

According to one embodiment of such a method the subject is seronegative at baseline and is from a region or travels to a region wherein the seroprevalence rate is high with respect to serotype 1 and/or serotype 2 i.e. 80%, or 90% or above.

According this embodiment the vaccine and corresponding method is safe for seronegative and seropositive subjects and thus does not require an analysis of the serostatus or a determination of a previous dengue infection or a high seroprevalence rate in the region. Such a method preferably provides a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline, preferably in at least 1,500 healthy 4 to 16 year old subjects seronegative at baseline, from first administration of the administration schedule until 12 to 18 months after the second administration of the administration schedule. Preferably, the 2-sided 95% confidence interval of the combined vaccine efficacy against virologically-confirmed dengue with hospitalization against all four serotypes when comparing seropositive and seronegative subjects provides for lower bounds of the 2-sided confidence interval which are within 10% points or within 15% points or within 20% points. The method is preferably safe with respect to serotype 1 and serotype 2 which may therefore be used in outbreak situations due to serotype 1 and/or serotype 2 or even for seronegative subjects (e.g. travelers) or subjects with unknown serostatus in regions with very high seroprevalence rates (>80%) due to serotype 1 and/or serotype 2.

The safety of the method is further described in more detail in the section "method of preventing, method of inoculating".

According to one embodiment such a method does not include the active surveillance with respect to febrile illness of the subject after the administration of the first- and second-unit dose. During active surveillance any subject with febrile illness (defined as fever ≥38° C. on any 2 of 3 consecutive days) will be asked to return to the site for dengue fever evaluation by the Investigator. Subjects/guardians will be contacted at least weekly to ensure robust identification of febrile illness by reminding subjects/guardians of their obligation to return to the site in case of febrile illness. This contact will be implemented through appropriate methods that may differ in each trial site (eg, phone calls, text messaging, home visits, school-based surveillance).

According to one embodiment such a method does not include vaccine immunogenicity analysis including GMTs for dengue neutralizing antibodies.

According to one embodiment such a method does not include a reactogenicity analysis. Such a reactogenicity analysis relates to solicited local AEs (injection site pain, injection site erythema, and injection site swelling) and solicited systemic AEs (child <6 years: fever, irritability/fussiness, drowsiness and loss of appetite; child ≥6 years: asthenia, fever, headache, malaise and myalgia) which will e.g. be assessed for 7 days and 14 days, respectively, following each vaccination (vaccination day included) via collection of diary cards.

According to one embodiment the method does not include an active surveillance, an immunogenicity analysis and a reactogenicity analysis.

According to such embodiments the vaccine and the corresponding method of inoculation are safe and therefore do not require further steps of surveillance or analysis.

In view of the above according to one embodiment the use is directed to a method comprises a primary vaccination consisting of the steps of:

(A) selecting a subject for administration of the unit doses of the tetravalent dengue virus composition in need for protection against dengue infection without determination of a previous dengue infection, and (B) administering a first unit dose of the tetravalent dengue virus composition to the subject, and (C) administering a second unit dose of the tetravalent dengue virus composition to the subject within 3 months of administration of the first unit dose.

Therefore the method of inoculating is finalized without determination of a previous dengue infection. The method however further optionally comprises at least 1 years after the administration of the second unit dose a booster dose of the unit dose.

Selecting the subject may include all types of considerations but preferably not the determination of a previous dengue infection. The selection may include consideration of the age, health conditions, and threat of infection. The threat of infection includes consideration of the seroprevalence rate in the region in which the subject normally lives or intends to travel, the serotype specific seroprevalence rate and an outbreak situation or serotype specific outbreak situations. The subject may be selected due to its exposure to serotype 1 and/or serotype 2 or due to the fact it requires protection against a specific dengue serotype, i.e. serotype 1 and/or serotype 2.

According to the invention the method is applicable to subjects of all kinds of ages. According to one embodiment the subject is under 9 years of age, or 4 to 5 years of age, or 6 to 11 years of age or 12 to 16 years, or 6 to 16 years of age or 4 to 16 years of age, or 2 to 17 years of age, or 9 years of age, or over 9 years of age, or 9 to 17 years of age, or 18 to 45 years of age, or 46 to 60 years of age, or over 60 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 10%, and the concentration of (iv) in pfu/0.5 mL is preferably at least 50%, and the concentration of (i) in pfu/0.5 mL is preferably at least 1%, and the concentration of (iii) in pfu/0.5 mL is preferably at least 8%, or more preferred at least 10%, or at least 12%, or at least 14%, or at least 16%, or at least 18% and the subject is 2 to 17 years of age or 4 to 16 years of age.

According to certain such embodiments the unit dose of the tetravalent dengue virus composition comprising (i), (ii), (iii), and (iv) upon reconstitution with a pharmaceutically acceptable diluent provides a total concentration of pfu/0.5 mL of (i), (ii), (iii), and (iv) and based on said total concentration the concentration of (ii) in pfu/0.5 mL is preferably less than 2%, the concentration of (iv) in pfu/0.5 mL is preferably at least 50%, the concentration of (i) in pfu/0.5 mL is at preferably least 1%, and the concentration of (iii) in pfu/0.5 mL is preferably at least 6% and the subject is 18 to 60 years of age.

Any method described herein above under the heading "Method of preventing" is to be understood to be also disclosed as the use of a unit dose for the manufacture of a medicament for preventing dengue disease in a subject or subject population with such a method irrespective of whether it is expressly stated below.

Further specific embodiments are described below.

The present invention is in part directed to the use of a unit dose of the invention as described herein for the manufacture of a medicament for preventing dengue disease in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein for the manufacture of a medicament for preventing dengue disease in a subject, comprising administering to the subject at least a first reconstituted unit dose of the invention as described herein, wherein certain ratios of neutralizing antibody titers at day 180 or 365 after administration of said first unit dose to the subject are achieved. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with the microneutralization test disclosed herein, for example according to the method described in Example 2.

In certain embodiments the invention is directed to said uses, wherein the reconstituted unit dose of the invention as described herein is administered by subcutaneous injection. According to some of these embodiments the subcutaneous injection is administered to the arm, preferably to the deltoid region of the arm.

In certain embodiments the invention is directed to said uses, wherein one reconstituted unit dose of the invention as described is administered by subcutaneous injection. According to some of these embodiments, the subcutaneous injection is administered to the arm, preferably to the deltoid region of the arm.

In certain embodiments the invention is directed to said uses, wherein two reconstituted unit doses of the invention as described herein are administered. In one embodiment, the two unit doses are administered within 12 months or more, or within six months, or within three months, such as at day 0 and day 90 or at day 1/0 and day 90. According to some of these embodiments a third unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments of the invention the subject is seronegative with respect to all dengue serotypes.

In certain other embodiments of the invention the subject is seropositive with respect to at least one dengue serotype.

In certain embodiments the invention is directed to said uses, wherein the reconstituted unit dose is administered to the seronegative subject by subcutaneous injection.

In certain embodiments the invention is directed to said uses, wherein the reconstituted unit dose is administered to a subject of unknown serostatus and/or wherein no test has been carried out to determine whether the subject is seropositive or seronegative before the unit dose is administered.

In certain embodiments the invention is directed to said uses, wherein the reconstituted unit dose of the invention as described herein is administered to a subject or subject population from a dengue endemic region. In some of these embodiments, the subject or subject population is from Singapore, Dominican Republic, Panama, Philippines, Colombia, Puerto Rico or Thailand, in particular from Singapore, Dominican Republic, Panama, or Philippines. In other embodiments, the subject or subject population is from a dengue non-endemic region. Such a subject population or subject may be vaccinated according to the invention in the context of traveling to a dengue endemic region. In certain embodiments, the reconstituted unit dose of the invention as described herein is administered subcutaneously to a subject or subject population from a dengue endemic region or from a dengue non-endemic region.

In certain embodiments the invention is directed to said uses, wherein the subject is of 2 to 60 years of age or more than 17 years, or more than 18 years, or 18 to 60 years of age. In certain embodiments the subject is 1 to 17 years of age, or less than 9 years of age, or less than 4 years of age or less than 2 years of age. In further embodiments, the subjects or subject population are adults of more than 21 years, or 21 to 60 years, or 21 to 45 years of age. According to some of these embodiments the subject is seronegative and from a dengue-endemic region.

In certain embodiments, the invention is directed to said uses, wherein the unit dose of the invention as described herein is administered to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

In certain embodiments, the invention is directed to said uses, wherein the reconstituted unit dose of the invention as described herein is administered subcutaneously to a pediatric subject or pediatric subject population of less than 2 years of age, preferably of 2 months to 2 years of age or 2 months to 1.5 years of age or 2 months to 1 year of age. According to some of these embodiments, the pediatric subject or pediatric subject population is seronegative and from a dengue endemic region.

The present invention is directed in part to the use of a unit dose of the invention as described herein for the manufacture of a medicament for preventing dengue disease in an elderly subject.

The present invention is directed in part to the use of a unit dose of the invention as described herein for the manufacture of a medicament for preventing dengue hemorrhagic fever (DHF) and dengue shock syndrome (DSS) in an elderly subject.

In certain embodiments the invention is directed to said uses, wherein the reconstituted unit dose of the invention as described herein is administered by subcutaneous injection. According to some of these embodiments the subcutaneous injection is administered to the arm, preferably to the deltoid region of the arm.

In certain embodiments the invention is directed to said uses, wherein two reconstituted unit doses of the invention as described herein are administered. In one embodiment, the two unit doses are administered within 12 months or more, or within six months, or within three months, such as at day 0/1 and day 90. According to some of these embodiments a third unit dose of the invention as described herein may be administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments of the invention the elderly subject is seronegative with respect to all dengue serotypes.

In certain other embodiments of the invention the elderly subject is seropositive with respect to at least one dengue serotype.

In certain embodiments the invention is directed to said uses, wherein the reconstituted unit dose is administered to the seronegative elderly subject by subcutaneous injection.

In certain embodiments the invention is directed to said uses, wherein the reconstituted unit dose of the invention as described herein is administered to an elderly subject from a dengue endemic region. In some of these embodiments, the elderly subject is from Singapore, Dominican Republic, Panama, Philippines, Colombia, Puerto Rico or Thailand, in particular from Singapore, Dominican Republic, Panama, or Philippines. In other embodiments, the elderly subject is from a dengue non-endemic region. Such an elderly subject may be vaccinated according to the invention in the context of traveling to a dengue endemic region. In certain embodiments, the reconstituted unit dose of the invention as described herein is administered subcutaneously to an elderly subject from a dengue endemic region or from a dengue non-endemic region.

In certain embodiments, the invention is directed to said uses, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to said uses, wherein the elderly subject has an impaired immune system.

Method of Preventing Dengue Disease and Yellow Fever and Uses

Method of Prevention

The present invention is directed in part to a method of preventing dengue disease as well as yellow fever in a subject. Thus, in certain embodiments the invention is directed to a method of preventing dengue disease in a subject, comprising administering to the subject a reconstituted unit dose of the invention as described herein, wherein the method further comprises preventing yellow fever in the subject by concomitant administration of a yellow fever vaccine, in particular YF-17D, to the subject.

The present invention is directed in part to a method of preventing dengue disease as well as yellow fever in a subject population. Thus, in certain embodiments the invention is directed to a method of preventing dengue disease in a subject population, comprising administering to the subject population a reconstituted unit dose of the invention as described herein, wherein the method further comprises preventing yellow fever in the subject population by concomitant administration of a yellow fever vaccine, in particular YF-17D, to the subject population.

The present invention is in part directed to said method for preventing dengue disease and yellow fever in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a yellow fever vaccine, in particular YF-17D, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and yellow fever in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a yellow fever vaccine, in particular YF-17D, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the yellow fever vaccine, in particular YF-17D, are administered simultaneously. In some of these embodiments the simultaneous administration is on day 0 or day 90, preferably on day 0. In other embodiments the administration of the unit dose of the invention as described herein and the yellow fever vaccine, in particular YF-17D, are done sequentially.

In certain embodiments the invention is directed to said methods, wherein the reconstituted unit dose of the invention as described herein is administered and the yellow fever vaccine, in particular YF-17D, are administered by subcutaneous injection. According to some embodiments, the subcutaneous injections are administered to the arm, preferably to the deltoid region of the arm. According to some of these embodiments the subcutaneous injections of the unit dose of the invention as described herein and yellow fever vaccine, in particular YF-17D, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and one dose of a yellow fever vaccine, in particular YF-17D, are administered, in particular according to the following schedule

- an administration of said yellow fever vaccine on day 0,
- a first administration of the first reconstituted unit dose after said yellow fever vaccine administration, such as 3 months later and preferably on day 90, and
- a second administration of the second reconstituted unit dose after said first administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule

- a first administration of the first reconstituted unit dose on day 0,
- a second administration of the second reconstituted unit dose after said first administration of the reconstituted unit dose, such as 3 months later and preferably on day 90, and
- an administration of said yellow fever vaccine after said second administration of the reconstituted unit dose, such as 3 months later and preferably on day 180.

In certain embodiments the invention is directed to said methods, wherein two reconstituted unit doses of the invention as described herein and one dose of a yellow fever vaccine, in particular YF-17D, are administered, in particular according to the following schedule

- a simultaneous administration of the first reconstituted unit dose and said yellow fever vaccine on day 0, and
- a second administration of the second reconstituted unit dose after said simultaneous administration, such as 3 months later and preferably on day 90.

In a preferred embodiment, the yellow fever vaccine and unit dose of the invention as described herein are administered simultaneously on day 0 or simultaneously on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the yellow fever vaccine, in particular YF-17D vaccine, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the yellow fever vaccine, in particular YF-17D, are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to said methods, wherein the reconstituted unit dose of the invention as described herein and of the yellow fever vaccine, in particular YF-17D, are administered subcutaneously to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and yellow fever non-endemic region. According to some of these embodiments, the subject or subject population are seronegative for all four dengue serotypes.

Unit Dose for Use in a Method of Prevention

The present invention is directed in part to the unit dose of the invention as described herein for use in a method of preventing dengue disease in a subject, wherein the method also comprises the prevention of yellow fever in the subject with a yellow fever vaccine, in particular YF-17D. In particular, the present invention is directed in part to a unit dose of a dengue vaccine composition as described herein and a yellow fever vaccine, in particular YF-17D, for use in a method of preventing dengue disease and yellow fever in a subject, respectively.

The present invention is directed in part to the unit dose of the invention as described herein for use in a method of preventing dengue disease in a subject population, wherein the method also comprises the prevention of yellow fever in the subject population with a yellow fever vaccine, in particular YF-17D. In particular, the present invention is directed in part to a unit dose of a dengue vaccine composition as described herein and a yellow fever vaccine, in particular YF-17D, for use in a method of preventing dengue disease and yellow fever in a subject population, respectively.

The present invention is in part directed to the unit dose of a dengue vaccine composition as described herein and the yellow fever vaccine, in particular YF-17D, for use in a method of preventing dengue disease and yellow fever in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a yellow fever vaccine, in particular YF-17D, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described 5 herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the yellow fever vaccine, in particular YF-17D, for use in a method of preventing dengue disease and yellow fever in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a yellow fever vaccine, in particular YF-17D, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the yellow fever vaccine, in particular YF-17D, for said uses, wherein said unit dose and said yellow fever vaccine are administered simultaneously. In some of these embodiments, the simultaneous administration is on day 0 or day 90, preferably on day 0. In other embodiments, the administration of said unit dose and said yellow fever vaccine, in particular YF-17D, are done sequentially.

In certain embodiments the invention is directed to the unit dose of the invention as described herein and the yellow fever vaccine, in particular YF-17D, for said uses, wherein said unit dose is administered by subcutaneous injection and wherein said yellow fever vaccine is administered by subcutaneous injection. According to some embodiments, the subcutaneous injections are administered to the arm, preferably to the deltoid region of the arm. According to some of these embodiments the subcutaneous injection of said unit dose and the subcutaneous injection of said yellow fever vaccine are administered to different anatomical sites, such as to opposite arms, in particular when the vaccines are administered simultaneously.

In certain embodiments the invention is directed to the unit dose of the invention as described herein and the yellow fever vaccine, in particular YF-17D, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the yellow fever vaccine, in particular YF-17D, for said uses, wherein two reconstituted unit doses of the invention as described herein and one dose of the yellow fever vaccine are administered, in particular according to the following schedule an administration of said yellow fever vaccine on day 0, a first administration of the first reconstituted unit dose after said yellow fever vaccine administration, such as 3 months later and preferably on day 90, and a second administration of the second reconstituted unit dose after said first administration of the reconstituted unit dose, such as 3 months later and preferably on day 180.

In another embodiment the invention is directed to the unit dose of the invention as described herein and the yellow fever vaccine, in particular YF-17D, for said uses, wherein two unit doses of the invention as described herein and one dose of the yellow fever vaccine are administered, in particular according to the following schedule a first administration of the first reconstituted unit on day 0, a second administration of the second reconstituted unit dose after said first administration of the reconstituted unit dose, such as 3 months later and preferably on day 90, and an administration of said yellow fever vaccine after said second administration of the reconstituted unit dose, such as 3 months later and preferably on day 180.

In another embodiment the invention is directed to the unit dose of the invention as described herein and the yellow fever vaccine, in particular YF-17D, for said uses, wherein two unit doses of the invention as described herein and one dose of the yellow fever vaccine are administered, in particular according to the following schedule a simultaneous administration of the first reconstituted unit dose and said yellow fever vaccine on day 0, and a second administration of the second reconstituted unit dose after said simultaneous administration, such as 3 months later and preferably on day 90.

In a preferred embodiment, the yellow fever vaccine and unit dose of the invention as described herein are administered simultaneously on day 0 or simultaneously on day 90.

In certain embodiments, the invention is directed to the unit dose of the invention as described herein and the yellow fever vaccine, in particular YF-17D, for said uses, wherein the subject or subject population is seronegative to all dengue serotypes. In certain embodiments, the invention is directed to the unit dose of the invention as described herein and the yellow fever vaccine, in particular YF-17D, for said uses, wherein said unit dose is reconstituted and administered subcutaneously to a subject or subject population and said yellow fever vaccine is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the yellow fever vaccine, in particular YF-17D, for said uses, wherein said unit dose and said yellow fever vaccine are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to the unit dose of the invention as described herein and the yellow fever vaccine, in particular YF-17D, for said uses, wherein the reconstituted unit dose of the invention as described herein and the yellow fever vaccine, in particular YF-17D, are administered subcutaneously to a subject or a subject population of more than 17 years, or more than 18 years, or 18 to 60 years of age. In some embodiments the subject or subject population is from a dengue endemic region. In another embodiment the subject or subject population is from a dengue non-endemic region, preferably from a dengue non-endemic and yellow fever non-endemic region. According to some of these embodiments, the subject or subject population is seronegative for all four dengue serotypes.

Use for the Manufacture of a Medicament in a Method of Prevention

The present invention is directed in part to the use of a unit dose of the invention as described herein for the manufacture of a medicament for preventing dengue disease in a subject, further comprising the use of a yellow fever vaccine, in particular YF-17D, for the manufacture of a medicament for preventing yellow fever in the subject. In particular, the present invention is directed in part to a use of a unit dose of a dengue vaccine composition as described herein and a yellow fever vaccine, in particular YF-17D, for the manufacture of a medicament for preventing dengue disease and yellow fever in a subject, respectively.

The present invention is directed in part to the use of a unit dose of the invention as described herein for the manufacture of a medicament for preventing dengue disease in a subject population, further comprising the use of a yellow fever vaccine, in particular YF-17D, for the manufacture of a medicament for preventing yellow fever in the subject population. In particular, the present invention is directed in part to a use of a unit dose of a dengue vaccine composition as described herein and a yellow fever vaccine, in particular YF-17D, for the manufacture of a medicament for preventing dengue disease and yellow fever in a subject population, respectively.

The present invention is in part directed to the use of a unit dose of the invention as described herein and a yellow fever vaccine, in particular YF-17D, for the manufacture of a medicament for preventing dengue disease and yellow fever in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a yellow fever vaccine, in particular YF-17D, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a yellow fever vaccine, in particular YF-17D, for the manufacture of a medicament for preventing dengue disease and yellow fever in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a yellow fever vaccine, in particular YF-17D, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the yellow fever vaccine, in particular YF-17D, are administered simultaneously. In some of these embodiments the simultaneous administration is on day 0 or day 90, preferably on day 0. In other embodiments the administration of the unit dose of the invention as described herein and the yellow fever vaccine, in particular YF-17D, are done sequentially.

In certain embodiments the invention is directed to said uses, wherein the unit dose of the invention as described herein is reconstituted and administered by subcutaneous injection and wherein the yellow fever vaccine, in particular YF-17D, is administered by subcutaneous injection. According to some embodiments the injections are administered to the arm, preferably to the deltoid region of the arm. According to some of these embodiments the subcutaneous injection of the unit dose of the invention as described herein and of the yellow fever vaccine, in particular YF-17D, are administered to different anatomical sites such as to opposite arms, in particular when the vaccines are administered simultaneously.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and one dose of a yellow fever vaccine, in particular YF-17D, are administered, in particular according to the following schedule

- an administration of said yellow fever vaccine on day 0,
- a first administration of the first reconstituted unit dose after said yellow fever vaccine administration, such as 3 months later and preferably on day 90, and
- a second administration of the second reconstituted unit dose after said first administration of the reconstituted unit dose, such as 3 months later and preferably on day 180.

In certain embodiments the invention is directed to said uses, wherein two unit doses of the invention as described herein and one dose of a yellow fever vaccine, in particular YF-17D, are administered, in particular according to the following schedule

- a first administration of the first reconstituted unit dose on day 0,
- a second administration of the second reconstituted unit dose said first administration of the reconstituted unit dose, such as 3 months later and preferably on day 90, and
- an administration of said yellow fever vaccine after said second administration of the reconstituted unit dose, such as 3 months later and preferably on day 180.

In certain embodiments the invention is directed to said uses, wherein two unit doses of the invention as described herein and one dose of a yellow fever vaccine, in particular YF-17D, are administered, in particular according to the following schedule

- a simultaneous administration of the first reconstituted unit dose and said yellow fever vaccine on day 0, and
- a second administration of the second reconstituted unit dose after said simultaneous administration, such as 3 months later and preferably on day 90.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the yellow fever vaccine, in particular YF-17D, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the yellow fever vaccine, in particular YF-17D, are administered to a subject or subject population from a dengue endemic region. In certain embodiments, the reconstituted unit dose of the invention as described herein and the yellow fever vaccine, in particular YF-17D, are administered subcutaneously to a subject or subject population from a dengue endemic region. In other embodiments, the subject or subject population is from a dengue non-endemic region. Such a subject population or such a subject may be vaccinated according to the present invention in the context of traveling to a dengue endemic region and yellow fever endemic region.

In certain embodiments the invention is directed to said uses, wherein the reconstituted unit dose of the invention as described herein and the yellow fever vaccine, in particular YF-17D, are administered subcutaneously to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and yellow fever non-endemic region. According to some of these embodiments, the subject or subject population is seronegative for all four dengue serotypes.

Method of Preventing Dengue Disease and Hepatitis a and Uses

Method of Prevention

The present invention is directed in part to a method of preventing dengue disease as well as hepatitis A in a subject. Thus, in certain embodiments the invention is directed to a method of preventing dengue disease in a subject, comprising administering to the subject a reconstituted unit dose of the invention as described herein, wherein the method further comprises preventing hepatitis A in the subject by concomitant administration of a hepatitis A vaccine, such as HAVRIX® or VAQTA®, to the subject.

The present invention is directed in part to a method of preventing dengue disease as well as hepatitis A in a subject population. Thus, in certain embodiments the invention is directed to a method of preventing dengue disease in a subject population, comprising administering to the subject population a reconstituted unit dose of the invention as described herein, wherein the method further comprises preventing hepatitis A in the subject population by concomitant administration of a hepatitis A vaccine, such as HAVRIX® or VAQTA®, to the subject population.

The present invention is in part directed to said method for preventing dengue disease and hepatitis A in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a hepatitis A vaccine, such as HAVRIX® or VAQTA®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or nor more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and hepatitis A in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a hepatitis A vaccine, such as HAVRIX® or VAQTA®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the hepatitis A vaccine, such as HAVRIX® or VAQTA®, are administered simultaneously. In some of these embodiments, the simultaneous administration is on day 0 or day 90, preferably on day 0. In other embodiments, the administration of the unit dose of the invention as described herein and the hepatitis A vaccine, such as HAVRIX® or VAQTA®, are done sequentially.

In certain embodiments, the invention is directed to said methods, wherein the reconstituted unit dose of the invention as described herein is administered by subcutaneous injection and wherein the hepatitis A vaccine, such as HAVRIX® or VAQTA®, is administered by intramuscular injection. According to some embodiments, the injections are administered to the arm, preferably to the deltoid region of the arm. According to some of these embodiments, the subcutaneous injection of the reconstituted unit dose of the invention as described herein and the intramuscular injection of the hepatitis A vaccine, such as HAVRIX® or VAQTA®, are administered to different anatomical sites, such as to opposite arms, in particular when the vaccines are administered simultaneously.

In certain embodiments, the invention is directed to said methods, wherein two unit doses of the invention as described herein are administered. In some embodiments, the two unit doses of the invention as described herein are administered within 12 month or more, or within 6 month, or within three months, such as at day 0/1 and day 90. According to some of these embodiments, a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to said methods, wherein two reconstituted unit doses of the invention as described herein and one dose of a hepatitis A vaccine, such as HAVRIX® or VAQTA®, are administered, in particular according to the following schedule a first simultaneous administration of the first reconstituted unit dose and said hepatitis A vaccine on day 0, and a second administration of the second reconstituted unit dose after said first simultaneous administration, such as 3 months later and preferably on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the hepatitis A vaccine, such as HAVRIX® or VAQTA®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the hepatitis A vaccine, such as HAVRIX® or VAQTA®, are administered to a subject or subject population from a dengue endemic region. In certain embodiments, the reconstituted unit dose of the invention as described herein is administered subcutaneously and the hepatitis A vaccine, such as HAVRIX® or VAQTA®, is administered intramuscularly to a subject or subject population from a dengue endemic region.

According to some embodiments, a second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 9 months after the first administration of the hepatitis A vaccine, such as on day 270.

In certain embodiments, the invention is directed to said methods, wherein the reconstituted unit dose of the invention as described herein is administered subcutaneously and wherein the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and a hepatitis A non-endemic region. According to certain embodiments, the subject or subject population is seronegative for all four dengue serotypes.

Unit Dose for Use in a Method of Prevention

The present invention is directed in part to the unit dose of the invention as described herein for use in a method of preventing dengue disease in a subject, wherein the method also comprises the prevention of hepatitis A in the subject with a hepatitis A vaccine, such as HAVRIX® or VAQTA®. In particular, the present invention is directed in part to a unit dose of a dengue vaccine composition as described herein and a hepatitis A vaccine, such as HAVRIX® or VAQTA®, for use in a method of preventing dengue disease and hepatitis A in a subject, respectively.

The present invention is directed in part to the unit dose of the invention as described herein for use in a method of preventing dengue disease in a subject population, wherein the method also comprises the prevention of hepatitis A in the subject population with a hepatitis A vaccine, such as HAVRIX® or VAQTA®. In particular, the present invention is directed in part to a unit dose of a dengue vaccine composition as described herein and a hepatitis A vaccine, such as HAVRIX® or VAQTA®, for use in a method of preventing dengue disease and hepatitis A in a subject population, respectively.

The present invention is in part directed to the unit dose of a dengue vaccine composition as described herein and the hepatitis A vaccine, such as HAVRIX® or VAQTA®, for use in a method of preventing dengue disease and hepatitis A in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a hepatitis A vaccine, such as HAVRIX® or VAQTA®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the hepatitis A vaccine, such as HAVRIX® or VAQTA®, for use in a method of preventing dengue disease and hepatitis A in a subject comprising administering to the subject a hepatitis A vaccine, such as HAVRIX® or VAQTA®, and at least a first reconstituted unit dose of the invention as described herein, wherein certain ratios of neutralizing antibody titers at day 180 or 365 after administration of said first unit dose to the subject are achieved, and concomitantly administering a hepatitis A vaccine, such as HAVRIX® or VAQTA®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20, wherein the method further comprises preventing hepatitis A in the subject by concomitant administration of a hepatitis A vaccine, such as HAVRIX® or VAQTA®, to the subject. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the hepatitis A vaccine, such as HAVRIX® or VAQTA®, for said uses, wherein said unit dose and said hepatitis A vaccine are administered simultaneously. In some of these embodiments, the simultaneous administration is on day 0 or day 90, preferably on day 0. In other embodiments, the administration of said unit dose and said hepatitis A vaccine are done sequentially.

In certain embodiments the invention is directed to the unit dose of the invention as described herein and the hepatitis A vaccine, such as HAVRIX® or VAQTA®, for said uses, wherein said unit dose is administered by subcutaneous injection and wherein said hepatitis A vaccine is administered by intramuscular injection. According to some embodiments, the injections are administered to the arm, preferably to the deltoid region of the arm. According to some of these embodiments, the subcutaneous injection of said unit dose and the intramuscular injection of said hepatitis A vaccine are administered to different anatomical sites, such as to opposite arms, in particular when the vaccines are administered simultaneously.

In certain embodiments, the invention is directed to the unit dose of the invention as described herein and the hepatitis A vaccine, such as HAVRIX® or VAQTA®, for said uses, wherein two reconstituted unit doses of the invention as described herein are administered. In some embodiments, the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to the unit dose of the invention as described herein and the hepatitis A vaccine, such as HAVRIX® or VAQTA®, for said uses, wherein two reconstituted unit doses of the invention as described herein and one dose of the hepatitis A vaccine are administered, in particular according to the following schedule a first simultaneous administration of the first reconstituted unit dose and a dose of said hepatitis A vaccine on day 0, and a second administration of the second reconstituted unit dose after said first simultaneous administration, such as 3 months later and preferably on day 90.

In certain embodiments, the invention is directed to the unit dose of the invention as described herein and the hepatitis A vaccine, such as HAVRIX® or VAQTA®, for said uses, wherein the subject or subject population is seronegative to all dengue serotypes. In certain embodiments, the invention is directed to the unit dose of the invention as described herein and the hepatitis A vaccine, such as HAVRIX® or VAQTA®, for said uses, wherein said unit dose is reconstituted and administered subcutaneously to a subject or subject population and said hepatitis A vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the hepatitis A vaccine, such as HAVRIX® or VAQTA®, for said uses, wherein said unit dose and said hepatitis A vaccine are administered to a subject or subject population from a dengue endemic region. In certain embodiments, the reconstituted unit dose of the invention as described herein is administered subcutaneously and the hepatitis A vaccine, such as HAVRIX® or VAQTA®, is administered intramuscularly to a subject or subject population from a dengue endemic region.

In certain embodiments, the invention is directed to the unit dose of the invention as described herein and the hepatitis A vaccine, such as HAVRIX® or VAQTA®, for said uses, wherein a further second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 9 months after the first administration of the hepatitis A vaccine, such as on day 270.

In some embodiments, the invention is directed to the unit dose of the invention as described herein and the hepatitis A vaccine, such as HAVRIX® or VAQTA®, for said uses, wherein the reconstituted unit dose of the invention as described herein is administered subcutaneously and the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and a hepatitis A non-endemic region. According to certain embodiments, the subject or subject population is seronegative for all four dengue serotypes.

Use for the Manufacture of a Medicament in a Method of Prevention

The present invention is directed in part to the use of a unit dose of the invention as described herein for the manufacture of a medicament for preventing dengue disease in a subject, further comprising the use of a hepatitis A vaccine, such as HAVRIX® or VAQTA®, for the manufacture of a medicament for preventing hepatitis A in the subject. In particular, the present invention is directed in part to a use of a unit dose of a dengue vaccine composition as described herein and a hepatitis A vaccine, such as HAVRIX® or VAQTA®, for the manufacture of a medicament for preventing dengue disease and hepatitis A in a subject, respectively.

The present invention is directed in part to the use of a unit dose of the invention as described herein for the manufacture of a medicament for preventing dengue disease in a subject population, further comprising the use of a hepatitis A vaccine, such as HAVRIX® or VAQTA®, for the manufacture of a medicament for preventing hepatitis A in the subject population. In particular, the present invention is directed in part to a use of a unit dose of a dengue vaccine composition as described herein and a hepatitis A vaccine, such as HAVRIX® or VAQTA®, for the manufacture of a medicament for preventing dengue disease and hepatitis A in a subject population, respectively.

The present invention is in part directed to the use of a unit dose of the invention as described herein and a hepatitis A vaccine, such as HAVRIX® or VAQTA®, for the manufacture of a medicament for preventing dengue disease and hepatitis A in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved and concomitantly administering a hepatitis A vaccine, such as HAVRIX® or VAQTA®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a hepatitis A vaccine, such as HAVRIX® or VAQTA®, for the manufacture of a medicament for preventing dengue disease and hepatitis A in a subject, comprising administering to the subject at least a first reconstituted unit dose of the invention as described herein, wherein certain ratios of neutralizing antibody titers at day 180 or 365 after administration of said first unit dose to the subject are achieved and concomitantly administering a hepatitis A vaccine, such as HAVRIX® or VAQTA®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the hepatitis A vaccine, such as HAVRIX® or VAQTA®, are administered simultaneously. In some of these embodiments, the simultaneous administration is on day 0 or day 90, preferably on day 0. In other embodiments, the administration of the unit dose of the invention as described herein and the hepatitis A vaccine, such as HAVRIX® or VAQTA®, are done sequentially.

In certain embodiments the invention is directed to said uses, wherein the unit dose of the invention as described herein is reconstituted and administered by subcutaneous injection and wherein the hepatitis A vaccine, such as HAVRIX® or VAQTA®, is administered by intramuscular injection. According to some embodiments, the injections are administered to the arm, preferably to the deltoid region of the arm. According to some embodiments the subcutaneous injection of the unit dose of the invention as described herein and the intramuscular injection of the hepatitis A vaccine, such as HAVRIX® or VAQTA®, are administered to different anatomical sites, such as to opposite arms, in particular when the vaccines are administered simultaneously.

In certain embodiments, the invention is directed to said uses, wherein two reconstituted unit doses of the invention as described herein are administered. In some embodiments, the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and one dose of a hepatitis A vaccine, such as HAVRIX® or VAQTA®, are administered, in particular according to the following schedule

- a first simultaneous administration of the first reconstituted unit dose and said hepatitis A vaccine on day 0, and
- a second administration of the second reconstituted unit dose after said first simultaneous administration, such as 3 months later and preferably on day 90.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the hepatitis A vaccine, such as HAVRIX® or VAQTA®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the hepatitis A vaccine, such as HAVRIX® or VAQTA®, are administered to a subject or subject population from a dengue endemic region. In certain embodiments, the reconstituted unit dose of the invention as described herein is administered subcutaneously and the hepatitis A vaccine, such as HAVRIX® or VAQTA®, is administered intramuscularly to a subject or subject population from a dengue endemic region.

In certain embodiments, the invention is directed to said uses, wherein a further second dose of a hepatitis A vaccine, such as HAVRIX® or VAQTA®, is administered. The second dose of the hepatitis A vaccine may be administered after the first administration of the hepatitis A vaccine. Such a second administration may act as a booster and may be administered 9 months after the first administration of the hepatitis A vaccine such as on day 270.

In certain embodiments, the invention is directed to said uses, wherein the reconstituted unit dose of the invention as described herein is administered subcutaneously and the hepatitis A vaccine, such as HAVRIX® or VAQTA®, is administered intramuscularly to a subject or subject population of more than 17 years, or more than 18 years, or 18 to 60 years of age. In further embodiments, the subjects or subject population are adults of more than 21 years, or 21 to 60 years, or 21 to 45 years of age. In some embodiments, the subject or subject population is from a dengue endemic region. In another embodiment, the subject or subject population is from a dengue non-endemic region, preferably from a dengue non-endemic and hepatitis A non-endemic region. According to some of these embodiments, the subject or subject population is seronegative for all four dengue serotypes.

Method of Preventing Dengue Disease and HPV Associated Diseases and Uses

Method of Prevention

The present invention is directed in part to a method of preventing dengue disease as well as HPV-associated cancers or genital warts in a subject. Thus, in certain embodiments the invention is directed to a method of preventing dengue disease in a subject, comprising administering to the subject a reconstituted unit dose of the invention as described herein, wherein the method further comprises preventing HPV-associated cancers or genital warts in the subject by concomitant administration of a HPV vaccine, in particular a 9vHPV vaccine, such as GARDASIL® 9, to the subject.

The present invention is directed in part to a method of preventing dengue disease as well as HPV-associated cancers or genital warts in a subject population. Thus, in certain embodiments the invention is directed to a method of preventing dengue disease in a subject population, comprising administering to the subject population a reconstituted unit dose of the invention as described herein, wherein the method further comprises preventing HPV-associated cancers or genital warts in the subject population by concomitant administration of a HPV vaccine, in particular a 9vHPV vaccine, such as GARDASIL® 9, to the subject population.

The present invention is in part directed to said method for preventing dengue disease and HPV-associated cancers or genital warts in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a HPV vaccine, in particular a 9vHPV vaccine, such as GARDASIL® 9, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and HPV-associated cancers or genital warts in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a HPV vaccine, in particular a 9vHPV vaccine, such as GARDASIL® 9, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the HPV vaccine, in particular a 9vHPV vaccine, such as GARDASIL® 9, are administered simultaneously. In some of these embodiments the simultaneous administration is on day 0 or day 90, preferably on day 0. In other embodiments the administration of the unit dose of the invention as described herein and the HPV vaccine, in particular a 9vHPV vaccine, such as GARDASIL® 9, are done sequentially.

In certain embodiments the invention is directed to said methods, wherein the reconstituted unit dose of the invention as described herein is administered by subcutaneous injection and wherein the HPV vaccine, in particular a 9vHPV vaccine, such as GARDASIL® 9, is administered by intramuscular injection. According to some embodiments the injections are administered to the arm, preferably to the deltoid region of the arm. According to some of these embodiments the subcutaneous injection of the unit dose of the invention as described herein and the intramuscular injection of the HPV vaccine, in particular a 9vHPV vaccine, such as GARDASIL® 9, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and two doses of a HPV vaccine, in particular a 9vHPV vaccine, such as GARDASIL® 9, are administered, in particular according to the following schedule

- a first simultaneous administration of the first reconstituted unit dose and the first dose of said HPV vaccine on day 0,
- a second administration of the second reconstituted unit dose after said first simultaneous administration, such as 3 month later and preferably on day 90, and
- a third administration of the second dose of said HPV vaccine after said second administration of the reconstituted unit dose, such as 3 month later and preferably on day 180.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the HPV vaccine, in particular a 9vHPV vaccine, such as GARDASIL® 9, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the HPV vaccine, in particular a 9vHPV vaccine, such as GARDASIL® 9, are administered to a subject or subject population from a dengue endemic region. In certain embodiments, the reconstituted unit dose of the invention as described herein is administered subcutaneously and the HPV vaccine, in particular a 9vHPV vaccine, such as GARDASIL® 9, is administered intramuscularly to a subject or subject population from a dengue endemic region.

In certain embodiments the invention is directed to said methods, wherein the reconstituted unit dose of the invention as described herein is administered subcutaneously and wherein the HPV vaccine, in particular a 9vHPV vaccine, such as GARDASIL® 9, is administered intramuscularly to a subject or subject population of 9 to 26 years of age, preferably 9 to 15 years of age. In some embodiments the subject or subject population is from a dengue endemic region. According to some of these embodiments, the subject or subject population is female. According to some of these embodiments, the subject or subject population is seronegative for all four dengue serotypes.

In a preferred embodiment the invention is directed to a method of preventing dengue disease and HPV-associated cancers or genital warts in a subject comprising administering to the subject a subcutaneous injection of the reconstituted unit dose of the invention as described herein and an intramuscular injection of the HPV vaccine, in particular a 9vHPV vaccine, such as GARDASIL® 9, according to the above described administration schedule, wherein the subject is a female subject of 9 to 15 years of age from a dengue endemic region.

Unit Dose for Use in a Method of Prevention

The present invention is directed in part to the unit dose of the invention as described herein for use in a method of preventing dengue disease in a subject, wherein the method also comprises the prevention of HPV-associated cancers or genital warts in the subject with a HPV vaccine, in particular a 9vHPV vaccine, such as GARDASIL® 9. In particular, the present invention is directed in part to a unit dose of a dengue vaccine composition as described herein and a HPV vaccine, in particular a 9vHPV vaccine, such as GARDASIL® 9, for use in a method of preventing dengue disease and HPV-associated cancers or genital warts in a subject, respectively.

The present invention is directed in part to the unit dose of the invention as described herein for use in a method of preventing dengue disease in a subject population, wherein the method also comprises the prevention of HPV-associated cancers or genital warts in the subject population with a HPV vaccine, in particular a 9vHPV vaccine, such as GARDASIL® 9. In particular, the present invention is directed in part to a unit dose of a dengue vaccine composition as described herein and a HPV vaccine, in particular a 9vHPV vaccine, such as GARDASIL® 9, for use in a method of preventing dengue disease and HPV-associated cancers or genital warts in a subject population, respectively.

The present invention is in part directed to the unit dose of a dengue vaccine composition as described herein and the HPV vaccine, in particular a 9vHPV vaccine, such as GARDASIL® 9, for use in a method of preventing dengue disease and HPV-associated cancers or genital warts in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a HPV vaccine, in particular a 9vHPV vaccine, such as GARDASIL® 9, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the HPV vaccine, in particular a 9vHPV vaccine, such as GARDASIL® 9, for use in a method of preventing dengue disease and HPV-associated cancers or genital warts in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a HPV vaccine, in particular a 9vHPV vaccine, such as GARDASIL® 9, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the HPV vaccine, in particular a 9vHPV vaccine, such as GARDASIL® 9, for said uses, wherein said unit dose and said HPV vaccine are administered simultaneously. In some of these embodiments the simultaneous administration is on day 0 or day 90, preferably on day 0. In other embodiments the administration of said unit dose and said HPV vaccine are done sequentially.

In certain embodiments the invention is directed to the unit dose of the invention as described herein and the HPV vaccine, in particular a 9vHPV vaccine, such as GARDASIL® 9, for said uses, wherein said unit dose is administered by subcutaneous injection and wherein said HPV vaccine is administered by intramuscular injection. According to some embodiments the injections are administered to the arm, preferably to the deltoid region of the arm. According to some of these embodiments the subcutaneous injection of said unit dose and the intramuscular injection of said HPV vaccine are administered to different anatomical sites, such as to opposite arms, in particular when the vaccines are administered simultaneously.

In certain embodiments the invention is directed to the unit dose of the invention as described herein and the HPV vaccine, in particular a 9vHPV vaccine, such as GARDASIL® 9, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the HPV vaccine, in particular a 9vHPV vaccine, such as GARDASIL® 9, for said uses, wherein two reconstituted unit doses of the invention as described herein and two doses of the HPV vaccine are administered, in particular according to the following schedule

- a first simultaneous administration of the first reconstituted unit dose and the first dose of said HPV vaccine on day 0,
- a second administration of the second reconstituted unit dose after said first simultaneous administration, such as 3 month later and preferably on day 90, and
- a third administration of the second dose of said HPV vaccine after said second administration of the reconstituted unit dose, such as 3 month later and preferably on day 180.

In certain embodiments, the invention is directed to the unit dose of the invention as described herein and the HPV vaccine, in particular a 9vHPV vaccine, such as GARDASIL® 9, for said uses, wherein the subject or subject population is seronegative to all dengue serotypes. In certain embodiments, the invention is directed to the unit dose of the invention as described herein and the HPV vaccine, in particular a 9vHPV vaccine, such as GARDASIL® 9, for said uses, wherein said unit dose is reconstituted and administered subcutaneously to a subject or subject population and said HPV vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the HPV vaccine, in particular a 9vHPV vaccine, such as GARDASIL® 9, for said uses, wherein said unit dose and said HPV vaccine are administered to a subject or subject population from a dengue endemic region. In certain embodiments, the reconstituted unit dose of the invention as described herein is administered subcutaneously and the HPV vaccine, in particular a 9vHPV vaccine, such as GARDASIL® 9, is administered intramuscularly to a subject or subject population from a dengue endemic region.

In certain embodiments the invention is directed to the unit dose of the invention as described herein and the HPV vaccine, in particular a 9vHPV vaccine, such as GARDASIL® 9, for said uses, wherein the reconstituted unit dose of the invention as described herein is administered subcutaneously and wherein the HPV vaccine, in particular a 9vHPV vaccine, such as GARDASIL® 9, is administered intramuscular to a subject or subject population of 9 to 25 years of age, preferably of 9 to 15 years of age. In some embodiments the subject or subject population is from a dengue endemic region. According to some of these embodiments, the subject or subject population is female. According to some of these embodiments, the subject or subject population is seronegative for all four dengue serotypes.

In a preferred embodiment the invention is directed to the unit dose of the invention as described herein and the HPV vaccine, in particular a 9vHPV vaccine, such as GARDASIL® 9, for use in a method of preventing dengue disease and HPV-associated cancers or genital warts in a subject comprising administering to the subject a subcutaneous injection of the reconstituted unit dose of the invention as described herein and an intramuscular injection of the HPV vaccine, in particular a 9vHPV vaccine, such as GARDASIL® 9, according to the above described administration schedule, wherein the subject is a female subject of 9 to 15 years of age from a dengue endemic region.

Use for the Manufacture of a Medicament in a Method of Prevention

The present invention is directed in part to the use of a unit dose of the invention as described herein for the manufacture of a medicament for preventing dengue disease in a subject, further comprising the use of a HPV vaccine, in particular a 9vHPV vaccine, such as GARDASIL® 9, for the manufacture of a medicament for preventing HPV-associated cancers or genital warts in the subject. In particular, the present invention is directed in part to a use of a unit dose of a dengue vaccine composition as described herein and a HPV vaccine, in particular a 9vHPV vaccine, such as GARDASIL® 9, for the manufacture of a medicament for preventing dengue disease and HPV-associated cancers or genital warts in a subject, respectively.

The present invention is directed in part to the use of a unit dose of the invention as described herein for the manufacture of a medicament for preventing dengue disease in a subject population, further comprising the use of a HPV vaccine, in particular a 9vHPV vaccine, such as GARDASIL® 9, for the manufacture of a medicament for preventing HPV-associated cancers or genital warts in the subject population. In particular, the present invention is directed in part to a use of a unit dose of a dengue vaccine composition as described herein and a HPV vaccine, in particular a 9vHPV vaccine, such as GARDASIL® 9, for the manufacture of a medicament for preventing dengue disease and HPV-associated cancers or genital warts in a subject population, respectively.

The present invention is in part directed to the use of a unit dose of the invention as described herein and a HPV vaccine, in particular a 9vHPV vaccine, such as GARDASIL® 9, for the manufacture of a medicament for preventing dengue disease and HPV-associated cancers or genital warts in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a HPV vaccine, in particular a 9vHPV vaccine, such as GARDASIL® 9, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a HPV vaccine, in particular a 9vHPV vaccine, such as GARDASIL® 9, for the manufacture of a medicament for preventing dengue disease and HPV-associated cancers or genital warts in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a HPV vaccine, in particular a 9vHPV vaccine, such as GARDASIL® 9, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the HPV vaccine, in particular a 9vHPV vaccine, such as GARDASIL® 9, are administered simultaneously. In some of these embodiments the simultaneous administration is on day 0 or day 90, preferably on day 0. In other embodiments the administration of the unit dose of the invention as described herein and the HPV vaccine, in particular a 9vHPV vaccine, such as GARDASIL® 9, are done sequentially.

In certain embodiments the invention is directed to said uses, wherein the unit dose of the invention as described herein is reconstituted and administered by subcutaneous injection and wherein the HPV vaccine, in particular a 9vHPV vaccine, such as GARDASIL® 9, is administered by intramuscular injection. According to some embodiments the injections are administered to the arm, preferably to the deltoid region of the arm. According to some of these embodiments the subcutaneous injection of the unit dose of the invention as described herein and the intramuscular injection of the HPV vaccine, in particular a 9vHPV vaccine, such as GARDASIL® 9, are administered to different anatomical sites such as to opposite arms, in particular when the vaccines are administered simultaneously.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and two doses of a HPV vaccine, in particular a 9vHPV vaccine, such as GARDASIL® 9, are administered, in particular according to the following schedule

- a first simultaneous administration of the first reconstituted unit dose and the first dose of said HPV vaccine on day 0,
- a second administration of the second reconstituted unit dose after said simultaneous administration, such as 3 month later and preferably on day 90, and
- a third administration of the second dose of said HPV vaccine after said second administration of the reconstituted unit dose, such as 3 month later and preferably on day 180.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the HPV vaccine, in particular a 9vHPV vaccine, such as GARDASIL® 9, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the HPV vaccine, in particular a 9vHPV vaccine, such as GARDASIL® 9, are administered to a subject or subject population from a dengue endemic region. In certain embodiments, the reconstituted unit dose of the invention as described herein is administered subcutaneously and the HPV vaccine, in particular a 9vHPV vaccine, such as GARDASIL® 9, is administered intramuscularly to a subject or subject population from a dengue endemic region.

In certain embodiments the invention is directed to said uses, wherein the reconstituted unit dose of the invention as described herein is administered subcutaneously and the HPV vaccine, in particular a 9vHPV vaccine, such as GARDASIL® 9, is administered intramuscularly to a subject or subject population of 9 years to 25 years of age, preferably of 9 to 15 years of age. In some embodiments the subject or subject population is from a dengue endemic region. According to some of these embodiments, the subject or subject population is female. According to some of these embodiments, the subject or subject population is seronegative for all four dengue serotypes.

In a preferred embodiment the invention is directed to the use of a unit dose of a dengue vaccine composition as described herein and a HPV vaccine, in particular a 9vHPV vaccine, such as GARDASIL® 9, for the manufacture of a medicament for preventing dengue disease and HPV-associated cancers or genital warts in a subject comprising administering to the subject a subcutaneous injection of the reconstituted unit dose of the invention as described herein and an intramuscular injection of the HPV vaccine, in particular a 9vHPV vaccine, such as GARDASIL® 9, according to the above described administration schedule, wherein the subject is a female subject of 9 to 15 years of age from a dengue endemic region.

Method of Preventing Dengue Disease and Measles, Mumps and Rubella and Uses

Method of Prevention

The present invention is directed in part to a method of preventing dengue disease as well as measles, mumps and rubella in a subject. Thus, in certain embodiments the invention is directed to a method of preventing dengue disease in a subject, comprising administering to the subject a reconstituted unit dose of the invention as described herein, wherein the method further comprises preventing measles, mumps and rubella in the subject by concomitant administration of a MMR vaccine, such as M-M-R® II, to the subject.

The present invention is directed in part to a method of preventing dengue disease as well as measles, mumps and rubella in a subject population. Thus, in certain embodiments the invention is directed to a method of preventing dengue disease in a subject population, comprising administering to the subject population a reconstituted unit dose of the invention as described herein, wherein the method further comprises preventing measles, mumps and rubella in the subject population by concomitant administration of a MMR vaccine, such as M-M-R® II, to the subject population.

The present invention is in part directed to said method for preventing dengue disease and measles, mumps and rubella in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a MMR vaccine, such as M-M-R® II, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and measles, mumps and rubella in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a MMR vaccine, such as M-M-R® II, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the MMR vaccine, such as M-M-R® II, are administered simultaneously. In some of these embodiments the simultaneous administration is on day 0 or day 90, preferably on day 0. In other embodiments the administration of the unit dose of the invention as described herein and the MMR vaccine, such as M-M-R® II, are done sequentially.

In certain embodiments the invention is directed to said methods, wherein the reconstituted unit dose of the invention as described herein is administered by subcutaneous injection and wherein the MMR vaccine, such as M-M-R® II, is administered by subcutaneous injection. According to some embodiments the injections are administered to the arm, preferably to the deltoid region of the arm. According to some of these embodiments the subcutaneous injection of the unit dose of the invention as described herein and the subcutaneous injection of the MMR vaccine, such as M-M-R® II, are administered to different anatomical sites, such as to opposite arms, in particular when the vaccines are administered simultaneously.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and two doses of a MMR vaccine, such as M-M-R® II, are administered, in particular according to the following schedule

- a first simultaneous administration of the first reconstituted unit dose and the first dose of said MMR vaccine on day 0,
- a second administration of the second reconstituted unit dose after said first simultaneous administration, such as 3 months later and preferably on day 90, and
- a third administration of the second dose of said MMR vaccine after said second administration of the second reconstituted unit dose, such as 3 to 6 years after said first simultaneous administration.

In certain embodiments, the invention is directed to said methods, wherein the subject or subject population is seronegative to all dengue serotypes. In certain embodiments, the invention is directed to said methods, wherein the reconstituted unit dose of the invention as described herein and the MMR vaccine, such as M-M-R® II, are administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the MMR vaccine, such as M-M-R® II, are administered to a subject or subject population from a dengue endemic region. In certain embodiments, the reconstituted unit dose of the invention as described herein and the MMR vaccine, such as M-M-R® II, are administered subcutaneously to a subject or subject population from a dengue endemic region.

In certain embodiments the invention is directed to said methods, wherein the reconstituted unit dose of the invention as described herein and wherein the MMR vaccine, such as M-M-R® II, are administered subcutaneously to a subject or subject population of 1 to 10 years of age, preferably 2 months to 7 years of age. In some embodiments the subject or subject population is from a dengue endemic region. In another embodiment, the subject or subject population is from a dengue non-endemic region. According to some of these embodiments, the subject or subject population is seronegative for all four dengue serotypes.

Unit Dose for Use in a Method of Prevention

The present invention is directed in part to the unit dose of the invention as described herein for use in a method of preventing dengue disease in a subject, wherein the method also comprises the prevention of measles, mumps and rubella in the subject with a MMR vaccine, such as M-M-R® II. In particular, the present invention is directed in part to a unit dose of a dengue vaccine composition as described herein and a MMR vaccine, such as M-M-R® II, for use in a method of preventing dengue disease and measles, mumps and rubella in a subject, respectively.

The present invention is directed in part to the unit dose of the invention as described herein for use in a method of preventing dengue disease in a subject population, wherein the method also comprises the prevention of measles, mumps and rubella in the subject population with a MMR vaccine, such as M-M-R® II. In particular, the present invention is directed in part to a unit dose of a dengue vaccine composition as described herein and a MMR vaccine, such as M-M-R® II, for use in a method of preventing dengue disease and measles, mumps and rubella in a subject population, respectively.

The present invention is in part directed to the unit dose of a dengue vaccine composition as described herein and the MMR vaccine, such as M-M-R® II, for use in a method of preventing dengue disease and measles, mumps and rubella in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a MMR vaccine, such as M-M-R® II, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the MMR vaccine, such as M-M-R® II, for use in a method of preventing dengue disease and measles, mumps and rubella in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a MMR vaccine, such as M-M-R® II, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2: neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the MMR vaccine, such as M-M-R® II, for said uses, wherein said unit dose and said MMR vaccine are administered simultaneously. In some of these embodiments the simultaneous administration is on day 0 or day 90, preferably on day 0. In other embodiments the administration of said unit dose and said MMR vaccine are done sequentially.

In certain embodiments the invention is directed to the unit dose of the invention as described herein and the MMR vaccine, such as M-M-R® II, for said uses, wherein said unit dose is administered by subcutaneous injection and wherein said MMR vaccine is administered by subcutaneous injection. According to some embodiments the injections are administered to the arm, preferably to the deltoid region of the arm. According to some of these embodiments the subcutaneous injection of said unit dose and the subcutaneous injection of said MMR vaccine are administered to different anatomical sites, such as to opposite arms, in particular when the vaccines are administered simultaneously.

In certain embodiments the invention is directed to the unit dose of the invention as described herein and the MMR vaccine, such as M-M-R® II, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the MMR vaccine, such as M-M-R® II, for said uses, wherein two reconstituted unit doses of the invention as described herein and two doses of the MMR vaccine are administered, in particular according to the following schedule

- a first simultaneous administration of the first reconstituted unit dose and the first dose of said MMR vaccine on day 0,
- a second administration of the second reconstituted unit dose after said first simultaneous administration, such as 3 months later and preferably on day 90, and
- a third administration of the second dose of said MMR vaccine after said second administration of the second reconstituted unit dose, such as 3 to 6 years after said first simultaneous administration.

In certain embodiments, the invention is directed to the unit dose of the invention as described herein and the MMR vaccine, such as M-M-R® II, for said uses, wherein the subject or subject population is seronegative to all dengue serotypes. In certain embodiments, the invention is directed to the unit dose of the invention as described herein and the MMR vaccine, such as M-M-R® II, for said uses, wherein said unit dose is reconstituted and administered subcutaneously to a subject or subject population and said MMR vaccine is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the MMR vaccine, such as M-M-R® II, for said uses, wherein said unit dose and said MMR vaccine are administered to a subject or subject population from a dengue endemic region. In certain embodiments, the reconstituted unit dose of the invention as described herein and the MMR vaccine, such as M-M-R® II, are administered subcutaneously to a subject or subject population from a dengue endemic region.

In certain embodiments the invention is directed to the unit dose of the invention as described herein and the MMR vaccine, such as M-M-R® II, for said uses, wherein the reconstituted unit dose of the invention as described herein and the MMR vaccine, such as M-M-R® II, are administered subcutaneously to a subject or subject population of 1 to 10 years of age, preferably of 2 months to 7 years of age. In some embodiments, the subject or subject population is from a dengue endemic region. In another embodiment, the subject or subject population is from a dengue non-endemic region. According to some of these embodiments, the subject or subject population is seronegative for all four dengue serotypes.

Use for the Manufacture of a Medicament in a Method of Prevention

The present invention is directed in part to the use of a unit dose of the invention as described herein for the manufacture of a medicament for preventing dengue disease in a subject, further comprising the use of a MMR vaccine, such as M-M-R® II, for the manufacture of a medicament for preventing measles, mumps and rubella in the subject. In particular, the present invention is directed in part to a use of a unit dose of a dengue vaccine composition as described herein and a MMR vaccine, such as M-M-R® II, for the manufacture of a medicament for preventing dengue disease and measles, mumps and rubella in a subject, respectively.

The present invention is directed in part to the use of a unit dose of the invention as described herein for the manufacture of a medicament for preventing dengue disease in a subject population, further comprising the use of a MMR vaccine, such as M-M-R® II, for the manufacture of a medicament for preventing measles, mumps and rubella in the subject population. In particular, the present invention is directed in part to a use of a unit dose of a dengue vaccine composition as described herein and a MMR vaccine, such as M-M-R® II, for the manufacture of a medicament for preventing dengue disease and measles, mumps and rubella in a subject population, respectively.

The present invention is in part directed to the use of a unit dose of the invention as described herein and a MMR vaccine, such as M-M-R® II, for the manufacture of a medicament for preventing dengue disease and measles, mumps and rubella in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a MMR vaccine, such as M-M-R® II, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a MMR vaccine, such as M-M-R® II, for the manufacture of a medicament for preventing dengue disease and measles, mumps and rubella in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a MMR vaccine, such as M-M-R® II, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the MMR vaccine, such as M-M-R® II, are administered simultaneously. In some of these embodiments the simultaneous administration is on day 0 or day 90, preferably on day 0. In other embodiments the administration of the unit dose of the invention as described herein and the MMR vaccine, such as M-M-R® II, are done sequentially.

In certain embodiments the invention is directed to said uses, wherein the unit dose of the invention as described herein is reconstituted and administered by subcutaneous injection and wherein the MMR vaccine, such as M-M-R® II, is administered by subcutaneous injection. According to some embodiments the injections are administered to the arm, preferably to the deltoid region of the arm. According to some of these embodiments the subcutaneous injection of the unit dose of the invention as described herein and the subcutaneous injection of the MMR vaccine, such as M-M-R® II, are administered to different anatomical sites such as to opposite arms, in particular when the vaccines are administered simultaneously.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and two doses of a MMR vaccine, such as M-M-R® II, are administered, in particular according to the following schedule

- a first simultaneous administration of the first reconstituted unit dose and the first dose of said MMR vaccine on day 0,
- a second administration of the second reconstituted unit dose after said first simultaneous administration, such as 3 months later and preferably on day 90, and
- a third administration of the second dose of said MMR vaccine after said second administration of the second reconstituted unit dose, such as 3 to 6 years after said first simultaneous administration.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the MMR vaccine, such as M-M-R® II, is administered subcutaneously to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the MMR vaccine, such as M-M-R® II, are administered to a subject or subject population from a dengue endemic region. In certain embodiments, the reconstituted unit dose of the invention as described herein and the MMR vaccine, such as M-M-R® II, are administered subcutaneously to a subject or subject population from a dengue endemic region.

In certain embodiments the invention is directed to said uses, wherein the reconstituted unit dose of the invention as described herein and the MMR vaccine, such as M-M-R® II, are administered subcutaneously to a subject or subject population of 1 to 10 years of age, preferably of 2 months to 7 years of age. In some embodiments, the subject or subject population is from a dengue endemic region. In another embodiment, the subject or subject population is from a dengue non-endemic region. According to some of these embodiments, the subject or subject population is seronegative for all four dengue serotypes.

Method of Preventing Dengue Disease and Tetanus, Diphtheria, and Pertussis and Uses

Method of Prevention

The present invention is directed in part to a method of preventing dengue disease, as well as tetanus, diphtheria, and pertussis in a subject. Thus, in certain embodiments the invention is directed to a method of preventing dengue disease in a subject, comprising administering to the subject a reconstituted unit dose of the invention as described herein, wherein the method further comprises preventing tetanus, diphtheria, and pertussis in the subject by concomitant administration of a Tdap vaccine, in particular a combined tetanus toxoid, reduced diphtheria toxoid and acellular pertussis (adsorbed) vaccine, such as BOOSTRIX®, to the subject.

The present invention is directed in part to a method of preventing dengue disease, as well as tetanus, diphtheria, and pertussis in a subject population. Thus, in certain embodiments the invention is directed to a method of preventing dengue disease, in a subject population, comprising administering to the subject population a reconstituted unit dose of the invention as described herein, wherein the method further comprises preventing tetanus, diphtheria, and pertussis in the subject population by concomitant administration of a Tdap vaccine, in particular a combined tetanus toxoid, reduced diphtheria toxoid and acellular pertussis (adsorbed) vaccine, such as BOOSTRIX®, to the subject population.

The present invention is in part directed to said method for preventing dengue disease and tetanus, diphtheria, and pertussis in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a Tdap vaccine, in particular a combined tetanus toxoid, reduced diphtheria toxoid and acellular pertussis (adsorbed) vaccine, such as BOOSTRIX®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or nor more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and tetanus, diphtheria, and pertussis in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a Tdap vaccine, in particular a combined tetanus toxoid, reduced diphtheria toxoid and acellular pertussis (adsorbed) vaccine, such as BOOSTRIX®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered simultaneously. In some of these embodiments, the simultaneous administration is on day 0 or day 90, preferably on day 0. In other embodiments, the administration of the unit dose of the invention as described herein and the Tdap vaccine, in particular combined tetanus toxoid, reduced diphtheria toxoid and acellular pertussis (adsorbed) vaccine, such as BOOSTRIX®, are done sequentially.

In certain embodiments, the invention is directed to said methods, wherein the reconstituted unit dose of the invention as described herein is administered by subcutaneous injection and wherein the Tdap vaccine, in particular a combined tetanus toxoid, reduced diphtheria toxoid and acellular pertussis (adsorbed) vaccine, such as BOOSTRIX®, is administered by intramuscular injection. According to some embodiments, the injections are administered to the arm, preferably to the deltoid region of the arm. According to some of these embodiments, the subcutaneous injection of the unit dose of the invention as described herein and the intramuscular injection of the Tdap vaccine, in particular a combined tetanus toxoid, reduced diphtheria toxoid and acellular pertussis (adsorbed) vaccine, such as BOOSTRIX®, are administered to different anatomical sites, such as to opposite arms, in particular when the vaccines are administered simultaneously.

In certain embodiments, the invention is directed to said methods, wherein two unit doses of the invention as described herein are administered. In some embodiments, the two unit doses of the invention as described herein are administered within 12 months or more, or within 6 months, or within 3 months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to said methods, wherein two reconstituted unit doses of the invention as described herein and one dose of a Tdap vaccine, in particular a combined tetanus toxoid, reduced diphtheria toxoid and acellular pertussis (adsorbed) vaccine, such as BOOSTRIX®, are administered, in particular according to the following schedule:

- a first simultaneous administration of the first reconstituted unit dose and said Tdap vaccine on day 0, and
- a second administration of the second reconstituted unit dose after said first simultaneous administration, such as 3 months later and preferably on day 90.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the Tdap vaccine, in particular a combined tetanus toxoid, reduced diphtheria toxoid and acellular pertussis (adsorbed) vaccine, such as BOOSTRIX®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered to a subject or subject population from a dengue endemic region. In certain embodiments, the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population from a dengue endemic region.

In certain embodiments, the invention is directed to said methods, wherein the reconstituted unit dose of the invention as described herein is administered subcutaneously and wherein the Tdap vaccine, in particular a combined tetanus toxoid, reduced diphtheria toxoid and acellular pertussis (adsorbed) vaccine, such as BOOSTRIX®, is administered intramuscularly to a subject or subject population of 10 to 18 years of age. In some embodiments, the subject or subject population is from a dengue endemic region. According to some of these embodiments, the subject or subject population is seronegative for all four dengue serotypes.

In a preferred embodiment, the invention is directed a method of preventing dengue disease, and tetanus, diphtheria and pertussis in a subject comprising administering to the subject a subcutaneous injection of the reconstituted unit dose of the invention as described herein and an intramuscular injection of the Tdap vaccine, in particular a combined tetanus toxoid, reduced diphtheria toxoid and acellular pertussis (adsorbed) vaccine, such as BOOSTRIX®, according to the above described administration schedule, wherein the subject is between 10 years and 18 years of age and from a dengue endemic region.

Unit Dose for Use in a Method of Prevention

The present invention is directed in part to the unit dose of the invention as described herein for use in a method of preventing dengue disease in a subject, wherein the method also comprises the prevention of tetanus, diphtheria, and pertussis in the subject with a Tdap vaccine, in particular a combined tetanus toxoid, reduced diphtheria toxoid and acellular pertussis (adsorbed) vaccine, such as BOOSTRIX®. In particular, the present invention is directed in part to a unit dose of a dengue vaccine composition as described herein and a Tdap vaccine, in particular a combined tetanus toxoid, reduced diphtheria toxoid and acellular pertussis (adsorbed) vaccine, such as BOOSTRIX®, for use in a method of preventing dengue disease, and tetanus, diphtheria, and pertussis in a subject, respectively.

The present invention is directed in part to the unit dose of the invention as described herein for use in a method of preventing dengue disease in a subject population, wherein the method also comprises the prevention of tetanus, diphtheria, and pertussis in a subject population with a Tdap vaccine, in particular a combined tetanus toxoid, reduced diphtheria toxoid and acellular pertussis (adsorbed) vaccine, such as BOOSTRIX®. In particular, the present invention is directed in part to a unit dose of a dengue vaccine composition as described herein and a Tdap vaccine, in particular a combined tetanus toxoid, reduced diphtheria toxoid and acellular pertussis (adsorbed) vaccine, such as BOOSTRIX®, for use in a method of preventing dengue disease, and tetanus, diphtheria, and pertussis in a subject population, respectively.

The present invention is in part directed to the unit dose of a dengue vaccine composition as described herein and the Tdap vaccine, in particular a combined tetanus toxoid, reduced diphtheria toxoid and acellular pertussis (adsorbed) vaccine, such as BOOSTRIX®, for use in a method of preventing dengue disease and tetanus, diphtheria, and pertussis in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a Tdap vaccine, in particular a combined tetanus toxoid, reduced diphtheria toxoid and acellular pertussis (adsorbed) vaccine, such as BOOSTRIX®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2: GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the Tdap vaccine, in particular a combined tetanus toxoid, reduced diphtheria toxoid and acellular pertussis (adsorbed) vaccine, such as BOOSTRIX®, for use in a method of preventing dengue disease and tetanus, diphtheria, and pertussis in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a Tdap vaccine, in particular a combined tetanus toxoid, reduced diphtheria toxoid and acellular pertussis (adsorbed) vaccine, such as BOOSTRIX®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for GMT DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose and said Tdap vaccine are administered simultaneously. In some of these embodiments, the simultaneous administration is on day 0 or day 90, preferably on day 0. In other embodiments the administration of said unit dose and said Tdap vaccine are done sequentially.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose is administered by subcutaneous injection and wherein said Tdap vaccine is administered by intramuscular injection. According to some embodiments, the injections are administered to the arm, preferably to the deltoid region of the arm. According to some of these embodiments, the subcutaneous injection of said unit dose and the intramuscular injection of said Tdap vaccine are administered to different anatomical sites, such as to opposite arms, in particular when the vaccines are administered simultaneously.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein two reconstituted unit doses of the invention as described herein are administered within 12 months or more, or within six months, or within three months, such as at day 0/1 and at day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 months after the first administration, such as 12 months (1 year) after the second administration or even 5 years or longer after the first or second administration.

In certain embodiments the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein two reconstituted unit doses of the invention as described herein and one dose of the Tdap vaccine are administered, in particular according to the following schedule

- a first simultaneous administration of the first reconstituted unit dose and said Tdap vaccine on day 0, and
- a second administration of the second reconstituted unit dose after said first simultaneous administration, such as 3 months later and preferably on day 90.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein the subject or subject population is seronegative to all dengue serotypes. In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose is reconstituted and administered subcutaneously to a subject or subject population and said Tdap vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein said unit dose and said Tdap vaccine are administered to a subject or subject population from a dengue endemic region. In certain embodiments, the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population from a dengue endemic region.

In certain embodiments the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for said uses, wherein the reconstituted unit dose of the invention as described herein is administered subcutaneously and wherein the Tdap vaccine, in particular a combined tetanus toxoid, reduced diphtheria toxoid and acellular pertussis (adsorbed) vaccine, such as BOOSTRIX®, is administered intramuscularly to a subject or subject population of 10 to 18 years of age. In some embodiments, the subject or subject population is from a dengue endemic region. According to some of these embodiments, the subject or subject population is seronegative for all four dengue serotypes.

In a preferred embodiment, the invention is directed to the unit dose of the invention as described herein and the Tdap vaccine, in particular a combined tetanus toxoid, reduced diphtheria toxoid and acellular pertussis (adsorbed) vaccine, such as BOOSTRIX®, for use in a method of preventing dengue disease and tetanus, diphtheria and pertussis in a subject comprising administering to the subject a subcutaneous injection of the reconstituted unit dose of the invention as described herein and an intramuscular injection of the Tdap vaccine, in particular a combined tetanus toxoid, reduced diphtheria toxoid and acellular pertussis (adsorbed) vaccine, such as BOOSTRIX®, according to the above described administration schedule, wherein the subject is of 10 to 18 years of age and from a dengue endemic region.

Use for the Manufacture of a Medicament in a Method of Prevention

The present invention is directed in part to the use of a unit dose of the invention as described herein for the manufacture of a medicament for preventing dengue disease in a subject, further comprising the use of a Tdap vaccine, in particular a combined tetanus toxoid, reduced diphtheria toxoid and acellular pertussis (adsorbed) vaccine, such as BOOSTRIX®, for the manufacture of a medicament for preventing tetanus, diphtheria, and pertussis in the subject. In particular, the present invention is directed in part to a use of a unit dose of a dengue vaccine composition as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis in a subject, respectively.

The present invention is directed in part to the use of a unit dose of the invention as described herein for the manufacture of a medicament for preventing dengue disease, in a subject population, further comprising the use of a Tdap vaccine, in particular a combined tetanus toxoid, reduced diphtheria toxoid and acellular pertussis (adsorbed) vaccine, such as BOOSTRIX®, for the manufacture of a medicament for preventing tetanus, diphtheria, and pertussis in the subject population. In particular, the present invention is directed in part to a use of a unit dose of a dengue vaccination composition as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis in a subject population, respectively.

The present invention is in part directed to the use of a unit dose of the invention as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a Tdap vaccine, in particular a combined tetanus toxoid, reduced diphtheria toxoid and acellular pertussis (adsorbed) vaccine, such as BOOSTRIX®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria, and pertussis in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a Tdap vaccine, in particular a combined tetanus toxoid, reduced diphtheria toxoid and acellular pertussis (adsorbed) vaccine, such as BOOSTRIX®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered simultaneously. In some of these embodiments, the simultaneous administration is on day 0 or day 90, preferably on day 0. In other embodiments, the administration of the unit dose of the invention as described herein and the Tdap vaccine, in particular a combined tetanus toxoid, reduced diphtheria toxoid and acellular pertussis (adsorbed) vaccine, such as BOOSTRIX®, are done sequentially.

In certain embodiments, the invention is directed to said uses, wherein the unit dose of the invention as described herein is reconstituted and administered by subcutaneous injection and wherein the Tdap vaccine, in particular a combined tetanus toxoid, reduced diphtheria toxoid and acellular pertussis (adsorbed) vaccine, such as BOOSTRIX®, is administered by intramuscular injection. According to some embodiments, the injections are administered to the arm, preferably to the deltoid region of the arm. According to some of these embodiments the subcutaneous injection of the unit dose of the invention as described herein and the intramuscular injection of the Tdap vaccine, in particular a combined tetanus toxoid, reduced diphtheria toxoid and acellular pertussis (adsorbed) vaccine, such as BOOSTRIX®, are administered to different anatomical sites, such as to opposite arms, in particular when the vaccines are administered simultaneously.

In certain embodiments, the invention is directed to said uses, wherein two reconstituted unit doses of the invention as described herein are administered. In some embodiments, the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments, the invention is directed to said uses, wherein two unit doses of the invention as described herein and one dose of a Tdap vaccine, in particular a combined tetanus toxoid, reduced diphtheria toxoid and acellular pertussis (adsorbed) vaccine, such as BOOSTRIX®, are administered, in particular according to the following schedule

- a first simultaneous administration of the first reconstituted unit dose and said Tdap vaccine on day 0, and
- a second administration of the second reconstituted unit dose after said first simultaneous administration, such as 3 months later and preferably on day 90.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the Tdap vaccine, in particular a combined tetanus toxoid, reduced diphtheria toxoid and acellular pertussis (adsorbed) vaccine, such as BOOSTRIX®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the Tdap vaccine, in particular a combined tetanus toxoid, reduced diphtheria toxoid and acellular pertussis (adsorbed) vaccine, such as BOOSTRIX®, are administered to a subject or subject population from a dengue endemic region. In certain embodiments, the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population from a dengue endemic region.

In certain embodiments, the invention is directed to said uses, wherein the reconstituted unit dose of the invention as described herein is administered subcutaneously and the Tdap vaccine, in particular a combined tetanus toxoid, reduced diphtheria toxoid and acellular pertussis (adsorbed) vaccine, such as BOOSTRIX®, is administered intramuscularly to a subject or subject population of 10 to 18 years of age. In some embodiments, the subject or subject population is from a dengue endemic region. According to some of these embodiments, the subject or subject population is seronegative for all four dengue serotypes.

In a preferred embodiment the invention is directed to the use of a unit dose of a dengue vaccine composition as described herein and the Tdap vaccine, in particular a combined tetanus toxoid, reduced diphtheria toxoid and acellular pertussis (adsorbed) vaccine, such as BOOSTRIX®, for the manufacture of a medicament for preventing dengue disease and tetanus, diphtheria and pertussis in a subject comprising administering to the subject a subcutaneous injection of the reconstituted unit dose of the invention as described herein and an intramuscular injection of the Tdap vaccine, in particular a combined tetanus toxoid, reduced diphtheria toxoid and acellular pertussis (adsorbed) vaccine, such as BOOSTRIX®, according to the above described administration schedule, wherein the subject is of 10 to 18 years of age and from a dengue endemic region.

Method of Preventing Dengue Disease and Diphtheria, Tetanus, Pertussis, Poliomyelitis and Diseases Caused by *Haemophilus influenzae* Type b and Uses

Method of Prevention

The present invention is directed in part to a method of preventing dengue disease as well as diphtheria, tetanus, pertussis, poliomyelitis and diseases caused by *Haemophilus*

*influenzae* type b in a subject. Thus, in certain embodiments the invention is directed to a method of preventing dengue disease in a subject, comprising administering to the subject a reconstituted unit dose of the invention as described herein, wherein the method further comprises preventing diphtheria, tetanus, pertussis, poliomyelitis and diseases caused by *Haemophilus influenzae* type b in the subject by concomitant administration of a DTaP/IPV/Hib vaccine, in particular a combined DTaP/IPV/Hib vaccine, such as Pentacel®, to the subject.

The present invention is directed in part to a method of preventing dengue disease as well as diphtheria, tetanus, pertussis, poliomyelitis and diseases caused by *Haemophilus influenzae* type b in a subject population. Thus, in certain embodiments the invention is directed to a method of preventing dengue disease in a subject population, comprising administering to the subject population a reconstituted unit dose of the invention as described herein, wherein the method further comprises preventing diphtheria, tetanus, pertussis, poliomyelitis and diseases caused by *Haemophilus influenzae* type b in the subject population by concomitant administration of a DTaP/IPV/Hib vaccine, in particular a combined DTaP/IPV/Hib vaccine, such as Pentacel®, to the subject population.

The present invention is in part directed to said method for preventing dengue disease and diphtheria, tetanus, pertussis, poliomyelitis and diseases caused by *Haemophilus influenzae* type b in a subject population comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a DTaP/IPV/Hib vaccine, in particular a combined DTaP/IPV/Hib vaccine, such as Pentacel®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to said method for preventing dengue disease and diphtheria, tetanus, pertussis, poliomyelitis and diseases caused by *Haemophilus influenzae* type b in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a DTaP/IPV/Hib vaccine, in particular a combined DTaP/IPV/Hib vaccine, such as Pentacel®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said methods, wherein the unit dose of the invention as described herein and the DTaP/IPV/Hib vaccine, in particular a combined DTaP/IPV/Hib vaccine, such as Pentacel®, are administered simultaneously. In some of these embodiments the simultaneous administration is on day 0 or day 90, preferably on day 0. In other embodiments the administration of the unit dose of the invention as described herein and the DTaP/IPV/Hib vaccine, in particular a combined DTaP/IPV/Hib vaccine, such as Pentacel®, are done sequentially.

In certain embodiments the invention is directed to said methods, wherein the reconstituted unit dose of the invention as described herein is administered by subcutaneous injection and wherein the DTaP/IPV/Hib vaccine, in particular a combined DTaP/IPV/Hib vaccine, such as Pentacel®, is administered by intramuscular injection. According to some embodiments, the unit dose of the invention as described herein is administered to the arm, preferably to the deltoid region of the arm. According to some embodiments, the subcutaneous injection of the unit dose of the invention as described herein and the intramuscular injection of the DTaP/IPV/Hib vaccine, in particular a combined DTaP/IPV/Hib vaccine, such as Pentacel®, are administered to different anatomical sites. According to some of these embodiments, said unit dose is administered subcutaneously to the arm, preferably to the deltoid region, and said DTaP/IPV/Hib vaccine is administered intramuscularly to the thigh, preferably to the anterolateral aspect of the thigh.

In certain embodiments the invention is directed to said methods, wherein two unit doses of the invention as described herein are administered. In some embodiments the two unit doses of the invention as described herein are administered within 12 month or more, or within 6 month, or within three months, such as at day 0/1 and day 90. According to some of these embodiments a further third unit dose of the invention as described herein is administered after the second. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said methods, wherein two reconstituted unit doses of the invention as described herein and four doses of a DTaP/IPV/Hib vaccine, in particular a combined DTaP/IPV/Hib vaccine, such as Pentacel®, are administered, in particular according to the following schedule

- a first simultaneous administration of the first reconstituted unit dose and the first dose of said DTaP/IPV/Hib vaccine on day 0,
- a second administration of the second dose of said DTaP/IPV/Hib vaccine after said first simultaneous administration, such as 2 months later and preferably on day 60,
- a third administration of the second reconstituted unit dose after said second administration, such as 3 months after the first simultaneous administration and preferably on day 90,
- a fourth administration of the third dose of said DTaP/IPV/Hib vaccine after said third administration, such as 4 months after the first simultaneous administration and preferably on day 120, and
- a fifth administration of the fourth dose of said DTaP/IPV/Hib vaccine after said fourth administration, such as 9 to 12 months later and preferably on day 390.

In certain embodiments the invention is directed to said methods, wherein two reconstituted unit doses of the invention as described herein and four doses of a DTaP/IPV/Hib vaccine, in particular a combined DTaP/IPV/Hib vaccine, such as Pentacel®, are administered, in particular according to the following schedule

- a first administration of the first dose of said DTaP/IPV/Hib vaccine on day 0,
- a second administration of the second dose of said DTaP/IPV/Hib vaccine after said first administration, such as 2 months later and preferably on day 60,
- a third administration of the third dose of said DTaP/IPV/Hib vaccine after said second administration, such as 4 months after the first administration and preferably on day 120,
- a fourth simultaneous administration of the first reconstituted unit dose and the fourth dose of said DTaP/IPV/Hib vaccine after said third administration, such as 9 to 12 months later and preferably on day 390, and
- a fifth administration of the second reconstituted unit dose after said fourth simultaneous administration, such as 3 months later and preferably on day 480.

According to some embodiments, a fifth dose of a DTaP/IPV/Hib vaccine, in particular a combined DTaP/IPV/Hib vaccine, such as Pentacel®, is administered after the administration of the fourth dose of said DTaP/IPV/Hib vaccine. For this purpose a commercially available combined diphtheria, tetanus, pertussis, and poliomyelitis (DTaP-IPV) vaccine marketed under the tradename Quadracel® from Sanofi Pasteur may be used. Quadracel® is a diphtheria and tetanus toxoids and acellular pertussis adsorbed and inactivated poliovirus vaccine and is indicated for active immunization against diphtheria, tetanus, pertussis and poliomyelitis. A single dose of Quadracel® is for use in children 4 through 6 years of age as a fifth dose in the diphtheria, tetanus, pertussis vaccination (DTaP) series and as a fourth or fifth dose in the inactivated poliovirus vaccination (IPV) series in children who have received 4 doses of Pentacel®. Accordingly, in some embodiments, a further sixth administration of a fifth dose of a DTaP/IPV/Hib vaccine, in particular a combined DTaP/IPV/Hib vaccine, such as Quadracel®, may be conducted 30 to 57 months after the administration of the fourth dose of a DTaP/IPV/Hib vaccine, in particular a combined DTaP/IPV/Hib vaccine, such as Pentacel®.

In certain embodiments, the invention is directed to said methods, wherein the subject or subject population is seronegative to all dengue serotypes. In certain embodiments, the invention is directed to said methods, wherein the reconstituted unit dose of the invention as described herein is administered subcutaneously to a subject or subject population and the DTaP/IPV/Hib vaccine, in particular a combined DTaP/IPV/Hib vaccine, such as Pentacel®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said methods, wherein the unit dose of the invention as described herein and the DTaP/IPV/Hib vaccine, in particular a combined DTaP/IPV/Hib vaccine, such as Pentacel®, are administered to a subject or subject population from a dengue endemic region. In certain embodiments, the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population from a dengue endemic region.

In certain embodiments the invention is directed to said methods, wherein the reconstituted unit dose of the invention as described herein is administered subcutaneously and wherein the DTaP/IPV/Hib vaccine, in particular a combined DTaP/IPV/Hib vaccine, such as Pentacel®, is administered intramuscularly to a subject or subject population of 2 months to 4 years of age. In some embodiments the subject or subject population is from a dengue endemic region. In other embodiments, the subject or subject population is from a dengue non-endemic region. According to some of these embodiments, the subject or subject population is seronegative for all four dengue serotypes.

In a preferred embodiment the invention is directed to a method of preventing dengue disease and diphtheria, tetanus, pertussis, poliomyelitis and diseases caused by *Haemophilus influenzae* type b in a subject comprising administering to the subject subcutaneous injections of the reconstituted unit dose of the invention as described herein and intramuscular injections of the DTaP/IPV/Hib vaccine, in particular a combined DTaP/IPV/Hib vaccine, such as Pentacel®, according to one of the above described administration schedule, wherein the subject is a subject of 2 months to 4 years of age from a dengue endemic region.

Unit Dose for Use in a Method of Prevention

The present invention is directed in part to the unit dose of the invention as described herein for use in a method of preventing dengue disease in a subject, wherein the method also comprises the prevention of diphtheria, tetanus, pertussis, poliomyelitis and diseases caused by *Haemophilus influenzae* type b in the subject with a DTaP/IPV/Hib vaccine, in particular a combined DTaP/IPV/Hib vaccine, such as Pentacel®. In particular, the present invention is directed in part to a unit dose of a dengue vaccine composition as described herein and a DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject, respectively.

The present invention is directed in part to the unit dose of the invention as described herein for use in a method of preventing dengue disease in a subject population, wherein the method also comprises the prevention of diphtheria, tetanus, pertussis, poliomyelitis and diseases caused by *Haemophilus influenzae* type b in the subject population with a DTaP/IPV/Hib vaccine, in particular a combined DTaP/IPV/Hib vaccine, such as Pentacel®. In particular, the present invention is directed in part to a unit dose of a dengue vaccine composition as described herein and a DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject population, respectively.

The present invention is in part directed to the unit dose of a dengue vaccine composition as described herein and the DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a DTaP/IPV/Hib vaccine, in particular a combined DTaP/IPV/Hib vaccine, such as Pentacel®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the unit dose of a dengue vaccine composition as described herein and the DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject comprising administering to the subject at least a first reconstituted unit dose of the invention as described herein, wherein certain ratios of neutralizing antibody titers at day 180 or 365 after administration of said first unit dose to the subject are achieved, and concomitantly administering a DTaP/IPV/Hib vaccine, in particular a combined DTaP/IPV/Hib vaccine, such as Pentacel®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to the unit dose of the invention as described herein and the DTaP/IPV/Hib vaccine, in particular a combined DTaP/IPV/Hib vaccine, such as Pentacel®, for said uses, wherein said unit dose and said DTaP/IPV/Hib vaccine are administered simultaneously. In some of these embodiments the simultaneous administration is on day 0 or day 90, preferably on day 0. In other embodiments the administration of said unit dose and said DTaP/IPV/Hib vaccine are done sequentially.

In certain embodiments the invention is directed to the unit dose of the invention as described herein and the DTaP/IPV/Hib vaccine, in particular a combined DTaP/IPV/Hib vaccine, such as Pentacel®, for said uses, wherein said unit dose is administered by subcutaneous injection and wherein said DTaP/IPV/Hib vaccine is administered by intramuscular injection. According to some embodiments, said unit dose is administered to the arm, preferably to the deltoid region of the arm. According to some embodiments, the subcutaneous injection of the unit dose of the invention as described herein and the intramuscular injection of the DTaP/IPV/Hib vaccine, in particular a combined DTaP/IPV/Hib vaccine, such as Pentacel®, are administered to different anatomical sites. According to some of these embodiments, said unit dose is administered subcutaneously to the arm, preferably to the deltoid region, and said DTaP/IPV/Hib vaccine is administered intramuscularly to the thigh, preferably to the anterolateral aspect of the thigh.

In certain embodiments the invention is directed to the unit dose of the invention as described herein and the DTaP/IPV/Hib vaccine, in particular a combined DTaP/IPV/Hib vaccine, such as Pentacel®, for said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third reconstituted unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to the unit dose of the invention as described herein and the DTaP/IPV/Hib vaccine, in particular a combined DTaP/IPV/Hib vaccine, such as Pentacel®, for said uses, wherein two reconstituted unit doses of the invention as described herein and four doses of the DTaP/IPV/Hib vaccine are administered, in particular according to the following schedule

- a first simultaneous administration of the first reconstituted unit dose and the first dose of said DTaP/IPV/Hib vaccine on day 0, a second administration of the second dose of said DTaP/IPV/Hib vaccine after said first simultaneous administration, such as 2 months later and preferably on day 60, a third administration of the second reconstituted unit dose after said second administration, such as 3 months after the first simultaneous administration and preferably on day 90, a fourth administration of the third dose of said DTaP/IPV/Hib vaccine after said third administration, such as 4 months after the first simultaneous administration and preferably on day 120, and a fifth administration of the fourth dose of said DTaP/IPV/Hib vaccine after said fourth administration, such as 9 to 12 months later and preferably on day 390.

In certain embodiments the invention is directed to the unit dose of the invention as described herein and the DTaP/IPV/Hib vaccine, in particular a combined DTaP/IPV/Hib vaccine, such as Pentacel®, for said uses, wherein two reconstituted unit doses of the invention as described herein and four doses of the DTaP/IPV/Hib vaccine are administered, in particular according to the following schedule a first administration of the first dose of said DTaP/IPV/Hib vaccine on day 0, a second administration of the second dose of said DTaP/IPV/Hib vaccine after said first administration, such as 2 months later and preferably on day 60, a third administration of the third dose of said DTaP/IPV/Hib vaccine after said second administration, such as 4 months after the first administration and preferably on day 120, a fourth simultaneous administration of the first reconstituted unit dose and the fourth dose of said DTaP/IPV/Hib vaccine after said third administration, such as 9 to 12 months later and preferably on day 390, and a fifth administration of the second reconstituted unit dose after said fourth simultaneous administration, such as 3 months later and preferably on day 480.

According to some embodiments, a fifth dose of a DTaP/IPV/Hib vaccine, in particular a combined DTaP/IPV/Hib vaccine, such as Pentacel®, is administered after the administration of the fourth dose of said DTaP/IPV/Hib vaccine. For this purpose a commercially available combined diphtheria, tetanus, pertussis, and poliomyelitis (DTaP-IPV) vaccine marketed under the tradename Quadracel® from Sanofi Pasteur may be used. Quadracel® is a diphtheria and tetanus toxoids and acellular pertussis adsorbed and inactivated poliovirus vaccine and is indicated for active immunization against diphtheria, tetanus, pertussis and poliomyelitis. A single dose of Quadracel® is for use in children 4 through 6 years of age as a fifth dose in the diphtheria, tetanus, pertussis vaccination (DTaP) series and as a fourth or fifth dose in the inactivated poliovirus vaccination (IPV) series in children who have received 4 doses of Pentacel®. Accordingly, in some embodiments, a further sixth administration of a fifth dose of a DTaP/IPV/Hib vaccine, in particular a combined DTaP/IPV/Hib vaccine, such as Quadracel®, may be conducted 30 to 57 months after the administration of the fourth dose of a DTaP/IPV/Hib vaccine, in particular a combined DTaP/IPV/Hib vaccine, such as Pentacel®.

In certain embodiments, the invention is directed to the unit dose of the invention as described herein and the DTaP/IPV/Hib vaccine, in particular a combined DTaP/IPV/Hib vaccine, such as Pentacel®, for said uses, wherein the subject or subject population is seronegative to all dengue serotypes. In certain embodiments, the invention is directed to the unit dose of the invention as described herein and the DTaP/IPV/Hib vaccine, in particular a combined DTaP/IPV/Hib vaccine, such as Pentacel®, for said uses, wherein said unit dose is reconstituted and administered subcutaneously to a subject or subject population and said DTaP/IPV/Hib vaccine is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to the unit dose of the invention as described herein and the DTaP/IPV/Hib vaccine, in particular a combined DTaP/IPV/Hib vaccine, such as Pentacel®, for said uses, wherein said unit dose and said DTaP/IPV/Hib vaccine are administered to a subject or subject population from a dengue endemic region. In certain embodiments, the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population from a dengue endemic region.

In certain embodiments the invention is directed to the unit dose of the invention as described herein and the DTaP/IPV/Hib vaccine, in particular a combined DTaP/IPV/Hib vaccine, such as Pentacel®, for said uses, wherein the reconstituted unit dose of the invention as described herein is administered subcutaneously and wherein the DTaP/IPV/Hib vaccine, in particular a combined DTaP/IPV/Hib vaccine, such as Pentacel®, is administered intramuscular to a subject or subject population of 2 months to 4 years of age. In some embodiments the subject or subject population is from a dengue endemic region. In other embodiments, the subject or subject population is from a dengue non-endemic region. According to some of these embodiments, the subject or subject population is seronegative for all four dengue serotypes.

In a preferred embodiment the invention is directed to the unit dose of the invention as described herein and the DTaP/IPV/Hib vaccine, in particular a combined DTaP/IPV/Hib vaccine, such as Pentacel®, for use in a method of preventing dengue disease and diphtheria, tetanus, pertussis, poliomyelitis and diseases caused by *Haemophilus influenzae* type b in a subject comprising administering to the subject subcutaneous injections of the reconstituted unit dose of the invention as described herein and intramuscular injections of the DTaP/IPV/Hib vaccine, in particular a combined DTaP/IPV/Hib vaccine, such as Pentacel®, according to one of the above described administration schedule, wherein the subject is a subject of 2 months to 4 years of age from a dengue endemic region.

Use for the Manufacture of a Medicament in a Method of Prevention

The present invention is directed in part to the use of a unit dose of the invention as described herein for the manufacture of a medicament for preventing dengue disease in a subject, further comprising the use of a DTaP/IPV/Hib vaccine, in particular a combined DTaP/IPV/Hib vaccine, such as Pentacel®, for the manufacture of a medicament for preventing diphtheria, tetanus, pertussis, poliomyelitis and diseases caused by *Haemophilus influenzae* type b in the subject. In particular, the present invention is directed in part to a use of a unit dose of a dengue vaccine composition as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject, respectively.

The present invention is directed in part to the use of a unit dose of the invention as described herein for the manufacture of a medicament for preventing dengue disease in a subject population, further comprising the use of a DTaP/IPV/Hib vaccine, in particular a combined DTaP/IPV/Hib vaccine, such as Pentacel®, for the manufacture of a medicament for preventing diphtheria, tetanus, pertussis, poliomyelitis and diseases caused by *Haemophilus influenzae* type b in the subject population. In particular, the present invention is directed in part to a use of a unit dose of a dengue vaccine composition as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject population, respectively.

The present invention is in part directed to the use of a unit dose of the invention as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject population, comprising administering to the subject population at least a first reconstituted unit dose of the invention as described herein, wherein certain ratios of geometric mean neutralizing antibody titers (GMTs) at day 180 or 365 after administration of said first unit dose to the subject population are achieved, and concomitantly administering a DTaP/IPV/Hib vaccine, in particular a combined DTaP/IPV/Hib vaccine, such as Pentacel®, to the subject population. According to some embodiments, the geometric mean neutralizing antibody titer for dengue serotype 2 (GMT DENV-2) and the geometric mean neutralizing antibody titer for dengue serotype 4 (GMT DENV-4) when tested in at least 40, or at least 50, or at least 60 subjects at day 180 or day 365 after at least a first administration of said reconstituted unit dose of the invention as described herein, and optionally a second administration of a reconstituted unit dose of the invention as described herein 90 days after said first administration, provide a ratio of GMT DENV-2:GMT DENV-4 of not more than 50, or not more than 40, or not more than 30, or not more than 20. In some of these embodiments, the ratio of GMT DENV-2:GMT DENV-1 is not more than 20, or not more than 18, or not more than 15 at day 180 or 365 after administration of said first reconstituted unit dose, and/or the ratio of GMT DENV-2:GMT DENV-3 is not more than 20, or not more than 18, or not more than 15 at day 180 or 365 after administration of said first reconstituted unit dose.

The present invention is in part directed to the use of a unit dose of the invention as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject, comprising administering to the subject at least a first reconstituted unit dose of the invention as described herein, wherein certain ratios of neutralizing antibody titers at day 180 or 365 after administration of said first unit dose to the subject are achieved, and concomitantly administering a DTaP/IPV/Hib vaccine, in particular a combined DTaP/IPV/Hib vaccine, such as Pentacel®, to the subject. According to some embodiments, the neutralizing antibody titer for dengue serotype 2 and the neutralizing antibody titer for dengue serotype 4 at day 180 or day 365 after at least a first administration of the reconstituted unit dose of the invention as described herein, and optionally a second administration of a reconstituted unit dose of the invention as described herein 90 days after said first administration, provide a ratio of neutralizing antibody titer for DENV-2:neutralizing antibody titer for DENV-4 of not more than 50, or not more than 40, or not more than 30, or not more than 20. In some of these embodiments, the ratio of the neutralizing antibody titers of DENV-2:DENV-1 is not more than 20, or not more than 18, or not more than 15 at day 180 or 365 after administration of said first reconstituted unit dose, and/or the ratio of the neutralizing antibody titers of DENV-2:DENV-3 is not more than 20, or not more than 18, or not more than 15 at day 180 or 365 after administration of said first reconstituted unit dose.

In some embodiments, the geometric mean neutralizing antibody titers (GMTs) of a subject population or the neutralizing antibody titers of a subject are determined in accordance with a microneutralization test, for example according to the method described in Example 2.

In certain embodiments the invention is directed to said uses, wherein the unit dose of the invention as described herein and the DTaP/IPV/Hib vaccine, in particular a combined DTaP/IPV/Hib vaccine, such as Pentacel®, are administered simultaneously. In some of these embodiments the simultaneous administration is on day 0 or day 90, preferably on day 0. In other embodiments the administration of the unit dose of the invention as described herein and the DTaP/IPV/Hib vaccine, in particular a combined DTaP/IPV/Hib vaccine, such as Pentacel®, are done sequentially.

In certain embodiments the invention is directed to said uses, wherein the unit dose of the invention as described herein is reconstituted and administered by subcutaneous injection and wherein the DTaP/IPV/Hib vaccine, in particular a combined DTaP/IPV/Hib vaccine, such as Pentacel®, is administered by intramuscular injection. According to some embodiments, the unit dose of the invention as described herein is administered to the arm, preferably to the deltoid region of the arm. According to some embodiments, the subcutaneous injection of the unit dose of the invention as described herein and the intramuscular injection of the DTaP/IPV/Hib vaccine, in particular a combined DTaP/IPV/Hib vaccine, such as Pentacel®, are administered to different anatomical sites. According to some of these embodiments, said unit dose is administered subcutaneously to the arm, preferably to the deltoid region, and said DTaP/IPV/Hib vaccine is administered intramuscularly to the thigh, preferably to the anterolateral aspect of the thigh.

In certain embodiments the invention is directed to said uses, wherein two reconstituted unit doses of the invention as described herein are administered. In some embodiments the two unit doses of the invention as described herein are administered within 12 months or more, or within six months, or within three months, such as at day 0/1 and day 90. According to some of these embodiments a further third unit dose of the invention as described herein is administered after the second administration. Such a third administration may act as a booster and may be administered between 6 to 12 months after the first administration, such as 12 months after the first administration, or later than 12 month after the first administration, such as 12 months (1 year) after the second administration or even 5 years or longer after the first or second administration.

In certain embodiments the invention is directed to said uses, wherein two unit doses of the invention as described herein and four doses of a DTaP/IPV/Hib vaccine, in particular a combined DTaP/IPV/Hib vaccine, such as Pentacel®, are administered, in particular according to the following schedule

- a first simultaneous administration of the first reconstituted unit dose and the first dose of said DTaP/IPV/Hib vaccine on day 0,
- a second administration of the second dose of said DTaP/IPV/Hib vaccine after said first simultaneous administration, such as 2 months later and preferably on day 60,
- a third administration of the second reconstituted unit dose after said second administration, such as 3 months after the first simultaneous administration and preferably on day 90,
- a fourth administration of the third dose of said DTaP/IPV/Hib vaccine after said third administration, such as 4 months after the first simultaneous administration and preferably on day 120, and
- a fifth administration of the fourth dose of said DTaP/IPV/Hib vaccine after said fourth administration, such as 9 to 12 months later and preferably on day 390.

In certain embodiments the invention is directed to said uses, wherein two unit doses of the invention as described herein and four doses of a DTaP/IPV/Hib vaccine, in particular a combined DTaP/IPV/Hib vaccine, such as Pentacel®, are administered, in particular according to the following schedule

- a first administration of the first dose of said DTaP/IPV/Hib vaccine on day 0,
- a second administration of the second dose of said DTaP/IPV/Hib vaccine after said first administration, such as 2 months later and preferably on day 60,
- a third administration of the third dose of said DTaP/IPV/Hib vaccine after said second administration, such as 4 months after the first administration and preferably on day 120,
- a fourth simultaneous administration of the first reconstituted unit dose and the fourth dose of said DTaP/IPV/Hib vaccine after said third administration, such as 9 to 12 months later and preferably on day 390, and
- a fifth administration of the second reconstituted unit dose after said fourth simultaneous administration, such as 3 months later and preferably on day 480.

According to some embodiments, a fifth dose of a DTaP/IPV/Hib vaccine, in particular a combined DTaP/IPV/Hib vaccine, such as Pentacel®, is administered after the administration of the fourth dose of said DTaP/IPV/Hib vaccine. For this purpose a commercially available combined diphtheria, tetanus, pertussis, and poliomyelitis (DTaP-IPV) vaccine marketed under the tradename Quadracel® from Sanofi Pasteur may be used. Quadracel® is a diphtheria and tetanus toxoids and acellular pertussis adsorbed and inactivated poliovirus vaccine and is indicated for active immunization against diphtheria, tetanus, pertussis and poliomyelitis. A single dose of Quadracel® is for use in children 4 through 6 years of age as a fifth dose in the diphtheria, tetanus, pertussis vaccination (DTaP) series and as a fourth or fifth dose in the inactivated poliovirus vaccination (IPV) series in children who have received 4 doses of Pentacel®. Accordingly, in some embodiments, a further sixth administration of a fifth dose of a DTaP/IPV/Hib vaccine, in particular a combined DTaP/IPV/Hib vaccine, such as Quadracel®, may be conducted 30 to 57 months after the administration of the fourth dose of a DTaP/IPV/Hib vaccine, in particular a combined DTaP/IPV/Hib vaccine, such as Pentacel®.

In certain embodiments, the invention is directed to said uses, wherein the subject or subject population is seronegative to all dengue serotypes. In certain embodiments, the invention is directed to said uses, wherein the unit dose of the invention as described herein is reconstituted and administered subcutaneously to a subject or subject population and the DTaP/IPV/Hib vaccine, in particular a combined DTaP/IPV/Hib vaccine, such as Pentacel®, is administered intramuscularly to a subject or subject population, and wherein the subject or the subject population is seronegative with respect to all dengue serotypes. In other embodiments, the subject or subject population is seropositive with respect to at least one dengue serotype.

In certain embodiments, the invention is directed to said uses, wherein the unit dose of the invention as described herein and the DTaP/IPV/Hib vaccine, in particular a combined DTaP/IPV/Hib vaccine, such as Pentacel®, are administered to a subject or subject population from a dengue endemic region. In certain embodiments, the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population from a dengue endemic region.

In certain embodiments the invention is directed to said uses, wherein the reconstituted unit dose of the invention as described herein is administered subcutaneously and the DTaP/IPV/Hib vaccine, in particular a combined DTaP/IPV/Hib vaccine, such as Pentacel®, is administered intramuscularly to a subject or subject population of 2 months to 4 years of age. In some embodiments the subject or subject population is from a dengue endemic region. In other embodiments, the subject or subject population is from a dengue non-endemic region. According to some of these embodiments, the subject or subject population is seronegative for all four dengue serotypes.

In a preferred embodiment the invention is directed to the use of a unit dose of a dengue vaccine composition as described herein and a DTaP/IPV/Hib vaccine, in particular a combined DTaP/IPV/Hib vaccine, such as Pentacel®, for the manufacture of a medicament for preventing dengue disease and diphtheria, tetanus, pertussis, poliomyelitis and diseases caused by *Haemophilus influenzae* type b in a subject comprising administering to the subject subcutaneous injections of the reconstituted unit dose of the invention as described herein and intramuscular injections of the DTaP/IPV/Hib vaccine, in particular a combined DTaP/IPV/Hib vaccine, such as Pentacel®, according to one of the above described administration schedule, wherein the subject is a subject of 2 months to 4 years of age from a dengue endemic region.

Method of Prevention Using Multiple Co-Vaccinations

In case multiple disease should be prevented the unit dose according to the invention (TDV) can be co-administered in at least any of the following combinations.

Double Vaccine Combinations:

TDV+YF, TDV+Hepatitis A, TDV+MMR, TDV+Tdap, TDV+DTap, or TDV+HPV

Triple Vaccine Combinations:

TDV+YF+Hepatitis A, TDV+YF+MMR, TDV+YF+Tdap, TDV+YF+Dtap, TDV+YF+HPV, TDV+Hepatitis A+MMR, TDV+Hepatitis A+Tdap, TDV+Hepatitis A+DTap, TDV+

Hepatitis A+HPV, TDV+MMR+Tdap, TDV+MMR+DTap, TDV+MMR+HPV, TDV+Tdap+DTap, TDV+Tdap+HPV, or TDV+DTap+HPV.

Quadruple Vaccine Combinations

TDV+YF+Hepatitis A+MMR, TDV+YF+Hepatitis A+Tdap, TDV+YF+Hepatitis A+DTap, TDV+YF+Hepatitis A+HPV, TDV+YF+MMR+Tdap, TDV+YF+MMR+DTap, TDV+YF+MMR+HPV, TDV+YF+Tdap+DTap, TDV+YF+Tdap+HPV, TDV+YF+DTap+HPV, TDV+Hepatitis A+MMR+Tdap, TDV+Hepatitis A+MMR+DTap, TDV+Hepatitis A+MMR+HPV, TDV+Hepatitis A+Tdap+DTap, TDV+Hepatitis A+Tdap+HPV, TDV+Hepatitis A+DTap+HPV, TDV+MMR+Tdap+DTap, TDV+MMR+Tdap+HPV, TDV+MMR+DTap+HPV, or TDV+Tdap+DTap+HPV.

Quintuple Vaccine Combinations

TDV+YF+Hepatitis A+MMR+Tdap, TDV+YF+Hepatitis A+MMR+Dtap, TDV+YF+Hepatitis A+MMR+HPV, TDV+YF+Hepatitis A+Tdap+DTap, TDV+YF+Hepatitis A+Tdap+HPV, TDV+YF+Hepatitis A+DTap+HPV, TDV+YF+MMR+Tdap+DTap, TDV+YF+MMR+Tdap+HPV, TDV+YF+MMR+DTap+HPV, TDV+YF+Tdap+DTap+HPV, TDV+Hepatitis A+MMR+Tdap+DTap, TDV+Hepatitis A+MMR+Tdap+HPV, TDV+Hepatitis A+MMR+DTap+HPV, TDV+Hepatitis A+Tdap+Dtap+HPV, or TDV+MMR+Tdap+DTap+HPV.

Sextuple Vaccine Combinations

TDV+YF+Hepatitis A+MMR+Tdap+DTap, TDV+YF+Hepatitis A+MMR+Tdap+HPV, TDV+YF+Hepatitis A+MMR+DTap+HPV, TDV+YF+Hepatitis A+Tdap+DTap+HPV, TDV+YF+MMR+Tdap+DTap+HPV, or TDV+Hepatitis A+MMR+Tdap+DTap+HPV.

Septuple Vaccine Combinations

TDV+YF+Hepatitis A+MMR+Tdap+DTap+HPV.

A preferred combination is e.g. TDV, YF and MMR.

Method of Co-Vaccinations with Other Dengue Vaccines

In certain embodiments of the invention the method is directed to a co-administration with other dengue vaccines such as Dengvaxia®. Dengvaxia® is a tetravalent dengue vaccine based on a yellow fever backbone, CYD-TDV (Dengvaxia®, Sanofi Pasteur, Lyon, France), and has been licensed in several countries based on the clinical demonstration of an overall vaccine efficacy (VE) against virologically-confirmed dengue (VCD) of 56-61% in children in Asia and Latin America (Capeding M R et al. Clinical efficacy and safety of a novel tetravalent dengue vaccine in healthy children in Asia: a phase 3, randomised, observer-masked, placebo-controlled trial. Lancet 2014, 384:1358-65; Villar L A et al. Safety and immunogenicity of a recombinant tetravalent dengue vaccine in 9-16 year olds: a randomized, controlled, phase II trial in Latin America. Pediatr Infect Dis J 2013, 32:1102-9). The preparation of these particular strains CYD1, CYD2, CYD3 and CYD4 has been described in detail in international patent applications WO 98/37911, WO 03/101397, WO07/021672, WO 08/007021, WO 08/047023 and WO 08/065315, to which reference may be made for a precise description of the processes for their preparation. The corresponding nucleotide sequences of the prM-E regions of CYD1, CYD2, CYD3 and CYD4 are provided in WO2016034629 and SEQID NOs are set out in Table 16.

Method of Co-Vaccinations with Other Travel Vaccines

In certain embodiments of the invention the method is directed to a co-administration with other travel vaccines such as Cholera, Hepatitis A, Hepatitis E, Japanese encephalitis, Meningococcal disease, Rabies, Tick-borne encephalitis, Typhoid fever, and Yellow fever.

According to one embodiment the dengue vaccine according to the invention is co-administered with all of the above vaccines.

According to one embodiment the dengue vaccine according to the invention is co-administered with one ore more of the above vaccines.

Method of Stimulating an Immune Response and Uses

Method of Stimulating an Immune Response

In certain embodiments the invention is directed to a method for stimulating an immune response, preferably a balanced immune response, to all four dengue serotypes in a subject, comprising administering to the subject a reconstituted unit dose of the invention as described herein.

In certain embodiments, the method includes a reconstituted unit dose/tetravalent dengue virus composition of a dengue vaccine composition administered for stimulating an immune response, preferably a balanced immune response, to all four dengue serotypes in a subject or subject population, the reconstituted unit dose comprising: a tetravalent virus composition including four live attenuated dengue virus strains, wherein the unit dose, described herein, is lyophilized and upon reconstitution with 0.5 mL of a pharmaceutically acceptable diluent the reconstituted unit dose is obtained, wherein the reconstituted unit dose comprises:

(i) a dengue serotype 1, such as a chimeric dengue serotype 2/1 strain, in a concentration of at least 3.3 log 10 pfu/0.5 ml, (ii) a dengue serotype 2, such as a dengue serotype 2 strain, in a concentration of at least 2.7 log 10 pfu/0.5 ml, (iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the reconstituted unit dose/tetravalent dengue virus composition is used in the method of stimulating an immune response of the present invention, wherein upon reconstitution of the unit dose with a pharmaceutically acceptable diluent dengue serotypes (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the reconstituted unit dose/tetravalent dengue virus composition is used in the method of stimulating an immune response of the present invention, wherein upon reconstitution with a pharmaceutically acceptable diluent dengue serotypes (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

The present invention is in part directed to a method for stimulating an immune response to all four serotypes of dengue virus in a subject, comprising administering to the subject a reconstituted unit dose of the invention as described herein by subcutaneous injection.

In certain embodiments, the invention is directed to said method, wherein the immune response to all four serotypes of dengue virus is balanced.

In certain embodiments, the invention is directed to said method, wherein the reconstituted unit dose is administered by subcutaneous injection to the arm, preferably to the deltoid region of the arm.

In certain embodiments, the invention is directed to said method, wherein the subject is seronegative to all dengue serotypes.

In certain embodiments, the invention is directed to said method, wherein two reconstituted unit doses of the invention as described herein are administered. In some embodiments, the two reconstituted doses are administered within 12 months or more, or within six months, or within three months, such as at day 0 and day 90 or at day 1 and day 90. According to some of these embodiments, a third unit dose of the invention as described herein is administered between 6 and 12 months after the administration of said first unit dose, such as 12 months after the first administration, or later than 12 month after the first administration, such as 12 months after the second administration.

In certain embodiments, the invention is directed to said method, wherein the unit dose of the invention as described herein is administered to a subject from a dengue endemic region. In some of these embodiments, the subject is from Singapore, Dominican Republic, Panama, Philippines, Colombia, Puerto Rico or Thailand, in particular from Singapore, Dominican Republic, Panama, or Philippines. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to said method, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to said method, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to said method, wherein the unit dose of the invention as described herein is administered to a subject of 2 to 60 years of age, or more than 17 years, or more than 18 years, or 18 to 60 years of age. In certain embodiments the subject is 1 to 17 years of age, or less than 9 years of age, or less than 4 years of age or less than 2 years of age. In further embodiments, the subjects or subject population are adults of more than 21 years, or 21 to 60 years, or 21 to 45 years of age. According to some of these embodiments the subject is seronegative and from a dengue-endemic region.

In certain embodiments, the invention is directed to said method, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said method, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a yellow fever vaccine, in particular YF-17D. It is particularly preferred that the reconstituted unit dose of the invention as described herein is administered concomitantly with a yellow fever vaccine, in particular YF-17D, as described in the previous section.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a HPV vaccine, in particular a 9vHPV vaccine, such as GARDASIL® 9. It is particularly preferred that the reconstituted unit dose of the invention as described herein is administered concomitantly with a HPV vaccine, in particular a 9vHPV vaccine, such as GARDASIL® 9, as described in the previous section.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a MMR vaccine, such as M-M-R® II. It is particularly preferred that the reconstituted unit dose of the invention as described herein is administered concomitantly with a MMR vaccine, such as M-M-R® II, as described in the previous section.

In certain embodiments, the invention is directed to said method, wherein the reconstituted unit dose of the invention as described herein is administered concomitantly with another vaccine. In one embodiments, the reconstituted unit dose of the invention as described herein is administered concomitantly with a DTaP/IPV/Hib vaccine, in particular a combined DTaP/IPV/Hib vaccine, such as Pentacel®. It is particularly preferred that the reconstituted unit dose of the invention as described herein is administered concomitantly with a DTaP/IPV/Hib vaccine, in particular a combined DTaP/IPV/Hib vaccine, such as Pentacel®, as described in the previous section.

In certain embodiments the invention is directed to a method for stimulating an immune response, preferably a balanced immune response, to all four dengue serotypes in an elderly subject, comprising administering to the elderly subject a reconstituted unit dose of the invention as described herein.

The present invention is in part directed to a method for stimulating an immune response to all four serotypes of dengue virus in an elderly subject, comprising administering to the elderly subject a reconstituted unit dose of the invention as described herein by subcutaneous injection.

In certain embodiments, the invention is directed to said method, wherein the immune response to all four serotypes of dengue virus is balanced.

In certain embodiments, the invention is directed to said method, wherein the reconstituted unit dose is administered by subcutaneous injection to the arm, preferably to the deltoid region of the arm.

In certain embodiments, the invention is directed to said method, wherein the elderly subject is seronegative to all dengue serotypes.

In certain embodiments, the invention is directed to said method, wherein two reconstituted unit doses of the invention as described herein are administered. In some embodiments, the two reconstituted doses are administered within 12 months or more, or within six months, or within three months, such as at day 0 and day 90. According to some of these embodiments, a third unit dose of the invention as described herein is administered between 6 and 12 months after the administration of said first unit dose, such as 12 months after the first administration, or later than 12 month after the first administration, such as 12 months after the second administration.

In certain embodiments, the invention is directed to said method, wherein the unit dose of the invention as described herein is administered to an elderly subject from a dengue endemic region. In some of these embodiments, the elderly subject is from Singapore, Dominican Republic, Panama, Philippines, Colombia, Puerto Rico or Thailand, in particular from Singapore, Dominican Republic, Panama, or Philippines. In other embodiments, the elderly subject is from a dengue non-endemic region. Such an elderly subject may be subject to a vaccination according to the invention in the context of traveling to a dengue endemic region. In certain embodiments, the reconstituted unit dose of the invention as described herein is administered subcutaneously to an elderly subject that is from a dengue endemic region or a dengue non-endemic region.

In certain embodiments, the invention is directed to said method, wherein the reconstituted unit dose of the invention as described herein is administered subcutaneously to an elderly subject that is seronegative with respect to all dengue serotypes. In other embodiments, the elderly subject is seropositive with respect to at least one dengue serotype.

In certain embodiments, the invention is directed to said method, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to said method, wherein the elderly subject has an impaired immune system.

Use for the Manufacture of a Medicament for Stimulating an Immune Response

The present invention is in part directed to the use of the reconstituted unit dose of the invention as described herein for the manufacture of a medicament for stimulating an immune response to all four serotypes of dengue virus in a subject. In one embodiment a reconstituted unit dose of the invention as described herein is administered by subcutaneous injection.

In certain embodiments, the present invention is directed to a use of the reconstituted unit dose/tetravalent dengue virus composition of a dengue vaccine composition for the manufacture of a medicament for stimulating an immune response to all four serotypes of dengue virus in a subject or in a subject population, wherein the reconstituted unit dose comprises a tetravalent virus composition including four live attenuated dengue virus strains, wherein a unit dose, as described herein, is lyophilized and upon reconstitution with 0.5 mL of a pharmaceutically acceptable diluent the reconstituted unit dose is obtained, wherein the reconstituted unit dose comprises:

(i) a dengue serotype 1, such as a chimeric dengue serotype 2/1 strain, in a concentration of at least 3.3 log 10 pfu/0.5 ml,
(ii) a dengue serotype 2, such as a dengue serotype 2 strain, in a concentration of at least 2.7 log 10 pfu/0.5 ml,
(iii) a dengue serotype 3, such as a chimeric dengue serotype 2/3 strain, in a concentration of at least 4.0 log 10 pfu/0.5 ml, and (vi) a dengue serotype 4, such as a chimeric dengue serotype 2/4 strain, in a concentration of at least 4.5 log 10 pfu/0.5 ml.

It is preferred that the use of the reconstituted unit dose/tetravalent dengue virus composition for the manufacture of a medicament in a method for stimulating an immune response to all four serotypes of dengue virus in a subject or in a subject population is obtained upon reconstitution of the unit dose with a pharmaceutically acceptable diluent and the dengue serotypes (i), (ii), (iii), and (iv) provide a total concentration of pfu/0.5 mL and based on said total concentration the concentration of (ii) in pfu/0.5 mL is less than 2%, the concentration of (iv) in pfu/0.5 mL is at least 50%, the concentration of (i) in pfu/0.5 mL is at least 1%, and the concentration of (iii) in pfu/0.5 mL is at least 6% and wherein the subject or subject population is of 18 to 60 years of age.

In another preferred embodiment, the use of reconstituted unit dose/tetravalent dengue virus composition for the manufacture of a medicament for a method for stimulating an immune response to all four serotypes of dengue virus in a subject or in a subject population is obtained upon reconstitution of the unit dose described herein with a pharmaceutically acceptable diluent and the dengue serotypes (i), (ii), (iii), and (iv) provide a total concentration of pfu/0.5 mL and based on said total concentration the concentration of (ii) in pfu/0.5 mL is less than 10%, and the concentration of (iv) in pfu/0.5 mL is at least 50%, and the concentration of (i) in pfu/0.5 mL is at least 1%, and the concentration of (iii) in pfu/0.5 mL is at least 8% and wherein the subject or subject population is of 2 to 17 years of age.

In certain embodiments, the invention is directed to said use, wherein the immune response to all four serotypes of dengue virus is balanced.

In certain embodiments, the invention is directed to said use, wherein the reconstituted unit dose is administered by subcutaneous injection to the arm, preferably to the deltoid region of the arm.

In certain embodiments, the invention is directed the reconstituted unit dose of the invention as described herein for said use, wherein the subject is seronegative to all dengue serotypes.

In certain embodiments, the invention is directed to said use, wherein two reconstituted unit doses of the invention as described herein are administered. In some embodiments, the two reconstituted unit doses are administered within 12 months or more, or within six months, or within three months, such as at day 0 and day 90 or at day 1 and day 90. According to some of these embodiments, a third reconstituted unit dose is administered 6 to 12 months after the administration of the first reconstituted unit dose, such as 12 months after the first administration, or later than 12 month after the first administration, such as 12 months (1 year) after the second administration or even 5 years or longer after the first or second administration.

In certain embodiments, the invention is directed to said use, wherein the subject is from a dengue endemic region. In other embodiments, the subject is from a dengue non-endemic region. Such a subject may be subject to a vaccination according to the invention in the context of traveling to a dengue endemic region. In certain embodiments, the reconstituted unit dose of the invention as described herein is administered subcutaneously to a subject that is from a dengue endemic region or a dengue non-endemic region.

In certain embodiments, the invention is directed to said use, wherein the reconstituted unit dose of the invention as described herein is administered subcutaneously to a subject that is seronegative with respect to all dengue serotypes. In other embodiments, the subject is seropositive with respect to at least one dengue serotype.

In certain embodiments, the invention is directed to said use, wherein the neutralizing antibody titers of the subject when tested at day 180 or day 365 after at least a first administration of said unit dose, and optionally a second administration of said unit dose 90 days after said first administration, provide a ratio of not more than 50, or not more than 40, or nor more than 30, or not more than 20 for the neutralizing antibody titer of dengue serotype 2 to the neutralizing antibody titer of dengue serotype 4. In certain embodiments, said neutralizing antibody titers of the subject further provide a ratio of not more than 20 for the neutralizing antibody titer of dengue serotype 2 to the neutralizing antibody titer of dengue serotype 1, and/or a ratio of not more than 20 for the neutralizing antibody titer of dengue serotype 2 to the neutralizing antibody titer of dengue serotype 3.

In certain embodiments, the invention is directed to said use, wherein the reconstituted unit dose of the invention as described herein is administered to a subject of 2 to 60 years of age or more than 17 years, or more than 18 years, or 18 to 60 years of age. In certain embodiments the subject is 1 to 17 years of age, or less than 9 years of age, or less than 4 years of age or less than 2 years of age. In further embodiments, the subjects or subject population are adults of more than 21 years, or 21 to 60 years, or 21 to 45 years of age. According to some of these embodiments the subject is seronegative and from a dengue-endemic region.

In certain embodiments, the invention is directed to said use, wherein the unit dose of the invention as described herein is administered to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed to said use, wherein the reconstituted unit dose of the invention as described herein is administered subcutaneously to a pediatric subject of less than 2 years of age, preferably of 2 months to 2 years of age or 2 months to 1.5 years of age or 2 months to 1 year of age. According to some of these embodiments, the pediatric subject is seronegative and from a dengue endemic region.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a yellow fever vaccine, in particular YF-17D. It is particularly preferred that the reconstituted unit dose of the invention as described herein is administered concomitantly with a yellow fever vaccine, in particular YF-17D, as described in the previous section.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a HPV vaccine, in particular a 9vHPV vaccine, such as GARDASIL® 9. It is particularly preferred that the reconstituted unit dose of the invention as described herein is administered concomitantly with a HPV vaccine, in particular a 9vHPV vaccine, such as GARDASIL® 9, as described in the previous section.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a MMR vaccine, such as M-M-R® II. It is particularly preferred that the reconstituted unit dose of the invention as described herein is administered concomitantly with a MMR vaccine, such as M-M-R® II, as described in the previous section.

In certain embodiments, the invention is directed said use, wherein the reconstituted unit dose of the invention as described herein is administered concomitantly with another vaccine. In one embodiments, the reconstituted unit dose of the invention as described herein is administered concomitantly with a DTaP/IPV/Hib vaccine, in particular a combined DTaP/IPV/Hib vaccine, such as Pentacel®. It is particularly preferred that the reconstituted unit dose of the invention as described herein is administered concomitantly with a DTaP/IPV/Hib vaccine, in particular a combined DTaP/IPV/Hib vaccine, such as Pentacel®, as described in the previous section.

The present invention is in part directed to the use of the reconstituted unit dose of the invention as described herein for the manufacture of a medicament for stimulating an immune response to all four serotypes of dengue virus in an elderly subject. In one embodiment a reconstituted unit dose of the invention as described herein is administered by subcutaneous injection.

In certain embodiments, the invention is directed to said use, wherein the immune response to all four serotypes of dengue virus is balanced.

In certain embodiments, the invention is directed to said use, wherein the reconstituted unit dose is administered by subcutaneous injection to the arm, preferably to the deltoid region of the arm.

In certain embodiments, the invention is directed the reconstituted unit dose of the invention as described herein for said use, wherein the elderly subject is seronegative to all dengue serotypes.

In certain embodiments, the invention is directed to said use, wherein two reconstituted unit doses of the invention as described herein are administered. In some embodiments, the two reconstituted unit doses are administered within 12 months or more, or within six months, or within three months, such as at day 0 and day 90. According to some of these embodiments, a third reconstituted unit dose is administered 6 to 12 months after the administration of the first reconstituted unit dose, such as 12 months after the first administration, or later than 12 month after the first administration, such as 12 months (1 year) after the second administration or even 5 years or longer after the first or second administration.

In certain embodiments, the invention is directed to said use, wherein the elderly subject is from a dengue endemic region. In other embodiments, the elderly subject is from a dengue non-endemic region. Such an elderly subject may be subject to a vaccination according to the invention in the context of traveling to a dengue endemic region. In certain embodiments, the reconstituted unit dose of the invention as described herein is administered subcutaneously to an elderly subject that is from a dengue endemic region or a dengue non-endemic region.

In certain embodiments, the invention is directed to said use, wherein the reconstituted unit dose of the invention as described herein is administered subcutaneously to an elderly subject that is seronegative with respect to all dengue serotypes. In other embodiments, the elderly subject is seropositive with respect to at least one dengue serotype.

In certain embodiments, the invention is directed to said use, wherein the elderly subject has at least one chronic condition or disease. The at least one chronic condition or disease may be selected from diabetes, hypertension, allergies, previous strokes, ischemic heart disease, chronic renal impairment and chronic obstructive pulmonary disease.

In certain embodiments, the invention is directed to said use, wherein the elderly subject has an impaired immune system.

Method for Determining the Titer of Neutralizing Antibodies

The present disclosure provides a method for determining the titer of neutralizing antibodies against each of dengue serotypes 1, 2, 3 and 4 in a blood serum sample, the method comprising the steps of:

(a) seeding cells from a dengue-susceptible cell line on 96-well assay plates and culturing the cells for a culture period;
(b) preparing serial dilutions of the blood serum sample;
(c) separately mixing the serially diluted blood serum samples prepared in step (b) with dengue serotype 1, dengue serotype 2, dengue serotype 3 and dengue serotype 4 to obtain separate mixtures for each dengue serotype and incubating the separate mixtures;
(d) adding the separate mixtures prepared in (c) to the cells seeded and cultured in step (a) and incubating the cells with the separate mixtures;
(e) providing an overlay for the inoculated cells and incubating the cells for an incubation period of 40 to 75 hours;
(f) determining the number of plaques in each well and comparing the number of plaques in each well to a control to determine the level of neutralizing antibodies against each of dengue serotypes 1, 2, 3 and 4.

Different incubation periods may be used in step (e) for the mixtures of different dengue serotypes. The incubation period for mixtures of dengue serotype 4 may be shorter than the incubation period for mixtures of dengue serotypes 1, 2 and 3, for example the incubation period for mixtures of dengue serotype 4 may be less than 50 hours, preferably 46±2 hours. In some embodiments, the incubation period for mixtures of dengue serotype 2 may be longer than the incubation period for mixtures of dengue serotypes 1, 3 and 4, for example the incubation period for mixtures of dengue serotype 2 may be between 60 and 70 hours, preferably 70±2 hours.

The dengue-susceptible cell line used in step (a) may be selected from Vero cells, LLC-MK2 cells and BHK-21 cells. The culture period of the cells may be 12 to 36 hours.

In step (c) the dengue serotype 1 may be DENV-1 strain 16007, dengue serotype 2 may be DENV-2 strain 16681, dengue serotype 3 may be DENV-3 strain 16562 and dengue serotype 4 may be DENV-4 strain 1036.

The separate mixtures in step (c) may be incubated overnight at a temperature of 2 to 8° C.

The overlay in step (e) may be selected from the group consisting of methylcellulose, carboxymethylcellulose and agarose. The cells with the overlay may be incubated at a temperature of 33° C. to 35° C.

The number of plaques in each well may be determined using serotype-specific anti-dengue monoclonal antibodies.

The disclosure also provides a method for determining the titer of neutralizing antibodies against each of dengue serotypes 1, 2, 3 and 4 in a blood serum sample, the method comprising the steps of:

(a) seeding Vero cells on 96-well assay plates and culturing the Vero cells for a period of 20 to 30 hours;
(b) preparing serial dilutions of the serum sample;
(c) separately mixing the serially diluted serum samples with dengue serotype 1, dengue serotype 2, dengue serotype 3 and dengue serotype 4 to prepare separate mixtures and incubating the separate mixtures overnight at a temperature of 2 to 8° C.;
(d) incubating the cells seeded and cultured in step (a) with the separate mixtures prepared in step (c) in separate wells for 90 to 120 minutes;
(e) providing a methylcellulose overlay for the inoculated cells and incubating the cells for an incubation period of 40 to 75 hours at 34° C.;
(f) determining the number of plaques in each well using serotype-specific anti-dengue monoclonal antibodies and comparing the number of plaques in each well to a control to determine the level of neutralizing antibodies against each of dengue serotypes 1, 2, 3 and 4.

The disclosure also provides the use of said method for determining the dengue serostatus of a subject before vaccination with a dengue virus vaccine or for analyzing a subject's immune response after vaccination with a dengue virus vaccine.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Preparation of the Dengue Virus Strains

The methods used to generate the chimeric dengue strains TDV-1, -3 and -4 were standard molecular cloning and DNA engineering methods and are described in Huang et al. (2003) J. Virology 77(21): 11436-11447. The following well-known methods were used to construct and introduce the prM-E genes of dengue serotypes 1, 3 and 4 into the TDV-2 backbone: Reverse-transcriptase PCR (RT-PCR), PCR, restriction enzyme digestion, DNA fragment ligation, bacterial transformations by electroporation, plasmid DNA preparations, in vitro transcription by T7 RNA polymerase, and transfection of Vero cells by electroporation.

After growing and purifying the different dengue serotypes separately as described in Huang et al. (2013) PLOS Neglected Dis, 7(5):e2243, they are mixed in the concentrations provided in Table 5. The mixture of dengue serotypes is present in a dengue vaccine composition and combined with a composition of pharmaceutically acceptable excipients resulting in a dengue vaccine composition comprising 15% w/v α,α trehalose dihydrate, 1% w/v poloxamer 407, 0.1% w/v human serum albumin and 100 mM sodium chloride. The dengue vaccine composition is lyophilized and represents a lyophilized unit dose of TDV. The lyophilized unit dose is reconstituted with 37 mM aqueous sodium chloride solution and the reconstituted unit dose comprises 15% w/v α,α trehalose dihydrate, 1% w/v poloxamer 407, 0.1% w/v human serum albumin and 137 mM sodium chloride.

Example 2: Microneutralization Test

Immunogenicity was measured by a microneutralization assay to each one of the four dengue serotypes with titers defined as the dilution resulting in a 50% reduction in plaque values (MNT50). Briefly, on day 1 Vero cells were seeded on 96-well assay plates in DMEM and 10% FBS at a density of $2.5\times10^5$ cells/ml and incubated at 37° C. for 24 hours. On day 2 serial dilutions of the heat-inactivated antibody-containing test and control sera samples (dilutions range 1:10 to 1:20480) were prepared and mixed with a constant concentration of dengue viruses, in particular DENV-1 strain 16007, DENV-2 strain 16681, DENV-3 strain 16562 and DENV-4 strain 1036, (target 60-80 pfu/well) in a 96 well microtiter plate and incubated overnight at 2-8° C. to enable the neutralization of the virus by the antibodies present in the sera. After the incubation the mixture of virus and antibodies was transferred onto the 96 well plates with Vero cells and the plates were incubated at 37° C. for 90-120 minutes to infect the Vero cells. A 1% methylcellulose overlay in DMEM was applied to the plate to restrict spread of progeny virus and the plate was incubated for 46-70 hours at 34° C. depending on the Dengue serotype:

DENV1—66±2 hours
DENV2—70±2 hours
DENV3—66±2 hours
DENV4—46±2 hours

After the incubation the cells were washed twice with PBS and fixed by adding cold methanol and incubating for 60 minutes at a temperature of ≤−20° C. After fixing the plates were dried and washed three times with washing buffer (lx PBS, pH 7.4 with 0.5% Tween), before 50 µl of serotype-specific anti-dengue monoclonal antibodies in blocking solution (2.5% nonfat dry milk in PBST) per well were added and incubated with the cells for 18±4 hours at 2-8° C.

The monoclonal antibodies were made as described in Gentry et al. (1982) Am. J. Trop. Med. Hyg. 31, 548-555; Henchal et al. (1985) Am. J. Trop. Med. Hyg. 34, 162-169; and Henchal et al. (1982) Am. J. Trop. Med. Hyg. 31(4): 830-6). Briefly, the anti-DENV-1 HBD was made against dengue 1 strain Hawaii, Envelope, the anti-DENV-2 was made against dengue 2 strain New Guinea C, Envelope, isotype 1, the anti-DENV-3 HBD was made against dengue 3 strain H87, Envelope, isotype 2A, and the anti-DENV-4 HBD was made against dengue 4 strain H241, Envelope, isotype 2A.

After incubation, the plates were washed three times with washing buffer and 50 µl of a secondary peroxidase labelled goat anti-mouse IgG (H+L) (KPL Cat #074-1806) in blocking solution was added and incubated for 90 to 120 minutes at 37° C. Then the plates were washed three times with washing buffer and 50 µl of precipitant substrate (2-amino-9-ethyl carbazole (AEC) tablet in 2.5 ml DMSO, 47.5 ml 50 mM acetate buffer and 250 µl hydrogen peroxide) were added and the mixture was incubated for 20 minutes at room temperature. Finally, the substrate was removed, the plates were rinsed with $dH_2O$ and dried.

Sample titers are calculated using the linear regression method and reported as MNT50 titers for each sample. Clinical data are reported as a geometric mean titer for all the individual MNT50 titers in each treatment group. Briefly, the number of infectious foci in each well was counted and the titer of neutralizing antibodies was determined by comparing the percent reduction of infectious foci centers in wells containing antibody (test samples) in comparison to wells containing virus alone. The MNT50 was calculated using the following linear regression equation:

$$MNT50=10\hat{}[(50-c)/m])$$

where c=y intercept of regression line and m=slope of regression line

Figure 2:
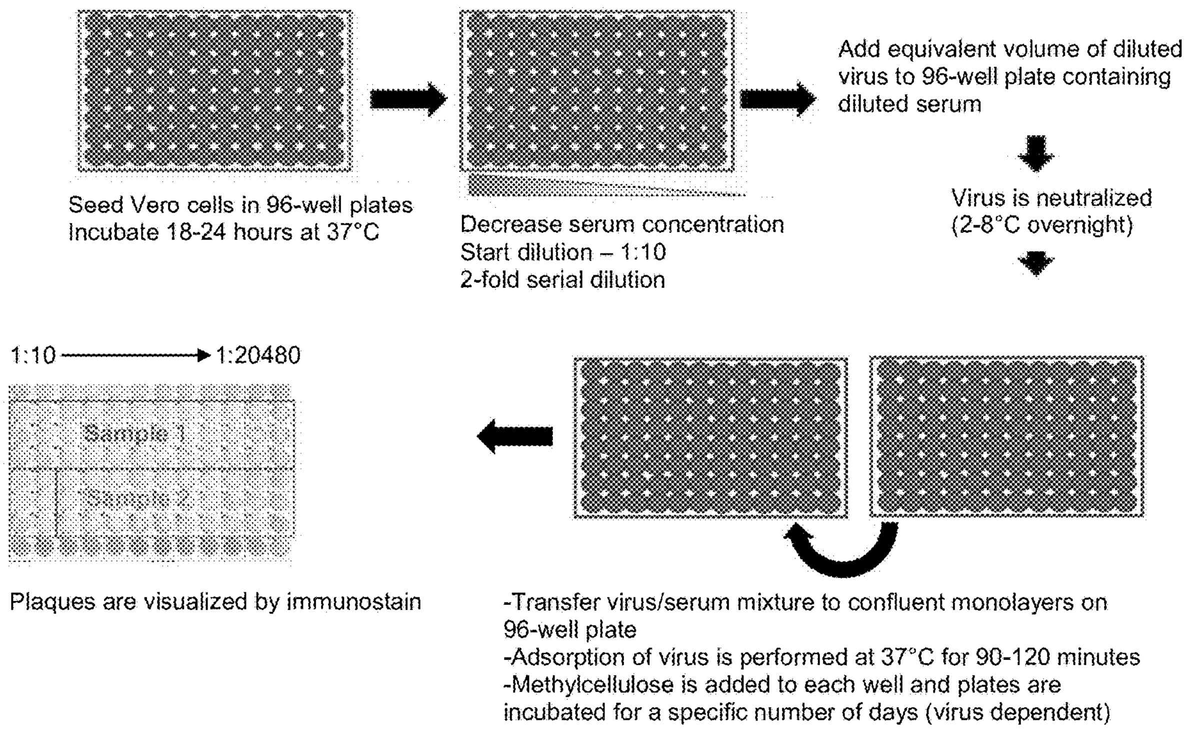
FIG. 2: Schematic drawing illustrating the microneutralization test (MNT) used to determine the titer of neutralizing antibodies.

Each test sample was tested in triplicates and the titer was calculated from the average of the triplicates. A schematic drawing of the steps performed in this test is provided in FIG. 2.

Example 3: Clinical Trial Comparing Two Different Unit Doses

A descriptive Phase II, double-blind, randomized, and controlled trial in 351 subjects aged 21 to 45 years living in Singapore was performed comparing two different formulations of a tetravalent dengue vaccine. Subjects were randomized (1:1), stratified by baseline dengue serostatus, into two treatment groups: groups 1 received one subcutaneous (SC) dose of HD-TDV and group 2 received one subcutaneous dose of TDV. The dengue vaccine formulations were prepared as described in Example 1. The concentration of the four dengue serotypes in the HD-TDV vaccine (high dose tetravalent dengue vaccine) and in the TDV vaccine (corresponding to the unit dose of the invention as described herein) is outlined in Table 5.

TABLE 5

Unit doses used in the trial.

| | |
|---|---|
| Comparative unit dose (HD-TDV) | 0.5 mL comprising TDV-1, TDV-2, TDV-3 and TDV-4 containing $3.2\times10^4$ PFU, $1.3\times10^5$ PFU, $2.5\times10^5$ PFU, and $4\times10^5$ PFU, respectively. Administered by subcutaneous injection on day 1. |
| Example 1 unit dose (TDV) | 0.5 mL comprising TDV-1, TDV-2, TDV-3 and TDV-4 containing $2.5\times10^4$ PFU, $6.3\times10^3$ PFU, $3.2\times10^4$ PFU, and $4\times10^5$ PFU, respectively. Administered by subcutaneous injection on day 1. |

Immunogenicity was evaluated at Days 15, 30, 90, 180, and 365 post-vaccination as geometric mean titers (GMTs) and seropositivity rates. Immunogenicity of the vaccines against each of the four dengue serotypes was assessed using a microneutralization assay, with titers corresponding to the dilution resulting in a 50% reduction in plaque reduction (MNT50) as described in Example 2. Primary immunogenicity endpoints were reported in terms of geometric mean titers (GMTs) of neutralizing antibodies, and seropositivity rates (which were defined as percentages of subjects with reciprocal neutralizing titers ≥10 for each of the DENV serotypes) in the overall trial population. As a secondary endpoint, GMTs and seropositivity rates were analyzed by dengue baseline seropositivity status. Seropositive at baseline was defined as being seropositive for at least one DENV serotype, whereas seronegative at baseline was defined as being seronegative for all four DENV serotypes.

Solicited and unsolicited adverse events (AEs) were assessed by severity and causality.

a) Seropositivity

Dengue seropositivity is based on the result of the microneutralization test (MNT) described in Example 2 and is defined as a reciprocal neutralizing antibody titer ≥10 for one or more dengue serotype at baseline. The baseline seropositivity rate for each dengue serotype is defined as the percentage of seropositive subjects for the given dengue serotype and was derived from the neutralizing antibodies titers of the dengue serotypes as measured in the subjects before administration of the first unit dose. The seropositivity rate at day 180 or day 365 is defined as the percentage of seropositive subjects and was derived from the neutralizing antibodies titers of the dengue serotypes as measured in the subjects 180 and 365 days after administration of the first unit dose, respectively.

In total, 187 subjects (53.6%) were seropositive, based on MNT50, for at least one dengue serotype at baseline: 48.7% were seropositive for DENV-1, 49.0% for DENV-2, 45.2% for DENV-3, and 41.2% for DENV-4. The seropositive status and rate at baseline of the two different vaccination groups is shown in Table 6.

TABLE 6

| Serostatus and seropositivity rate at baseline | | |
|---|---|---|
| | Comparative unit dose | Example 1 unit dose |
| Baseline seropositivity status (count of participants) | | |
| Seropositive for at least one dengue serotype | 92 | 95 |
| Seronegative for all dengue serotypes | 83 | 80 |
| Baseline seropositivity rate for each serotype (percentage of participants) | | |
| TDV-1 | 48.6 | 48.6 |
| TDV-2 | 47.4 | 50.3 |
| TDV-3 | 44.0 | 46.3 |
| TDV-4 | 41.7 | 40.6 |

Figure 3:
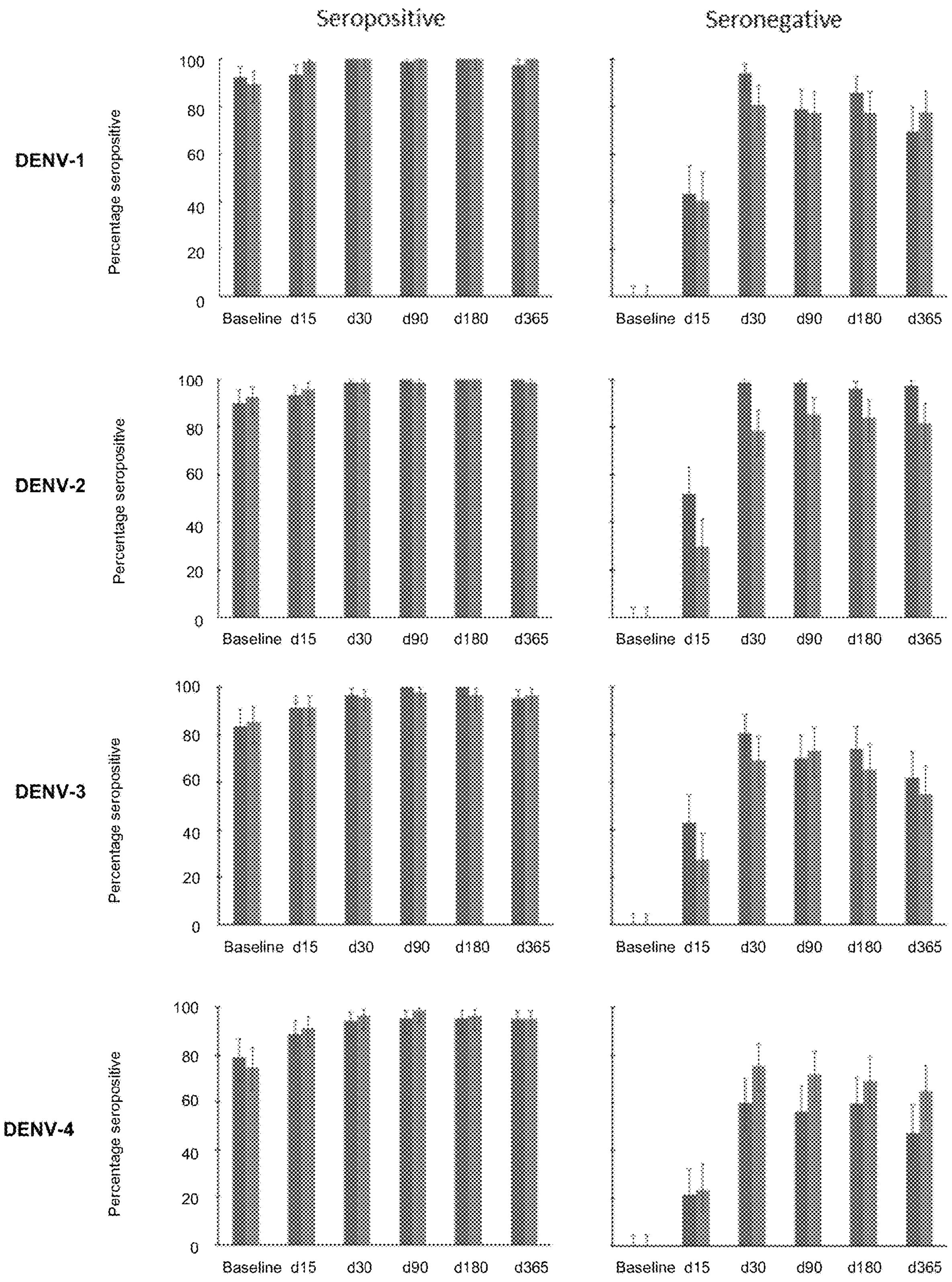
FIG. 3: Percentage of subjects (±95% confidence intervals) who were seropositive (reciprocal neutralizing titer ≥10) for each of the dengue serotypes at different time points of the trial in the HD-TDV group (dark colored, left bar) and TDV group (light colored, right bar) throughout the trial. Time points shown are baseline, day 15 (d15), day 30 (d30), day 90 (d90), day 180 (d180) and day 365 (d365). Part A shows the results for participants seropositive (set of graphs on the left) and seronegative (set of graphs on the right) at baseline, per-protocol set. Part B shows the results for the entire trial population (all) per-protocol set
Figure 3:
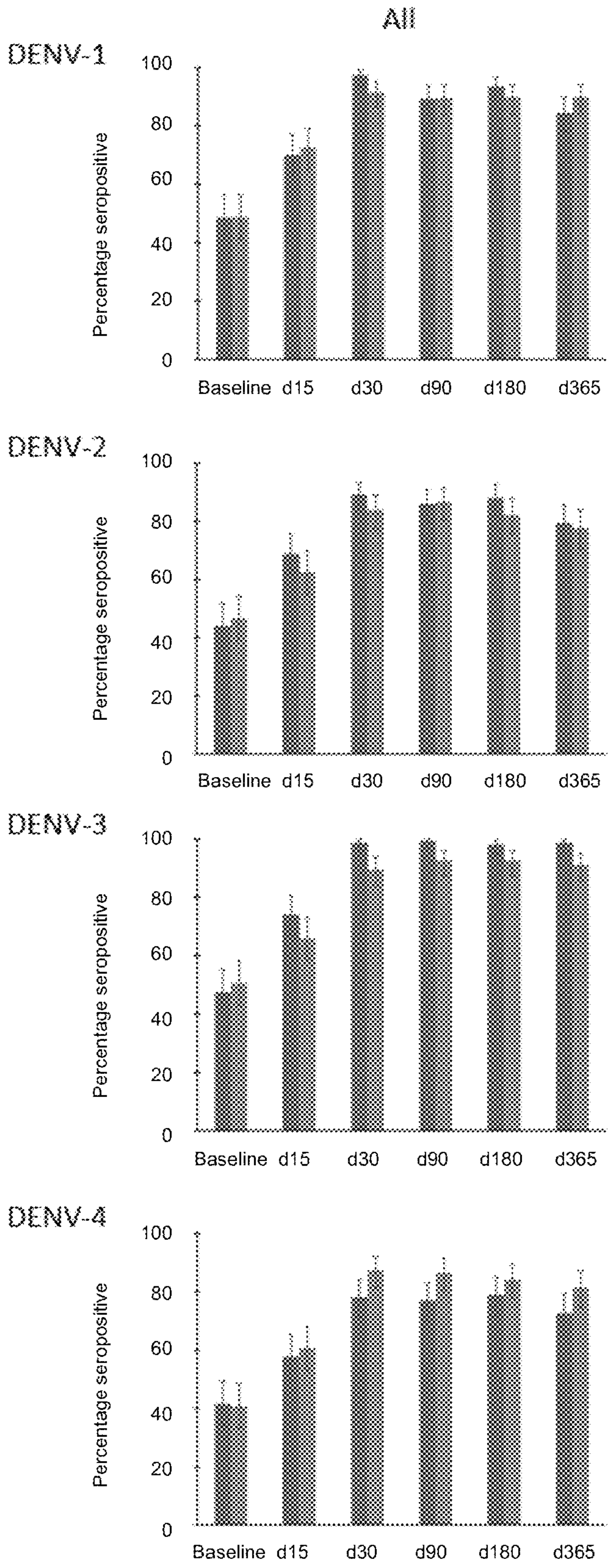

Seropositivity rates increased to Day 30 after administration of the unit doses, and remained high through to Day 365 for each of the four serotypes (FIG. 3). For the overall trial population, the percentages of subjects who were seropositive for DENV-1 and DENV-3 were similar in the HD-TDV and TDV groups, whereas higher post-baseline seropositivity rates were seen for the HD-TDV group against DENV-2, and for the TDV group against DENV-4 (FIG. 3B). In general, higher seropositivity rates were seen in subjects already seropositive at baseline than in seronegative subjects. Seropositivity rates rose to nearly 100% against all four dengue serotypes in the seropositive vaccine groups by Day 30, and remained at this level through to Day 365; no difference was seen between HD-TDV and TDV (FIG. 3A). In the seronegative group, the seropositivity rates increased more gradually to a peak at Day 30, with limited decline until Day 365. The rates were consistently higher for HD-TDV than TDV against DENV-2, but were higher for TDV than HD-TDV against DENV-4, through to Day 365 (FIG. 3A).

TABLE 7

| Seropositivity rate at day 180 | | |
|---|---|---|
| | Comparative unit dose | Example 1 unit dose |
| Overall number of participants analyzed | 166 | 163 |
| Seropositivity rate at day 180 (95% Confidence Interval) | | |
| Day 180, TDV-1 | 93.4 (88.5 to 96.6) | 89.6 (83.8 to 93.8) |
| Day 180, TDV-2 | 98.2 (94.8 to 99.6) | 92.6 (87.5 to 96.1) |
| Day 180, TDV-3 | 88.0 (82.0 to 92.5) | 82.2 (75.5 to 87.7) |
| Day 180, TDV-4 | 78.9 (71.9 to 84.9) | 84.0 (77.5 to 89.3) |

TABLE 8

| Seropositivity rate at day 365 | | |
|---|---|---|
| | Comparative unit dose | Example 1 unit dose |
| Overall number of participants analyzed | 160 | 156 |
| Seropositivity rate at day 365 (95% Confidence Interval) | | |
| Day 365, TDV-1 | 84.4 (77.8 to 89.6) | 89.7 (83.9 to 94.0) |
| Day 365, TDV-2 | 98.8 (95.6 to 99.8) | 91.0 (85.4 to 95.0) |
| Day 365, TDV-3 | 79.4 (72.3 to 85.4) | 77.6 (70.2 to 83.8) |
| Day 365, TDV-4 | 72.5 (64.9 to 79.3) | 81.4 (74.4 to 87.2) |

b) Geometric Mean Neutralizing Antibody Titers (GMTs)

Neutralizing antibody titers (GMTs) for each dengue serotype were determined in a serum sample of a subject taken before administration of the first unit dose of the dengue vaccine composition and 180 or 365 days after administration of the first unit dose of the dengue vaccine composition using the microneutralization (MNT) assay as described in Example 2.

Figure 4:
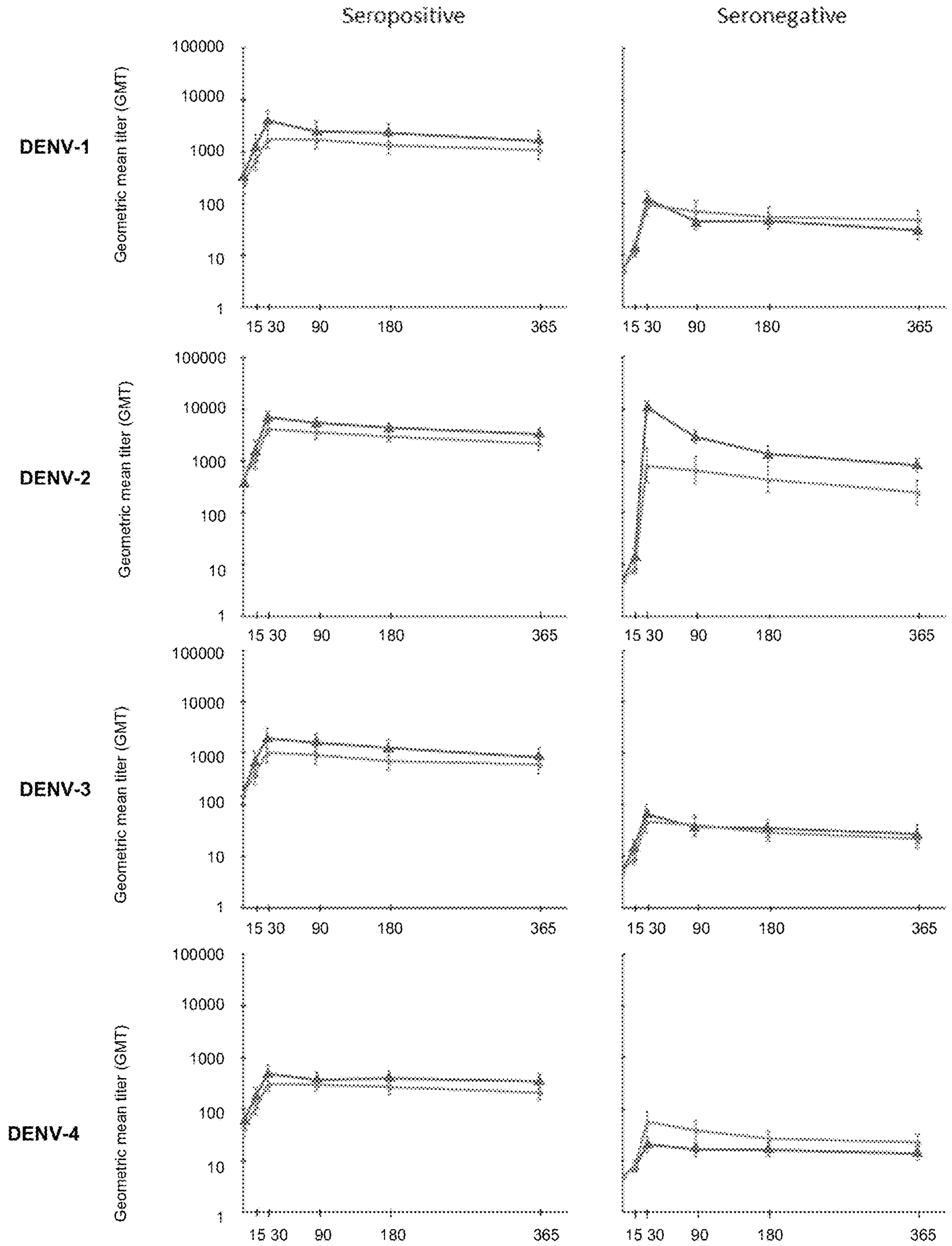
FIG. 4: Geometric mean titers (GMTs) (±95% confidence intervals) of neutralizing antibodies against each of the four dengue serotypes during the course of the trial for HD-TDV (dark line with triangles) and TDV (light line with circles) recipients, for the entire trial population (part B) and for participants seropositive and seronegative at baseline (part A), per-protocol set.
Figure 4:
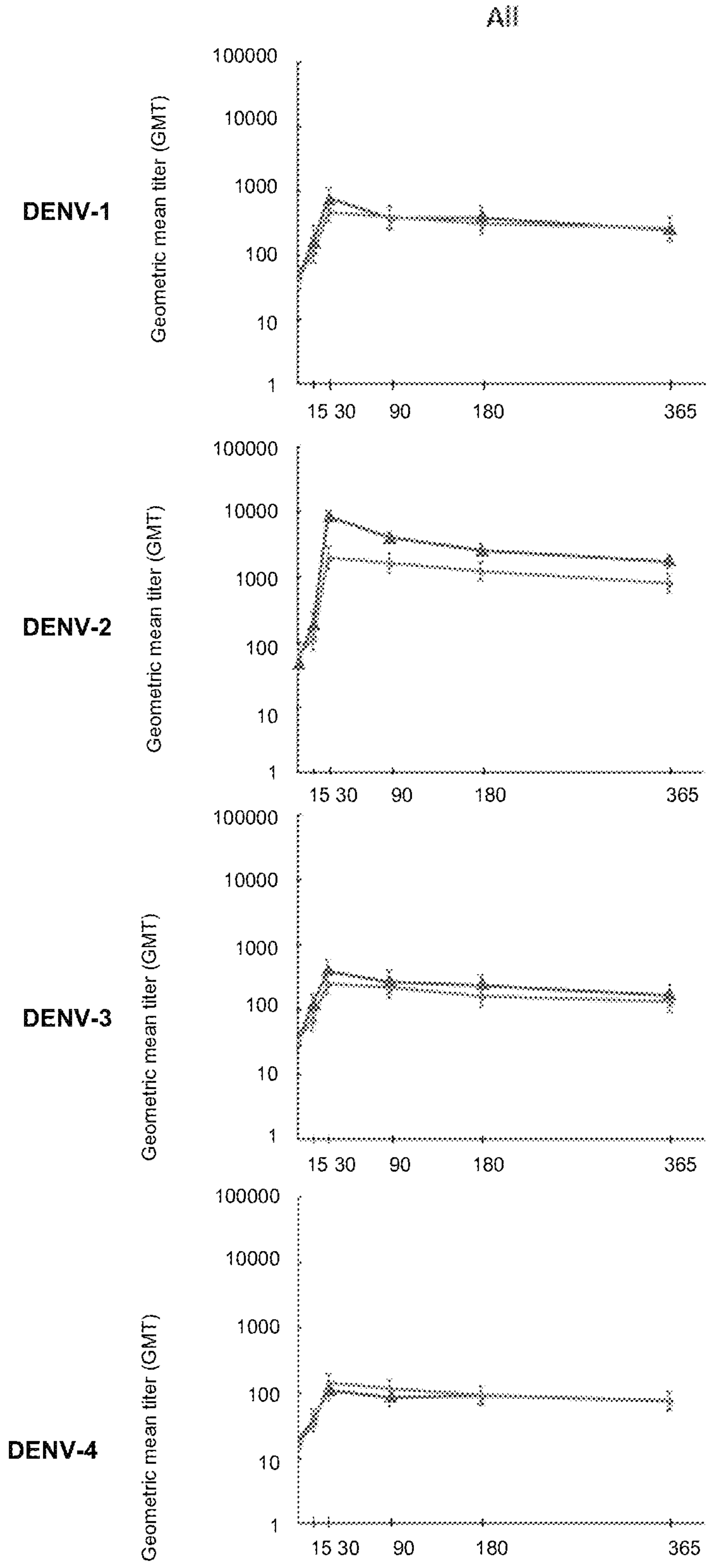

For both HD-TDV and TDV, an increase in GMTs was observed by Day 15, reaching a maximum by Day 30 (FIG. 4). Antibody titers remained above baseline levels throughout the trial for both unit doses. In the overall trial population, no substantial differences were seen in GMT titers between the two unit dose groups, except against DENV-2, where the response was higher for the HD-TDV group compared with the TDV group (8640.3 versus 1992.7 at Day 30). When assessed by baseline seropositivity status, the GMT profiles were similar as for the entire population, with a rise by Day 15, peak at Day 30, and gradual decline thereafter (FIG. 4B). In the group who were seropositive at baseline, the difference between the unit dose groups in response to DENV-2 was reduced, with GMTs of 6970.3 and 4193.3 at Day 30 for the HD-TDV and TDV groups, respectively. Responses were higher against DENV-1, DENV-3, and DENV-4 in the baseline seropositive group, compared with the baseline seronegative group, across both unit doses. Against DENV-2, a lower response was seen in baseline seronegative subjects receiving TDV, compared with HD-TDV; Day 30 GMTs were 812.9 in the TDV group, compared with 10965.9 in the HD-TDV group. The response in these subjects also differed against DENV-4, with a higher response being observed in the TDV group (Day 30 GMTs of 57.7, compared with 20.9 in the HD-TDV group); this difference persisted to Day 365 (FIG. 4A).

TABLE 9

| Geometric mean neutralizing antibody titers (GMTs) at day 180 | | |
|---|---|---|
| | Comparative unit dose | Example 1 unit dose |
| Overall number of participants analyzed | 166 | 163 |
| GMTs (95% Confidence Interval) [units: Titer] | | |
| Day 180, TDV-1 | 379.4 (252.3 to 570.3) | 312.2 (212.2 to 459.2) |
| Day 180, TDV-2 | 2585.5 (2088.8 to 3200.3) | 1235.0 (890.7 to 1712.5) |
| Day 180, TDV-3 | 236.2 (162.2 to 344.0) | 161.0 (110.5 to 234.6) |
| Day 180, TDV-4 | 91.0 (65.7 to 125.9) | 92.9 (68.9 to 125.4) |

TABLE 10

| Ratio of geometric mean neutralizing antibody titers (GMTs) at day 180 | | |
|---|---|---|
| | Comparative unit dose | Example 1 unit dose |
| TDV-2:TDV-1 | 7 | 4 |
| TDV-2:TDV-3 | 11 | 8 |
| TDV-2:TDV-4 | 28 | 13 |

TABLE 11

| Geometric mean neutralizing antibody titers (GMTs) at day 365 | | |
|---|---|---|
| | Comparative unit dose | Example 1 unit dose |
| Overall number of participants analyzed | 160 | 156 |
| GMTs (95% Confidence Interval) [units: Titer] | | |
| Day 365, TDV-1 | 247.3 (160.9 to 380.2) | 264.1 (181.1 to 385.1) |
| Day 365, TDV-2 | 1726.0 (1392.6 to 2139.3) | 809.5 (576.6 to 1136.4) |
| Day 365, TDV-3 | 163.2 (110.0 to 242.3) | 132.6 (89.9 to 195.5) |
| Day 365, TDV-4 | 75.3 (53.8 to 105.4) | 77.0 (56.9 to 104.2) |

TABLE 12

| Ratio of geometric mean neutralizing antibody titers (GMTs) at day 365 | | |
|---|---|---|
| | Comparative unit dose | Example 1 unit dose |
| TDV-2:TDV-1 | 7 | 3 |
| TDV-2:TDV-3 | 11 | 6 |
| TDV-2:TDV-4 | 23 | 11 |

TABLE 13

| Geometric mean neutralizing antibody titers (GMTs) of all four dengue serotypes assessed by dengue baseline seropositivity status at day 180 | | |
|---|---|---|
| | Comparative unit dose | Example 1 unit dose |
| Seropositive | 89 Participants | 88 Participants |
| Day 180, TDV-1 (Seropositive) | 2327.2 (1550.4 to 3493.3) | 1356.2 (905.5 to 2031.2) |
| Day 180, TDV-2 (Seropositive) | 4412.0 (3586.6 to 5427.4) | 2952.0 (2358.2 to 3695.4) |

TABLE 13-continued

Geometric mean neutralizing antibody titers (GMTs) of all four dengue serotypes assessed by dengue baseline seropositivity status at day 180

| | Comparative unit dose | Example 1 unit dose |
|---|---|---|
| Day 180, TDV-3 (Seropositive) | 1248.3 (879.7 to 1771.3) | 693.6 (459.6 to 1046.6) |
| Day 180, TDV-4 (Seropositive) | 399.5 (291.3 to 547.9) | 268.3 (190.2 to 378.6) |
| Seronegative | 77 Participants | 75 Participants |
| Day 180, TDV-1 (Seronegative) | 46.6 (32.0 to 67.9) | 55.7 (35.6 to 87.1) |
| Day 180, TDV-2 (Seronegative) | 1394.1 (983.2 to 1976.6) | 444.3 (247.2 to 798.5) |
| Day 180, TDV-3 (Seronegative) | 34.5 (23.4 to 50.7) | 29.0 (19.4 to 43.3) |
| Day 180, TDV-4 (Seronegative) | 16.4 (12.3 to 22.0) | 26.8 (19.0 to 37.7) |

TABLE 14

Ratio of geometric mean neutralizing antibody titers (GMTs) assessed by dengue baseline seropositivity status at day 180 and 365

| | Comparative unit dose | Example 1 unit dose |
|---|---|---|
| Seropositive 180 Days | | |
| TDV-2:TDV-1 | 1.9 | 2.2 |
| TDV-2:TDV-3 | 3.5 | 4.3 |
| TDV-2:TDV-4 | 11.0 | 11.0 |
| Seronegative 180 Days | | |
| TDV-2:TDV-1 | 29.9 | 8.0 |
| TDV-2:TDV-3 | 40.4 | 15.3 |
| TDV-2:TDV-4 | 85.0 | 16.6 |

TABLE 15

Geometric mean neutralizing antibody titers (GMTs) of all four dengue serotypes assessed by dengue baseline seropositivity status at day 365

| | Comparative unit dose | Example 1 unit dose |
|---|---|---|
| Seropositive | 84 Participants | 85 Participants |
| Day 365, TDV-1 (Seropositive) | 1633.3 (1055.8 to 2526.7) | 1081.5 (724.0 to 1615.6) |
| Day 365, TDV-2 (Seropositive) | 3316.0 (2623.8 to 4190.9) | 2177.3 (1613.5 to 2938.1) |
| Day 365, TDV-3 (Seropositive) | 830.6 (551.2 to 1251.5) | 600.2 (402.3 to 895.3) |
| Day 365, TDV-4 (Seropositive) | 346.3 (249.2 to 481.1) | 212.6 (152.2 to 296.9) |
| Seronegative | 76 Participants | 71 Participants |
| Day 365, TDV-1 (Seronegative) | 30.7 (20.4 to 46.2) | 48.8 (32.1 to 74.2) |
| Day 365, TDV-2 (Seronegative) | 838.7 (621.9 to 1131.1) | 247.6 (143.9 to 426.1) |
| Day 365, TDV-3 (Seronegative) | 27.0 (17.8 to 41.1) | 21.7 (14.3 to 33.1) |
| Day 365, TDV-4 (Seronegative) | 13.9 (10.3 to 19.0) | 22.9 (15.8 to 33.1) |

TABLE 16

Ratio of geometric mean neutralizing antibody titers (GMTs) assessed by dengue baseline seropositivity status at day 365

| | Comparative unit dose | Example 1 unit dose |
|---|---|---|
| Seropositive 365 Days | | |
| TDV-2:TDV-1 | 2.0 | 2.0 |
| TDV-2:TDV-3 | 4.0 | 3.6 |
| TDV-2:TDV-4 | 9.6 | 10.2 |
| Seronegative 365 Days | | |
| TDV-2:TDV-1 | 27.3 | 5.1 |
| TDV-2:TDV-3 | 31.1 | 11.4 |
| TDV-2:TDV-4 | 60.3 | 10.8 |

c) Safety

Overall, rates of solicited local and systemic adverse events (AEs), unsolicited AEs, and serious adverse events (SAEs) were similar across the two unit dose groups. No deaths or AEs leading to discontinuation were recorded in the trial. Three subjects in each unit dose group experienced SAEs, one of these events in the HD-TDV group was considered by the sponsor to be vaccine-related based on temporal association. The SAE was polyarthritis which began six days following receipt of the vaccine. Rates of solicited reactions were similar across unit dose groups, and seropositivity status at baseline. Overall, 47.4% and 53.7% of subjects reported local reactions, and 52.0% and 50.9% reported solicited systemic AEs, in the HD-TDV and TDV groups, respectively. Most reactions were mild or moderate. The most commonly reported local adverse reaction was injection site pain (46.3% in the HD-TDV group, 52.0% in the TDV group) and the most common systemic AE was headache (28.6% in the HD-TDV group, 34.9% in the TDV group).

d) Conclusion

Both unit doses showed an acceptable safety profile. The results show a more balanced immune response with the new TDV unit dose compared to the early HD-TDV unit dose, particularly in the subjects who were seronegative prior to vaccination: (i) in baseline seronegative subjects, response to DENV-2 was less dominant with TDV and (ii) DENV-4 seropositivity rates and GMTs were also higher with TDV in these subjects.

Example 4: Cell-Mediated Immunity Stimulated by the Dengue Vaccine

A gamma interferon (IFNγ) enzyme-linked immunosorbent spot (ELISPOT) assay was performed using peripheral blood mononuclear cells (PBMCs) from the subjects taking part in the clinical trial of Example 3 and the commercial ELISpot assay kit available from Mabtech according to the manufacturer's instructions. Briefly, cryopreserved PBMCs were thawed and left to rest overnight, then incubated with various peptide pools for 18-22 hours in plates coated with anti-IFNγ antibodies. PBMCs were then removed and spots were developed and then counted. Results were reported as mean spot forming cells (SFC) per $10^6$ PBMCs. Peptide pools matched selected DENV-derived proteins, covering the entire DENV-2 proteome with NS1, NS3, and NS5 proteins from New Guinea C (NGC) and Thailand/16681/84 strains; and C, prM+E, NS2 and NS4 proteins from Thailand/16681/84 only plus TDV-1, TDV-3 and TDV-4 prM+E inserts from DENV-1, -3 and -4 strains Thailand/16007/1964, Philippines/16562/1964 and Indonesia/1036/1976, respectively.

Figure 5:
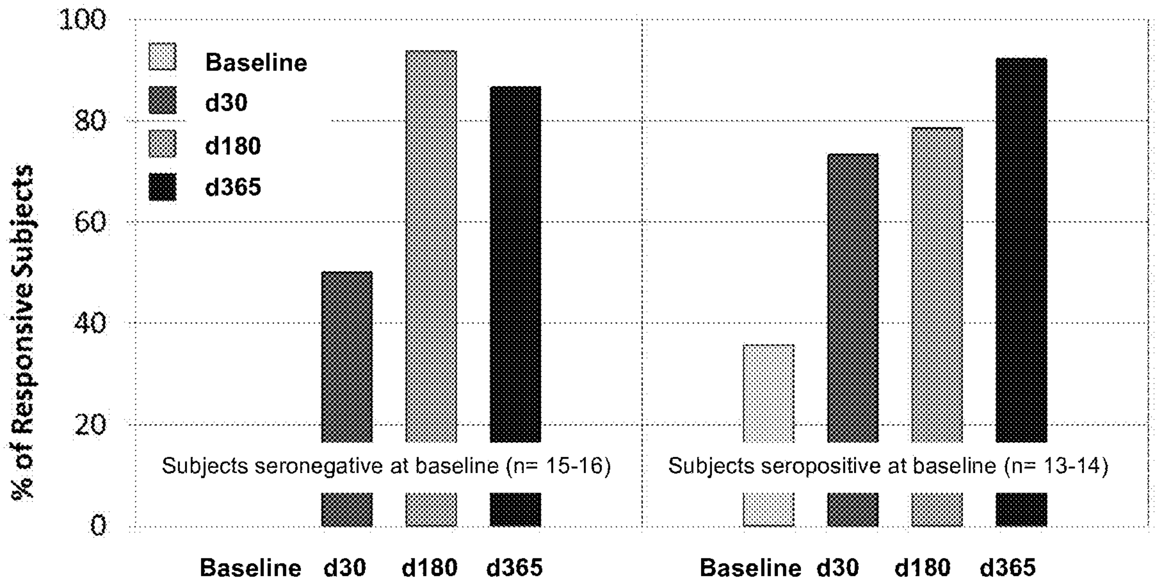
FIG. 5: IFNγ ELISpot analysis of peripheral blood mononuclear cells before vaccination (baseline) and at different time points after administration of TDV. Shown are the response frequencies to the entire DENV-2 proteome. A subject was considered responsive if response to more than one peptide pool from DENV-2 was positive (i.e. ≥4× mean of negative control and ≥50 SFC/$10^6$ PBMCs).

Response rates to DENV-2 proteome at 6 and 12 months post-single dose of TDV were >90%, and were comparable between subjects seronegative and seropositive at baseline (FIG. 5).

Figure 6:
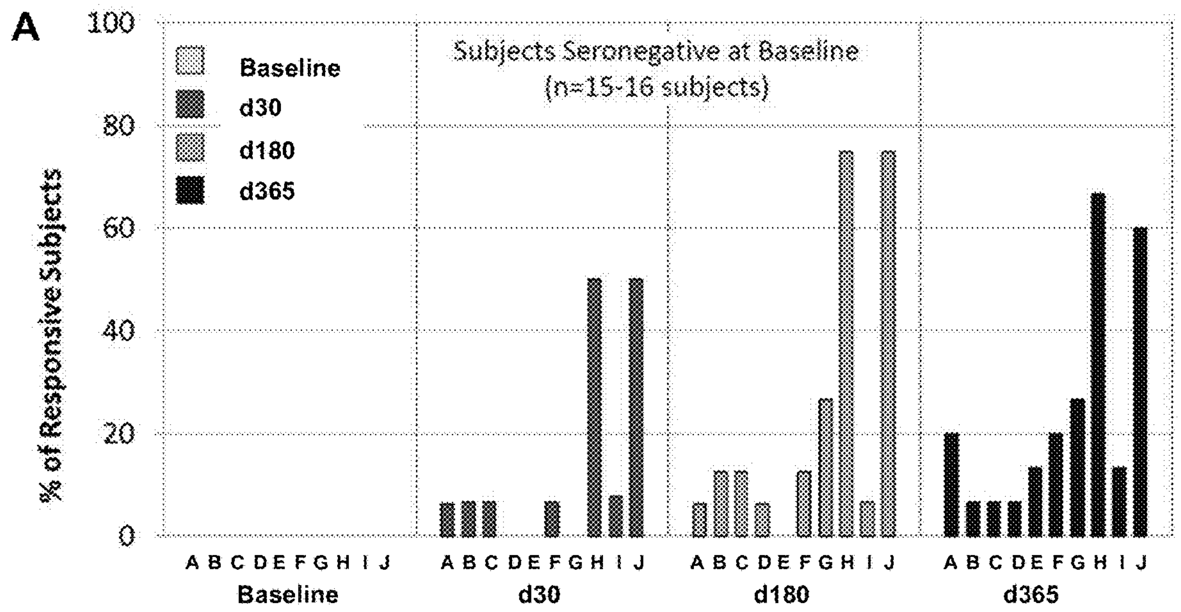
FIG. 6: IFNγ ELISpot analysis of peripheral blood mononuclear cells before vaccination (baseline) and at different time points after administration of TDV. Shown are the response frequencies to peptide pools matching selected DENV-derived proteins as indicated. A subject was considered responsive if response to more than one peptide pool from DENV-2 was positive (i.e. ≥4× mean of negative control and ≥50 SFC/$10^6$ PBMCs). A=DENV-2 C; B=DENV-1 prM+E; C=DENV-2 prM+E; D=DENV-3 prM+E; E=DENV-4 prM+E; F=DENV-2 NS1; G=DENV-2 NS2; H=DENV-2 NS3; I=DENV-2 NS4; J=DENV-2 NS5.
Figure 6:
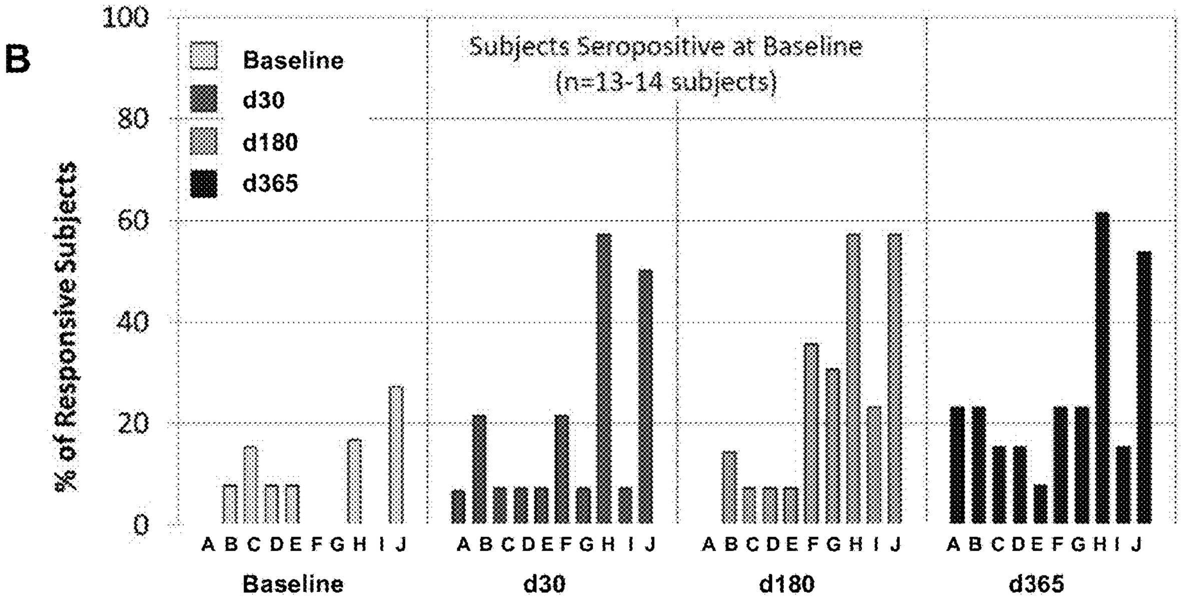

The response was primarily directed to the NS proteins, particularly in subjects seronegative at baseline (FIG. 6).

The NS3 and NS5 proteins were the most recognized antigens (by 50-75% of subjects). Immunodominance of NS3 and NS5 was independent of baseline serostatus. Durability of the response was maintained equally between NS3 and NS5 throughout the 12-month post-single vaccination follow-up.

Example 5: Antibody Responses to Non-Structural Proteins

The non-structural protein NS-1 from all four dengue serotypes can induce endothelial hyperpermeability of human pulmonary microvascular endothelial cells (HP-MEC) as measured by transendothelial electrical resistance (TEER) (Puerta-Guardo et al. (2016) PloS Pathog. 12(7): e1005738). It also interacts with endothelial cells to induce degradation of the glycocalyx via activation of sialidases and the cathepsin L/heparanase pathway (Glasner et al. (2017) PloS Pathog. 13(11): e1006673). In view of these effects, it was investigated whether the comparative unit dose induces antibodies against NS1 and inhibits NS1-mediated physiological effects.

a) Anti-NS1 Antibodies

Serum samples were collected at day 0 before vaccination and day 120 after administration of the first unit dose. Serum was collected from 6 dengue seronegative and 6 dengue seropositive subjects at both day 0 and day 120, and Ab concentrations were determined by ELISA.

The anti-NS1 antibody concentration in seronegative and seropositive subjects at day 0 and day 120 is shown in Tables 17 and 18:

TABLE 17

Anti-NS1 antibody concentration in seronegative subjects at day 0 and day 120
Dengue seronegative subjects
Anti-NS1 antibody concentration (RU/ml)

| | DENV1 | | DENV2 | | DENV3 | | DENV4 | |
|---|---|---|---|---|---|---|---|---|
| Subj. | d0 | d120 | d0 | d120 | d0 | d120 | d0 | d120 |
| 1023014 | 13.49 | 602.56 | 16.22 | 2570.40 | 10.00 | 489.78 | 28.18 | 302.00 |
| 1025011 | 66.07 | 173.78 | 35.48 | 794.33 | 67.61 | 117.49 | 42.66 | 85.11 |
| 1025013 | 5.62 | 380.19 | 24.55 | 2454.71 | 16.98 | 316.23 | 10.00 | 186.21 |
| 1035002 | 34.67 | 177.83 | 31.62 | 977.24 | 17.78 | 114.82 | 19.05 | 44.67 |
| 1035005 | 50.12 | 467.74 | 20.42 | 1659.59 | 104.71 | 309.03 | 66.07 | 288.40 |
| 1035001 | 40.74 | 186.21 | 52.48 | 489.78 | 44.67 | 169.82 | 51.29 | 177.83 |

TABLE 18

Anti-NS1 antibody concentration in seropositive subjects at day 0 and day 120
Dengue seropositive subjects
Anti-NS1 antibody concentration (RU/ml)

| | DENV1 | | DENV2 | | DENV3 | | DENV4 | |
|---|---|---|---|---|---|---|---|---|
| Subj. | d0 | d120 | d0 | d120 | d0 | d120 | d0 | d120 |
| 1052010 | 691.83 | 11481.54 | 309.03 | 12022.64 | 436.52 | 7585.78 | 245.47 | 4677.35 |
| 1052014 | 758.58 | 1445.44 | 407.38 | 891.25 | 758.58 | 1122.02 | 724.44 | 707.95 |
| 1052015 | 3890.45 | 3467.37 | 2570.40 | 2344.23 | 3235.94 | 2818.38 | 660.69 | 707.95 |
| 1071007 | 478.63 | 851.14 | 239.88 | 478.63 | 660.69 | 1202.26 | 870.96 | 1258.93 |
| 1071012 | 691.83 | 776.25 | 724.44 | 676.08 | 776.25 | 812.83 | 346.74 | 446.68 |
| 1082009 | 5888.44 | 5370.32 | 7413.10 | 6309.57 | 5248.07 | 4897.79 | 891.25 | 794.33 |

These data show that the vaccine induces antibodies against NS1 from all dengue serotypes in both seropositive and seronegative subjects.

b) Transendothelial Electrical Resistance (TEER)

The effect of recombinant NS1 proteins from dengue serotypes 1, 2, 3 and 4 and sera from vaccinated seronegative and seropositive subjects on endothelial permeability was evaluated by measuring TEER of HPMEC grown on a 24-well Transwell polycarbonate membrane system (Transwell® permeable support, 0.4 μM, 6.5 mm insert; Corning Inc.) as previously described (Beatty et al. (2015) Sci. Transl. Med. 7(304): 304ra141; Puerta-Guardo et al. (2016) PloS Pathog. 12(7):e1005738). Briefly, TEER was measured in Ohms (Ω) at sequential 2-hour time-points following the addition of test proteins using an Epithelial Volt Ohm Meter (EVOM) with "chopstick" electrodes (World Precision Instruments). Untreated endothelial cells grown on Transwell inserts were used as negative untreated controls, and inserts with medium alone were used for blank resistance measurements. Relative TEER represents a ratio of resistance values (Ω) as follows: (Ω experimental condition−Ω medium alone)/(Ω non-treated endothelial cells−Ω medium alone). After 24 hours of treatment, 50% of upper and lower chamber media was replaced by fresh endothelial cell medium. For experiments using sera, 30 μl of culture supernatant was removed from the apical chamber and replaced with 30 μl of serum samples immediately before the addition of 5 μg/ml DENV-2 NS1.

Figure 7:
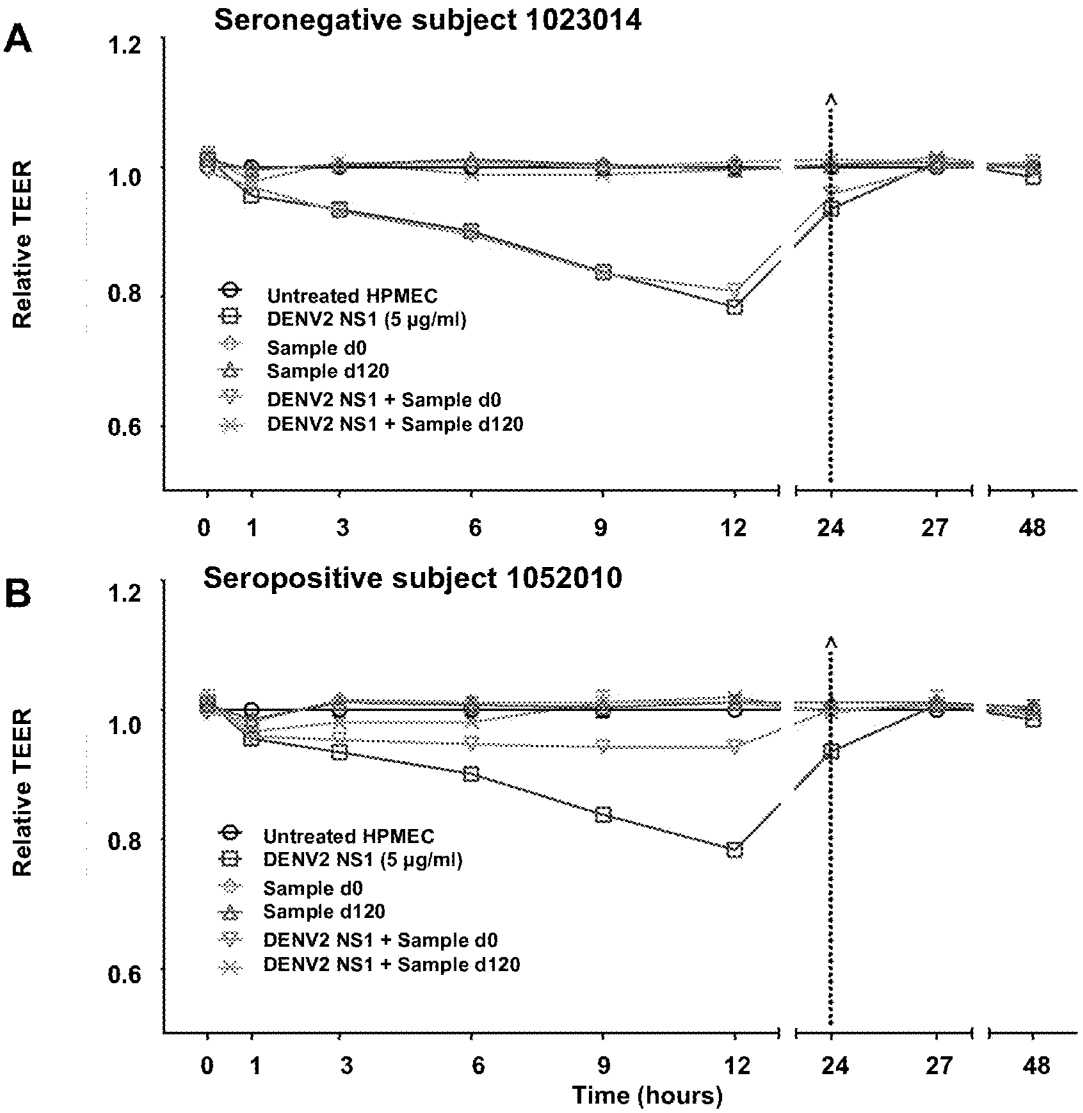
FIG. 7: Effect of sera from a seronegative subject (A) and a seropositive subject (A) to whom TDV was administered on DENV-2 NS1-induced hyperpermeability as determined by TEER. HPMEC were grown on Transwell semi-permeable membranes (0.4 μm pore size), and serum samples (30 μl) were added to the apical chamber in the presence or absence of DENV2 NS1 (5 μg/ml). DENV2 NS1 is depicted as squares; day 0 serum alone is depicted as diamonds; day 120 serum alone is depicted as triangles; day 0 serum+DENV2 NS1, is depicted as upside-down triangles; day 120 serum+DENV2 NS1 is depicted as X's. (^) represents media change. Endothelial permeability was measured at indicated time-points over 48 hours. Relative TEER values from one independent experiment performed in duplicate are plotted. Error bars indicate standard error of the mean (SEM).

Day 0 serum samples from seronegative subjects did not protect against NS1-mediated barrier dysfunction, but day 120 samples from all seronegative subjects blocked decreases in TEER values induced by NS1 (see FIG. 7A). Day 0 samples from seropositive subjects produced varying levels of protection, and all day 120 samples from seropositive subjects completely abrogated NS1-induced hyperpermeability (see FIG. 7B).

c) Degradation of Glycocalyx-Like Layer (EGL)

Microscopy was performed as previously described (Puerta-Guardo et al. (2016) PloS Pathog. 12(7):e1005738). For imaging experiments, HPMEC were grown on coverslips coated with 0.2% gelatin (Sigma) and imaged on a Zeiss LSM 710 Axio Observer inverted fluorescence microscope equipped with a 34-channel spectral detector. Images acquired using the Zen 2010 software (Zeiss) were processed and analyzed with ImageJ software. All RGB images were converted to grayscale, then mean grayscale values and integrated density from selected areas were taken, along with adjacent background readings, and plotted as mean fluorescence intensity (MFI). To assess the effect of sera from vaccinated subjects on DENV2 NS1-induced EGL disruption, the distribution of sialic acid and heparan sulfate was examined on confluent HPMEC monolayers treated with DENV2 NS1 (5 μg/ml)+negative control serum (30 μl), NS1+positive control serum (30 μl), or NS1+serum from vaccinated subjects (30 μl) and fixed with 4% paraformaldehyde (PFA) at 6 hours post-treatment. Primary antibodies (Wheat germ agglutinin (WGA) lectin conjugated to Alexa Fluor 647 (WGA-A647, Molecular Probes) to stain N-acetyl neuraminic acid (sialic acid); Ab Heparan Sulfate, purified (clone F58-10E4, Amsbio) were incubated overnight at 4° C., and detection was performed using secondary species-specific anti-IgG or anti-IgM antibodies conjugated to Alexa fluorophores (488 and 647).

Figure 8:
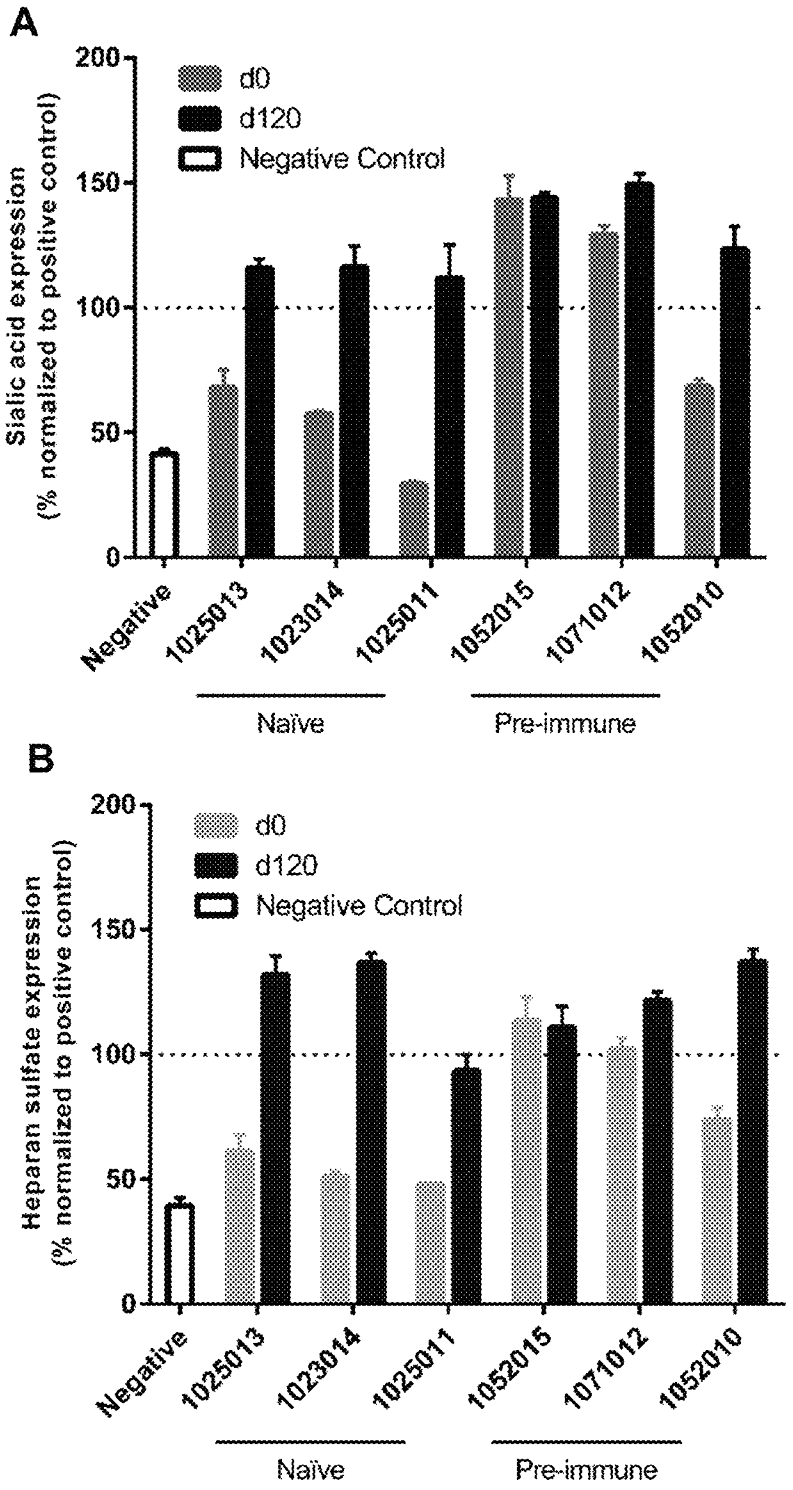
FIG. 8: Effect of sera from seronegative and seropositive subjects to which TDV was administered on NS1-induced sialic acid and heparan sulfate degradation. Shown is the quantification of mean fluorescence intensity (MFI) of (A) sialic acid and (B) heparan sulfate expression after staining with sialic acid- and heparan sulfate-specific fluorescent antibodies as visualized by confocal microscopy. Values are normalized to MFI from the NS1+positive control serum group (represented by dotted line at 100%) and expressed as percentage of control. Error bars indicate SEM. The left bar for each subject shows the results at day 0 (d0), the right car for each subject shows the results at day 120 (d120).

Day 0 sera from seronegative subjects had no substantial protective effect, while day 120 sera from seronegative subjects completely blocked degradation of both sialic acid and heparan sulfate. Similarly, day 0 samples from seropositive subjects exhibited varying levels of protection, and sera from seropositive subjects at day 120 were completely protective (see FIG. 8). Positive control serum was used as a baseline for protection, and negative control serum represented maximum NS1-mediated disruption. These results show that the anti-NS1 antibody response stimulated by the dengue vaccine can protect against NS1-induced hyperpermeability by preventing the degradation of key EGL components.

Taken together, these results suggest that the dengue vaccine stimulates robust and protective anti-DENV2 NS1 Ab responses following vaccination.

Example 6: Phase III Clinical Trial in Children

A Phase III, double-blind, randomized, and placebo-controlled trial in 20100 subjects aged 4 to 16 years living in Thailand, Sri Lanka, Philippines, Panama, Nicaragua, Dominican Republic, Colombia or Brazil was performed evaluating the efficacy, safety and immunogenicity of a tetravalent dengue vaccine referred to hereinafter as TDV. The trial includes 3 parts. Part 1 evaluates vaccine efficacy (VE) and lasts until both of the following 2 criteria are fulfilled: (i) 120 cases of dengue fever are confirmed and (ii) minimum duration of subject follow-up of 12 months post-second vaccination. Part 2 is for an additional 6 months to evaluate VE and for secondary efficacy analyses. Part 3 will evaluate long-term safety by following participants for side effects and will last an additional 3 years.

Part 1: Active surveillance for the primary assessment of efficacy in all subjects. During this time subjects were contacted at least weekly to ensure identification of febrile illness that could potentially be due to dengue. This part commenced on the day of vaccination and finished once both of the following 2 criteria were fulfilled: (i) 120 cases of dengue fever are confirmed and (ii) minimum duration of subject follow-up of 12 months post-second vaccination. The end of Part 1 was defined for each subject so that the duration of follow up after the second vaccination was approximately the same for all subjects. Virologically-confirmed cases in Part 1 count towards the primary efficacy objective if occurring at least 30 days post-second vaccination. Part 1 was finished 12 months post-second vaccination Part 2: Active surveillance for an additional 6 months for each subject following the completion of Part 1, I, i.e. 18 month post second vaccination. During this time subjects were contacted at least weekly to ensure identification of febrile illness that could potentially be due to dengue. Virologically-confirmed cases in Parts 1 and 2 contribute towards the secondary efficacy objectives.

Part 3: Modified active surveillance for the assessment of safety in all subjects following the completion of Part 2 and lasting 3 years for each subject. The modified surveillance during Part 3 will maintain at least weekly contacts through Part 3 of the trial, but the intensity of investigation will be modified based on the need for hospitalization. Surveillance will identify febrile illness of any severity that could potentially be due to dengue.

Criteria for Inclusion include:

The subject was aged 4 to 16 years inclusive, at the time of randomization.

Individuals who were in good health at the time of entry into the trial as determined by medical history, physical examination (including vital signs) and clinical judgment of the Investigator.

The subject and/or the subject's parent/guardian signed and dated an assent/written informed consent form where applicable, and any required privacy authorization prior to the initiation of any trial procedures, after the nature of the trial has been explained according to local regulatory requirements.

Individuals who can comply with trial procedures and are available for the duration of follow-up.

Exclusion criteria include:

1. Febrile illness (temperature ≥38° C.) or moderate or severe acute illness or infection at the time of randomization.
2. History or any illness that, in the opinion of the Investigator, might interfere with the results of the trial or pose an additional risk to the subject due to participation in the trial, including but not limited to:
   a. Known hypersensitivity or allergy to any of the vaccine components.
   b. Female subjects (post-menarche) who are pregnant or breastfeeding.
   c. Individuals with any serious chronic or progressive disease according to judgment of the Investigator (e.g., neoplasm, insulin-dependent diabetes, cardiac, renal or hepatic disease, neurologic or seizure disorder or Guillain-Barré syndrome).
   d. Known or suspected impairment/alteration of immune function, including:
      i. Chronic use of oral steroids (equivalent to 20 mg/day prednisone ≥12 weeks/≥2 mg/kg body weight/day prednisone ≥2 weeks) within 60 days prior to Day 1 (Month 0) (use of inhaled, intranasal, or topical corticosteroids is allowed).
      ii. Receipt of parenteral steroids (equivalent to 20 mg/day prednisone ≥12 weeks/≥2 mg/kg body weight/day prednisone ≥2 weeks) within 60 days prior to Day 1 (Month 0).
      iii. Administration of immunoglobulins and/or any blood products within the 3 months prior to Day 1 (Month 0) or planned administration during the trial.
      iv. Receipt of immunostimulants within 60 days prior to Day 1 (Month 0).
      v. Immunosuppressive therapy such as anti-cancer chemotherapy or radiation therapy within 6 months prior to Day 1 (Month 0).
      vi. Human Immunodeficiency Virus (HIV) infection or HIV-related disease.
      vii. Genetic immunodeficiency.
3. Receipt of any other vaccine within 14 days (for inactivated vaccines) or 28 days (for live vaccines) prior to Day 1 (Month 0) or planning to receive any vaccine within 28 days after Day 1 (Month 0).
4. Participation in any clinical trial with another investigational product 30 days prior to Day 1 (Month 0) or intent to participate in another clinical trial at any time during the conduct of this trial.
5. Previous participation in any clinical trial of a dengue candidate vaccine, or previous receipt of a dengue vaccine.
6. First degree relatives of individuals involved in trial conduct.
7. Females of childbearing potential who are sexually active, and who have not used any of the acceptable contraceptive method for at least 2 months prior to Day 1 (Month 0).
8. Females of childbearing potential who are sexually active, and who refuse to use an acceptable contraceptive method up to 6 weeks post-second vaccination.
9. Deprived of freedom by administrative or court order, or in an emergency setting, or hospitalized involuntarily.
10. Current alcohol abuse or drug addiction that may interfere with the subject's ability to comply with trial procedures.
11. Identified as an employee of the Investigator or trial center, with direct involvement in the proposed trial or other trials under the direction of that Investigator or trial center.

Eligible subjects were randomized (2:1) into two treatment groups: groups 1 received one subcutaneous (SC) dose of TDV in the upper arm on Day 1 and on Day 90, and group 2 received one subcutaneous dose of placebo in the upper arm on Day 1 and on Day 90. Randomization was stratified by region (Asia Pacific and Latin America) and age range (children aged 4-5 years, 6-11 years, and 12-16 years) to ensure each age range has the appropriate ratio of TDV to placebo in each region. After randomization dropouts were not replaced. Study Day 1 is defined to be the date of the first dose administration of TDV or placebo. The TDV was prepared as described in Example 1. Each subcutaneous dose of TDV was 0.5 mL and the concentration of the four dengue serotypes in the TDV vaccine in each dose was 3.6 $\log_{10}$ PFU/dose, 4.0 $\log_{10}$ PFU/dose, 4.6 $\log_{10}$ PFU/dose and 5.1 $\log_{10}$ PFU/dose of TDV-1, TDV-2, TDV-3 and TDV-4, respectively.

The "total concentration in pfu/0.5 ml" which serves as a base value for the calculation of the percentage concentration for each individual component of a tetravalent dengue vaccine is shown for one exemplary tetravalent vaccine composition comprising dengue serotype 1 in a concentration of 3.60 $\log_{10}$ pfu/0.5 ml, a dengue serotype 2 concentration of 4.00 $\log_{10}$ pfu/0.5 ml, a dengue serotype 3 concentration of 4.60 log 10 pfu/0.5 ml and a dengue serotype 4 concentration of 5.11 $\log_{10}$ pfu/0.5 ml.

Primarily, the logarithmic values of the concentrations are converted into numerical values. The results of this conversion are $4\times10^3$ pfu/0.5 ml for serotype 1, $1\times10^4$ pfu/0.5 ml for serotype 2, $4\times10^4$ pfu/0.5 ml for serotype 3 and $1.3\times10^5$ pfu/0.5 ml for serotype 4. The total concentration in pfu/0.5 ml is the sum of the preceding numerical values resulting in $1.84\times10^5$ pfu/0.5 ml.

The "percentage concentration" for each of the serotypes 1, 2, 3 and 4 is obtained by dividing the numerical concentration value (expressed as pfu/0.5 ml) of an individual serotype by the total concentration (expressed in pfu/0.5 ml) and multiplying the result by 100 i.e.:

$$\text{Percentage concentration of serotype } 1=(4\times10^3 \text{ pfu/0.5 ml}\div1.84\times10^5 \text{ pfu/0.5 ml})\times100=2\%$$

$$\text{Percentage concentration of serotype } 2=(1\times10^4 \text{ pfu/0.5 ml}\div1.84\times10^5 \text{ pfu/0.5 ml})\times100=5\%$$

$$\text{Percentage concentration of serotype } 3=(4\times10^4 \text{ pfu/0.5 ml}\div1.84\times10^5 \text{ pfu/0.5 ml})\times100=22\%$$

$$\text{Percentage concentration of serotype } 4=(1.3\times10^5 \text{ pfu/0.5 ml}\div1.84\times10^5 \text{ pfu/0.5 ml})\times100=71\%.$$

The percentage concentrations are rounded to whole numbers.

Primary Outcome Measures included the vaccine efficacy (VE) of two doses of TDV in preventing virologically-confirmed dengue (VCD) fever induced by any dengue serotype [time frame: 30 days post-second vaccination (Day 120) until the end of Part 1]. VE is defined as $1-(\lambda v/\lambda c)$, wherein $\lambda v$ and $\lambda c$ denote the hazard rates for the TDV and placebo groups, respectively. A virologically-confirmed dengue case is defined as febrile illness (defined as temperature ≥38° C. on any 2 of 3 consecutive days) or illness clinically suspected to be dengue by the Investigator with a positive serotype-specific reverse transcriptase polymerase chain reaction (RT-PCR). A febrile illness will require an interval of at least 14 days from a previous febrile illness to avoid overlap of acute and convalescent visits from one episode with those from a second episode.

Secondary Outcome Measures include:

1) VE of two doses of TDV in preventing virologically-confirmed dengue fever induced by each dengue serotype [time frame: from 30 days post-second vaccination (Day 120) until the end of Part 2].
2) VE of two doses of TDV in preventing virologically-confirmed dengue fever induced by any dengue serotype in participants dengue seronegative at baseline [time frame: from 30 days post-second vaccination (Day 120) until the end of Part 2 (up to 21 months)].
3) VE of two doses of TDV in preventing virologically-confirmed dengue fever induced by any dengue serotype in participants dengue seropositive at baseline [time frame: from 30 days post-second vaccination (Day 120) until the end of Part 2].
4) VE of two doses of TDV in preventing hospitalization due to virologically-confirmed dengue fever induced by any dengue serotype [time frame: from 30 days post-second vaccination (Day 120) until the end of Part 2].
5) VE of two doses of TDV in preventing virologically-confirmed severe dengue fever induced by any dengue serotype [time frame: from 30 days post-second vaccination (Day 120) until the end of Part 2].
6) Percentage of participants with solicited local injection site adverse events (AEs) in the safety subset [time frame: Days 1 through 7 after each vaccination] and severity of solicited local injection AEs. Solicited local AEs at injection site are defined as pain, erythema and swelling that occurred within 7 days after each vaccination.
7) Percentage of participants with solicited systemic adverse events (AEs) in the safety subset [time frame: Days 1 through 14 after each vaccination] and severity of solicited systemic AEs. Solicited systemic AEs in children (<6 years) are defined as fever, irritability/fussiness, drowsiness and loss of appetite that occurred within 14 days after each vaccination. Solicited systemic AEs in children (≥6 years) are defined as fever, headache, asthenia, malaise and myalgia that occurred within 14 days after each vaccination.
8) Percentage of participants with any unsolicited adverse events (AEs) in the safety subset [time frame: Days 1 through 28 after each vaccination]. Unsolicited AEs are any AEs that are not solicited local or systemic AEs, as defined above.
9) Percentage of participants with serious adverse events (SAEs) during Parts 1 and 2 [time frame: from Day 1 until the end of Parts 1 and 2]. A serious adverse event (SAE) is any untoward medical occurrence or effect that at any dose results in death, is life-threatening, requires inpatient hospitalization or prolongation of existing hospitalization, results in persistent or significant disability/incapacity, is a congenital anomaly/birth defect or is medically important due to other reasons than the above mentioned criteria.
10) Percentage of participants with fatal SAEs and SAEs related to study drug during the first and second half of Part 3 [time frame: for 3 years (18 month halves) beginning at the end of Part 2 (approximately 21 months after the first vaccination)].
11) Percentage of participants with a seropositive response for each of the four dengue serotypes in the immunogenicity subset [time frame: Day 1 and months 1, 3, 4, 9, 15 and then annually (up to 3 years)]. Seropositive response is defined as a reciprocal neutralizing titer ≥10. The four DENV serotypes are DEN-1, DEN-2, DEN-3 and DEN-4.
12) Percentage of participants with a seropositive response for multiple dengue serotypes in the immunogenicity subset [time frame: Day 1 and months 1, 3, 4, 9, 15 and then annually (up to 3 years)].
13) Geometric Mean Titers (GMTs) of neutralizing antibodies for each of the four dengue serotypes in the immunogenicity subset [time frame: Day 1 and months 1, 3, 4, 9, 15 and then annually (up to 3 years)]. GMTs of neutralizing antibodies will be measured via microneutralization test (MNT) as described in Example 2.

a) Study Population

Figure 9:
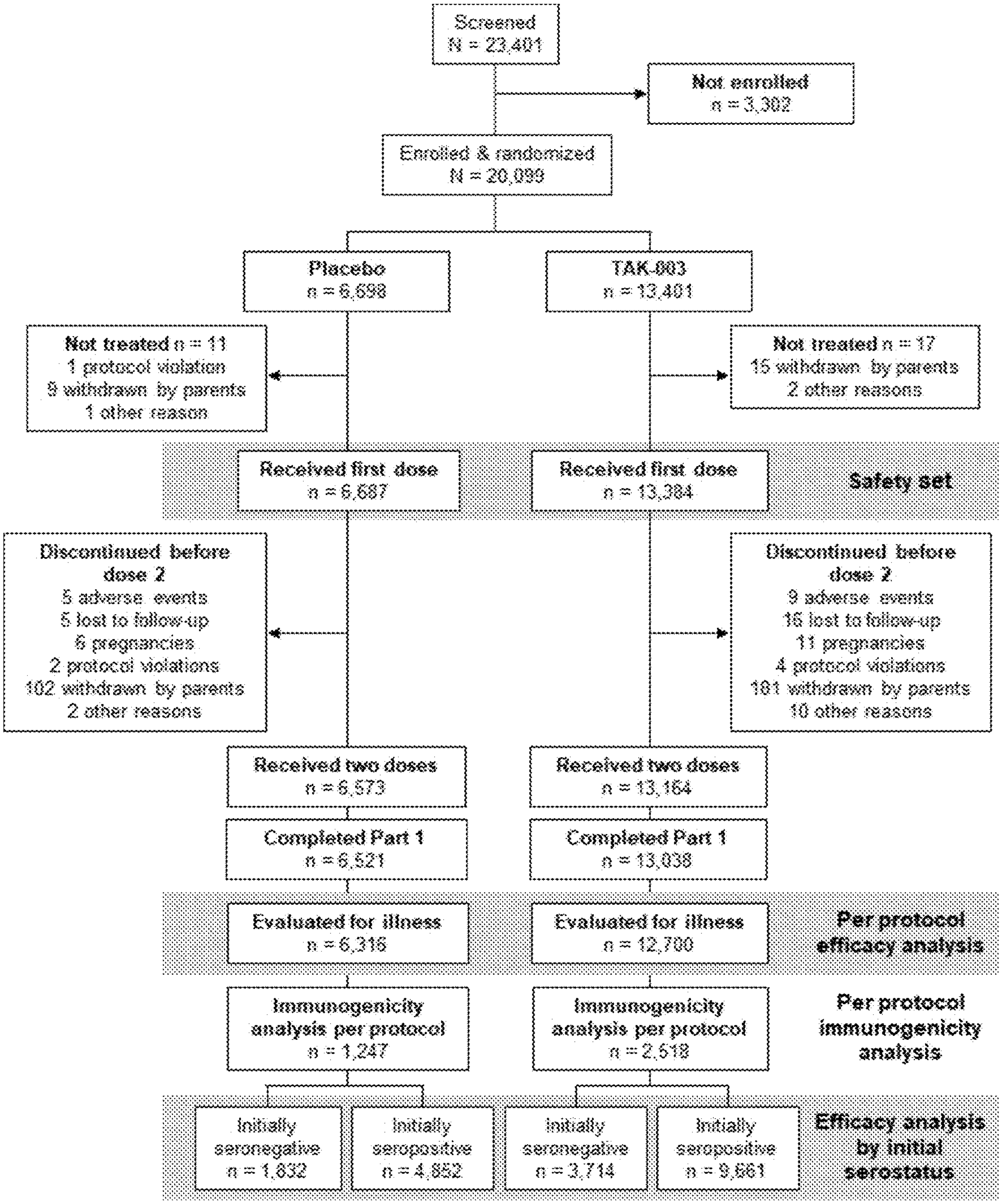
FIG. 9: Flow diagram of the clinical trial of Example 6.

After screening, 20,099 participants were randomized, and 20,071 received at least one injection. In total, 97.4% of placebo participants (n/N: 6,521/6,698) and 97.3% of vaccinees (n/N: 13,038/13,401) completed Part 1 of the study (FIG. 9). Reasons for study withdrawals included AEs, participants lost to follow-up, pregnancy, protocol violations, and withdrawal by participants (or parents/guardians). Baseline characteristics were similar across both treatment groups (Table 19). Mean age of study participants was 9.6 years, with baseline seronegativity of 27.7%, and enrollment was broadly balanced across regions (46.5% in Asia, 53.5% in Latin America). The highest seronegative rate was in Panama (62.2%), followed by Sri Lanka (38.5%), Thailand (34.4%), Brazil (28.8%), Nicaragua (22.3%), Colombia (15.4%), the Philippines (12.4%), and the Dominican Republic (2.8%).

TABLE 19

Baseline characteristics of study population (number, %)

| | TDV | Placebo | Total |
|---|---|---|---|
| Per Protocol Set | | | |
| Number of Participants | 12,704 | 6,317 | 19,021 |
| Mean Age (Years, SD) | 9.6 (3.35) | 9.6 (3.34) | 9.6 (3.35) |
| Baseline Seronegative[a] | 3,533 (27.8) | 1,726 (27.3) | 5,259 (27.7) |
| Female | 6,314 (49.7) | 3,098 (49.0) | 9,412 (49.5) |
| Male | 6,390 (50.3) | 3,219 (51.0) | 9,609 (50.5) |
| Asia Pacific | 5,896 (46.4) | 2,942 (46.6) | 8,838 (46.5) |
| Baseline Seronegative[a] | 1,503 (25.5) | 773 (26.3) | 2,276 (25.8) |
| Latin America | 6,808 (53.6) | 3,375 (53.4) | 10,183 (53.5) |
| Baseline Seronegative[a] | 2,030 (29.8) | 953 (28.2) | 2,983 (29.3) |
| Safety Set[b] | | | |
| Number of Participants | 13,380 | 6,687 | 20,071 |
| Mean Age (Years, SD) | 9.6 (3.36) | 9.6 (3.34) | 9.6 (3.35) |
| Baseline Seronegative[a] | 3,714 (27.8) | 1,832 (27.4) | 5,547 (27.6) |
| Female | 6,651 (49.7) | 3,276 (49.0) | 9,929 (49.5) |
| Male | 6,729 (50.3) | 3,411 (51.0) | 10,142 (50.5) |

TABLE 19-continued

| Baseline characteristics of study population (number, %) | | | |
|---|---|---|---|
| | TDV | Placebo | Total |
| Safety Set of Subset[b] | | | |
| Number of Participants | 2,663 | 1,329 | 3,993 |
| Baseline Seronegative[3] | 740 (27.8) | 369 (27.8) | 1,109 (27.8) |

[a]Seronegative for all serotypes; seropositive defined as reciprocal neutralizing antibody titer ≥10; SD, standard deviation.
[b]numbers of participants in TVD plus placebo groups are not equal to total numbers shown because misallocated participants (i.e. those who received both TVD and placebo due to an administrative error) are not included in the TDV and placebo group data.

b) Febrile Illnesses and VCD

During Part 1, 5,754 and 4,663 episodes of febrile illness were reported in Asian and Latin American sites, respectively. Acute samples were obtained in 99.5% and 96.6% of these cases, with 98.3% and 85.1% of samples taken within five days, in Asia and Latin America, respectively. There were 278 VCD cases (76 hospitalized) in the safety set during the entire Part 1 period, of which 210 (58 hospitalized) were 30 days post-second vaccination in the PPS (Table 20; Table 22) and were included in primary endpoint analysis.

c) Distribution of VCD Included in Primary Endpoint Analysis

DENV-1 was reported in all countries with VCD and included all the 21 cases in Panama. In Sri Lanka, 54 of 60 VCD were DENV-2, and 87 of 109 VCD in the Philippines were DENV-3. All seven DENV-4 VCD were reported in the Philippines. No VCD were reported in Nicaragua or the Dominican Republic. Of the associated 58 hospitalized VCD, 43 were reported in Sri Lanka. A total of two severe dengue (both DENV-3) and five dengue hemorrhagic fever (DHF; three DENV-2; two DENV-3) cases were reported (Table 21). These seven were also the only such cases in the entire part 1 safety set.

d) Vaccine Efficacy

Figure 10:
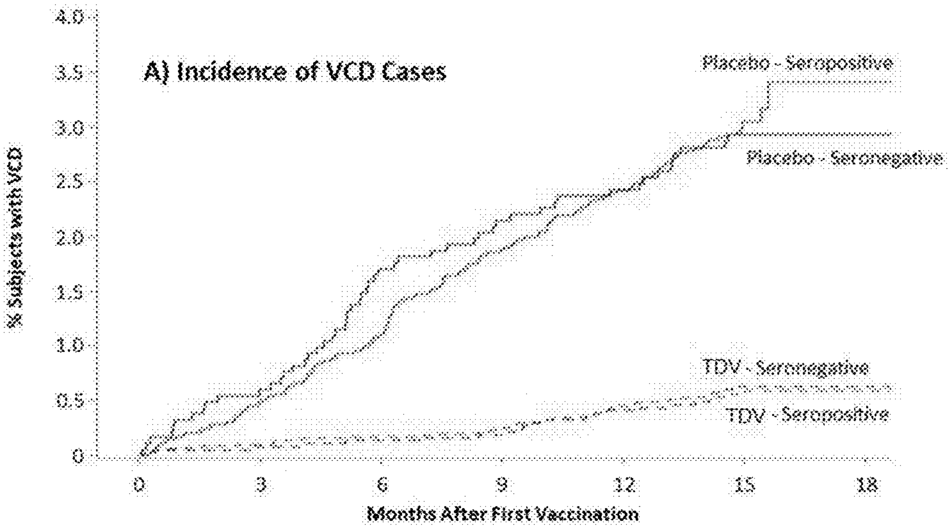
FIG. 10: Cumulative incidence of A) virologically-confirmed dengue cases and B) hospitalized virologically-confirmed dengue cases over time during Part 1 study period by baseline serostatus (safety set data; data presented truncated at Month 18). Tables show numbers of participants under follow-up at various time points to end of Part 1 study period.
Figure 10:
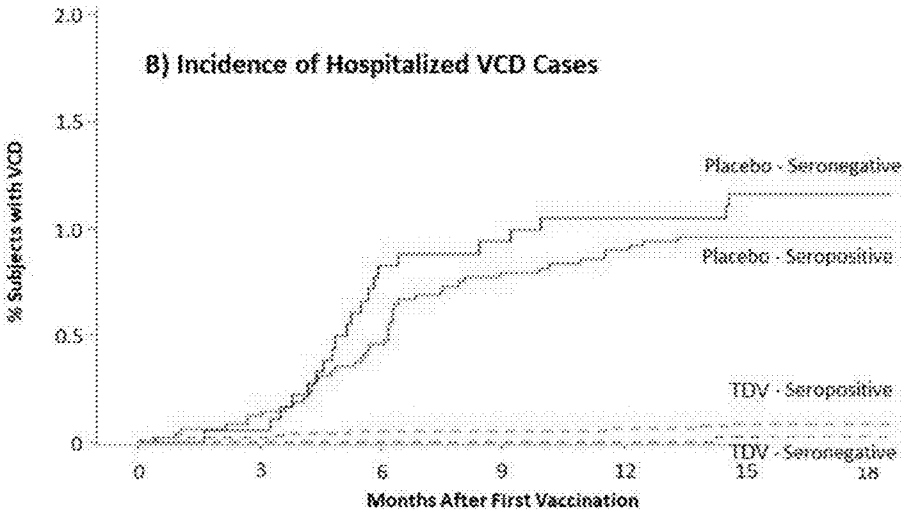
Figure 11:
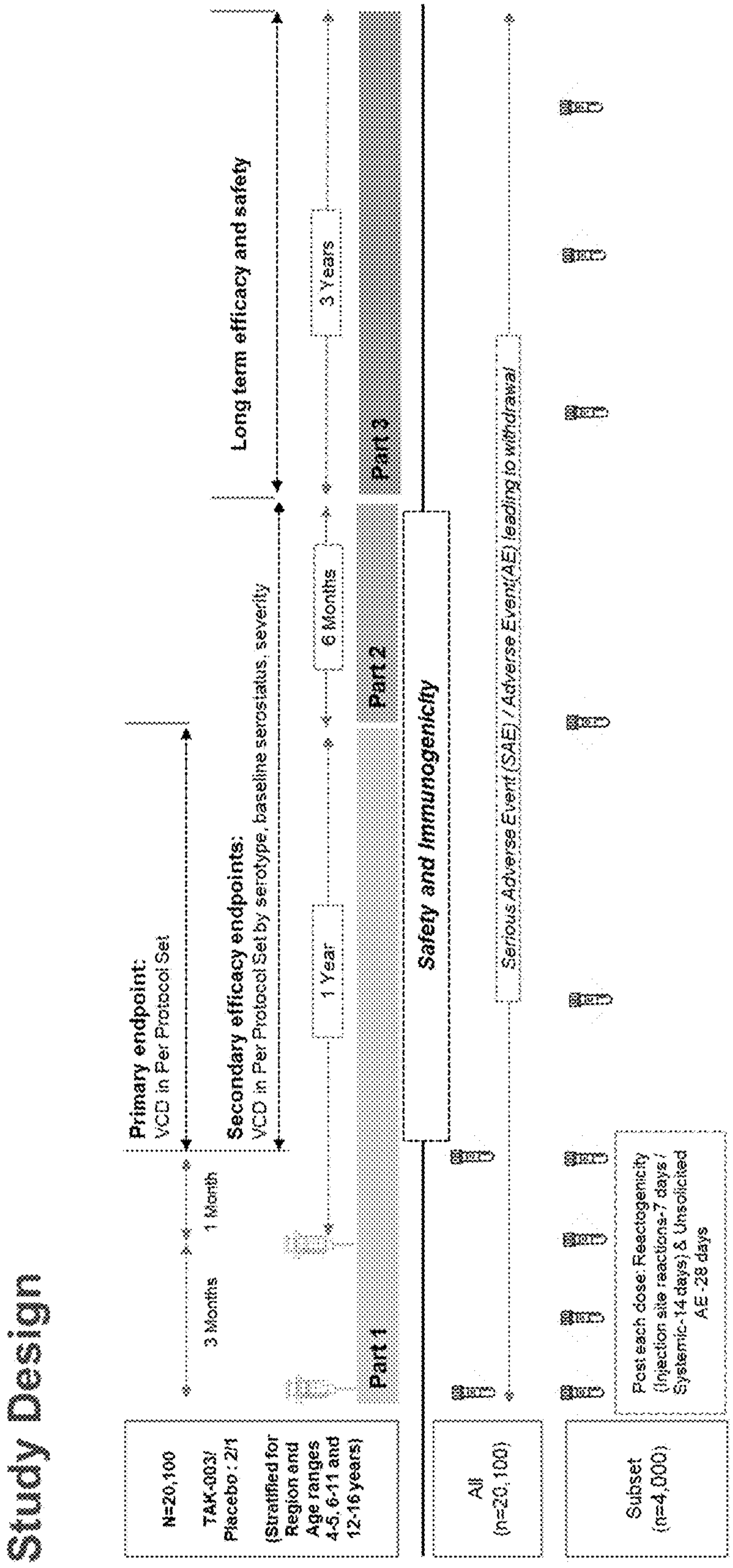
FIG. 11: Study design of phase III study described in example 6

VE against VCD of any serotype was 80.2% (95% CI: 73.3-85.3; P<0.001). A similar efficacy of 81% (95% CI: 64.1-90.0) between the doses and from first dose onwards in the safety set (Table 20) suggests that the vaccine was efficacious after the first dose. Exploratory analysis of the secondary efficacy endpoints showed a trend of differential efficacy by serotype, with the highest efficacy against DENV-2 (97.7%), followed by DENV-1 (73.7%), DENV-4 (63.2% with CI containing zero), and DENV-3 (62.6%; Table 3). Overall, efficacy was similar in baseline seronegatives (74.9%) and seropositives (82.2%; FIG. 10A); however, this varied by serotype. Efficacy against DENV-2 was not impacted by serostatus; efficacy against DENV-1 was slightly higher in baseline seropositives (79.8%; 95% CI: 51.3-91.6) than baseline seronegatives (67.2%; 95% CI: 23.2-86.0). No efficacy was observed against DENV-3 in baseline seronegatives (−38.7%; 95% CI: −335.7-55.8) compared to baseline seropositives (71.3%; 95% CI: 54.2-82.0). Efficacy by serostatus could not be calculated for DENV-4 because no cases were observed in baseline seronegatives. In the primary endpoint timeframe of the PPS, only five VCD requiring hospitalization were reported in the vaccine group compared with 53 cases in the placebo group, with a VE of 95.4% (95% CI: 88.4-98.2; 97.2% for baseline seronegatives and 94.4% for baseline seropositives; Table 21; FIG. 10B), consistent with a VE of 93.3% (95% CI: 86.7-96.7) in the safety set from first dose onwards.

The primary vaccine efficacy (VE) of two doses of TDV in preventing virologically-confirmed dengue (VCD) fever induced by any dengue serotype is shown in Table 20.

TABLE 20

Vaccine efficacy of TDV in preventing virologically-confirmed dengue (VCD) fever against any serotype from 30 days post-second vaccination until end of part 1 Per Protocol Set (PPS), i.e. 12 months post-second vaccination. Safety set analysis from first dose to end of Part 1 study period, i.e. 12 months post-second vaccination

| | Placebo n = 6317 | TDV (PPS) n = 12,704 |
|---|---|---|
| number of subject evaluated | 6,316 | 12,700 |
| number of subjects with febrile illness | 1,712 | 3,195 |
| number of febrile illness cases | 2,591 | 4,692 |
| virologically confirmed dengue fever (n [%]) | 149 [2.4] | 61 [0.5] |
| Person-years at risk | 5,670.1 | 11,578.7 |
| incident density | 2.6 | 0.5 |
| relative risk | 0.20 | |
| 95% CI of relative risk | (0.15, 0.27) | |
| vaccine efficacy (%) | 80.2 | |
| 95% CI of vaccine efficacy | (73.3, 85.3) | |
| p-value for vaccine efficacy | <0.001 | |
| | **Placebo** | **TDV (Safety Set)*** |
| number of subject evaluated | 6,687 | 13,380 |
| virologically confirmed dengue fever (n [%]) | 199 [3.0] | 78 [0.6] |
| Person-years at risk | 8,072.0 | 16,351.5 |
| incident density | 2.5 | 0.5 |
| vaccine efficacy (%) | 80.9 | |
| 95% CI of vaccine efficacy | (75.2, 85.3) | |

Note 1:
Percentage of virologically confirmed dengue (VCD) fever are based on number of subjects evaluated.
Note 2:
Person-years at risks is defined as cumulative time in years until start of VCD fever or until end of Part 1 study period or discontinuation date, whichever comes first. Incident density is defined as the number of cases per 100 person-years at risk. Percentages are based on total number (denominator) of analysis set participants evaluate and may not be equal to the total number of participants in the per protocol analysis set.
*One participant had two instances of VCD during Part 1, only the first VCD was included in efficacy calculation
Note 3:
Vaccine efficacy (VE) and 2-sided 95% CIs are estimated from a Cox proportional hazard model with TDV as a factor, adjusted for age and stratified by region.
Note 4:
Statistical significance will be concluded if the lower bound of the 95% CI for VE is above 25%. Since the hypotheses will be tested in a confirmatory manner at a 2-sided significance level of 5%, the calculated p-value should be compared with 0.025.
Note 5:
Relative risk is calculated as the number of events divided by the number of subjects evaluated in the TDV group, over the number of events divided by the number of subjects evaluated in the placebo group.

For the efficacy evaluation shown in Table 20, a case of VCD was defined as febrile illness (defined as fever ≥38° C. on any 2 of 3 consecutive days) with a positive serotype-specific RT-PCR (i.e., positive dengue detection RT-PCR) and occurring at any time starting from 30 days post-second vaccination (Day 120 [Month 4]) through the end of Part 1. The analysis was performed on the Per-Protocol Set (PPS) and Safety Set.

As used herein, the "Per-Protocol Set (PPS)" consist of all subjects in the Full Analysis Set (FAS) consisting of all randomized subjects who received at least one dose of TDV or placebo who had no major protocol violations. Major protocol violations are not receiving both doses of TDV or placebo administration, not receiving both doses in the correct interval, not having the correct administration of TDV or placebo, use of prohibited medications/vaccines by the subject, the subject meets any of the exclusion criteria of 2d, 3, 4 or 5 defined above or product preparation error.

The p-value is obtained by solving the critical value Z in the following equation:

$$\text{Upper bound of 1-sided}(1-p\ \%)CI \text{ of } HR=0.75,$$

wherein HR is the hazard ratio and defined as HR=λV/λC.

$$e\hat{}[\beta\hat{}+Z*S\hat{}E]=0.75,$$

wherein β^ defines the treatment and S^E the related standard error.

The 1-sided p-value is 1−(area to the left of the critical value Z from a standard normal distribution). Since the hypotheses will be tested in a confirmatory manner 2-sided at a significance level of 5%, the calculated 1-sided p-value should be compared with 0.025.

In summary in Part 1 of this study, a high vaccine efficacy of 80.2% against virologically-confirmed dengue of any serotype in children 4-16 years of age was found. It included an efficacy of 74.9% in baseline seronegatives and a robust 95.4% reduction in hospitalizations. Onset of protection could be seen after the first dose with 81% efficacy between doses. Overall, these results suggest a potential benefit for each vaccine recipient regardless of prior dengue exposure or age. This finding is significant because vaccine development against dengue has been challenging, especially for dengue naïve individuals, and dengue remains one of the WHO's top ten threats to global health in 2019.19 Furthermore, the onset of protection after the first dose has potential utility in the context of outbreak control or travel vaccination, offering a reduction in the risk of dengue after only one dose.

Severe forms of dengue were assessed as follows: Dengue Hemorrhagic Fever (DHF) as defined by the 1997 WHO definition. Severe Dengue through the Dengue Case Adjudication Committee. The Dengue Case Adjudication Committee (DCAC) consisted of four members: a voting chairperson, two voting members, and an independent non-voting statistician. The three DCAC voting members are all physicians and clinical dengue experts. DCAC members are not study investigators and do not have any conflict of interest that would bias their review of the trial data. All non-hospitalized cases were considered non-severe. The DCAC severe dengue case criteria applied in a blinded manner to virologically-confirmed hospitalized dengue cases are as follows: 1) bleeding abnormality, for a case to be considered severe there needs to be a significant intervention required in response to the bleeding episode such as blood transfusion, nasal packing, hormonal therapy, or, bleeding occurred into critical organs such as the brain; 2) plasma leakage, for a case to be considered severe there needs to be evidence of both plasma leakage and functional impairment (plasma leakage includes clinical evidence, radiological evidence, or hematocrit elevated >20% above normal levels or baseline; functional impairment defined as shock or respiratory distress); 3) liver, for a case to be considered severe there needs to be evidence of both hepatitis and functional impairment (hepatitis defined as an aspartate aminotransferase [AST] or alanine aminotransferase [ALT] >10 upper limit of normal range [ULN]; functional impairment defined as prothrombin [PT] >1.5 ULN or hypoalbuminemia); 4) renal, serum creatinine >2.5 times ULN or requiring dialysis; 5) cardiac, abnormalities intrinsic to the heart (i.e. not resulting from intravascular volume depletion) and with evidence of functional impairment (examples of intrinsic abnormality: myocarditis, pericarditis, and myopericarditis; example of functional impairment: new conduction abnormality resulting in irregular heart rhythm [i.e. not transient first-degree heart block]); 6) central nervous system, any abnormality with the exception of a simple febrile convulsion or a brief delirium; 7) shock, all shock cases considered severe. At least 1 functional impairment (of criterion 3, 4, 5, 6), needs to be present but the totality of data were considered by the members in their assessment.

Further results of part 1 and part 2 are presented in Tables 21a to c.

TABLE 21a

Distribution of cases contributing to primary endpoint by per protocol set subgroup (30 days after second vaccination until end of Part 1, i.e. 12 months after second vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Baseline Seropositive[a] | 41/9,165 (0.4%) | 0.5 | 110/4,587 (2.4%) | 2.7 | 82.2% (74.5%-87.6%) |
| Baseline Seronegative[a] | 20/3,531 (0.6%) | 0.6 | 39/1,726 (2.3%) | 2.5 | 74.9% (57.0%-85.4%) |
| DENV-1 | 16/12,700 (0.1%) | 0.1 | 30/6,316 (0.5%) | 0.5 | 73.7% (51.7%-85.7%) |
| DENV-2 | 3/12,700 (<0.1%) | <0.1 | 64/6,316 (1.0%) | 1.1 | 97.7% (92.7%-99.3%) |
| DENV-3 | 39/12,700 (0.3%) | 0.3 | 51/6,316 (0.8%) | 0.9 | 62.6% (43.3%-75.4%) |
| DENV-4[d] | 3/12,700 (<0.1%) | <0.1 | 4/6,316 (<0.1%) | <0.1 | 63.2% (−64.6%-91.8%) |
| 4-5 Years Old | 13/1,619 (0.8%) | 0.9 | 23/801 (2.9%) | 3.2 | 72.8% (46.2%-86.2%) |
| 6-11 Years Old | 34/7,009 (0.5%) | 0.5 | 85/3,491 (2.4%) | 2.7 | 80.7% (71.3%-87.0%) |
| 12-16 Years Old | 14/4,072 (0.3%) | 0.4 | 41/2,024 (2.0%) | 2.2 | 83.3% (69.3%-90.9%) |
| Asia | 54/5,894 (0.9%) | 1.0 | 127/2,942 (4.3%) | 4.9 | 79.5% (71.8%-85.1%) |
| Latin America | 7/6,806 (0.1%) | 0.1 | 22/3,374 (0.7%) | 0.7 | 84.3% (63.1%-93.3%) |
| Hospitalized VCD cases | | | | | |
| Baseline Seropositive[a] | 4/9,165 (<0.1%) | <0.1 | 35/4,587 (0.8%) | 0.8 | 94.4% (84.3%-98.0%) |
| Baseline Seronegative[a] | 1/3,531 (<0.1%) | <0.1 | 18/1,726 (1.0%) | 1.2 | 97.2% (79.1%-99.6%) |
| Cases of DHF[b] | | | | | |
| All participants | 1/12,700 (<0.1%) | <0.1 | 4/6,316 (<0.1%) | <0.1 | 87.3% (−13.5%-98.6%) |
| Severe VCD Cases[c] | | | | | |
| All participants | 1/12,700 (<0.1%) | <0.1 | 1/6,316 (<0.1%) | <0.1 | 50.8% (−686.9%-96.9%) |

VCD, virologically-confirmed dengue;

DHF, dengue hemorrhagic fever

[a]Seronegative for all serotypes; baseline seropositive defined as reciprocal neutralizing antibody titer ≥10 to one or more serotypes.

[b]VCD cases meeting WHO 1997 DHF criteria; incidence density defined as the number of cases per 100 person-years at risk; percentages are based on total number (denominator) of per protocol set participants evaluated.

[c]two severe VCD were not classified as DHF.

[d]The number of cases identified was sufficient to provide reasonably precise estimates of vaccine efficacy against all individual serotypes, except DENV-4.

TABLE 21b

Distribution of cases contributing to secondary endpoint by per protocol set subgroup (30 days after second vaccination until end of Part 2, i.e. 18 months after second vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 73.3% (66.5%-78.8%) |
| Baseline Seropositive[a] | 75 | 0.6 | 150 | 2.4 | 76.1% (68.5%-81.9%) |
| Baseline Seronegative[a] | 39 | 0.8 | 56 | 2.4 | 66.2% (49.1%-77.5%) |
| DENV-1 | 38 | 0.2 | 62 | 0.7 | 69.8% (54.8%-79.9%) |
| Baseline Seropositive[a] | 21 | 0.2 | 37 | 0.6 | 72.0 (52.2%-83.6%) |
| Baseline Seronegative[a] | 17 | 0.3 | 25 | 1 | 67.8 (40.3%-82.6%) |
| DENV-2 | 8 | <0.1 | 80 | 0.9 | 95.1% (89.9%-97.6%) |
| Baseline Seropositive[a] | 7 | <0.1 | 54 | 0.9 | 93.7 (86.1%-97.1%) |
| Baseline Seronegative[a] | 1 | <0.1 | 26 | 1.1 | 98.1 (85.8%-99.7%) |
| Hospitalized VCD cases | | | | | |
| Overall | 13 | <0.1 | 66 | 0.8 | 90.4% (82.6%-94.7%) |
| Baseline Seropositive[a] | 8 | <0.1 | 45 | 0.7 | 91.4% (81.7%-95.9%) |
| Baseline Seronegative[a] | 5 | 0.1 | 21 | 0.9 | 88.1% (68.5%-95.5%) |

VCD, virologically-confirmed dengue;

[a]Seronegative for all serotypes; baseline seropositive defined as reciprocal neutralizing antibody titer ≥10 to one or more serotypes.

TABLE 21c

Distribution of cases contributing to secondary endpoint by safety set (first vaccination until end of Part 2, i.e. 21 months after first vaccination)

| | TDV Dengue Cases | TDV Incidence Density | Placebo Dengue Cases | Placebo Incidence Density | Vaccine Efficacy (95% CI) |
|---|---|---|---|---|---|
| VCD cases | | | | | |
| Overall | | | | | 75.3% (69.5%-80.0%) |
| Overall in between[a] | | | | | 81.0% (64.1%-90.0%) |
| Baseline Seropositive[b] | 89 | 0.5 | 187 | 2.3 | 77.2% (70.6%-82.3%) |
| Baseline Seronegative[b] | 42 | 0.7 | 70 | 2.3 | 70.6% (56.9%-79.9%) |
| DENV-1 | 41 | 0.2 | 78 | 0.7 | 73.9% (61.9%-82.1%) |
| DENV-2 | 14 | <0.1 | 109 | 1.0 | 93.7% (89.0%-96.4%) |
| Hospitalized VCD cases | | | | | |
| Overall | 17 | <0.1 | 81 | 0.7 | 89.7% (82.6%-93.9%) |

VCD, virologically-confirmed dengue;

[a]In between: VCD after first vaccination and before second vaccination.

[b]Seronegative for all serotypes; baseline seropositive defined as reciprocal neutralizing antibody titer ≥10 to one or more serotypes.

TABLE 21d

Dengvaxia ® VCD (first vaccination until 25 months after first vaccination (i.e. 13 month after third vaccination), ITT from CYD15, 9 to 16 years of age)[a]

| | Vaccine Efficacy (95% CI) |
|---|---|
| Overall VCD | 64.7% (58.7%-69.8%) |
| Baseline Seropositive[b] | 83.7% (62.2%-93.7%) |
| Baseline Seronegative[b] | 43.2% (−61.5%-80.0%) |
| DENV-1 | 58.8% (40.2%-65.9%) |
| DENV-2 | 50.2% (31.8%-63.6%) |
| Overall Hospitalized VCD | 80.3% (64.7%-89.5%) |

[a]Luis Villar et al. Efficacy of a tetravalent dengue vaccine in Children in Latin America: N Engl J of Med 2015 Vol. 372 No2, 113-123

Clinical signs and symptoms of virologically-confirmed dengue cases during Part 1 study period in safety set data are shown in Table 22.

TABLE 22

Clinical signs and symptoms of virologically-confirmed dengue cases during Part 1 study period (safety set data)

| | TDV (N = 13,380) | Placebo (N = 6,687) | Relative Risk |
|---|---|---|---|
| Number of VCD Cases | 78 | 200 | — |
| Median Duration of Febrile Illness (days; 95% CI)[a] | 6.0 (5.7-7.4) | 6.0 (5.9-6.8) | — |
| Median Duration of Fever (days; 95% CI) | 4.0 (3.9-4.6) | 5.0 (4.5-5.0) | — |
| Number of Hospitalized VCD Cases | 9 | 67 | — |
| Median Duration of Hospitalization (days; 95% CI) | 5.0 (2.8-5.4) | 5.0 (4.6-5.4) | — |
| Evidence of Bleeding (%, n/N) | 3.8% (3/78) | 3.5% (7/200) | 1.10 |
| Plasma Leakage (%, n/N) | 2.6% (2/78) | 6.5% (13/200) | 0.39 |
| Plasma Leakage - Pleural Effusion (%, n/N) | 1.3% (1/78) | 1.5% (3/200) | — |
| Plasma Leakage - Ascites (%, n/N) | 1.3% (1/78) | 3.0% (6/200) | — |
| Plasma Leakage - Radiological Signs (%, n/N) | 40.0% (2/5) | 19.6% (10/51) | — |
| Plasma Leakage - Hematocrit Increase ≥20% (%, n/N)[b] | 3.8% (2/53) | 9.5% (13/137) | — |
| Platelet Count ≤100 × $10^9$ (%, n/N)[c] | 6.4% (5/78) | 22.0% (44/200) | 0.29 |
| Platelet Count ≤50 × $10^9$ (%, n/N)[c] | 3.8% (3/78) | 11.0% (22/200) | 0.35 |
| ALT or AST ≥1000 U/L (%, n/N)[c] | 0% (0/78) | 0% (0/200) | — |

VCD, virologically-confirmed dengue;

ALT, alanine aminotransferase;

AST, aspartate aminotransferase

[a]Duration of febrile illness defined as start date of earliest symptom to end date of latest symptom plus one day (symptoms considered include fever and any general symptoms).

[b]Hematocrit increase defined as maximum hematocrit between Day 3 and Day 7 inclusive, from onset of fever ≥20% increase over minimum hematocrit before Day 3 or after Day 7 from onset of fever.

[c]For platelet, ALT, and AST data, assessments within 14 days of onset of febrile illness have been considered.

N refers to number of VCD cases with available data for the specific parameter e) Immunogenicity The highest geometric mean titers (GMTs) were observed against DENV-2 regardless of baseline serostatus (Table 24). A very high tetravalent seropositivity rate (99.5%) in baseline seronegatives one month after the second dose (Tables 23 and 24) was observed.

Seropositivity rate (% of seropositive subjects) for each of the four dengue serotypes is determined at prevaccination on Day 1 (Month 0), post-first vaccination on Day 30 (Month 1), prevaccination on Day 90 (Month 3), post-second vaccination on Day 120 (Month 4), Day 270 (Month 9), Day 450 (Month 15), and then annually. Seropositivity rates (% participants, 95% CI) by dengue serotype per protocol set for immunogenicity data for Day 0, Day 30, Day 90, Day 120, and Day 270 are shown in Table 23.

Seropositivity rates (% participants, 95% CI) by dengue serotype against three or more serotypes (trivalent) and against all four serotypes (tetravalent) per protocol set for immunogenicity data for Day 0, Day 30, Day 90, Day 120, and Day 270 are shown in Table 23. The tetravalent seropositivity rates were high (>91%) in baseline seronegatives six months after second dose.

TABLE 23

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| DENV-1 | | | |
| 89.1 (87.6-90.5) | 90.6 (88.5-92.4) | 0 (0-0.5) | 0 (0-1.1) |
| 99.5 (99.1-99.8) | 88.6 (86.3-90.7) | 94.1 (92.0-95.8) | 4.9 (2.8-7.8) |
| 99.3 (98.8-99.6) | 90.2 (88.1-92.1) | 91.6 (89.3-93.5) | 6.1 (3.8-9.2) |
| >99.9 (99.7-100) | 90.3 (88.1-92.3) | 99.5 (98.6-99.9) | 8.3 (5.5-11.9) |
| 99.6 (99.1-99.8) | 89.8 (87.5-91.8) | 95.1 (93.0-96.6) | 9.0 (6.0-12.8) |
| DENV-2 | | | |
| 96.5 (95.6-97.3) | 97.2 (95.9-98.2) | 0 (0-0.5) | 0 (0-1.1) |
| 99.9 (99.6-100) | 93.3 (91.4-94.9) | 98.6 (97.4-99.4) | 10.7 (7.5-14.5) |
| >99.9 (99.7-100) | 94.0 (92.2-95.5) | 99.0 (98.0-99.6) | 12.2 (8.9-16.1) |
| 99.9 (99.6-100) | 93.6 (91.7-95.2) | 100 (99.4-100) | 14.7 (11.0-19.1) |
| 100 (99.8-100) | 94.6 (92.8-96.1) | 100 (99.4-100) | 18.3 (14.1-23.2) |
| DENV-3 | | | |
| 88.1 (86.5-89.6) | 88.0 (85.7-90.1) | 0 (0-0.5) | 0 (0-1.1) |
| 99.8 (99.4-99.9) | 87.6 (85.1-89.7) | 96.1 (94.3-97.4) | 4.0 (2.1-6.7) |

TABLE 23-continued

Seropositivity rates (% participants, 95% CI) by dengue serotype (per protocol set for immunogenicity data)

| BASELINE SEROPOSITIVE | | BASELINE SERONEGATIVE | |
|---|---|---|---|
| TDV N = 1,816 | Placebo N = 902 | TDV N = 702 | Placebo N = 345 |
| 99.5 (99.1-99.8) | 87.3 (84.9-89.4) | 94.4 (92.5-96.0) | 2.0 (0.8-4.1) |
| 99.8 (99.5-100) | 87.9 (85.5-90.1) | 100 (99.4-100) | 5.1 (2.9-8.2) |
| 99.7 (99.4-99.9) | 87.1 (84.6-89.4) | 96.4 (94.6-97.7) | 7.7 (4.9-11.3) |
| DENV-4 | | | |
| 88.1 (86.5-89.6) | 87.4 (85.0-89.5) | 0 (0-0.5) | 0 (0-1.1) |
| 99.6 (99.2-99.9) | 86.6 (84.1-88.8) | 90.5 (88.0-92.6) | 1.8 (0.7-3.9) |
| 99.3 (98.8-99.7) | 86.9 (84.5-89.0) | 92.0 (89.8-93.9) | 2.9 (1.4-5.3) |
| >99.9 (99.7-100) | 88.3 (85.9-90.4) | 99.8 (99.1-100) | 4.8 (2.7-7.8) |
| 99.7 (99.3-99.9) | 87.6 (85.1-89.9) | 97.0 (95.4-98.2) | 6.3 (3.9-9.7) |
| Three or More Serotypes | | | |
| 87.5 (85.9-89.0) | 87.3 (84.9-89.4) | 0 (0-0.5) | 0 (0-1.1) |
| 99.8 (99.5-100) | 87.2 (84.7-89.4) | 96.5 (94.8-97.8) | 1.2 (0.3-3.1) |
| 99.7 (99.3-99.9) | 87.7 (85.3-89.7) | 94.9 (93.0-96.4) | 1.7 (0.6-3.7) |
| 99.9 (99.6-100) | 88.4 (86.0-90.5) | 99.8 (99.1-100) | 4.2 (2.2-7.0) |
| 99.7 (99.4-99.9) | 87.3 (84.7-89.5) | 97.5 (96.0-98.6) | 5.7 (3.3-8.9) |
| All Four Serotypes | | | |
| 83.5 (81.7-85.2) | 83.5 (80.9-85.8) | 0 (0-0.5) | 0 (0-1.1) |
| 99.1 (98.5-99.5) | 82.9 (80.2-85.4) | 85.3 (82.4-87.9) | 0.9 (0.2-2.6) |
| 98.6 (97.9-99.1) | 83.6 (81.0-86.0) | 84.3 (81.4-86.9) | 1.4 (0.5-3.3) |
| 99.8 (99.5-100) | 85.2 (82.6-87.6) | 99.5 (98.6-99.9) | 3.5 (1.8-6.2) |
| 99.2 (98.7-99.6) | 84.6 (81.9-87.0) | 91.3 (88.7-93.4) | 5.3 (3.1-8.5) |

Seropositivity rates (% participants, 95% CI) by dengue serotype (per protocol set for immunogenicity data; seropositive defined as a reciprocal neutralizing antibody titer ≥10; baseline seronegative defined as seronegative to all serotype; baseline seropositive defined as seropositive to one or more serotypes; N refers to number of participants in the analysis set; number of participants evaluated at each time-point may vary)

Geometric mean titers (GMTs) of neutralizing antibodies (microneutralization test [MNT]) for each dengue serotype are determined at pre-vaccination on Day 1 (Month 0), post-first vaccination on Day 30 (Month 1), pre-vaccination on Day 90 (Month 3), post-second vaccination on Day 120 (Month 4), Day 270 (Month 9), Day 450 (Month 15), and then annually. Geometric mean titers (95% CI) by dengue serotype per protocol set for immunogenicity data for Day 0, Day 30, Day 90, Day 120, and Day 270 are shown in Table 24.

TABLE 24

Geometric mean titers (95% CI) by dengue serotype (per protocol set for immunogenicity data)

| | BASELINE SEROPOSITIVE | | BASELINE SERONEGATIVE | |
|---|---|---|---|---|
| | TDV N = 1,816 | Placebo N-902 | TDV N = 702 | Placebo N = 345 |
| DENV-1 | | | | |
| Day 1 | 410 (365-461) | 445 (377-524) | 5.0 (5.0-5.0) | 5.0 (5.0-5.0) |
| Day 30 | 2,404 (2,204-2,622) | 430 (361-512) | 118 (106-131) | 5.8 (5.3-6.3) |
| Day 90 | 1,945 (1,791-2,112) | 410 (349-481) | 91 (82-102) | 5.9 (5.4-6.3) |
| Day 120 | 2,115 (1,957-2,286) | 451 (381-534) | 184 (169-201) | 6.3 (5.7-7.0) |
| Day 270 | 1,447 (1,329-1,574) | 415 (350-492) | 87 (79-97) | 6.3 (5.7-6.9) |
| DENV-2 | | | | |
| Day 1 | 745 (674-825) | 802 (697-924) | 5.0 (5.0-5.0) | 5.0 (5.0-5.0) |
| Day 30 | 6,697 (6,301-7,117) | 744 (635-870) | 6,277 (5,648-6,977) | 6.6 (6.0-7.3) |
| Day 90 | 4,826 (4,571-5,096) | 729 (629-845) | 1,682 (1,544-1,834) | 7.0 (6.3-7.9) |
| Day 120 | 4,897 (4,646-5,163) | 766 (655-896) | 1,730 (1,614-1,855) | 7.7 (6.7-8.8) |
| Day 270 | 3,692 (3,496-3,898) | 776 (665-906) | 929 (856-1,010) | 8.7 (7.4-10.2) |
| DENV-3 | | | | |
| Day 1 | 357 (321-398) | 356 (305-415) | 5.0 (5.0-5.0) | 5.0 (5.0-5.0) |
| Day 30 | 2,255 (2,094-2,428) | 349 (298-409) | 194 (173-218) | 5.5 (5.2-5.9) |
| Day 90 | 1,563 (1,453-1,682) | 321 (277-374) | 94 (85-104) | 5.5 (5.1-5.9) |
| Day 120 | 1,761 (1,646-1,885) | 353 (301-414) | 228 (212-246) | 6.0 (5.4-6.6) |
| Day 270 | 1,089 (1,009-1,175) | 307 (261-360) | 72 (66-78) | 6.3 (5.7-7.0) |

TABLE 24-continued

| Geometric mean titers (95% CI) by dengue serotype (per protocol set for immunogenicity data) | | | | |
|---|---|---|---|---|
| | BASELINE SEROPOSITIVE | | BASELINE SERONEGATIVE | |
| | TDV N = 1,816 | Placebo N-902 | TDV N = 702 | Placebo N = 345 |
| DENV-4 | | | | |
| Day 1 | 218 (198-241) | 234 (203-270) | 5.0 (5.0-5.0) | 5.0 (5.0-5.0) |
| Day 30 | 1,303 (1,221-1,391) | 222 (191-258) | 111 (98-125) | 5.4 (5.0-5.7) |
| Day 90 | 1,002 (940-1,069) | 215 (187-248) | 63 (57-70) | 5.5 (5.1-5.9) |
| Day 120 | 1,129 (1,066-1,196) | 241 (208-280) | 144 (134-155) | 5.8 (5.3-6.4) |
| Day 270 | 778 (730-830) | 229 (197-266) | 64 (59-70) | 6.2 (5.6-6.9) |

Vaccine viremia is assessed by three PCRs: dengue detection RT-PCR, vaccine screening PCR and TDV sequencing in subjects with febrile illness within 30 days after each vaccination.

f) Safety

Rates of serious adverse events (SAEs) were similar in the vaccine and placebo groups (3.1% and 3.8% of participants, respectively; Table 25). One vaccinee and four placebo recipients experienced SAEs considered to be related to receiving blinded investigational product by the investigator (two experienced hypersensitivity, two were diagnosed with dengue, and one with DHF). There were five deaths during Part 1, and all were considered unrelated to the investigational product or study procedures. Total rates of unsolicited AEs were similar between the vaccine and placebo groups. The most commonly (≥1% of vaccine-recipients) reported unsolicited AEs within four weeks of any dose by preferred term were pyrexia (vaccine group 1.5%; placebo 1.4%), nasopharyngitis (vaccine 2.7%; placebo 3.0%), upper respiratory tract infection (vaccine 2.6%; placebo 2.9%), and viral infection (vaccine 1.1%; placebo 0.9%). Solicited local reactions were reported more frequently in the vaccine group.

TABLE 25a

| Overview of safety data. Subjects with at least one adverse event after any vaccine dose. Data presented as number of events (percentage of subjects; number [n] of subjects/total [N] subjects) unless otherwise stated (safety set data) | | |
|---|---|---|
| | TDV | Placebo |
| Safety Set | N = 13,380 | N = 6,687 |
| SAEs | 3.1% (409/13,380) | 3.8% (255/6,687) |
| Non-IP-Related[a] SAEs | 3.0% (408/13,380) | 3.8% (251/6,687) |
| IP-Related[a] SAEs | <0.1% (1/13,380) | <0.1% (4/6,687) |
| SAEs Leading to IP Withdrawal and/or Trial Discontinuation | 0.1% (18/13,380) | 0.1% (8/6,687) |
| Deaths | <0.1% (4/13,380) | <0.1% (1/6,687) |
| IP-Related Deaths | 0% (0/13,380) | 0% (0/6,687) |
| Safety Subset | N = 2,663 | N = 1,329 |
| Unsolicited AEs Occurring Within 4 Weeks of Any Dose | 18.4% (490/2,663) | 18.8% (250/1,329) |
| IP-Related[a] Unsolicited AEs Occurring Within 4 Weeks of Any Dose | 1.0% (27/2,663) | 1.6% (21/1,329) |
| Solicited Systemic AEs Occurring Within 2 Weeks of Any Dose[b] | 42.0% (1,107/2,635) | 38.0% (501/1,317) |
| IP-Related[a] Solicited Systemic AEs Occurring Within 2 Weeks of Any Dose | 31.2% (821/2,635) | 28.2% (371/1,317) |
| Solicited Local Reactions Occurring Within 1 Week of Any Dose[c] | 36.7% (967/2,633) | 25.7% (338/1,317) |

AE, adverse event;

SAE, serious adverse event;

IP, investigational product/TDV

[a]IP-related, defined as related to the investigational product as assessed by investigator

[b]only participants with diary data available were evaluated

[c]all injection site (solicited local) reactions considered to be IP-related

TABLE 25b

Number of participants (%) with serious adverse events after any vaccination during Part 1 by MedDRA (Medical Dictionary for Regulatory Activities) System Organ Class in the order of decreasing frequency (safety set data presented by TDV and placebo group for events that occurred in >3 participants due to risk of unblinding).

| MedDRA System Organ Class | TDV N = 13,380 | Placebo N = 6,687 | Total* N = 20,071 |
|---|---|---|---|
| Any Serious Adverse Events | 409 (3.1) | 255 (3.8) | 664 (3.3) |
| Infections and infestations | 235 (1.8) | 179 (2.7) | 414 (2.1) |
| Injury, poisoning and procedural complications | 87 (0.7) | 37 (0.6) | 124 (0.6) |
| Gastrointestinal disorders | 23 (0.2) | 9 (0.1) | 32 (0.2) |
| Nervous system disorders | 14 (0.1) | 6 (<0.1) | 20 (<0.1) |
| Respiratory, thoracic and mediastinal disorders | 14 (0.1) | 6 (<0.1) | 20 (<0.1) |
| Renal and urinary disorders | 15 (0.1) | 3 (<0.1) | 18 (<0.1) |
| Blood and lymphatic system disorders | 8 (<0.1) | 2 (<0.1) | 10 (<0.1) |
| Pregnancy, puerperium and perinatal conditions | 8 (<0.1) | 2 (<0.1) | 10 (<0.1) |
| Skin and subcutaneous tissue disorders | 7 (<0.1) | 3 (<0.1) | 10 (<0.1) |
| Psychiatric disorders | 7 (<0.1) | 2 (<0.1) | 9 (<0.1) |
| General disorders and administration site conditions | 5 (<0.1) | 3 (<0.1) | 8 (<0.1) |
| Immune system disorders | 3 (<0.1) | 4 (<0.1) | 7 (<0.1) |
| Metabolism and nutrition disorders | 6 (<0.1) | 1 (<0.1) | 7 (<0.1) |
| Musculoskeletal and connective tissue | 1 (<0.1) | 5 (<0.1) | 6 (<0.1) |
| Social circumstances | 2 (<0.1) | 4 (<0.1) | 6 (<0.1) |
| Congenital, familial and genetic disorders | 3 (<0.1) | 2 (<0.1) | 5 (<0.1) |
| Neoplasms benign, malignant and unspecified (including cysts and polyps) | 3 (<0.1) | 1 (<0.1) | 4 (<0.1) |
| Endocrine disorders | — | — | 3 (<0.1) |
| Hepatobiliary disorders | — | — | 3 (<0.1) |
| Reproductive system and breast disorders | — | — | 3 (<0.1) |
| Vascular disorders | — | — | 3 (<0.1) |
| Cardiac disorders | — | — | 2 (<0.1) |
| Eye disorders | — | — | 2 (<0.1) |
| Investigations | — | — | 1 (<0.1) |
| Product issues | — | — | 1 (<0.1) |
| Surgical and medical procedures | — | — | 1 (<0.1) |

*Total column includes participants who received both TAK-003 and placebo due to administration error and are excluded from the TAK-003 and placebo groups. N in column header refers to number of participants in the safety set TABLE 25c Number of participants (%) with unsolicited adverse events of any severity up to 28-days after any vaccination by MedDRA System Organ Class in the order of decreasing frequency (Subset of safety set data presented by TDV and placebo group for events that occurred in >6 participants due to risk of unblinding).

| MedDRA System Organ Class | TDV N = 2,663 | Placebo N = 1,329 | Total N = 3,993 |
|---|---|---|---|
| Any Unsolicited Adverse Events | 487 (18.3) | 249 (18.7) | 736 (18.4) |
| Infections and infestations | 368 (13.8) | 190 (14.3) | 556 (14.0) |
| Injury, poisoning and procedural complications | 21 (0.8) | 22 (1.7) | 43 (1.1) |
| Gastrointestinal disorders | 33 (1.2) | 9 (0.7) | 42 (1.1) |
| General disorders and administration site conditions | 30 (1.1) | 11 (0.8) | 41 (1.0) |
| Skin and subcutaneous tissue disorders | 27 (1.0) | 7 (0.5) | 34 (0.9) |
| Nervous system disorders | 18 (0.7) | 13 (1.0) | 31 (0.8) |
| Respiratory, thoracic and mediastinal disorders | 18 (0.7) | 10 (0.8) | 28 (0.7) |
| Blood and lymphatic system disorders | 6 (0.2) | 5 (0.4) | 11 (0.3) |
| Musculoskeletal and connective tissue disorders | 6 (0.2) | 5 (0.4) | 11 (0.3) |
| Immune system disorders | — | — | 6 (0.2) |

TABLE 25c-continued

Number of participants (%) with unsolicited adverse events of any severity up to 28-days after any vaccination by MedDRA System Organ Class in the order of decreasing frequency (Subset of safety set data presented by TDV and placebo group for events that occurred in >6 participants due to risk of unblinding).

| MedDRA System Organ Class | TDV N = 2,663 | Placebo N = 1,329 | Total N = 3,993 |
|---|---|---|---|
| Psychiatric disorders | — | — | 3 (<0.1) |
| Reproductive system and breast disorders | — | — | 3 (<0.1) |
| Ear and labyrinth disorders | — | — | 2 (<0.1) |
| Cardiac disorders | — | — | 1 (<0.1) |
| Congenital, familial and genetic disorders | — | — | 1 (<0.1) |
| Eye disorders | — | — | 1 (<0.1) |
| Renal and urinary disorders | — | — | 1 (<0.1) |
| Social circumstances | — | — | 1 (<0.1) |

*Total column includes participants who received both TAK-003 and placebo due to administration error and are excluded from the TAK-003 and placebo groups. N in column header refers to number of participants in the subset of safety set.

TABLE 25d

Summary of diary reported injection site reactions up to 7 days and systemic adverse events up to 14 days after any vaccination (Subset of safety set data). Data presented as number of participants with events/number of evaluated participants in the analysis set (% of evaluated participants with events).

| Solicited Events | TDV | Placebo |
|---|---|---|
| Injection site reactions (Age <6 years) | | |
| Any | 106/331 (32.0) | 43/169 (25.4) |
| Pain | 104/331 (31.4) | 43/169 (25.4) |
| Erythema | 5/331 (1.5) | 1/169 (0.6) |
| Swelling | 11/331 (3.3) | 2/169 (1.2) |
| Injection site reactions (Age ≥6 years) | | |
| Any | 861/2302 (37.4) | 295/1148 (25.7) |
| Pain | 853/2302 (37.1) | 293/1148 (25.5) |
| Erythema | 33/2301 (1.4) | 1/1147 (<0.1) |
| Swelling | 33/2300 (1.4) | 6/1147 (0.5) |
| Systemic adverse events (Age <6 years) | | |
| Any | 88/331 (26.6) | 35/169 (20.7) |
| Irritability/Fussiness | 41/331 (12.4) | 16/169 (9.5) |
| Drowsiness | 45/331 (13.6) | 21/169 (12.4) |
| Loss of Appetite | 57/331 (17.2) | 22/169 (13.0) |
| Fever (Body temperature >= 38° C. or 100.4° F.) | 45/327 (13.8) | 23/169 (13.6) |
| Systemic adverse events (Age ≥6 years) | | |
| Any | 941/2302 (40.9) | 422/1147 (36.8) |
| Headache | 715/2302 (31.1) | 326/1147 (28.4) |
| Asthenia | 404/2302 (17.5) | 187/1147 (16.3) |
| Malaise | 510/2301 (22.2) | 226/1147 (19.7) |
| Myalgia | 554/2302 (24.1) | 216/1147 (18.8) |
| Fever (Body temperature >= 38° C. or 100.4° F.) | 221/2279 (9.7) | 124/1134 (10.9) |

Example 7: Concomitant Administration of a Yellow Fever Vaccine and a Dengue Vaccine A phase 3, observer-blind, randomized, multi-center trial will be conducted in about 900 healthy adults aged 18 to 60 years in non-endemic areas for dengue disease and yellow fever to investigate the immunogenicity and safety of the concomitant and sequential administration of the unit dose as described herein (TDV) and YF-17D vaccine. Subjects will be randomized equally (1:1:1 ratio) to one of the following 3 trial groups (300 subjects per trial group):

Group 1: YF-17D vaccine and placebo concomitantly administered on day 0 (month 0), first dose of TDV administered on day 90 (month 3), and second dose of TDV administered on day 180 (month 6).

Group 2: first dose of TDV and placebo concomitantly administered on day 0 (month 0), second dose of TDV administered on day 90 (month 3), and YF-17D vaccine administered on day 180 (month 6).

Group 3: first dose of TDV and YF-17D vaccine concomitantly administered on day 0 (month 0), second dose of TDV administered on day 90 (month 3), and placebo administered on day 180 (month 6).

Concomitantly administered vaccines will be injected to opposite arms. All subjects will be followed-up for 6 months after the third vaccination (administered approximately 6 months after the first vaccination), so the trial duration will be approximately 360 days (12 months) for each subject.

For evaluation of the immune response to TDV and YF-17D blood samples will be collected and analyzed. Blood samples for the measurement of dengue neutralizing antibodies (microneutralization test 50% (MNT50)) will be collected at pre-first vaccination (Day 0 (month 0)), 1 month post first vaccination (Day 30 (month 1)), pre-second vaccination (Day 90 (month 3)), 1 month post second vaccination (Day 120 (month 4)), pre-third vaccination (Day 180 (month 6)), and 1 month post third vaccination (Day 210 (month 7)). Blood samples for the measurement of YF neutralizing antibodies (plaque reduction neutralization test (PRNT)) will be collected at pre-first vaccination (Day 0 (month 0)), 1 month post first vaccination (Day 30 (month 1)), pre-third vaccination (Day 180 (month 6)), and 1 month post third vaccination (Day 210 (month 7)).

Example 8: Concomitant Administration of a Hepatitis a Vaccine and a Dengue Vaccine A randomized, observer blind, phase 3 trial will be conducted in about 900 healthy adult subjects aged 18 to 60 years (distributed across the entire age range) in non-endemic countries for dengue and hepatitis A virus (HAV) to investigate the immunogenicity and safety of 2 doses of tetravalent dengue vaccine TDV (subcutaneous (SC) injection), and of the co-administration of a single dose of HAV vaccine (intramuscular (IM) injection) and TDV (SC injection). Subjects will be randomized equally (1:1:1 ratio) to one of the following 3 trial groups (300 subjects per group):

Group 1: HAV vaccine (IM) and placebo (SC), co-administered at day 0 (month 0); placebo (SC) administered at day 90 (month 3).

Group 2: TDV (SC) and placebo (IM), co-administered at day 0 (month 0); TDV (SC) administered at day 90 (month 3).

Group 3: TDV (SC) and HAV vaccine (IM), co-administered at day 0 (month 0); TDV (SC) administered at day 90 (month 3).

Co-administered trial vaccines will be injected to opposite arms. Normal saline solution for injection (0.9% NaCl) will be used as placebo. A blood sample for an anti-HAV antibody test will be collected at screening from all subjects to exclude subjects who are positive for anti-HAV antibodies. All subjects will be followed-up for 6 months after the second vaccination at day 90 (month 3), so the trial duration will be 270 days or 9 months for each subject (not including the screening period). Outside the context of this trial, subjects in Groups 1 and 3 will be offered a HAV vaccine booster dose after the completion of trial procedures at day 270 (month 9).

Dengue neutralizing antibodies (microneutralization test (MNT50)) will be measured using blood samples collected at pre-first trial vaccination (day 0 (month 0)), 1 month post first trial vaccination (day 30 (month 1)), and 1 month post second trial vaccination (day 120 (month 4)). Blood samples for the measurement of anti-HAV antibodies (enzyme-linked immunosorbent assay (ELISA)) will be collected at pre-first trial vaccination (day 0 (month 0)) and 1 month post first trial vaccination (day 30 (month 1)).

The primary endpoint includes the proportion of HAV/DENV-naive subjects at baseline who are seroprotected against HAV at day 30 (month 1) as measured by enzyme-linked immunosorbent assay (ELISA) (seroprotection rate) in a subset of 120 subjects in each group (immunogenicity subset) will be determined. Seroprotection is defined as serum anti-HAV antibody levels ≥10 mIU/mL. Immunological naivety to HAV/DENV is defined as anti-HAV antibody levels <10 mIU/mL and reciprocal neutralizing titers for all 4 dengue serotypes <10.

The secondary endpoints include the geometric mean titers of neutralizing antibodies (GMTs) (microneutralization test (MNT50)) for each of the 4 dengue serotypes at day 30 (month 1) and day 120 (month 4) will be determined in HAV/DENV-naive subjects at baseline, the proportion of HAV/DENV-naive subjects at baseline who are seropositive for each of the 4 dengue serotypes at day 30 (month 1) and day 120 (month 4) (seropositivity rate), and Geometric mean concentrations (GMC) of anti-HAV antibodies at day 30 (month 1) in subjects HAV/DENV-naive at baseline.

Seropositivity for dengue virus is defined as a reciprocal neutralizing titer ≥10 for any of the four dengue serotypes.

Example 9: Concomitant Administration of a HPV Vaccine and a Dengue Vaccine

A phase 3, open-label, randomized, multicenter trial will be conducted in about 430 healthy females aged ≥9 to <15 years in dengue endemic regions to investigate the immunogenicity and safety of the co-administration of TDV and 9vHPV vaccine vs 9vHPV vaccine alone. Subjects will be randomized equally to 1 of 2 groups (about 215 subjects per trial group):

Group 1: first doses of 9vHPV vaccine+TDV co-administered on day 0 (month 0), second dose of TDV administered on Day 90 (month 3), second dose of 9vHPV vaccine administered on Day 180 (month 6).

Group 2: first dose of 9vHPV vaccine administered on day 0 (month 0), second dose of 9vHPV vaccine administered on Day 180 (month 6).

Concomitantly administered vaccines will be injected to opposite arms. All subjects will be followed-up for 6 months after the last trial vaccination, so the trial duration will be approximately 360 days (or 12 months) for each subject.

Blood samples for the measurement of HPV neutralizing antibodies (Merck assay) for both Groups 1 and 2 will be collected at pre-first vaccination (day 0 (Month 0)) and at 1 month post-second 9vHPV vaccination (day 210 (month 7)). Blood samples for the measurement of dengue neutralizing antibodies (by microneutralization test 50% (MNT50)) will be collected for Group 1 only at pre-first vaccination (day 0 (month 0)) and at 1 month post-second TDV vaccination (day 120 (month 4)).

The primary endpoints includes the geometric mean titers (GMTs) for HPV Types 6, 11, 16, 18, 31, 33, 45, 52, 58 on day 210 (month 7).

The secondary endpoints includes seropositivity rates (% of subjects seropositive) for HPV Types 6, 11, 16, 18, 31, 33, 45, 52 and 58 on day 210 (month 7) as measured by competitive Luminex immunoassay (cLIA) or equivalent assay, GMTs of neutralizing antibodies (by MNT50) for each of the 4 dengue serotypes on day 120 (month 4), and seropositivity rates (% of subjects seropositive) for each of the 4 dengue serotypes and for multiple (2, 3 or 4) dengue serotypes on day 120 (month 4).

Seropositivity for dengue virus is defined as a reciprocal neutralizing antibody titer ≥10 for any of the 4 dengue serotypes.

Seropositivity for HPV is defined as an anti-HPV titer greater than or equal to the pre-specified serostatus cut-off for a given HPV type. Seronegativity is defined as an anti-HPV titer less than the pre-specified serostatus cut-off for a given HPV type. The serostatus cut-off is the antibody titer level above the assay's lower limit of quantification that reliably distinguishes sera samples classified by clinical likelihood of HPV infection and positive or negative status by previous versions of cLIA or equivalent assay. The lower limits of quantification and serostatus cut-offs for each of the 9 vaccine HPV types are shown below.

TABLE 26

Competitive Luminex Immunoassay Limits of Quantification and Serostatus Cutoffs for 9vHPV types

| HPV type | cLIA Lower Limit of Quantification (mMU[a]/mL) | cLIA Serostatus Cutoff (mMU[a]/mL) |
|---|---|---|
| HPV 6 | 16 | 30 |
| HPV 11 | 6 | 16 |
| HPV 16 | 12 | 20 |
| HPV 18 | 8 | 24 |
| HPV 31 | 4 | 10 |
| HPV 33 | 4 | 8 |
| HPV 45 | 3 | 8 |
| HPV 52 | 3 | 8 |
| HPV 58 | 4 | 8 |

[a]mMU = milli-Merck Units

Serum antibodies to HPV types 6, 11, 16, 18, 31, 33, 45, 52, and 58 will be measured with a competitive Luminex immunoassay or equivalent assay. Titers will be reported in milli Merck Units/mL with the use of the Luminex immunoassay.

Example 10: Concomitant Administration of a Tdap Vaccine and a Dengue Vaccine

A phase 3, open-label, randomized trial will be conducted in about 840 healthy subjects aged of ≥10 to <18 years in dengue endemic areas, where the Tdap vaccine is licensed for children and adolescents from 10 up to 18 years of age to investigate the immunogenicity and safety of the co-administration of TDV and the Tdap vaccine BOOSTRIX® vs BOOSTRIX® alone.

TDV will be administered subcutaneously and BOOSTRIX® will be administered intramuscularly. Subjects will be randomized equally (1:1 ratio) to each one of the following 2 trial groups (about 420 subjects per trial group):

Group 1: first dose of TDV+Tdap vaccine co-administered on day 0 (month 0); and second dose of TDV administered on day 90 (month 3).

Group 2: Tdap vaccine administered on day 0 (month 0).

Concomitantly administered vaccines will be injected to opposite arms. All subjects will be followed up for 9 months (270 days) after the first vaccination, so the trial duration will be approximately 270 days for each subject.

For each subject there will be 5 scheduled clinic visits: day 0 (month 0), day 30 (month 1), day 90 (month 3), day 120 (month 4), and day 270 (month 9). Blood samples for the measurement of antibody response to the Tdap vaccine will be collected on day 0 (month 0) and on day 30 (month 1) from all subjects in Group 1 and 2. Antibodies against the following antigens will be measured:

pertussis antigens (inactivated pertussis toxin (iPT), formaldehyde-treated filamentous hemagglutinin (FHA)), and pertactin (PRN)), tetanus toxoid antigen, and diphtheria toxoid antigen.

Blood samples for the measurement of dengue neutralizing antibodies (by microneutralization test 50% (MNT50)) will be collected from Group 1 on day 0 (month 0), day 30 (month 1), and day 120 (month 4). Blood samples will also be collected prior to vaccination.

The primary endpoints include:

(i) the proportion of subjects seroprotected for diphtheria as measured by Neutralizing Toxin Assay (NTA) or equivalent assay on day 30 (month 1), wherein seroprotection is defined as anti-diphtheria antibody levels (NTA or equivalent assay) ≥0.1 IU/mL in serum (ii) The proportion of subjects seroprotected for tetanus as measured by Enzyme Linked Immunosorbent Assay (ELISA) or equivalent assay on day 30 (month 1), wherein seroprotection is defined as anti-tetanus antibody levels (ELISA or equivalent assay) ≥0.1 IU/mL in the serum.

(iii) Geometric mean concentration (GMC) of acellular pertussis antibodies (anti-iPT antibodies, anti-FHA antibodies, anti-PRN antibodies,) as measured by ELISA or equivalent assay on day 30 (month 1).

The secondary endpoints include evaluations include geometric mean neutralizing antibody titers (GMTs) of antibodies (by MNT50) for each of the four dengue serotypes on day 30 (month 1) following a first dose with TDV and on day 120 (month 4) following a second dose of TDV, seropositivity rates (% of subjects seropositive) for each of the four dengue serotypes and for multiple (2, 3 or 4) dengue serotypes on day 30 (month 1) following a first dose with TDV and on day 120 (month 4) following a second dose of TDV, wherein seropositive for each dengue serotype is defined as the percentage of subjects with a reciprocal neutralizing antibody titer of ≥10.

What is claimed is:

1. A method of vaccinating against virologically confirmable dengue disease in a subject population, the method providing a combined vaccine efficacy of at least 60% which is represented by at least 60% reduction in dengue disease occurrence in vaccinated subjects compared to unvaccinated subjects, in each of seropositive subjects and seronegative subjects, for at least 18 months after a second unit dose administration of a tetravalent dengue virus composition wherein the method comprises a primary vaccination comprising:

selecting a subject from the subject population without determining whether the subject had a previous dengue infection, administering a first unit dose of the tetravalent dengue virus composition to the subject population comprising seropositive subjects, seronegative subjects, or a combination thereof, the tetravalent dengue virus composition comprising four dengue virus strains representing serotype 1, serotype 2, serotype 3 and serotype 4, and administering a second unit dose of the tetravalent dengue virus composition to the subject population within 3 months of administration of the first unit dose, wherein the first dose and the second dose each comprises a tetravalent dengue virus composition including four dengue virus strains representing serotype 1, serotype 2, serotype 3 and serotype 4, represented by a chimeric dengue serotype 2/1 strain, a dengue serotype 2 strain, a chimeric dengue serotype 2/3 strain, and a chimeric dengue serotype 2/4 strain, the dengue serotype 2 strain being derived from the wild type virus strain DEN-2 16681 and differing in at least three nucleotides from the wild type as follows:

a) 5'-noncoding region (NCR)-57 b) NS1-53 Gly-to-Asp c) NS3-250 Glu-to-Val; and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera, and wherein the first unit dose corresponding to a dose of 0.5 ml comprising:

(i) the dengue serotype 1 has a concentration of at least 3.3 log 10 pfu/0.5 mL, (ii) the dengue serotype 2 has a concentration of at least 2.7 log 10 pfu/0.5 mL, (iii) the dengue serotype 3 has a concentration of at least 4.0 log 10 pfu/0.5 mL, and (iv) the dengue serotype 4 has a concentration of at least 4.5 log 10 pfu/0.5 mL, and the second unit dose corresponding to a dose of 0.5 ml comprising:

(i) the dengue serotype 1 has a concentration of at least 3.3 log 10 pfu/0.5 mL, (ii) the dengue serotype 2 has a concentration of at least 2.7 log 10 pfu/0.5 mL, (iii) the dengue serotype 3 has a concentration of at least 4.0 log 10 pfu/0.5 mL, and (iv) the dengue serotype 4 has a concentration of at least 4.5 log 10 pfu/0.5 mL.

2. The method according to claim 1, wherein the subject population is from a region wherein the seroprevalence rate is unknown and/or wherein the seroprevalence is below 80%, or below 70%, or below 60%.

3. The method according to claim 1, wherein the subject population is exposed to a dengue outbreak.

4. The method according to claim 3, wherein the outbreak is due to a dengue serotype 2, and/or due to a dengue serotype 1.

5. The method according to claim 1, wherein the virologically confirmable dengue disease is due to a dengue serotype 2, and/or due to a dengue serotype 1.

6. The method according to claim 1, wherein the subject population is under 9 years of age, 4 to 5 years of age, 6 to 11 years of age or 12 to 16 years, or 6 to 16 years of age, or 4 to 16 years of age, or 2 to 17 years of age, or 9 years of age, or over 9 years of age, or 9 to 19 years of age, or 4 years of age to over 60 years of age, or 18 to 60 years of age, or 18 to 45 years of age, or 46 to 60 years of age, or over 60 years of age.

7. A method of vaccinating against virologically confirmable dengue disease with hospitalization in subjects, the method providing a combined vaccine efficacy against virologically confirmable dengue disease with hospitalization of at least 65% which is represented by a reduction of at least 65% dengue disease with hospitalization occurrence in vaccinated subjects compared to unvaccinated subjects, in each of seropositive subjects and seronegative subjects, for at least 18 months after a second unit dose administration, by administering a tetravalent dengue virus composition including four live attenuated dengue virus strains representing serotype 1, serotype 2, serotype 3 and serotype 4, the method comprises a primary vaccination consisting of the steps of:

administering a first unit dose of the tetravalent dengue virus composition to the subject population comprising seropositive subjects, seronegative subjects, or a combination thereof, and administering a second unit dose of the tetravalent dengue virus composition to the subject population within 3 months of administration of the first unit dose, wherein the first dose and the second dose each comprises a tetravalent dengue virus composition including four dengue virus strains representing serotype 1, serotype 2, serotype 3 and serotype 4, represented by a chimeric dengue serotype 2/1 strain, a dengue serotype 2 strain, a chimeric dengue serotype 2/3 strain, and a chimeric dengue serotype 2/4 strain, the dengue serotype 2 strain being derived from the wild type virus strain DEN-2 16681 and differing in at least three nucleotides from the wild type as follows:

a) 5'-noncoding region (NCR)-57)

b) NS1-53 Gly-to-Asp c) NS3-250 Glu-to-Val; and the three chimeric dengue strains being derived from the serotype 2 strain by replacing the structural proteins prM and E from serotype 2 strain with the corresponding structural proteins from the other dengue serotypes, resulting in the following chimeric dengue strains:

a DENV-2/1 chimera, a DENV-2/3 chimera and a DENV-2/4 chimera, and wherein the first unit dose corresponding to a dose of 0.5 ml comprising:

(i) the dengue serotype 1 has a concentration of at least 3.3 log 10 pfu/0.5 mL, (ii) the dengue serotype 2 has a concentration of at least 2.7 log 10 pfu/0.5 mL, (iii) the dengue serotype 3 has a concentration of at least 4.0 log 10 pfu/0.5 mL, and (iv) the dengue serotype 4 has a concentration of at least 4.5 log 10 pfu/0.5 mL, and the second unit dose corresponding to a dose of 0.5 ml comprises:

(i) the dengue serotype 1 has a concentration of at least 3.3 log 10 pfu/0.5 mL, (ii) the dengue serotype 2 has a concentration of at least 2.7 log 10 pfu/0.5 mL, (iii) the dengue serotype 3 has a concentration of at least 4.0 log 10 pfu/0.5 mL, and (iv) the dengue serotype 4 has a concentration of at least 4.5 log 10 pfu/0.5 mL.

8. The method according to claim 7, wherein the subject population is from a region wherein the seroprevalence rate is unknown and/or wherein the seroprevalence is below 80%, or below 70%, or below 60%.

9. The method according to claim 7, wherein the subject population is under 9 years of age, 4 to 5 years of age, 6 to 11 years of age or 12 to 16 years, or 6 to 16 years of age, or 4 to 16 years of age, or 2 to 17 years of age, or 9 years of age, or over 9 years of age, or 9 to 19 years of age, or 4 years of age to over 60 years of age, or 18 to 60 years of age, 18 to 45 years of age, or 46 to 60 years of age, or over 60 years of age.

10. The method according to claim 7, wherein upon reconstitution with a pharmaceutically acceptable diluent provide a total concentration of pfu/0.5 mL and based on said total concentration the concentration of dengue serotype 2 in pfu/0.5 mL is less than 10%, and the concentration of dengue serotype 4 in pfu/0.5 mL is at least 50%, and the concentration of dengue serotype 1 in pfu/0.5 mL is at least 1%, and the concentration of dengue serotype 3 in pfu/0.5 mL is at least 8%, or at least 10%, or at least 12%, or at least 14%, or at least 16%, or at least 18%, and wherein the subject population is 2 to 17 years of age or 4 to 16 years of age.

11. The method according to claim 7, wherein upon reconstitution with a pharmaceutically acceptable diluent provide a total concentration of pfu/0.5 mL and based on said total concentration the concentration of dengue serotype 2 in pfu/0.5 mL is less than 2%, the concentration of dengue serotype 4 in pfu/0.5 mL is at least 50%, the concentration of dengue serotype 1 in pfu/0.5 mL is at least 1%, and the concentration of dengue serotype 3 in pfu/0.5 mL is at least 6%, wherein the subject is 18 to 60 years of age.

12. The method of claim 7, providing a combined vaccine efficacy against virologically-confirmed dengue with hospitalization against all four serotypes with a 2-sided 95% confidence interval, wherein the lower bound is more than 70%, when measured against placebo in a subject population of at least 5,000 healthy 4 to 16 year old subjects irrespective of serostatus at baseline from first administration of the administration schedule until 12 to 18 months after the second administration of the administration schedule.

13. The method of claim 7, providing a combined vaccine efficacy against all four serotypes, in preventing virologically confirmable dengue disease with hospitalization with a 2-sided 95% confidence interval, wherein the lower bound is more than 70%, when measured against placebo in a subject population of at least 5,000 healthy subjects irrespective of serostatus at baseline and 4 to 16 years of age, from the first administration of the administration schedule until 18 months after the second administration of the administration schedule.

14. The method of claim 7, providing a combined vaccine efficacy against all four serotypes, in preventing virologically confirmable dengue disease with hospitalization with a 2-sided 95% confidence interval, wherein the lower bound is more than 60%, when measured against placebo in a subject population of at least 1,500 or at least 2,000 healthy subjects seronegative against all serotypes at baseline and 4 to 16 years of age, from 30 days after the second administration of the administration schedule until 18 months after the second administration of the administration schedule.

15. The method of claim 7, providing a combined vaccine efficacy against virologically-confirmed dengue with hospitalization against all four serotypes with a 2-sided 95% confidence interval, wherein the lower bound is more than 65%, when measured against placebo in a subject population of at least 5,000 healthy 4 to 16 year old subjects irrespective of serostatus at baseline from first administration of the administration schedule until 12 to 18 months after the last administration of the administration schedule.

16. The method of claim 1, providing a combined vaccine efficacy against all four serotypes, in preventing virologically confirmable dengue disease with a 2-sided 95% confidence interval, wherein the lower bound is more than 60%, when measured against placebo in a subject population of at least 5,000 healthy subjects irrespective of serostatus at baseline and 4 to 16 years of age, from the first administration of the administration schedule until 18 months after the last administration of the administration schedule.

17. The method of claim 1, providing a combined vaccine efficacy against all four serotypes, in preventing virologically confirmable dengue disease with a 2-sided 95% confidence interval, wherein the lower bound is more than 45%, when measured against placebo in a subject population of at least 1,500 or at least 2,000 healthy subjects seronegative against all serotypes at baseline and 4 to 16 years of age, from 30 days after the last administration of the administration schedule until 18 months after the last administration of the administration schedule.

* * * * *

SEQUENCE LISTING

```
<160> NUMBER OF SEQ ID NOS: 16

<210> SEQ ID NO 1
<211> LENGTH: 10723
<212> TYPE: DNA
<213> ORGANISM: chimeric dengue seroytpe 2/1 (MVS)

<400> SEQUENCE: 1

agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acgcgtgggg gagagccgca tatgatagtt    480

agcaagcagg aaagaggaaa gtcacttttg ttcaagacct ctgcaggtgt caacatgtgc    540

accctcattg cgatggattt gggagagttg tgtgaggaca cgatgaccta caaatgcccc    600

cggatcactg aggcggaacc agatgacgtt gactgttggt gcaatgccac ggacacatgg    660

gtgacctatg gaacgtgctc tcaaactggc gaacaccgac gagacaaacg ttccgtcgca    720

ttggccccac acgtggggct tggcctagaa acaagagccg aaacgtggat gtcctctgaa    780

ggtgcttgga aacagataca aaaagtagag acttgggctc tgagacatcc aggattcacg    840
```

gtgatagccc tttttctagc acatgccata ggaacatcca tcacccagaa agggatcatt 900
ttcattttgc tgatgctggt aacaccatct atggccatgc gatgcgtggg aataggcaac 960
agagacttcg tggaaggact gtcaggagca acatgggtgg atgtggtact ggagcatgga 1020
agttgcgtca ccaccatggc aaaaaacaaa ccaacactgg acattgaact cttgaagacg 1080
gaggtcacaa accctgcagt tctgcgtaaa ttgtgcattg aagctaaaat atcaaacacc 1140
accaccgatt cgagatgtcc aacacaagga gaagccacac tggtggaaga acaagacgcg 1200
aactttgtgt gccgacgaac gttcgtggac agaggctggg gcaatggctg tgggctattc 1260
ggaaaaggta gtctaataac gtgtgccaag tttaagtgtg tgacaaaact agaaggaaag 1320
atagttcaat atgaaaacct aaaatattca gtgatagtca ccgtccacac tggagatcag 1380
caccaggtgg gaaatgagac tacagaacat ggaacaactg caaccataac acctcaagct 1440
cctacgtcgg aaatacagct gaccgactac ggaaccctta cattagattg ttcacctagg 1500
acagggctag attttaacga gatggtgttg ctgacaatga aagaaagatc atggcttgtc 1560
cacaaacaat ggttcctaga cttaccactg ccttggacct ctggggcttc aacatcccaa 1620
gagacttgga acagacaaga tttactggtc acatttaaga cagctcatgc aaagaagcag 1680
gaagtagtcg tactaggatc acaagaagga gcaatgcaca ctgcgctgac tggagcgaca 1740
gaaatccaaa cgtcaggaac gacaacaatt ttcgcaggac acctaaaatg cagactaaaa 1800
atggacaaac taactttaaa agggatgtca tatgtgatgt gcacaggctc attcaagtta 1860
gagaaagaag tggctgagac ccagcatgga actgttctgg tgcaggttaa atatgaagga 1920
acagacgcac catgcaagat tcccttttcg acccaagatg agaaaggagc aacccagaat 1980
gggagattaa taacagccaa ccccatagtc actgacaaag aaaaaccagt caatattgag 2040
gcagaaccac cctttggtga gagctacatc gtggtaggag caggtgaaaa agctttgaaa 2100
ctaagctggt tcaagaaagg aagcagcata gggaaaatgt ttgaagcaac tgcccgagga 2160
gcacgaagga tggccattct gggagacacc gcatgggact tcggttctat aggaggagtg 2220
ttcacgtcta tgggaaaact ggtacaccag gtttttggaa ctgcatatgg agttttgttt 2280
agcggagttt cttggaccat gaaaatagga atagggattc tgctgacatg gctaggatta 2340
aattcaagga acacgtccct ttcgatgatg tgcatcgcag ccggcattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180

-continued

```
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccctaccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagatcaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
```

-continued

```
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc gaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
```

-continued

```
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
```

```
catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 2
<211> LENGTH: 3391
<212> TYPE: PRT
<213> ORGANISM: chimeric dengue serotype 2/1 (MVS)

<400> SEQUENCE: 2

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Ala Glu Pro Asp
                165                 170                 175

Asp Val Asp Cys Trp Cys Asn Ala Thr Asp Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Ala Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300
```

```
Leu Glu His Gly Ser Cys Val Thr Thr Met Ala Lys Asn Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350

Arg Cys Pro Thr Gln Gly Glu Ala Thr Leu Val Glu Glu Gln Asp Ala
        355                 360                 365

Asn Phe Val Cys Arg Arg Thr Phe Val Asp Arg Gly Trp Gly Asn Gly
    370                 375                 380

Cys Gly Leu Phe Gly Lys Gly Ser Leu Ile Thr Cys Ala Lys Phe Lys
385                 390                 395                 400

Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720
```

```
Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
```

1130 1135 1140

Leu Phe Leu Glu Glu Met Leu Arg Thr Arg Val Gly Thr Lys His
1145 1150 1155

Ala Ile Leu Leu Val Ala Val Ser Phe Val Thr Leu Ile Thr Gly
1160 1165 1170

Asn Met Ser Phe Arg Asp Leu Gly Arg Val Met Val Met Val Gly
1175 1180 1185

Ala Thr Met Thr Asp Asp Ile Gly Met Gly Val Thr Tyr Leu Ala
1190 1195 1200

Leu Leu Ala Ala Phe Lys Val Arg Pro Thr Phe Ala Ala Gly Leu
1205 1210 1215

Leu Leu Arg Lys Leu Thr Ser Lys Glu Leu Met Met Thr Thr Ile
1220 1225 1230

Gly Ile Val Leu Leu Ser Gln Ser Thr Leu Pro Glu Thr Ile Leu
1235 1240 1245

Glu Leu Thr Asp Ala Leu Ala Leu Gly Met Met Val Leu Lys Met
1250 1255 1260

Val Arg Asn Met Glu Lys Tyr Gln Leu Ala Val Thr Ile Met Ala
1265 1270 1275

Ile Leu Cys Val Pro Asn Ala Val Ile Leu Gln Asn Ala Trp Lys
1280 1285 1290

Val Ser Cys Thr Ile Leu Ala Val Val Ser Val Ser Pro Leu Phe
1295 1300 1305

Leu Thr Ser Ser Gln Gln Lys Thr Asp Trp Ile Pro Leu Ala Leu
1310 1315 1320

Thr Ile Lys Gly Leu Asn Pro Thr Ala Ile Phe Leu Thr Thr Leu
1325 1330 1335

Ser Arg Thr Ser Lys Lys Arg Ser Trp Pro Leu Asn Glu Ala Ile
1340 1345 1350

Met Ala Val Gly Met Val Ser Ile Leu Ala Ser Ser Leu Leu Lys
1355 1360 1365

Asn Asp Ile Pro Met Thr Gly Pro Leu Val Ala Gly Gly Leu Leu
1370 1375 1380

Thr Val Cys Tyr Val Leu Thr Gly Arg Ser Ala Asp Leu Glu Leu
1385 1390 1395

Glu Arg Ala Ala Asp Val Lys Trp Glu Asp Gln Ala Glu Ile Ser
1400 1405 1410

Gly Ser Ser Pro Ile Leu Ser Ile Thr Ile Ser Glu Asp Gly Ser
1415 1420 1425

Met Ser Ile Lys Asn Glu Glu Glu Asp Gln Thr Leu Thr Ile Leu
1430 1435 1440

Ile Arg Thr Gly Leu Leu Val Ile Ser Gly Leu Phe Pro Val Ser
1445 1450 1455

Ile Pro Ile Thr Ala Ala Ala Trp Tyr Leu Trp Glu Val Lys Lys
1460 1465 1470

Gln Arg Ala Gly Val Leu Trp Asp Val Pro Ser Pro Pro Pro Met
1475 1480 1485

Gly Lys Ala Glu Leu Glu Asp Gly Ala Tyr Arg Ile Lys Gln Lys
1490 1495 1500

Gly Ile Leu Gly Tyr Ser Gln Ile Gly Ala Gly Val Tyr Lys Glu
1505 1510 1515

Gly Thr Phe His Thr Met Trp His Val Thr Arg Gly Ala Val Leu
1520 1525 1530

-continued

```
Met His  Lys Gly Lys Arg Ile  Glu Pro Ser Trp Ala  Asp Val Lys
    1535                 1540                 1545

Lys Asp  Leu Ile Ser Tyr Gly  Gly Gly Trp Lys Leu  Glu Gly Glu
    1550                 1555                 1560

Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Val  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920
```

```
Val Thr His Ser Ser Ala Ala Gln Arg Arg Gly Arg Ile Gly Arg
    1925                1930                1935

Asn Pro Lys Asn Glu Asn Asp Gln Tyr Ile Tyr Met Gly Glu Pro
    1940                1945                1950

Leu Glu Asn Asp Glu Asp Cys Ala His Trp Lys Glu Ala Lys Met
    1955                1960                1965

Leu Leu Asp Asn Ile Asn Thr Pro Glu Gly Ile Ile Pro Ser Met
    1970                1975                1980

Phe Glu Pro Glu Arg Glu Lys Val Asp Ala Ile Asp Gly Glu Tyr
    1985                1990                1995

Arg Leu Arg Gly Glu Ala Arg Lys Thr Phe Val Asp Leu Met Arg
    2000                2005                2010

Arg Gly Asp Leu Pro Val Trp Leu Ala Tyr Arg Val Ala Ala Glu
    2015                2020                2025

Gly Ile Asn Tyr Ala Asp Arg Arg Trp Cys Phe Asp Gly Val Lys
    2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
    2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
    2090                2095                2100

Gly Arg Leu Pro Thr Phe Met Thr Gln Lys Ala Arg Asp Ala Leu
    2105                2110                2115

Asp Asn Leu Ala Val Leu His Thr Ala Glu Ala Gly Gly Arg Ala
    2120                2125                2130

Tyr Asn His Ala Leu Ser Glu Leu Pro Glu Thr Leu Glu Thr Leu
    2135                2140                2145

Leu Leu Leu Thr Leu Leu Ala Thr Val Thr Gly Gly Ile Phe Leu
    2150                2155                2160

Phe Leu Met Ser Ala Arg Gly Ile Gly Lys Met Thr Leu Gly Met
    2165                2170                2175

Cys Cys Ile Ile Thr Ala Ser Ile Leu Leu Trp Tyr Ala Gln Ile
    2180                2185                2190

Gln Pro His Trp Ile Ala Ala Ser Ile Ile Leu Glu Phe Phe Leu
    2195                2200                2205

Ile Val Leu Leu Ile Pro Glu Pro Glu Lys Gln Arg Thr Pro Gln
    2210                2215                2220

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys
    2240                2245                2250

Lys Asp Leu Gly Leu Gly Ser Ile Ala Thr Gln Gln Pro Glu Ser
    2255                2260                2265

Asn Ile Leu Asp Ile Asp Leu Arg Pro Ala Ser Ala Trp Thr Leu
    2270                2275                2280

Tyr Ala Val Ala Thr Thr Phe Val Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
```

```
    2315                2320                2325

Lys Met  Asp Ile Gly Val Pro  Leu Leu Ala Ile Gly  Cys Tyr Ser
    2330                2335                2340

Gln Val  Asn Pro Ile Thr Leu  Thr Ala Ala Leu Phe  Leu Leu Val
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415

Leu Cys  Val Thr Gln Val Leu  Met Met Arg Thr Thr  Trp Ala Leu
    2420                2425                2430

Cys Glu  Ala Leu Thr Leu Ala  Thr Gly Pro Ile Ser  Thr Leu Trp
    2435                2440                2445

Glu Gly  Asn Pro Gly Arg Phe  Trp Asn Thr Thr Ile  Ala Val Ser
    2450                2455                2460

Met Ala  Asn Ile Phe Arg Gly  Ser Tyr Leu Ala Gly  Ala Gly Leu
    2465                2470                2475

Leu Phe  Ser Ile Met Lys Asn  Thr Thr Asn Thr Arg  Arg Gly Thr
    2480                2485                2490

Gly Asn  Ile Gly Glu Thr Leu  Gly Glu Lys Trp Lys  Ser Arg Leu
    2495                2500                2505

Asn Ala  Leu Gly Lys Ser Glu  Phe Gln Ile Tyr Lys  Lys Ser Gly
    2510                2515                2520

Ile Gln  Glu Val Asp Arg Thr  Leu Ala Lys Glu Gly  Ile Lys Arg
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715
```

```
Ile Val  Ser Ser Val Asn Met  Ile Ser Arg Met Leu  Ile Asn Arg
    2720                 2725                 2730

Phe Thr  Met Arg Tyr Lys Lys  Ala Thr Tyr Glu Pro  Asp Val Asp
    2735                 2740                 2745

Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105
```

-continued

```
Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```

<210> SEQ ID NO 3
<211> LENGTH: 10723
<212> TYPE: DNA
<213> ORGANISM: dengue serotype 2 (MVS)

<400> SEQUENCE: 3

```
agttgttagt ctacgtggac cgacaaagac agattctttg agggagctaa gctcaatgta      60

gttctaacag ttttttaatt agagagcaga tctctgatga ataaccaacg gaaaaaggcg     120

aaaaacacgc ctttcaatat gctgaaacgc gagagaaacc gcgtgtcgac tgtgcaacag     180

ctgacaaaga gattctcact tggaatgctg cagggacgag gaccattaaa actgttcatg     240

gccctggtgg cgttccttcg tttcctaaca atcccaccaa cagcagggat attgaagaga     300

tggggaacaa ttaaaaaatc aaaagctatt aatgttttga gagggttcag gaaagagatt     360

ggaaggatgc tgaacatctt gaataggaga cgcagatctg caggcatgat cattatgctg     420
```

-continued

```
attccaacag tgatggcgtt ccatttaacc acacgtaacg gagaaccaca catgatcgtc    480
agcagacaag agaaagggaa aagtcttctg tttaaaacag aggttggcgt gaacatgtgt    540
accctcatgg ccatggacct tggtgaattg tgtgaagaca caatcacgta cgagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatc    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
```

-continued ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160

-continued

```
cggggtttga gaacattaat cttggccccc actagagttg tggcagctga aatggaggaa   5220
gcccttagag gacttccaat aagataccag accccagcca tcagagctgt gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgca   6600
aggggcatag ggaagatgac cctgggaatg tgctgcataa tcacggctag catcctccta   6660
tggtacgcac aaatacagcc acactggata gcagcttcaa taatactgga gtttttttctc   6720
atagttttgc ttattccaga acctgaaaaa cagagaaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
```

```
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccgtattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
```

```
gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 4
<211> LENGTH: 3391
<212> TYPE: PRT
<213> ORGANISM: dengue seroytpe 2 (MVS)

<400> SEQUENCE: 4

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Val Gly
    130                 135                 140

Val Asn Met Cys Thr Leu Met Ala Met Asp Leu Gly Glu Leu Cys Glu
145                 150                 155                 160

Asp Thr Ile Thr Tyr Glu Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
```

-continued

```
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655
```

```
Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                1015                1020

Gly Pro  Val Ser Gln His Asn  Tyr Arg Pro Gly Tyr  His Thr Gln
    1025                1030                1035

Ile Thr  Gly Pro Trp His Leu  Gly Lys Leu Glu Met  Asp Phe Asp
    1040                1045                1050

Phe Cys  Asp Gly Thr Thr Val  Val Val Thr Glu Asp  Cys Gly Asn
    1055                1060                1065
```

```
Arg Gly  Pro Ser Leu Arg Thr  Thr Thr Ala Ser Gly  Lys Leu Ile
    1070                1075                1080

Thr Glu  Trp Cys Cys Arg Ser  Cys Thr Leu Pro Pro  Leu Arg Tyr
    1085                1090                1095

Arg Gly  Glu Asp Gly Cys Trp  Tyr Gly Met Glu Ile  Arg Pro Leu
    1100                1105                1110

Lys Glu  Lys Glu Glu Asn Leu  Val Asn Ser Leu Val  Thr Ala Gly
    1115                1120                1125

His Gly  Gln Val Asp Asn Phe  Ser Leu Gly Val Leu  Gly Met Ala
    1130                1135                1140

Leu Phe  Leu Glu Glu Met Leu  Arg Thr Arg Val Gly  Thr Lys His
    1145                1150                1155

Ala Ile  Leu Leu Val Ala Val  Ser Phe Val Thr Leu  Ile Thr Gly
    1160                1165                1170

Asn Met  Ser Phe Arg Asp Leu  Gly Arg Val Met Val  Met Val Gly
    1175                1180                1185

Ala Thr  Met Thr Asp Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Lys Glu Leu Met Met  Thr Thr Ile
    1220                1225                1230

Gly Ile  Val Leu Leu Ser Gln  Ser Thr Ile Pro Glu  Thr Ile Leu
    1235                1240                1245

Glu Leu  Thr Asp Ala Leu Ala  Leu Gly Met Met Val  Leu Lys Met
    1250                1255                1260

Val Arg  Asn Met Glu Lys Tyr  Gln Leu Ala Val Thr  Ile Met Ala
    1265                1270                1275

Ile Leu  Cys Val Pro Asn Ala  Val Ile Leu Gln Asn  Ala Trp Lys
    1280                1285                1290

Val Ser  Cys Thr Ile Leu Ala  Val Val Ser Val Ser  Pro Leu Phe
    1295                1300                1305

Leu Thr  Ser Ser Gln Gln Lys  Thr Asp Trp Ile Pro  Leu Ala Leu
    1310                1315                1320

Thr Ile  Lys Gly Leu Asn Pro  Thr Ala Ile Phe Leu  Thr Thr Leu
    1325                1330                1335

Ser Arg  Thr Ser Lys Lys Arg  Ser Trp Pro Leu Asn  Glu Ala Ile
    1340                1345                1350

Met Ala  Val Gly Met Val Ser  Ile Leu Ala Ser Ser  Leu Leu Lys
    1355                1360                1365

Asn Asp  Ile Pro Met Thr Gly  Pro Leu Val Ala Gly  Gly Leu Leu
    1370                1375                1380

Thr Val  Cys Tyr Val Leu Thr  Gly Arg Ser Ala Asp  Leu Glu Leu
    1385                1390                1395

Glu Arg  Ala Ala Asp Val Lys  Trp Glu Asp Gln Ala  Glu Ile Ser
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
```

```
1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560

Trp Lys  Glu Gly Glu Glu Val  Gln Val Leu Ala Leu  Glu Pro Gly
    1565                1570                1575

Lys Asn  Pro Arg Ala Val Gln  Thr Lys Pro Gly Leu  Phe Lys Thr
    1580                1585                1590

Asn Ala  Gly Thr Ile Gly Ala  Val Ser Leu Asp Phe  Ser Pro Gly
    1595                1600                1605

Thr Ser  Gly Ser Pro Ile Ile  Asp Lys Lys Gly Lys  Val Val Gly
    1610                1615                1620

Leu Tyr  Gly Asn Gly Val Val  Thr Arg Ser Gly Ala  Tyr Val Ser
    1625                1630                1635

Ala Ile  Ala Gln Thr Glu Lys  Ser Ile Glu Asp Asn  Pro Glu Ile
    1640                1645                1650

Glu Asp  Asp Ile Phe Arg Lys  Arg Arg Leu Thr Ile  Met Asp Leu
    1655                1660                1665

His Pro  Gly Ala Gly Lys Thr  Lys Arg Tyr Leu Pro  Ala Ile Val
    1670                1675                1680

Arg Glu  Ala Ile Lys Arg Gly  Leu Arg Thr Leu Ile  Leu Ala Pro
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860
```

Thr Phe Asp Ser Glu Tyr Val Lys Thr Arg Thr Asn Asp Trp Asp
1865 1870 1875

Phe Val Val Thr Thr Asp Ile Ser Glu Met Gly Ala Asn Phe Lys
1880 1885 1890

Ala Glu Arg Val Ile Asp Pro Arg Arg Cys Met Lys Pro Val Ile
1895 1900 1905

Leu Thr Asp Gly Glu Glu Arg Val Ile Leu Ala Gly Pro Met Pro
1910 1915 1920

Val Thr His Ser Ser Ala Ala Gln Arg Arg Gly Arg Ile Gly Arg
1925 1930 1935

Asn Pro Lys Asn Glu Asn Asp Gln Tyr Ile Tyr Met Gly Glu Pro
1940 1945 1950

Leu Glu Asn Asp Glu Asp Cys Ala His Trp Lys Glu Ala Lys Met
1955 1960 1965

Leu Leu Asp Asn Ile Asn Thr Pro Glu Gly Ile Ile Pro Ser Met
1970 1975 1980

Phe Glu Pro Glu Arg Glu Lys Val Asp Ala Ile Asp Gly Glu Tyr
1985 1990 1995

Arg Leu Arg Gly Glu Ala Arg Lys Thr Phe Val Asp Leu Met Arg
2000 2005 2010

Arg Gly Asp Leu Pro Val Trp Leu Ala Tyr Arg Val Ala Ala Glu
2015 2020 2025

Gly Ile Asn Tyr Ala Asp Arg Arg Trp Cys Phe Asp Gly Val Lys
2030 2035 2040

Asn Asn Gln Ile Leu Glu Glu Asn Val Glu Val Glu Ile Trp Thr
2045 2050 2055

Lys Glu Gly Glu Arg Lys Lys Leu Lys Pro Arg Trp Leu Asp Ala
2060 2065 2070

Arg Ile Tyr Ser Asp Pro Leu Ala Leu Lys Glu Phe Lys Glu Phe
2075 2080 2085

Ala Ala Gly Arg Lys Ser Leu Thr Leu Asn Leu Ile Thr Glu Met
2090 2095 2100

Gly Arg Leu Pro Thr Phe Met Thr Gln Lys Ala Arg Asp Ala Leu
2105 2110 2115

Asp Asn Leu Ala Val Leu His Thr Ala Glu Ala Gly Gly Arg Ala
2120 2125 2130

Tyr Asn His Ala Leu Ser Glu Leu Pro Glu Thr Leu Glu Thr Leu
2135 2140 2145

Leu Leu Leu Thr Leu Leu Ala Thr Val Thr Gly Gly Ile Phe Leu
2150 2155 2160

Phe Leu Met Ser Ala Arg Gly Ile Gly Lys Met Thr Leu Gly Met
2165 2170 2175

Cys Cys Ile Ile Thr Ala Ser Ile Leu Leu Trp Tyr Ala Gln Ile
2180 2185 2190

Gln Pro His Trp Ile Ala Ala Ser Ile Ile Leu Glu Phe Phe Leu
2195 2200 2205

Ile Val Leu Leu Ile Pro Glu Pro Glu Lys Gln Arg Thr Pro Gln
2210 2215 2220

Asp Asn Gln Leu Thr Tyr Val Val Ile Ala Ile Leu Thr Val Val
2225 2230 2235

Ala Ala Thr Met Ala Asn Glu Met Gly Phe Leu Glu Lys Thr Lys
2240 2245 2250

```
Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475

Leu Phe  Ser Ile Met Lys Asn  Thr Thr Asn Thr Arg  Arg Gly Thr
    2480                 2485                 2490

Gly Asn  Ile Gly Glu Thr Leu  Gly Glu Lys Trp Lys  Ser Arg Leu
    2495                 2500                 2505

Asn Ala  Leu Gly Lys Ser Glu  Phe Gln Ile Tyr Lys  Lys Ser Gly
    2510                 2515                 2520

Ile Gln  Glu Val Asp Arg Thr  Leu Ala Lys Glu Gly  Ile Lys Arg
    2525                 2530                 2535

Gly Glu  Thr Asp His His Ala  Val Ser Arg Gly Ser  Ala Lys Leu
    2540                 2545                 2550

Arg Trp  Phe Val Glu Arg Asn  Met Val Thr Pro Glu  Gly Lys Val
    2555                 2560                 2565

Val Asp  Leu Gly Cys Gly Arg  Gly Gly Trp Ser Tyr  Tyr Cys Gly
    2570                 2575                 2580

Gly Leu  Lys Asn Val Arg Glu  Val Lys Gly Leu Thr  Lys Gly Gly
    2585                 2590                 2595

Pro Gly  His Glu Glu Pro Ile  Pro Met Ser Thr Tyr  Gly Trp Asn
    2600                 2605                 2610

Leu Val  Arg Leu Gln Ser Gly  Val Asp Val Phe Phe  Ile Pro Pro
    2615                 2620                 2625

Glu Lys  Cys Asp Thr Leu Leu  Cys Asp Ile Gly Glu  Ser Ser Pro
    2630                 2635                 2640

Asn Pro  Thr Val Glu Ala Gly  Arg Thr Leu Arg Val  Leu Asn Leu
```

```
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715

Ile Val  Ser Ser Val Asn Met  Ile Ser Arg Met Leu  Ile Asn Arg
    2720                2725                2730

Phe Thr  Met Arg Tyr Lys Lys  Ala Thr Tyr Glu Pro  Asp Val Asp
    2735                2740                2745

Leu Gly  Ser Gly Thr Arg Asn  Ile Gly Ile Glu Ser  Glu Ile Pro
    2750                2755                2760

Asn Leu  Asp Ile Ile Gly Lys  Arg Ile Glu Lys Ile  Lys Gln Glu
    2765                2770                2775

His Glu  Thr Ser Trp His Tyr  Asp Gln Asp His Pro  Tyr Lys Thr
    2780                2785                2790

Trp Ala  Tyr His Gly Ser Tyr  Glu Thr Lys Gln Thr  Gly Ser Ala
    2795                2800                2805

Ser Ser  Met Val Asn Gly Val  Val Arg Leu Leu Thr  Lys Pro Trp
    2810                2815                2820

Asp Val  Val Pro Met Val Thr  Gln Met Ala Met Thr  Asp Thr Thr
    2825                2830                2835

Pro Phe  Gly Gln Gln Arg Val  Phe Lys Glu Lys Val  Asp Thr Arg
    2840                2845                2850

Thr Gln  Glu Pro Lys Glu Gly  Thr Lys Lys Leu Met  Lys Ile Thr
    2855                2860                2865

Ala Glu  Trp Leu Trp Lys Glu  Leu Gly Lys Lys Lys  Thr Pro Arg
    2870                2875                2880

Met Cys  Thr Arg Glu Glu Phe  Thr Arg Lys Val Arg  Ser Asn Ala
    2885                2890                2895

Ala Leu  Gly Ala Val Phe Thr  Asp Glu Asn Lys Trp  Lys Ser Ala
    2900                2905                2910

Arg Glu  Ala Val Glu Asp Ser  Arg Phe Trp Glu Leu  Val Asp Lys
    2915                2920                2925

Glu Arg  Asn Leu His Leu Glu  Gly Lys Cys Glu Thr  Cys Val Tyr
    2930                2935                2940

Asn Met  Met Gly Lys Arg Glu  Lys Lys Leu Gly Glu  Phe Gly Lys
    2945                2950                2955

Ala Lys  Gly Ser Arg Ala Ile  Trp Tyr Met Trp Leu  Gly Ala Arg
    2960                2965                2970

Phe Leu  Glu Phe Glu Ala Leu  Gly Phe Leu Asn Glu  Asp His Trp
    2975                2980                2985

Phe Ser  Arg Glu Asn Ser Leu  Ser Gly Val Glu Gly  Glu Gly Leu
    2990                2995                3000

His Lys  Leu Gly Tyr Ile Leu  Arg Asp Val Ser Lys  Lys Glu Gly
    3005                3010                3015

Gly Ala  Met Tyr Ala Asp Asp  Thr Ala Gly Trp Asp  Thr Arg Ile
    3020                3025                3030

Thr Leu  Glu Asp Leu Lys Asn  Glu Glu Met Val Thr  Asn His Met
    3035                3040                3045
```

```
Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135

Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```

<210> SEQ ID NO 5
<211> LENGTH: 10717
<212> TYPE: DNA
<213> ORGANISM: chimeric dengue serotype 2/3 (MVS)

<400> SEQUENCE: 5

```
agttgttagt ctacgtggac cgacaaagac agattctttg agggagctaa gctcaatgta     60
```

```
gttctaacag ttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acgcgtgatg gagagccgcg catgattgtg    480
gggaagaatg aaagaggaaa atccctactt ttcaagacag cctctggaat caacatgtgc    540
acactcatag ctatggatct gggagagatg tgtgatgaca cggtcactta caaatgcccc    600
cacattaccg aagtggagcc tgaagacatt gactgctggt gcaaccttac atcgacatgg    660
gtgacttatg gaacatgcaa tcaagctgga gagcatagac gcgataagag atcagtggcg    720
ttagctcccc atgttggcat gggactggac acacgcactc aaacctggat gtcggctgaa    780
ggagcttgga gacaagtcga gaaggtagag acatgggccc ttaggcaccc agggtttacc    840
atactagccc tatttcttgc ccattacata ggcacttcct tgacccagaa agtggttatt    900
tttatactat taatgctggt taccccatcc atgacaatga gatgtgtagg agtaggaaac    960
agagattttg tggaaggcct atcgggagct acgtgggttg acgtggtgct cgagcacggt   1020
gggtgtgtga ctaccatggc taagaacaag cccacgctgg acatagagct tcagaagacc   1080
gaggccaccc aactggcgac cctaaggaag ctatgcattg agggaaaaat taccaacata   1140
acaaccgact caagatgtcc cacccaaggg gaagcgattt tacctgagga gcaggaccag   1200
aactacgtgt gtaagcatac atacgtggac agaggctggg gaaacggttg tggtttgttt   1260
ggcaagggaa gcttggtgac atgcgcgaaa tttcaatgtt tagaatcaat agagggaaaa   1320
gtggtgcaac atgagaacct caaatacacc gtcatcatca cagtgcacac aggagaccaa   1380
caccaggtgg gaaatgaaac gcagggagtc acggctgaga taacacccca ggcatcaacc   1440
gctgaagcca ttttacctga atatggaacc ctcgggctag aatgctcacc acggacaggt   1500
ttggatttca atgaaatgat ctcattgaca atgaagaaca aagcatggat ggtacataga   1560
caatggttct ttgacttacc cctaccatgg acatcaggag cttcagcaga aacaccaact   1620
tggaacagga aagagcttct tgtgacattt aaaaatgcac atgcaaaaaa gcaagaagta   1680
gttgttcttg gatcacaaga gggagcaatg catacagcac tgacaggagc tacagagatc   1740
caaacctcag gaggcacaag tatctttgcg gggcacttaa aatgtagact caagatggac   1800
aaattggaac tcaaggggat gagctatgca atgtgcttga gtagctttgt gttgaagaaa   1860
gaagtctccg aaacgcagca tgggacaata ctcattaagg ttgagtacaa aggggaagat   1920
gcaccctgca agattccttt ctccacggag gatggacaag gaaaagctct caatggcaga   1980
ctgatcacag ccaatccagt ggtgaccaag aaggaggagc ctgtcaacat tgaggctgaa   2040
cctccttttg gagaaagtaa catagtaatt ggaattggag acaaagccct gaaaatcaac   2100
tggtacaaga agggaagctc gattgggaag atgttcgagg ccactgccag aggtgcaagg   2160
cgcatggcca tcttgggaga cacagcctgg gactttggat cagtgggtgg tgttttgaat   2220
tcattaggga aaatggtcca ccaaatattt gggagtgctt acacagccct atttggtgga   2280
gtctcctgga tgatgaaaat tggaataggt gtcctcttaa cctggatagg gttgaactca   2340
aaaaatactt ctatgtcatt ttcatgcatc gcggccggca ttgtgacact gtatttggga   2400
```

-continued

```
gtcatggtgc aggccgatag tggttgcgtt gtgagctgga aaaacaaaga actgaaatgt   2460
ggcagtggga ttttcatcac agacaacgtg cacacatgga cagaacaata caagttccaa   2520
ccagaatccc cttcaaaact agcttcagct atccagaaag cccatgaaga ggacatttgt   2580
ggaatccgct cagtaacaag actggagaat ctgatgtgga aacaaataac accagaattg   2640
aatcacattc tatcagaaaa tgaggtgaag ttaactatta tgacaggaga catcaaagga   2700
atcatgcagg caggaaaacg atctctgcgg cctcagccca ctgagctgaa gtattcatgg   2760
aaaacatggg gcaaagcaaa aatgctctct acagagtctc ataaccagac ctttctcatt   2820
gatggccccg aaacagcaga atgccccaac acaaatagag cttggaattc gttggaagtt   2880
gaagactatg gctttggagt attcaccacc aatatatggc taaaattgaa agaaaaacag   2940
gatgtattct gcgactcaaa actcatgtca gcggccataa aagacaacag agccgtccat   3000
gccgatatgg gttattggat agaaagtgca ctcaatgaca catggaagat agagaaagcc   3060
tctttcattg aagttaaaaa ctgccactgg ccaaaatcac acaccctctg gagcaatgga   3120
gtgctagaaa gtgagatgat aattccaaag aatctcgctg gaccagtgtc tcaacacaac   3180
tatagaccag gctaccatac acaaataaca ggaccatggc atctaggtaa gcttgagatg   3240
gactttgatt tctgtgatgg aacaacagtg gtagtgactg aggactgcgg aaatagagga   3300
ccctctttga gaacaaccac tgcctctgga aaactcataa cagaatggtg ctgccgatct   3360
tgcacattac caccgctaag atacagaggt gaggatgggt gctggtacgg gatggaaatc   3420
agaccattga aggagaaaga agagaatttg gtcaactcct tggtcacagc tggacatggg   3480
caggtcgaca acttttcact aggagtcttg ggaatggcat tgttcctgga ggaaatgctt   3540
aggacccgag taggaacgaa acatgcaata ctactagttg cagtttcttt tgtgacattg   3600
atcacaggga acatgtcctt tagagacctg ggaagagtga tggttatggt aggcgccact   3660
atgacggatg acataggtat gggcgtgact tatcttgccc tactagcagc cttcaaagtc   3720
agaccaactt ttgcagctgg actactcttg agaaagctga cctccaagga attgatgatg   3780
actactatag gaattgtact cctctcccag agcaccatac cagagaccat tcttgagttg   3840
actgatgcgt tagccttagg catgatggtc ctcaaaatgg tgagaaatat ggaaaagtat   3900
caattggcag tgactatcat ggctatcttg tgcgtcccaa acgcagtgat attacaaaac   3960
gcatggaaag tgagttgcac aatattggca gtggtgtccg tttccccact gttcttaaca   4020
tcctcacagc aaaaaacaga ttggatacca ttagcattga cgatcaaagg tctcaatcca   4080
acagctattt ttctaacaac cctctcaaga accagcaaga aaaggagctg gccattaaat   4140
gaggctatca tggcagtcgg gatggtgagc attttagcca gttctctcct aaaaaatgat   4200
attcccatga caggaccatt agtggctgga gggctcctca ctgtgtgcta cgtgctcact   4260
ggacgatcgg ccgatttgga actggagaga gcagccgatg tcaaatggga agaccaggca   4320
gagatatcag gaagcagtcc aatcctgtca ataacaatat cagaagatgg tagcatgtcg   4380
ataaaaaatg aagaggaaga acaaacactg accatactca ttagaacagg attgctggtg   4440
atctcaggac tttttcctgt atcaatacca atcacggcag cagcatggta cctgtgggaa   4500
gtgaagaaac aacgggccgg agtattgtgg gatgttcctt cacccccacc catgggaaag   4560
gctgaactgg aagatggagc ctatagaatt aagcaaaaag ggattcttgg atattcccag   4620
atcggagccg gagtttacaa agaaggaaca ttccatacaa tgtggcatgt cacacgtggc   4680
gctgttctaa tgcataaagg aaagaggatt gaaccatcat gggcggacgt caagaaagac   4740
ctaatatcat atggaggagg ctggaagtta gaaggagaat ggaaggaagg agaagaagtc   4800
```

```
caggtattgg cactggagcc tggaaaaaat ccaagagccg tccaaacgaa acctggtctt   4860
ttcaaaacca acgccggaac aataggtgct gtatctctgg acttttctcc tggaacgtca   4920
ggatctccaa ttatcgacaa aaaaggaaaa gttgtgggtc tttatggtaa tggtgttgtt   4980
acaaggagtg gagcatatgt gagtgctata gcccagactg aaaaaagcat tgaagacaac   5040
ccagagatcg aagatgacat tttccgaaag agaagactga ccatcatgga cctccaccca   5100
ggagcgggaa agacgaagag ataccttccg gccatagtca gagaagctat aaaacggggt   5160
ttgagaacat taatcttggc ccccactaga gttgtggcag ctgaaatgga ggaagccctt   5220
agaggacttc caataagata ccagacccca gccatcagag ctgtgcacac cgggcgggag   5280
attgtggacc taatgtgtca tgccacattt accatgaggc tgctatcacc agttagagtg   5340
ccaaactaca acctgattat catggacgaa gcccatttca cagacccagc aagtatagca   5400
gctagaggat acatctcaac tcgagtggag atgggtgagg cagctgggat tttatgaca    5460
gccactcccc cgggaagcag agacccattt cctcagagca atgcaccaat catagatgaa   5520
gaaagagaaa tccctgaacg ctcgtggaat tccggacatg aatgggtcac ggattttaaa   5580
gggaagactg tttggttcgt tccaagtata aaagcaggaa atgatatagc agcttgcctg   5640
aggaaaaatg gaaagaaagt gatacaactc agtaggaaga cctttgattc tgagtatgtc   5700
aagactagaa ccaatgattg ggacttcgtg gttacaactg acatttcaga aatgggtgcc   5760
aatttcaagg ctgagagggt tatagacccc agacgctgca tgaaaccagt catactaaca   5820
gatggtgaag agcgggtgat tctggcagga cctatgccag tgacccactc tagtgcagca   5880
caaagaagag ggagaatagg aagaaatcca aaaaatgaga atgaccagta catatacatg   5940
ggggaacctc tggaaaatga tgaagactgt gcacactgga aagaagctaa aatgctccta   6000
gataacatca acacgccaga aggaatcatt cctagcatgt tcgaaccaga gcgtgaaaag   6060
gtggatgcca ttgatggcga ataccgcttg agaggagaag caaggaaaac ctttgtagac   6120
ttaatgagaa gaggagacct accagtctgg ttggcctaca gagtggcagc tgaaggcatc   6180
aactacgcag acagaaggtg gtgttttgat ggagtcaaga acaaccaaat cctagaagaa   6240
aacgtggaag ttgaaatctg gacaaaagaa ggggaaagga agaaattgaa acccagatgg   6300
ttggatgcta ggatctattc tgacccactg gcgctaaaag aatttaagga atttgcagcc   6360
ggaagaaagt ctctgaccct gaacctaatc acagaaatgg gtaggctccc aaccttcatg   6420
actcagaagg caagagacgc actggacaac ttagcagtgc tgcacacggc tgaggcaggt   6480
ggaagggcgt acaaccatgc tctcagtgaa ctgccggaga ccctggagac attgctttta   6540
ctgacacttc tggctacagt cacgggaggg atctttttat tcttgatgag cgcaaggggc   6600
atagggaaga tgaccctggg aatgtgctgc ataatcacgg ctagcatcct cctatggtac   6660
gcacaaatac agccacactg gatagcagct tcaataatac tggagttttt tctcatagtt   6720
ttgcttattc cagaacctga aaaacagaga acaccccaag acaaccaact gacctacgtt   6780
gtcatagcca tcctcacagt ggtggccgca accatggcaa acgagatggg tttcctagaa   6840
aaaacgaaga aagatctcgg attgggaagc attgcaaccc agcaacccga gagcaacatc   6900
ctggacatag atctacgtcc tgcatcagca tggacgctgt atgccgtggc cacaacattt   6960
gttacaccaa tgttgagaca tagcattgaa aattcctcag tgaatgtgtc cctaacagct   7020
atagccaacc aagccacagt gttaatgggt ctcgggaaag gatggccatt gtcaaagatg   7080
gacatcggag ttccccttct cgccattgga tgctactcac aagtcaaccc cataactctc   7140
```

-continued

```
acagcagctc ttttcttatt ggtagcacat tatgccatca tagggccagg actccaagca   7200
aaagcaacca gagaagctca gaaaagagca gcggcgggca tcatgaaaaa cccaactgtc   7260
gatggaataa cagtgattga cctagatcca ataccttatg atccaaagtt tgaaaagcag   7320
ttgggacaag taatgctcct agtcctctgc gtgactcaag tattgatgat gaggactaca   7380
tgggctctgt gtgaggcttt aaccttagct accgggccca tctccacatt gtgggaagga   7440
aatccaggga ggttttggaa cactaccatt gcggtgtcaa tggctaacat ttttagaggg   7500
agttacttgg ccggagctgg acttctcttt tctattatga agaacacaac caacacaaga   7560
aggggaactg gcaacatagg agagacgctt ggagagaaat ggaaaagccg attgaacgcg   7620
ttgggaaaaa gtgaattcca gatctacaag aaaagtggaa tccaggaagt ggatagaacc   7680
ttagcaaaag aaggcattaa aagaggagaa acggaccatc acgctgtgtc gcgaggctca   7740
gcaaaactga gatggttcgt tgagagaaac atggtcacac cagaagggaa agtagtggac   7800
ctcggttgtg gcagaggagg ctggtcatac tattgtggag gactaaagaa tgtaagagaa   7860
gtcaaaggcc taacaaaagg aggaccagga cacgaagaac ccatccccat gtcaacatat   7920
gggtggaatc tagtgcgtct tcaaagtgga gttgacgttt tcttcatccc gccagaaaag   7980
tgtgacacat tattgtgtga catagggggag tcatcaccaa atcccacagt ggaagcagga   8040
cgaacactca gagtccttaa cttagtagaa aattggttga acaacaacac tcaattttgc   8100
ataaaggttc tcaacccata tatgccctca gtcatagaaa aaatggaagc actacaaagg   8160
aaatatggag gagccttagt gaggaatcca ctctcacgaa actccacaca tgagatgtac   8220
tgggtatcca atgcttccgg gaacatagtg tcatcagtga acatgatttc aaggatgttg   8280
atcaacagat ttacaatgag atacaagaaa gccacttacg agccggatgt tgacctcgga   8340
agcggaaccc gtaacatcgg gattgaaagt gagataccaa acctagatat aattgggaaa   8400
agaatagaaa aaataaagca agagcatgaa acatcatggc actatgacca agaccaccca   8460
tacaaaacgt gggcatacca tggtagctat gaaacaaaac agactggatc agcatcatcc   8520
atggtcaacg gagtggtcag gctgctgaca aaaccttggg acgtcgtccc catggtgaca   8580
cagatggcaa tgacagacac gactccattt ggacaacagc gcgtttttaa agagaaagtg   8640
gacacgagaa cccaagaacc gaaagaaggc acgaagaaac taatgaaaat aacagcagag   8700
tggctttgga aagaattagg gaagaaaaag acacccagga tgtgcaccag agaagaattc   8760
acaagaaagg tgagaagcaa tgcagccttg ggggccatat tcactgatga gaacaagtgg   8820
aagtcggcac gtgaggctgt tgaagatagt aggttttggg agctggttga caaggaaagg   8880
aatctccatc ttgaaggaaa gtgtgaaaca tgtgtgtaca acatgatggg aaaaagagag   8940
aagaagctag gggaattcgg caaggcaaaa ggcagcagag ccatatggta catgtggctt   9000
ggagcacgct tcttagagtt tgaagcccta ggattcttaa atgaagatca ctggttctcc   9060
agagagaact ccctgagtgg agtggaagga gaagggctgc acaagctagg ttacattcta   9120
agagacgtga gcaagaaaga gggaggagca atgtatgccg atgacaccgc aggatgggat   9180
acaagaatca cactagaaga cctaaaaaat gaagaaatgg taacaaacca catggaagga   9240
gaacacaaga aactagccga ggccattttc aaactaacgt accaaaacaa ggtggtgcgt   9300
gtgcaaagac caacaccaag aggcacagta atggacatca tatcgagaag agaccaaaga   9360
ggtagtggac aagttggcac ctatggactc aatactttca ccaatatgga agcccaacta   9420
atcagacaga tggagggaga aggagtcttt aaaagcattc agcacctaac aatcacagaa   9480
gaaatcgctg tgcaaaactg gttagcaaga gtggggcgcg aaaggttatc aagaatggcc   9540
```

```
atcagtggag atgattgtgt tgtgaaacct ttagatgaca ggttcgcaag cgctttaaca   9600

gctctaaatg acatgggaaa gattaggaaa gacatacaac aatgggaacc ttcaagagga   9660

tggaatgatt ggacacaagt gcccttctgt tcacaccatt tccatgagtt aatcatgaaa   9720

gacggtcgcg tactcgttgt tccatgtaga aaccaagatg aactgattgg cagagcccga   9780

atctcccaag gagcagggtg gtctttgcgg gagacggcct gtttggggaa gtcttacgcc   9840

caaatgtgga gcttgatgta cttccacaga cgcgacctca ggctggcggc aaatgctatt   9900

tgctcggcag taccatcaca ttgggttcca acaagtcgaa caacctggtc catacatgct   9960

aaacatgaat ggatgacaac ggaagacatg ctgacagtct ggaacagggt gtggattcaa  10020

gaaaacccat ggatggaaga caaaactcca gtggaatcat gggaggaaat cccatacttg  10080

gggaaaagag aagaccaatg gtgcggctca ttgattgggt taacaagcag ggccacctgg  10140

gcaaagaaca tccaagcagc aataaatcaa gttagatccc ttataggcaa tgaagaatac  10200

acagattaca tgccatccat gaaaagattc agaagagaag aggaagaagc aggagttctg  10260

tggtagaaag caaaactaac atgaaacaag gctagaagtc aggtcggatt aagccatagt  10320

acggaaaaaa ctatgctacc tgtgagcccc gtccaaggac gttaaaagaa gtcaggccat  10380

cataaatgcc atagcttgag taaactatgc agcctgtagc tccacctgag aaggtgtaaa  10440

aaatccggga ggccacaaac catggaagct gtacgcatgg cgtagtggac tagcggttag  10500

aggagacccc tcccttacaa atcgcagcaa caatgggggc ccaaggcgag atgaagctgt  10560

agtctcgctg gaaggactag aggttagagg agaccccccc gaaacaaaaa acagcatatt  10620

gacgctggga aagaccagag atcctgctgt ctcctcagca tcattccagg cacagaacgc  10680

cagaaaatgg aatggtgctg ttgaatcaac aggttct                           10717
```

<210> SEQ ID NO 6
<211> LENGTH: 3389
<212> TYPE: PRT
<213> ORGANISM: chimeric dengue serotype 2/3 (MVS)

<400> SEQUENCE: 6

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160
```

-continued

```
Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Ala Glu Ala Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Ser Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
```

```
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

Leu Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685

Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ala Gly Ile Val Thr Leu Tyr Leu Gly
        755                 760                 765

Val Met Val Gln Ala Asp Ser Gly Cys Val Val Ser Trp Lys Asn Lys
    770                 775                 780

Glu Leu Lys Cys Gly Ser Gly Ile Phe Ile Thr Asp Asn Val His Thr
785                 790                 795                 800

Trp Thr Glu Gln Tyr Lys Phe Gln Pro Glu Ser Pro Ser Lys Leu Ala
                805                 810                 815

Ser Ala Ile Gln Lys Ala His Glu Glu Asp Ile Cys Gly Ile Arg Ser
            820                 825                 830

Val Thr Arg Leu Glu Asn Leu Met Trp Lys Gln Ile Thr Pro Glu Leu
        835                 840                 845

Asn His Ile Leu Ser Glu Asn Glu Val Lys Leu Thr Ile Met Thr Gly
    850                 855                 860

Asp Ile Lys Gly Ile Met Gln Ala Gly Lys Arg Ser Leu Arg Pro Gln
865                 870                 875                 880

Pro Thr Glu Leu Lys Tyr Ser Trp Lys Thr Trp Gly Lys Ala Lys Met
                885                 890                 895

Leu Ser Thr Glu Ser His Asn Gln Thr Phe Leu Ile Asp Gly Pro Glu
            900                 905                 910

Thr Ala Glu Cys Pro Asn Thr Asn Arg Ala Trp Asn Ser Leu Glu Val
        915                 920                 925

Glu Asp Tyr Gly Phe Gly Val Phe Thr Thr Asn Ile Trp Leu Lys Leu
    930                 935                 940

Lys Glu Lys Gln Asp Val Phe Cys Asp Ser Lys Leu Met Ser Ala Ala
945                 950                 955                 960

Ile Lys Asp Asn Arg Ala Val His Ala Asp Met Gly Tyr Trp Ile Glu
                965                 970                 975

Ser Ala Leu Asn Asp Thr Trp Lys Ile Glu Lys Ala Ser Phe Ile Glu
            980                 985                 990

Val Lys Asn Cys His Trp Pro Lys  Ser His Thr Leu Trp  Ser Asn Gly
        995                 1000                1005
```

```
Val Leu Glu Ser Glu Met Ile Ile Pro Lys Asn Leu Ala Gly Pro
    1010                1015                1020

Val Ser Gln His Asn Tyr Arg Pro Gly Tyr His Thr Gln Ile Thr
    1025                1030                1035

Gly Pro Trp His Leu Gly Lys Leu Glu Met Asp Phe Asp Phe Cys
    1040                1045                1050

Asp Gly Thr Thr Val Val Val Thr Glu Asp Cys Gly Asn Arg Gly
    1055                1060                1065

Pro Ser Leu Arg Thr Thr Thr Ala Ser Gly Lys Leu Ile Thr Glu
    1070                1075                1080

Trp Cys Cys Arg Ser Cys Thr Leu Pro Pro Leu Arg Tyr Arg Gly
    1085                1090                1095

Glu Asp Gly Cys Trp Tyr Gly Met Glu Ile Arg Pro Leu Lys Glu
    1100                1105                1110

Lys Glu Glu Asn Leu Val Asn Ser Leu Val Thr Ala Gly His Gly
    1115                1120                1125

Gln Val Asp Asn Phe Ser Leu Gly Val Leu Gly Met Ala Leu Phe
    1130                1135                1140

Leu Glu Glu Met Leu Arg Thr Arg Val Gly Thr Lys His Ala Ile
    1145                1150                1155

Leu Leu Val Ala Val Ser Phe Val Thr Leu Ile Thr Gly Asn Met
    1160                1165                1170

Ser Phe Arg Asp Leu Gly Arg Val Met Val Met Val Gly Ala Thr
    1175                1180                1185

Met Thr Asp Asp Ile Gly Met Gly Val Thr Tyr Leu Ala Leu Leu
    1190                1195                1200

Ala Ala Phe Lys Val Arg Pro Thr Phe Ala Ala Gly Leu Leu Leu
    1205                1210                1215

Arg Lys Leu Thr Ser Lys Glu Leu Met Met Thr Thr Ile Gly Ile
    1220                1225                1230

Val Leu Leu Ser Gln Ser Thr Ile Pro Glu Thr Ile Leu Glu Leu
    1235                1240                1245

Thr Asp Ala Leu Ala Leu Gly Met Met Val Leu Lys Met Val Arg
    1250                1255                1260

Asn Met Glu Lys Tyr Gln Leu Ala Val Thr Ile Met Ala Ile Leu
    1265                1270                1275

Cys Val Pro Asn Ala Val Ile Leu Gln Asn Ala Trp Lys Val Ser
    1280                1285                1290

Cys Thr Ile Leu Ala Val Val Ser Val Ser Pro Leu Phe Leu Thr
    1295                1300                1305

Ser Ser Gln Gln Lys Thr Asp Trp Ile Pro Leu Ala Leu Thr Ile
    1310                1315                1320

Lys Gly Leu Asn Pro Thr Ala Ile Phe Leu Thr Thr Leu Ser Arg
    1325                1330                1335

Thr Ser Lys Lys Arg Ser Trp Pro Leu Asn Glu Ala Ile Met Ala
    1340                1345                1350

Val Gly Met Val Ser Ile Leu Ala Ser Ser Leu Leu Lys Asn Asp
    1355                1360                1365

Ile Pro Met Thr Gly Pro Leu Val Ala Gly Gly Leu Leu Thr Val
    1370                1375                1380

Cys Tyr Val Leu Thr Gly Arg Ser Ala Asp Leu Glu Leu Glu Arg
    1385                1390                1395
```

-continued

```
Ala Ala  Asp Val Lys Trp Glu  Asp Gln Ala Glu Ile  Ser Gly Ser
    1400                 1405                 1410

Ser Pro  Ile Leu Ser Ile Thr  Ile Ser Glu Asp Gly  Ser Met Ser
    1415                 1420                 1425

Ile Lys  Asn Glu Glu Glu Glu  Gln Thr Leu Thr Ile  Leu Ile Arg
    1430                 1435                 1440

Thr Gly  Leu Leu Val Ile Ser  Gly Leu Phe Pro Val  Ser Ile Pro
    1445                 1450                 1455

Ile Thr  Ala Ala Ala Trp Tyr  Leu Trp Glu Val Lys  Lys Gln Arg
    1460                 1465                 1470

Ala Gly  Val Leu Trp Asp Val  Pro Ser Pro Pro Pro  Met Gly Lys
    1475                 1480                 1485

Ala Glu  Leu Glu Asp Gly Ala  Tyr Arg Ile Lys Gln  Lys Gly Ile
    1490                 1495                 1500

Leu Gly  Tyr Ser Gln Ile Gly  Ala Gly Val Tyr Lys  Glu Gly Thr
    1505                 1510                 1515

Phe His  Thr Met Trp His Val  Thr Arg Gly Ala Val  Leu Met His
    1520                 1525                 1530

Lys Gly  Lys Arg Ile Glu Pro  Ser Trp Ala Asp Val  Lys Lys Asp
    1535                 1540                 1545

Leu Ile  Ser Tyr Gly Gly Gly  Trp Lys Leu Glu Gly  Glu Trp Lys
    1550                 1555                 1560

Glu Gly  Glu Glu Val Gln Val  Leu Ala Leu Glu Pro  Gly Lys Asn
    1565                 1570                 1575

Pro Arg  Ala Val Gln Thr Lys  Pro Gly Leu Phe Lys  Thr Asn Ala
    1580                 1585                 1590

Gly Thr  Ile Gly Ala Val Ser  Leu Asp Phe Ser Pro  Gly Thr Ser
    1595                 1600                 1605

Gly Ser  Pro Ile Ile Asp Lys  Lys Gly Lys Val Val  Gly Leu Tyr
    1610                 1615                 1620

Gly Asn  Gly Val Val Thr Arg  Ser Gly Ala Tyr Val  Ser Ala Ile
    1625                 1630                 1635

Ala Gln  Thr Glu Lys Ser Ile  Glu Asp Asn Pro Glu  Ile Glu Asp
    1640                 1645                 1650

Asp Ile  Phe Arg Lys Arg Arg  Leu Thr Ile Met Asp  Leu His Pro
    1655                 1660                 1665

Gly Ala  Gly Lys Thr Lys Arg  Tyr Leu Pro Ala Ile  Val Arg Glu
    1670                 1675                 1680

Ala Ile  Lys Arg Gly Leu Arg  Thr Leu Ile Leu Ala  Pro Thr Arg
    1685                 1690                 1695

Val Val  Ala Ala Glu Met Glu  Glu Ala Leu Arg Gly  Leu Pro Ile
    1700                 1705                 1710

Arg Tyr  Gln Thr Pro Ala Ile  Arg Ala Val His Thr  Gly Arg Glu
    1715                 1720                 1725

Ile Val  Asp Leu Met Cys His  Ala Thr Phe Thr Met  Arg Leu Leu
    1730                 1735                 1740

Ser Pro  Val Arg Val Pro Asn  Tyr Asn Leu Ile Ile  Met Asp Glu
    1745                 1750                 1755

Ala His  Phe Thr Asp Pro Ala  Ser Ile Ala Ala Arg  Gly Tyr Ile
    1760                 1765                 1770

Ser Thr  Arg Val Glu Met Gly  Glu Ala Ala Gly Ile  Phe Met Thr
    1775                 1780                 1785

Ala Thr  Pro Pro Gly Ser Arg  Asp Pro Phe Pro Gln  Ser Asn Ala
```

```
    1790                1795                1800

Pro Ile  Ile Asp Glu Glu Arg  Glu Ile Pro Glu Arg  Ser Trp Asn
    1805                1810                1815

Ser Gly  His Glu Trp Val Thr  Asp Phe Lys Gly Lys  Thr Val Trp
    1820                1825                1830

Phe Val  Pro Ser Ile Lys Ala  Gly Asn Asp Ile Ala  Ala Cys Leu
    1835                1840                1845

Arg Lys  Asn Gly Lys Lys Val  Ile Gln Leu Ser Arg  Lys Thr Phe
    1850                1855                1860

Asp Ser  Glu Tyr Val Lys Thr  Arg Thr Asn Asp Trp  Asp Phe Val
    1865                1870                1875

Val Thr  Thr Asp Ile Ser Glu  Met Gly Ala Asn Phe  Lys Ala Glu
    1880                1885                1890

Arg Val  Ile Asp Pro Arg Arg  Cys Met Lys Pro Val  Ile Leu Thr
    1895                1900                1905

Asp Gly  Glu Glu Arg Val Ile  Leu Ala Gly Pro Met  Pro Val Thr
    1910                1915                1920

His Ser  Ser Ala Ala Gln Arg  Arg Gly Arg Ile Gly  Arg Asn Pro
    1925                1930                1935

Lys Asn  Glu Asn Asp Gln Tyr  Ile Tyr Met Gly Glu  Pro Leu Glu
    1940                1945                1950

Asn Asp  Glu Asp Cys Ala His  Trp Lys Glu Ala Lys  Met Leu Leu
    1955                1960                1965

Asp Asn  Ile Asn Thr Pro Glu  Gly Ile Ile Pro Ser  Met Phe Glu
    1970                1975                1980

Pro Glu  Arg Glu Lys Val Asp  Ala Ile Asp Gly Glu  Tyr Arg Leu
    1985                1990                1995

Arg Gly  Glu Ala Arg Lys Thr  Phe Val Asp Leu Met  Arg Arg Gly
    2000                2005                2010

Asp Leu  Pro Val Trp Leu Ala  Tyr Arg Val Ala Ala  Glu Gly Ile
    2015                2020                2025

Asn Tyr  Ala Asp Arg Arg Trp  Cys Phe Asp Gly Val  Lys Asn Asn
    2030                2035                2040

Gln Ile  Leu Glu Glu Asn Val  Glu Val Glu Ile Trp  Thr Lys Glu
    2045                2050                2055

Gly Glu  Arg Lys Lys Leu Lys  Pro Arg Trp Leu Asp  Ala Arg Ile
    2060                2065                2070

Tyr Ser  Asp Pro Leu Ala Leu  Lys Glu Phe Lys Glu  Phe Ala Ala
    2075                2080                2085

Gly Arg  Lys Ser Leu Thr Leu  Asn Leu Ile Thr Glu  Met Gly Arg
    2090                2095                2100

Leu Pro  Thr Phe Met Thr Gln  Lys Ala Arg Asp Ala  Leu Asp Asn
    2105                2110                2115

Leu Ala  Val Leu His Thr Ala  Glu Ala Gly Gly Arg  Ala Tyr Asn
    2120                2125                2130

His Ala  Leu Ser Glu Leu Pro  Glu Thr Leu Glu Thr  Leu Leu Leu
    2135                2140                2145

Leu Thr  Leu Leu Ala Thr Val  Thr Gly Gly Ile Phe  Leu Phe Leu
    2150                2155                2160

Met Ser  Ala Arg Gly Ile Gly  Lys Met Thr Leu Gly  Met Cys Cys
    2165                2170                2175

Ile Ile  Thr Ala Ser Ile Leu  Leu Trp Tyr Ala Gln  Ile Gln Pro
    2180                2185                2190
```

```
His Trp  Ile Ala Ala Ser Ile  Ile Leu Glu Phe Phe  Leu Ile Val
    2195                 2200                 2205

Leu Leu  Ile Pro Glu Pro Glu  Lys Gln Arg Thr Pro  Gln Asp Asn
    2210                 2215                 2220

Gln Leu  Thr Tyr Val Val Ile  Ala Ile Leu Thr Val  Val Ala Ala
    2225                 2230                 2235

Thr Met  Ala Asn Glu Met Gly  Phe Leu Glu Lys Thr  Lys Lys Asp
    2240                 2245                 2250

Leu Gly  Leu Gly Ser Ile Ala  Thr Gln Gln Pro Glu  Ser Asn Ile
    2255                 2260                 2265

Leu Asp  Ile Asp Leu Arg Pro  Ala Ser Ala Trp Thr  Leu Tyr Ala
    2270                 2275                 2280

Val Ala  Thr Thr Phe Val Thr  Pro Met Leu Arg His  Ser Ile Glu
    2285                 2290                 2295

Asn Ser  Ser Val Asn Val Ser  Leu Thr Ala Ile Ala  Asn Gln Ala
    2300                 2305                 2310

Thr Val  Leu Met Gly Leu Gly  Lys Gly Trp Pro Leu  Ser Lys Met
    2315                 2320                 2325

Asp Ile  Gly Val Pro Leu Leu  Ala Ile Gly Cys Tyr  Ser Gln Val
    2330                 2335                 2340

Asn Pro  Ile Thr Leu Thr Ala  Ala Leu Phe Leu Leu  Val Ala His
    2345                 2350                 2355

Tyr Ala  Ile Ile Gly Pro Gly  Leu Gln Ala Lys Ala  Thr Arg Glu
    2360                 2365                 2370

Ala Gln  Lys Arg Ala Ala Ala  Gly Ile Met Lys Asn  Pro Thr Val
    2375                 2380                 2385

Asp Gly  Ile Thr Val Ile Asp  Leu Asp Pro Ile Pro  Tyr Asp Pro
    2390                 2395                 2400

Lys Phe  Glu Lys Gln Leu Gly  Gln Val Met Leu Leu  Val Leu Cys
    2405                 2410                 2415

Val Thr  Gln Val Leu Met Met  Arg Thr Thr Trp Ala  Leu Cys Glu
    2420                 2425                 2430

Ala Leu  Thr Leu Ala Thr Gly  Pro Ile Ser Thr Leu  Trp Glu Gly
    2435                 2440                 2445

Asn Pro  Gly Arg Phe Trp Asn  Thr Thr Ile Ala Val  Ser Met Ala
    2450                 2455                 2460

Asn Ile  Phe Arg Gly Ser Tyr  Leu Ala Gly Ala Gly  Leu Leu Phe
    2465                 2470                 2475

Ser Ile  Met Lys Asn Thr Thr  Asn Thr Arg Arg Gly  Thr Gly Asn
    2480                 2485                 2490

Ile Gly  Glu Thr Leu Gly Glu  Lys Trp Lys Ser Arg  Leu Asn Ala
    2495                 2500                 2505

Leu Gly  Lys Ser Glu Phe Gln  Ile Tyr Lys Lys Ser  Gly Ile Gln
    2510                 2515                 2520

Glu Val  Asp Arg Thr Leu Ala  Lys Glu Gly Ile Lys  Arg Gly Glu
    2525                 2530                 2535

Thr Asp  His His Ala Val Ser  Arg Gly Ser Ala Lys  Leu Arg Trp
    2540                 2545                 2550

Phe Val  Glu Arg Asn Met Val  Thr Pro Glu Gly Lys  Val Val Asp
    2555                 2560                 2565

Leu Gly  Cys Gly Arg Gly Gly  Trp Ser Tyr Tyr Cys  Gly Gly Leu
    2570                 2575                 2580
```

-continued

```
Lys Asn  Val Arg Glu Val Lys  Gly Leu Thr Lys Gly  Gly Pro Gly
    2585                 2590                 2595

His Glu  Glu Pro Ile Pro Met  Ser Thr Tyr Gly Trp  Asn Leu Val
    2600                 2605                 2610

Arg Leu  Gln Ser Gly Val Asp  Val Phe Phe Ile Pro  Pro Glu Lys
    2615                 2620                 2625

Cys Asp  Thr Leu Leu Cys Asp  Ile Gly Glu Ser Ser  Pro Asn Pro
    2630                 2635                 2640

Thr Val  Glu Ala Gly Arg Thr  Leu Arg Val Leu Asn  Leu Val Glu
    2645                 2650                 2655

Asn Trp  Leu Asn Asn Asn Thr  Gln Phe Cys Ile Lys  Val Leu Asn
    2660                 2665                 2670

Pro Tyr  Met Pro Ser Val Ile  Glu Lys Met Glu Ala  Leu Gln Arg
    2675                 2680                 2685

Lys Tyr  Gly Gly Ala Leu Val  Arg Asn Pro Leu Ser  Arg Asn Ser
    2690                 2695                 2700

Thr His  Glu Met Tyr Trp Val  Ser Asn Ala Ser Gly  Asn Ile Val
    2705                 2710                 2715

Ser Ser  Val Asn Met Ile Ser  Arg Met Leu Ile Asn  Arg Phe Thr
    2720                 2725                 2730

Met Arg  Tyr Lys Lys Ala Thr  Tyr Glu Pro Asp Val  Asp Leu Gly
    2735                 2740                 2745

Ser Gly  Thr Arg Asn Ile Gly  Ile Glu Ser Glu Ile  Pro Asn Leu
    2750                 2755                 2760

Asp Ile  Ile Gly Lys Arg Ile  Glu Lys Ile Lys Gln  Glu His Glu
    2765                 2770                 2775

Thr Ser  Trp His Tyr Asp Gln  Asp His Pro Tyr Lys  Thr Trp Ala
    2780                 2785                 2790

Tyr His  Gly Ser Tyr Glu Thr  Lys Gln Thr Gly Ser  Ala Ser Ser
    2795                 2800                 2805

Met Val  Asn Gly Val Val Arg  Leu Leu Thr Lys Pro  Trp Asp Val
    2810                 2815                 2820

Val Pro  Met Val Thr Gln Met  Ala Met Thr Asp Thr  Thr Pro Phe
    2825                 2830                 2835

Gly Gln  Gln Arg Val Phe Lys  Glu Lys Val Asp Thr  Arg Thr Gln
    2840                 2845                 2850

Glu Pro  Lys Glu Gly Thr Lys  Lys Leu Met Lys Ile  Thr Ala Glu
    2855                 2860                 2865

Trp Leu  Trp Lys Glu Leu Gly  Lys Lys Lys Thr Pro  Arg Met Cys
    2870                 2875                 2880

Thr Arg  Glu Glu Phe Thr Arg  Lys Val Arg Ser Asn  Ala Ala Leu
    2885                 2890                 2895

Gly Ala  Ile Phe Thr Asp Glu  Asn Lys Trp Lys Ser  Ala Arg Glu
    2900                 2905                 2910

Ala Val  Glu Asp Ser Arg Phe  Trp Glu Leu Val Asp  Lys Glu Arg
    2915                 2920                 2925

Asn Leu  His Leu Glu Gly Lys  Cys Glu Thr Cys Val  Tyr Asn Met
    2930                 2935                 2940

Met Gly  Lys Arg Glu Lys Lys  Leu Gly Glu Phe Gly  Lys Ala Lys
    2945                 2950                 2955

Gly Ser  Arg Ala Ile Trp Tyr  Met Trp Leu Gly Ala  Arg Phe Leu
    2960                 2965                 2970

Glu Phe  Glu Ala Leu Gly Phe  Leu Asn Glu Asp His  Trp Phe Ser
```

2975 2980 2985

Arg Glu Asn Ser Leu Ser Gly Val Glu Gly Glu Gly Leu His Lys
2990 2995 3000

Leu Gly Tyr Ile Leu Arg Asp Val Ser Lys Lys Glu Gly Gly Ala
3005 3010 3015

Met Tyr Ala Asp Asp Thr Ala Gly Trp Asp Thr Arg Ile Thr Leu
3020 3025 3030

Glu Asp Leu Lys Asn Glu Glu Met Val Thr Asn His Met Glu Gly
3035 3040 3045

Glu His Lys Lys Leu Ala Glu Ala Ile Phe Lys Leu Thr Tyr Gln
3050 3055 3060

Asn Lys Val Val Arg Val Gln Arg Pro Thr Pro Arg Gly Thr Val
3065 3070 3075

Met Asp Ile Ile Ser Arg Arg Asp Gln Arg Gly Ser Gly Gln Val
3080 3085 3090

Gly Thr Tyr Gly Leu Asn Thr Phe Thr Asn Met Glu Ala Gln Leu
3095 3100 3105

Ile Arg Gln Met Glu Gly Glu Gly Val Phe Lys Ser Ile Gln His
3110 3115 3120

Leu Thr Ile Thr Glu Glu Ile Ala Val Gln Asn Trp Leu Ala Arg
3125 3130 3135

Val Gly Arg Glu Arg Leu Ser Arg Met Ala Ile Ser Gly Asp Asp
3140 3145 3150

Cys Val Val Lys Pro Leu Asp Asp Arg Phe Ala Ser Ala Leu Thr
3155 3160 3165

Ala Leu Asn Asp Met Gly Lys Ile Arg Lys Asp Ile Gln Gln Trp
3170 3175 3180

Glu Pro Ser Arg Gly Trp Asn Asp Trp Thr Gln Val Pro Phe Cys
3185 3190 3195

Ser His His Phe His Glu Leu Ile Met Lys Asp Gly Arg Val Leu
3200 3205 3210

Val Val Pro Cys Arg Asn Gln Asp Glu Leu Ile Gly Arg Ala Arg
3215 3220 3225

Ile Ser Gln Gly Ala Gly Trp Ser Leu Arg Glu Thr Ala Cys Leu
3230 3235 3240

Gly Lys Ser Tyr Ala Gln Met Trp Ser Leu Met Tyr Phe His Arg
3245 3250 3255

Arg Asp Leu Arg Leu Ala Ala Asn Ala Ile Cys Ser Ala Val Pro
3260 3265 3270

Ser His Trp Val Pro Thr Ser Arg Thr Thr Trp Ser Ile His Ala
3275 3280 3285

Lys His Glu Trp Met Thr Thr Glu Asp Met Leu Thr Val Trp Asn
3290 3295 3300

Arg Val Trp Ile Gln Glu Asn Pro Trp Met Glu Asp Lys Thr Pro
3305 3310 3315

Val Glu Ser Trp Glu Glu Ile Pro Tyr Leu Gly Lys Arg Glu Asp
3320 3325 3330

Gln Trp Cys Gly Ser Leu Ile Gly Leu Thr Ser Arg Ala Thr Trp
3335 3340 3345

Ala Lys Asn Ile Gln Ala Ala Ile Asn Gln Val Arg Ser Leu Ile
3350 3355 3360

Gly Asn Glu Glu Tyr Thr Asp Tyr Met Pro Ser Met Lys Arg Phe
3365 3370 3375

Arg Arg Glu Glu Glu Glu Ala Gly Val Leu Trp
3380 3385

<210> SEQ ID NO 7
<211> LENGTH: 10723
<212> TYPE: DNA
<213> ORGANISM: chimeric dengue seroytpe 2/4 (MVS)
<220> FEATURE:
<221> NAME/KEY: r
<222> LOCATION: (3773)..(3773)
<223> OTHER INFORMATION: a or g

<400> SEQUENCE: 7
agttgttagt ctacgtggac cgacaaagac agattctttg agggagctaa gctcaatgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gacctttaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagctctg caggcatgat cattatgctg 420
attccaacag tgatggcgtt ccatttaacc acgcgtgatg gcgaacccct catgatagtg 480
gcaaaacatg aaagggggag acctctcttg tttaagacaa cagaggggat caacaaatgc 540
actctcattg ccatggactt gggtgaaatg tgtgaggaca ctgtcacgta taaatgcccc 600
ttactggtca ataccgaacc tgaagacatt gattgctggt gcaatctcac gtctacctgg 660
gtcatgtatg ggacatgcac ccagagcgga gaacggagac gagagaagcg ctcagtagct 720
ttaacaccac attcaggaat gggattggaa acaagagctg agacatggat gtcatcggaa 780
ggggcttgga agcatgctca gagagtagag agctggatac tcagaaaccc aggattcgcg 840
ctcttggcag gatttatggc ttatatgatt gggcaaacag gaatccagcg aactgtcttc 900
tttgtcctaa tgatgctggt cgccccatcc tacggaatgc gatgcgtagg agtaggaaac 960
agagactttg tggaaggagt ctcaggtgga gcatgggtcg atctggtgct agaacatgga 1020
ggatgcgtca caaccatggc ccagggaaaa ccaaccttgg attttgaact gactaagaca 1080
acagccaagg aagtggctct gttaagaacc tattgcattg aagcctcaat atcaaacata 1140
accacggcaa caagatgtcc aacgcaagga gagccttatc taaaagagga acaagaccaa 1200
cagtacattt gccggagaga tgtggtagac agagggtggg gcaatggctg tggcttgttt 1260
ggaaaaggag gagttgtgac atgtgcgaag ttttcatgtt cggggaagat aacaggcaat 1320
ttggtccaaa ttgagaacct tgaatacaca gtggttgtaa cagtccacaa tggagacacc 1380
catgcagtag gaaatgacac gtccaatcat ggagttacag ccacgataac tcccaggtca 1440
ccatcggtgg aagtcaaatt gccggactat ggagaactaa cactcgattg tgaacccagg 1500
tctggaattg actttaatga gatgattctg atgaaaatga aaaagaaaac atggcttgtg 1560
cataagcaat ggtttttgga tctacctcta ccatggacag caggagcaga cacatcagag 1620
gttcactgga attacaaaga gagaatggtg acatttaagg ttcctcatgc caagagacag 1680
gatgtgacag tgctgggatc tcaggaagga gccatgcatt ctgccctcgc tggagccaca 1740
gaagtggact ccggtgatgg aaatcacatg tttgcaggac atctcaagtg caaagtccgt 1800
atggagaaat tgagaatcaa gggaatgtca tacacgatgt gttcaggaaa gttctcaatt 1860
gacaaagaga tggcagaaac acagcatggg acaacagtgg tgaaagtcaa gtatgaaggt 1920
gctggagctc cgtgtaaagt ccccatagag ataagagatg tgaacaagga aaaagtggtt 1980
gggcgtatca tctcatccac ccctttggct gagaatacca acagtgtaac caacatagag 2040
ttagaacccc cctttgggga cagctacata gtgataggtg ttggaaacag tgcattaaca 2100
ctccattggt tcaggaaagg gagttccatt ggcaagatgt ttgagtccac atacagaggt 2160
gcaaaacgaa tggccattct aggtgaaaca gcttgggatt ttggttccgt tggtggactg 2220
ttcacatcat tgggaaaggc tgtgcaccag gtttttggaa gtgtgtatac aaccctgttt 2280
ggaggagtct catggatgat tagaatccta attgggttcc tagtgttgtg gattggcacg 2340
aactcaagga acacttcaat ggctatgacg tgcatagctg ccggcattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagaggac 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cgggtgacat aggtatgggc gtgacttatc ttgccctact agcagccttc 3720
aaagtcagac caacttttgc agctggacta ctcttgagaa agctgacctc carggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgttc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctgt gcacaccggg 5280
cgggagattg tggacctaat gtgtcatgcc acatttacca tgaggctgct atcaccagtt 5340
agagtgccaa actacaacct gattatcatg gacgaagccc atttcacaga tccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgctcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggtaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttattcttt gatgagcgca 6600
aggggcatag ggaagatgac cctgggaatg tgctgcataa tcacggctag catcctccta 6660

```
tggtacgcac aaatacagcc acactggata gcagcttcaa taatactgga gtttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagccatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
```

-continued

```
tggcttggag cacgcttctt agagtttgaa gccctaggat tcttaaatga agatcactgg   9060

ttctccagag agaactccct gagtggagtg gaaggagaag ggctgcacaa gctaggttac   9120

attctaagag acgtgagcaa gaaagaggga ggagcaatgt atgccgatga caccgcagga   9180

tgggatacaa gaatcacact agaagaccta aaaaatgaag aaatggtaac aaaccacatg   9240

gaaggagaac acaagaaact agccgaggcc attttcaaac taacgtacca aaacaaggtg   9300

gtgcgtgtgc aaagaccaac accaagaggc acagtaatgg acatcatatc gagaagagac   9360

caaagaggta gtggacaagt tggcacctat ggactcaata ctttcaccaa tatggaagcc   9420

caactaatca gacagatgga gggagaagga gtctttaaaa gcattcagca cctaacaatc   9480

acagaagaaa tcgctgtgca aaactggtta gcaagagtgg ggcgcgaaag gttatcaaga   9540

atggccatca gtggagatga ttgtgttgtg aaacctttag atgacaggtt cgcaagcgct   9600

ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttccc tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgaacaac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 8
<211> LENGTH: 3391
<212> TYPE: PRT
<213> ORGANISM: chimeric dengue serotype 2/4 (MVS)
<220> FEATURE:
<221> NAME/KEY: Xaa
<222> LOCATION: (1226)..(1226)
<223> OTHER INFORMATION: Arg or Lys

<400> SEQUENCE: 8

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45
```

-continued

```
Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Ser Ser Ala Gly Met Ile Ile Met Leu Ile Pro Thr Val
            100                 105                 110

Met Ala Phe His Leu Thr Thr Arg Asp Gly Glu Pro Leu Met Ile Val
        115                 120                 125

Ala Lys His Glu Arg Gly Arg Pro Leu Leu Phe Lys Thr Thr Glu Gly
    130                 135                 140

Ile Asn Lys Cys Thr Leu Ile Ala Met Asp Leu Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Leu Thr Ser Thr Trp Val Met Tyr Gly
            180                 185                 190

Thr Cys Thr Gln Ser Gly Glu Arg Arg Arg Glu Lys Arg Ser Val Ala
        195                 200                 205

Leu Thr Pro His Ser Gly Met Gly Leu Glu Thr Arg Ala Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Ala Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Thr Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Gly Val Val Thr Cys Ala Lys Phe Ser
385                 390                 395                 400

Cys Ser Gly Lys Ile Thr Gly Asn Leu Val Gln Ile Glu Asn Leu Glu
                405                 410                 415

Tyr Thr Val Val Val Thr Val His Asn Gly Asp Thr His Ala Val Gly
            420                 425                 430

Asn Asp Thr Ser Asn His Gly Val Thr Ala Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
```

-continued

```
465                 470                 475                 480

Met Lys Lys Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Ala Gly Ala Thr Glu Val Asp Ser Gly Asp Gly Asn His Met Phe Ala
545                 550                 555                 560

Gly His Leu Lys Cys Lys Val Arg Met Glu Lys Leu Arg Ile Lys Gly
                565                 570                 575

Met Ser Tyr Thr Met Cys Ser Gly Lys Phe Ser Ile Asp Lys Glu Met
            580                 585                 590

Ala Glu Thr Gln His Gly Thr Thr Val Val Lys Val Lys Tyr Glu Gly
        595                 600                 605

Ala Gly Ala Pro Cys Lys Val Pro Ile Glu Ile Arg Asp Val Asn Lys
    610                 615                 620

Glu Lys Val Val Gly Arg Ile Ile Ser Ser Thr Pro Leu Ala Glu Asn
625                 630                 635                 640

Thr Asn Ser Val Thr Asn Ile Glu Leu Glu Pro Pro Phe Gly Asp Ser
                645                 650                 655

Tyr Ile Val Ile Gly Val Gly Asn Ser Ala Leu Thr Leu His Trp Phe
            660                 665                 670

Arg Lys Gly Ser Ser Ile Gly Lys Met Phe Glu Ser Thr Tyr Arg Gly
        675                 680                 685

Ala Lys Arg Met Ala Ile Leu Gly Glu Thr Ala Trp Asp Phe Gly Ser
    690                 695                 700

Val Gly Gly Leu Phe Thr Ser Leu Gly Lys Ala Val His Gln Val Phe
705                 710                 715                 720

Gly Ser Val Tyr Thr Thr Leu Phe Gly Gly Val Ser Trp Met Ile Arg
                725                 730                 735

Ile Leu Ile Gly Phe Leu Val Leu Trp Ile Gly Thr Asn Ser Arg Asn
            740                 745                 750

Thr Ser Met Ala Met Thr Cys Ile Ala Ala Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Asp Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895
```

-continued

```
Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                 1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
    1160                 1165                 1170

Asn Met  Ser Phe Arg Asp Leu  Gly Arg Val Met Val  Met Val Gly
    1175                 1180                 1185

Ala Thr  Met Thr Gly Asp Ile  Gly Met Gly Val Thr  Tyr Leu Ala
    1190                 1195                 1200

Leu Leu  Ala Ala Phe Lys Val  Arg Pro Thr Phe Ala  Ala Gly Leu
    1205                 1210                 1215

Leu Leu  Arg Lys Leu Thr Ser  Xaa Glu Leu Met Met  Thr Thr Ile
    1220                 1225                 1230

Gly Ile  Val Leu Leu Ser Gln  Ser Thr Ile Pro Glu  Thr Ile Leu
    1235                 1240                 1245

Glu Leu  Thr Asp Ala Leu Ala  Leu Gly Met Met Val  Leu Lys Met
    1250                 1255                 1260

Val Arg  Asn Met Glu Lys Tyr  Gln Leu Ala Val Thr  Ile Met Ala
    1265                 1270                 1275

Ile Leu  Cys Val Pro Asn Ala  Val Ile Leu Gln Asn  Ala Trp Lys
    1280                 1285                 1290
```

-continued

Val Ser Cys Thr Ile Leu Ala Val Val Ser Val Ser Pro Leu Phe
1295 1300 1305

Leu Thr Ser Ser Gln Gln Lys Thr Asp Trp Ile Pro Leu Ala Leu
1310 1315 1320

Thr Ile Lys Gly Leu Asn Pro Thr Ala Ile Phe Leu Thr Thr Leu
1325 1330 1335

Ser Arg Thr Ser Lys Lys Arg Ser Trp Pro Leu Asn Glu Ala Ile
1340 1345 1350

Met Ala Val Gly Met Val Ser Ile Leu Ala Ser Ser Leu Leu Lys
1355 1360 1365

Asn Asp Ile Pro Met Thr Gly Pro Leu Val Ala Gly Gly Leu Leu
1370 1375 1380

Thr Val Cys Tyr Val Leu Thr Gly Arg Ser Ala Asp Leu Glu Leu
1385 1390 1395

Glu Arg Ala Ala Asp Val Lys Trp Glu Asp Gln Ala Glu Ile Ser
1400 1405 1410

Gly Ser Ser Pro Ile Leu Ser Ile Thr Ile Ser Glu Asp Gly Ser
1415 1420 1425

Met Ser Ile Lys Asn Glu Glu Glu Glu Gln Thr Leu Thr Ile Leu
1430 1435 1440

Ile Arg Thr Gly Leu Leu Val Ile Ser Gly Leu Phe Pro Val Ser
1445 1450 1455

Ile Pro Ile Thr Ala Ala Ala Trp Tyr Leu Trp Glu Val Lys Lys
1460 1465 1470

Gln Arg Ala Gly Val Leu Trp Asp Val Pro Ser Pro Pro Pro Met
1475 1480 1485

Gly Lys Ala Glu Leu Glu Asp Gly Ala Tyr Arg Ile Lys Gln Lys
1490 1495 1500

Gly Ile Leu Gly Tyr Ser Gln Ile Gly Ala Gly Val Tyr Lys Glu
1505 1510 1515

Gly Thr Phe His Thr Met Trp His Val Thr Arg Gly Ala Val Leu
1520 1525 1530

Met His Lys Gly Lys Arg Ile Glu Pro Ser Trp Ala Asp Val Lys
1535 1540 1545

Lys Asp Leu Ile Ser Tyr Gly Gly Gly Trp Lys Leu Glu Gly Glu
1550 1555 1560

Trp Lys Glu Gly Glu Glu Val Gln Val Leu Ala Leu Glu Pro Gly
1565 1570 1575

Lys Asn Pro Arg Ala Val Gln Thr Lys Pro Gly Leu Phe Lys Thr
1580 1585 1590

Asn Ala Gly Thr Ile Gly Ala Val Ser Leu Asp Phe Ser Pro Gly
1595 1600 1605

Thr Ser Gly Ser Pro Ile Ile Asp Lys Lys Gly Lys Val Val Gly
1610 1615 1620

Leu Tyr Gly Asn Gly Val Val Thr Arg Ser Gly Ala Tyr Val Ser
1625 1630 1635

Ala Ile Ala Gln Thr Glu Lys Ser Ile Glu Asp Asn Pro Glu Ile
1640 1645 1650

Glu Asp Asp Ile Phe Arg Lys Arg Arg Leu Thr Ile Met Asp Leu
1655 1660 1665

His Pro Gly Ala Gly Lys Thr Lys Arg Tyr Leu Pro Ala Ile Val
1670 1675 1680

Arg Glu Ala Ile Lys Arg Gly Leu Arg Thr Leu Ile Leu Ala Pro

```
    1685                1690                1695

Thr Arg  Val Val Ala Ala Glu  Met Glu Glu Ala Leu  Arg Gly Leu
    1700                1705                1710

Pro Ile  Arg Tyr Gln Thr Pro  Ala Ile Arg Ala Val  His Thr Gly
    1715                1720                1725

Arg Glu  Ile Val Asp Leu Met  Cys His Ala Thr Phe  Thr Met Arg
    1730                1735                1740

Leu Leu  Ser Pro Val Arg Val  Pro Asn Tyr Asn Leu  Ile Ile Met
    1745                1750                1755

Asp Glu  Ala His Phe Thr Asp  Pro Ala Ser Ile Ala  Ala Arg Gly
    1760                1765                1770

Tyr Ile  Ser Thr Arg Val Glu  Met Gly Glu Ala Ala  Gly Ile Phe
    1775                1780                1785

Met Thr  Ala Thr Pro Pro Gly  Ser Arg Asp Pro Phe  Pro Gln Ser
    1790                1795                1800

Asn Ala  Pro Ile Ile Asp Glu  Glu Arg Glu Ile Pro  Glu Arg Ser
    1805                1810                1815

Trp Asn  Ser Gly His Glu Trp  Val Thr Asp Phe Lys  Gly Lys Thr
    1820                1825                1830

Val Trp  Phe Val Pro Ser Ile  Lys Ala Gly Asn Asp  Ile Ala Ala
    1835                1840                1845

Cys Leu  Arg Lys Asn Gly Lys  Lys Val Ile Gln Leu  Ser Arg Lys
    1850                1855                1860

Thr Phe  Asp Ser Glu Tyr Val  Lys Thr Arg Thr Asn  Asp Trp Asp
    1865                1870                1875

Phe Val  Val Thr Thr Asp Ile  Ser Glu Met Gly Ala  Asn Phe Lys
    1880                1885                1890

Ala Glu  Arg Val Ile Asp Pro  Arg Arg Cys Met Lys  Pro Val Ile
    1895                1900                1905

Leu Thr  Asp Gly Glu Glu Arg  Val Ile Leu Ala Gly  Pro Met Pro
    1910                1915                1920

Val Thr  His Ser Ser Ala Ala  Gln Arg Arg Gly Arg  Ile Gly Arg
    1925                1930                1935

Asn Pro  Lys Asn Glu Asn Asp  Gln Tyr Ile Tyr Met  Gly Glu Pro
    1940                1945                1950

Leu Glu  Asn Asp Glu Asp Cys  Ala His Trp Lys Glu  Ala Lys Met
    1955                1960                1965

Leu Leu  Asp Asn Ile Asn Thr  Pro Glu Gly Ile Ile  Pro Ser Met
    1970                1975                1980

Phe Glu  Pro Glu Arg Glu Lys  Val Asp Ala Ile Asp  Gly Glu Tyr
    1985                1990                1995

Arg Leu  Arg Gly Glu Ala Arg  Lys Thr Phe Val Asp  Leu Met Arg
    2000                2005                2010

Arg Gly  Asp Leu Pro Val Trp  Leu Ala Tyr Arg Val  Ala Ala Glu
    2015                2020                2025

Gly Ile  Asn Tyr Ala Asp Arg  Arg Trp Cys Phe Asp  Gly Val Lys
    2030                2035                2040

Asn Asn  Gln Ile Leu Glu Glu  Asn Val Glu Val Glu  Ile Trp Thr
    2045                2050                2055

Lys Glu  Gly Glu Arg Lys Lys  Leu Lys Pro Arg Trp  Leu Asp Ala
    2060                2065                2070

Arg Ile  Tyr Ser Asp Pro Leu  Ala Leu Lys Glu Phe  Lys Glu Phe
    2075                2080                2085
```

```
Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Val Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Ala Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
    2345                 2350                 2355

Ala His  Tyr Ala Ile Ile Gly  Pro Gly Leu Gln Ala  Lys Ala Thr
    2360                 2365                 2370

Arg Glu  Ala Gln Lys Arg Ala  Ala Ala Gly Ile Met  Lys Asn Pro
    2375                 2380                 2385

Thr Val  Asp Gly Ile Thr Val  Ile Asp Leu Asp Pro  Ile Pro Tyr
    2390                 2395                 2400

Asp Pro  Lys Phe Glu Lys Gln  Leu Gly Gln Val Met  Leu Leu Val
    2405                 2410                 2415

Leu Cys  Val Thr Gln Val Leu  Met Met Arg Thr Thr  Trp Ala Leu
    2420                 2425                 2430

Cys Glu  Ala Leu Thr Leu Ala  Thr Gly Pro Ile Ser  Thr Leu Trp
    2435                 2440                 2445

Glu Gly  Asn Pro Gly Arg Phe  Trp Asn Thr Thr Ile  Ala Val Ser
    2450                 2455                 2460

Met Ala  Asn Ile Phe Arg Gly  Ser Tyr Leu Ala Gly  Ala Gly Leu
    2465                 2470                 2475
```

```
Leu Phe Ser Ile Met Lys Asn Thr Thr Asn Thr Arg Arg Gly Thr
    2480                2485                2490

Gly Asn Ile Gly Glu Thr Leu Gly Glu Lys Trp Lys Ser Arg Leu
    2495                2500                2505

Asn Ala Leu Gly Lys Ser Glu Phe Gln Ile Tyr Lys Lys Ser Gly
    2510                2515                2520

Ile Gln Glu Val Asp Arg Thr Leu Ala Lys Glu Gly Ile Lys Arg
    2525                2530                2535

Gly Glu Thr Asp His His Ala Val Ser Arg Gly Ser Ala Lys Leu
    2540                2545                2550

Arg Trp Phe Val Glu Arg Asn Met Val Thr Pro Glu Gly Lys Val
    2555                2560                2565

Val Asp Leu Gly Cys Gly Arg Gly Gly Trp Ser Tyr Tyr Cys Gly
    2570                2575                2580

Gly Leu Lys Asn Val Arg Glu Val Lys Gly Leu Thr Lys Gly Gly
    2585                2590                2595

Pro Gly His Glu Glu Pro Ile Pro Met Ser Thr Tyr Gly Trp Asn
    2600                2605                2610

Leu Val Arg Leu Gln Ser Gly Val Asp Val Phe Phe Ile Pro Pro
    2615                2620                2625

Glu Lys Cys Asp Thr Leu Leu Cys Asp Ile Gly Glu Ser Ser Pro
    2630                2635                2640

Asn Pro Thr Val Glu Ala Gly Arg Thr Leu Arg Val Leu Asn Leu
    2645                2650                2655

Val Glu Asn Trp Leu Asn Asn Asn Thr Gln Phe Cys Ile Lys Val
    2660                2665                2670

Leu Asn Pro Tyr Met Pro Ser Val Ile Glu Lys Met Glu Ala Leu
    2675                2680                2685

Gln Arg Lys Tyr Gly Gly Ala Leu Val Arg Asn Pro Leu Ser Arg
    2690                2695                2700

Asn Ser Thr His Glu Met Tyr Trp Val Ser Asn Ala Ser Gly Asn
    2705                2710                2715

Ile Val Ser Ser Val Asn Met Ile Ser Arg Met Leu Ile Asn Arg
    2720                2725                2730

Phe Thr Met Arg Tyr Lys Lys Ala Thr Tyr Glu Pro Asp Val Asp
    2735                2740                2745

Leu Gly Ser Gly Thr Arg Asn Ile Gly Ile Glu Ser Glu Ile Pro
    2750                2755                2760

Asn Leu Asp Ile Ile Gly Lys Arg Ile Glu Lys Ile Lys Gln Glu
    2765                2770                2775

His Glu Thr Ser Trp His Tyr Asp Gln Asp His Pro Tyr Lys Thr
    2780                2785                2790

Trp Ala Tyr His Gly Ser Tyr Glu Thr Lys Gln Thr Gly Ser Ala
    2795                2800                2805

Ser Ser Met Val Asn Gly Val Val Arg Leu Leu Thr Lys Pro Trp
    2810                2815                2820

Asp Val Val Pro Met Val Thr Gln Met Ala Met Thr Asp Thr Thr
    2825                2830                2835

Pro Phe Gly Gln Gln Arg Val Phe Lys Glu Lys Val Asp Thr Arg
    2840                2845                2850

Thr Gln Glu Pro Lys Glu Gly Thr Lys Lys Leu Met Lys Ile Thr
    2855                2860                2865

Ala Glu Trp Leu Trp Lys Glu Leu Gly Lys Lys Lys Thr Pro Arg
```

```
    2870                2875                2880

Met Cys  Thr Arg Glu Glu Phe  Thr Arg Lys Val Arg  Ser Asn Ala
    2885                2890                2895

Ala Leu  Gly Ala Ile Phe Thr  Asp Glu Asn Lys Trp  Lys Ser Ala
    2900                2905                2910

Arg Glu  Ala Val Glu Asp Ser  Arg Phe Trp Glu Leu  Val Asp Lys
    2915                2920                2925

Glu Arg  Asn Leu His Leu Glu  Gly Lys Cys Glu Thr  Cys Val Tyr
    2930                2935                2940

Asn Met  Met Gly Lys Arg Glu  Lys Lys Leu Gly Glu  Phe Gly Lys
    2945                2950                2955

Ala Lys  Gly Ser Arg Ala Ile  Trp Tyr Met Trp Leu  Gly Ala Arg
    2960                2965                2970

Phe Leu  Glu Phe Glu Ala Leu  Gly Phe Leu Asn Glu  Asp His Trp
    2975                2980                2985

Phe Ser  Arg Glu Asn Ser Leu  Ser Gly Val Glu Gly  Glu Gly Leu
    2990                2995                3000

His Lys  Leu Gly Tyr Ile Leu  Arg Asp Val Ser Lys  Lys Glu Gly
    3005                3010                3015

Gly Ala  Met Tyr Ala Asp Asp  Thr Ala Gly Trp Asp  Thr Arg Ile
    3020                3025                3030

Thr Leu  Glu Asp Leu Lys Asn  Glu Glu Met Val Thr  Asn His Met
    3035                3040                3045

Glu Gly  Glu His Lys Lys Leu  Ala Glu Ala Ile Phe  Lys Leu Thr
    3050                3055                3060

Tyr Gln  Asn Lys Val Val Arg  Val Gln Arg Pro Thr  Pro Arg Gly
    3065                3070                3075

Thr Val  Met Asp Ile Ile Ser  Arg Arg Asp Gln Arg  Gly Ser Gly
    3080                3085                3090

Gln Val  Gly Thr Tyr Gly Leu  Asn Thr Phe Thr Asn  Met Glu Ala
    3095                3100                3105

Gln Leu  Ile Arg Gln Met Glu  Gly Glu Gly Val Phe  Lys Ser Ile
    3110                3115                3120

Gln His  Leu Thr Ile Thr Glu  Glu Ile Ala Val Gln  Asn Trp Leu
    3125                3130                3135

Ala Arg  Val Gly Arg Glu Arg  Leu Ser Arg Met Ala  Ile Ser Gly
    3140                3145                3150

Asp Asp  Cys Val Val Lys Pro  Leu Asp Asp Arg Phe  Ala Ser Ala
    3155                3160                3165

Leu Thr  Ala Leu Asn Asp Met  Gly Lys Ile Arg Lys  Asp Ile Gln
    3170                3175                3180

Gln Trp  Glu Pro Ser Arg Gly  Trp Asn Asp Trp Thr  Gln Val Pro
    3185                3190                3195

Phe Cys  Ser His His Phe His  Glu Leu Ile Met Lys  Asp Gly Arg
    3200                3205                3210

Val Leu  Val Val Pro Cys Arg  Asn Gln Asp Glu Leu  Ile Gly Arg
    3215                3220                3225

Ala Arg  Ile Ser Gln Gly Ala  Gly Trp Ser Leu Arg  Glu Thr Ala
    3230                3235                3240

Cys Leu  Gly Lys Ser Tyr Ala  Gln Met Trp Ser Leu  Met Tyr Phe
    3245                3250                3255

His Arg  Arg Asp Leu Arg Leu  Ala Ala Asn Ala Ile  Cys Ser Ala
    3260                3265                3270
```

```
Val Pro Ser His Trp Val Pro Thr Ser Arg Thr Thr Trp Ser Ile
    3275                3280                3285

His Ala Lys His Glu Trp Met Thr Thr Glu Asp Met Leu Thr Val
    3290                3295                3300

Trp Asn Arg Val Trp Ile Gln Glu Asn Pro Trp Met Glu Asp Lys
    3305                3310                3315

Thr Pro Val Glu Ser Trp Glu Glu Ile Pro Tyr Leu Gly Lys Arg
    3320                3325                3330

Glu Asp Gln Trp Cys Gly Ser Leu Ile Gly Leu Thr Ser Arg Ala
    3335                3340                3345

Thr Trp Ala Lys Asn Ile Gln Ala Ala Ile Asn Gln Val Arg Ser
    3350                3355                3360

Leu Ile Gly Asn Glu Glu Tyr Thr Asp Tyr Met Pro Ser Met Lys
    3365                3370                3375

Arg Phe Arg Arg Glu Glu Glu Glu Ala Gly Val Leu Trp
    3380                3385                3390
```

```
<210> SEQ ID NO 9
<211> LENGTH: 10735
<212> TYPE: DNA
<213> ORGANISM: dengue virus

<400> SEQUENCE: 9

agttgttagt ctacgtggac cgacaagaac agtttcgaat cggaagcttg cttaacgtag     60
ttctaacagt tttttattag agagcagatc tctgatgatc aaccaacgaa aaaagacggg    120
tcgaccgtct ttcaatatgc tgaaacgcgc gagaaaccgc gtgtcaactg tttcacagtt    180
ggcgaagaga ttctcaaaag gattgctctc aggccaagga cccatgaaat tggtgatggc    240
tttcatagca ttcttaagat ttctagccat acccccaaca gcaggaattt tggctagatg    300
gggctcattc aagaagaatg gagcgattaa agtgttacgg ggtttcaaga gagaaatctc    360
aaacatgcta aacataatga acaggaggaa aagatccgtg accatgctcc ttatgctgct    420
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggacacg atgacctaca aatgccccg     600
gatcactgag gcggaaccag atgacgttga ctgttggtgc aatgccacgg acacatgggt    660
gacctatgga acgtgctctc aaactggcga acaccgacga gacaaacgtt ccgtcgcatt    720
ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agttcaatat gaaaacctaa aatattcagt gatagtcacc gtccacactg gagatcagca   1380
```

-continued

```
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa gaaagatcat ggcttgtcca   1560
caaacaatgg tttctagact taccactgcc ttggacctct ggggcttcaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt ttttggaact gcatatggag ttttgtttag   2280
cggagtttct tggaccatga aaataggaat agggattctg ctgacatggc taggattaaa   2340
ttcaaggaac acgtcccttt cgatgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg gagatgttag   2700
tggaatcttg gcccaaggga aaaaaatgat taggccacaa cccatggaac acaaatactc   2760
gtggaaaagc tggggaaaag ccaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
atcttgtacg ctacccccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
```

-continued tcttcttaca attggcttga gcctggtggc atccgtggag ctaccaagtt ccctagagga 3840
gctgggggat ggacttgcaa taggcatcat gatgttgaaa ttattgactg attttcagtc 3900
acaccagcta tgggctactc tgctatcctt gacatttatt aaaacaactt tttcattgca 3960
ctatgcatgg aagacaatgg ctatggtact gtcaattgta tctctcttcc ctttatgcct 4020
gtccacgacc tctcaaaaaa caacatggct tccggtgctg ttgggatctc ttggatgcaa 4080
accactaccc atgtttctta taacagaaaa caaaatctgg ggaaggaaga gttggcccct 4140
caatgaagga attatggctg ttggaatagt tagtattcta ctaagttcac ttttaaaaaa 4200
tgatgtgccg ctagccggcc cattaatagc tggaggcatg ctaatagcat gttatgtcat 4260
atccggaagc tcagctgatt tatcactgga gaaagcggct gaggtctcct gggaggaaga 4320
agcagaacac tcaggcgcct cacacaacat actagtagag gttcaagatg atggaaccat 4380
gaagataaaa gatgaagaga gagatgacac gctcaccatt ctccttaaag caactctgct 4440
ggcagtctca ggggtgtacc caatgtcaat accagcgacc ctttttgtgt ggtatttttg 4500
gcagaaaaag aaacagagat caggagtgct atgggacaca cccagccccc cagaagtgga 4560
aagagcagtt cttgatgatg gcatctatag aattttgcaa agaggactgt tgggcaggtc 4620
ccaagtagga gtaggagttt tccaagaagg cgtgttccac acaatgtggc acgtcactag 4680
gggagctgtc ctcatgtatc aaggaaaaag gctggaacca agctgggcca gtgtcaaaaa 4740
agacttgatc tcatatggag gaggttggag gtttcaagga tcctggaaca cgggagaaga 4800
agtacaggtg attgctgttg aaccgggaaa aaaccccaaa aatgtacaaa caacgccggg 4860
taccttcaag acccctgaag gcgaagttgg agccatagcc ttagacttta aacctggcac 4920
atctggatct cccatcgtaa acagagaggg aaaaatagta ggtctttatg gaaatggagt 4980
ggtgacaaca agcggaactt acgttagtgc catagctcaa gctaaggcat cacaagaagg 5040
gcctctacca gagattgagg acgaggtgtt taggaaaaga aacttaacaa taatggacct 5100
acatccagga tcgggaaaaa caagaagata ccttccagcc atagtccgtg aggccataaa 5160
aaggaagctg cgcacgctaa tcctagctcc cacaagagtt gtcgcttctg aaatggcaga 5220
ggcactcaag ggagtgccaa taaggtatca gacaacagca gtgaagagtg aacacacagg 5280
aaaggagata gttgacctta tgtgccacgc cactttcacc atgcgcctcc tgtctcccgt 5340
gagagttccc aattataaca tgattatcat ggatgaagca cacttcaccg atccagccag 5400
catagcagcc agagggtaca tctcaacccg agtgggtatg ggtgaagcag ctgcgatctt 5460
tatgacagcc actcccccag gatcggtgga ggcctttcca cagagcaatg caattatcca 5520
agatgaggaa agagacattc ctgagagatc atggaactca ggctatgact ggatcactga 5580
ttttccaggt aaaacagtct ggtttgttcc aagcatcaaa tcaggaaatg acattgccaa 5640
ctgtttaaga aaaaacggga aacgggtgat ccaattgagc agaaaaacct ttgacactga 5700
gtaccagaaa acaaaaaaca acgactggga ctatgtcgtc acaacagaca tttccgaaat 5760
gggagcaaat ttccgggccg acagggtaat agacccaagg cggtgtctga aaccggtaat 5820
actaaaagat ggtccagagc gcgtcattct agccggaccg atgccagtga ctgtggccag 5880
tgccgcccag aggagaggaa gaattggaag gaaccaaaac aaggaaggtg atcagtatat 5940
ttacatggga cagcctttaa acaatgatga ggaccacgct cattggacag aagcaaagat 6000
gctccttgac aatataaaca caccagaagg gattatccca gccctctatg agccggagag 6060
agaaaagagt gcagctatag acggggaata cagactgcgg ggtgaagcaa ggaaaacgtt 6120

```
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcatgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacaa ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaagct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
```

ctcatccatg gtcaatggcg tggtgagatt gctcaccaaa ccatgggatg ttatccccat 8580
ggtcacacaa atagccatga ctgataccac accctttgga caacagaggg tgtttaaaga 8640
gaaagttgac acgcgcacac caaaagcaaa acgtggcaca gcacaaatta tggaagtgac 8700
agccaggtgg ttatggggtt tcctttctag aaacaaaaaa cccagaattt gcacaagaga 8760
ggagtttaca agaaaagtta ggtcaaacgc agctattgga gcagtgttcg ttgatgaaaa 8820
tcaatggaac tcggcaaaag aagcagtgga agacgaacgg ttctgggaac ttgtccacag 8880
agagagggag cttcataaac aggggaaatg tgccacgtgt gtctacaata tgatggggaa 8940
gagagagaaa aaattaggag agttcggaaa ggcaaaagga agtcgtgcaa tatggtacat 9000
gtggttggga gcacgcttcc tagagtttga agcccttggt ttcatgaatg aagatcactg 9060
gttcagtaga gagaattcac tcagtggagt ggaaggagaa ggactccaca aacttggata 9120
catactcaga gacatatcaa ggattccagg ggggaacatg tatgcagatg acacagccgg 9180
atgggacaca agaataacag aggatgatct ccagaatgag gctaaaatca ctgacatcat 9240
ggagcccgaa catgccctgc tggctacgtc aatctttaag ctgacctacc aaaataaggt 9300
ggtaagggtg cagagaccag caaaaaatgg aaccgtgatg gatgttatat ccagacgtga 9360
ccagagaggc agtggacagg ttggaactta tggcttaaac actttcacca acatggaggc 9420
ccaactgata agacaaatgg agtccgaggg aatcttttta cccagcgaat tggaaacccc 9480
aaatctagcc ggaagagttc tcgactggtt ggaaaaatat ggtgtcgaaa ggctgaaaag 9540
aatggcaatc agcggagatg actgtgtggt gaaaccaatt gatgacaggt tcgcaacagc 9600
cttaacagct ttgaatgaca tgggaaaagt aagaaaagac ataccacaat gggaaccttc 9660
aaaaggatgg aatgattggc aacaagtgcc tttctgttca caccacttcc accagctaat 9720
tatgaaggat gggagggaga tagtggtgcc atgccgcaac caagatgaac ttgtggggag 9780
ggccagagta tcacaaggcg ccggatggag cctgagagaa accgcatgcc taggcaagtc 9840
atatgcacaa atgtggcagc tgatgtattt ccacaggaga gacctgagac tggcggctaa 9900
cgctatttgt tcagccgttc cagttgattg ggtcccaacc agccgcacca cctggtcgat 9960
ccatgcccat caccaatgga tgacaacaga agacatgtta tcagtatgga atagggtctg 10020
gatagaggaa aacccatgga tggaggataa gactcatgtg tccagttggg aagaagttcc 10080
atacctagga aagagggaag atcagtggtg tggatccctg ataggcttaa cagcaagggc 10140
cacctgggcc actaatatac aagtggccat aaaccaagtg agaaggctca ttgggaatga 10200
gaattatcta gattacatga catcaatgaa gagattcaag aatgagagtg atcccgaagg 10260
ggcactctgg taagtcaaca cattcacaaa ataaaggaaa ataaaaaatc aaatgaggca 10320
agaagtcagg ccagattaag ccatagtacg gtaagagcta tgctgcctgt gagccccgtc 10380
caaggacgta aaatgaagtc aggccgaaag ccacggtttg agcaagccgt gctgcctgtg 10440
gctccatcgt ggggatgtaa aaacccggga ggctgcaacc catggaagct gtacgcatgg 10500
ggtagcagac tagtggttag aggagacccc tcccaagaca caacgcagca gcggggccca 10560
acaccagggg aagctgtacc ctggtggtaa ggactagagg ttagaggaga ccccccgcgt 10620
aacaataaac agcatattga cgctgggaga gaccagagat cctgctgtct ctacagcatc 10680
attccaggca cagaacgcca gaaaatggaa tggtgctgtt gaatcaacag gttct 10735

<210> SEQ ID NO 10
<211> LENGTH: 3392
<212> TYPE: PRT

<213> ORGANISM: dengue virus

<400> SEQUENCE: 10

Met Ile Asn Gln Arg Lys Lys Thr Gly Arg Pro Ser Phe Asn Met Leu
1 5 10 15

Lys Arg Ala Arg Asn Arg Val Ser Thr Val Ser Gln Leu Ala Lys Arg
20 25 30

Phe Ser Lys Gly Leu Leu Ser Gly Gln Gly Pro Met Lys Leu Val Met
35 40 45

Ala Phe Ile Ala Phe Leu Arg Phe Leu Ala Ile Pro Pro Thr Ala Gly
50 55 60

Ile Leu Ala Arg Trp Gly Ser Phe Lys Lys Asn Gly Ala Ile Lys Val
65 70 75 80

Leu Arg Gly Phe Lys Arg Glu Ile Ser Asn Met Leu Asn Ile Met Asn
85 90 95

Arg Arg Lys Arg Ser Val Thr Met Leu Leu Met Leu Leu Pro Thr Ala
100 105 110

Leu Ala Phe His Leu Thr Thr Arg Gly Gly Glu Pro His Met Ile Val
115 120 125

Ser Lys Gln Glu Arg Gly Lys Ser Leu Leu Phe Lys Thr Ser Ala Gly
130 135 140

Val Asn Met Cys Thr Leu Ile Ala Met Asp Leu Gly Glu Leu Cys Glu
145 150 155 160

Asp Thr Met Thr Tyr Lys Cys Pro Arg Ile Thr Glu Ala Glu Pro Asp
165 170 175

Asp Val Asp Cys Trp Cys Asn Ala Thr Asp Thr Trp Val Thr Tyr Gly
180 185 190

Thr Cys Ser Gln Thr Gly Glu His Arg Arg Asp Lys Arg Ser Val Ala
195 200 205

Leu Ala Pro His Val Gly Leu Gly Leu Glu Thr Arg Ala Glu Thr Trp
210 215 220

Met Ser Ser Glu Gly Ala Trp Lys Gln Ile Gln Lys Val Glu Thr Trp
225 230 235 240

Ala Leu Arg His Pro Gly Phe Thr Val Ile Ala Leu Phe Leu Ala His
245 250 255

Ala Ile Gly Thr Ser Ile Thr Gln Lys Gly Ile Ile Phe Ile Leu Leu
260 265 270

Met Leu Val Thr Pro Ser Met Ala Met Arg Cys Val Gly Ile Gly Asn
275 280 285

Arg Asp Phe Val Glu Gly Leu Ser Gly Ala Thr Trp Val Asp Val Val
290 295 300

Leu Glu His Gly Ser Cys Val Thr Thr Met Ala Lys Asn Lys Pro Thr
305 310 315 320

Leu Asp Ile Glu Leu Leu Lys Thr Glu Val Thr Asn Pro Ala Val Leu
325 330 335

Arg Lys Leu Cys Ile Glu Ala Lys Ile Ser Asn Thr Thr Thr Asp Ser
340 345 350

Arg Cys Pro Thr Gln Gly Glu Ala Thr Leu Val Glu Glu Gln Asp Ala
355 360 365

Asn Phe Val Cys Arg Arg Thr Phe Val Asp Arg Gly Trp Gly Asn Gly
370 375 380

Cys Gly Leu Phe Gly Lys Gly Ser Leu Ile Thr Cys Ala Lys Phe Lys
385 390 395 400

-continued

```
Cys Val Thr Lys Leu Glu Gly Lys Ile Val Gln Tyr Glu Asn Leu Lys
                405                 410                 415

Tyr Ser Val Ile Val Thr Val His Thr Gly Asp Gln His Gln Val Gly
            420                 425                 430

Asn Glu Thr Thr Glu His Gly Thr Thr Ala Thr Ile Thr Pro Gln Ala
        435                 440                 445

Pro Thr Ser Glu Ile Gln Leu Thr Asp Tyr Gly Thr Leu Thr Leu Asp
    450                 455                 460

Cys Ser Pro Arg Thr Gly Leu Asp Phe Asn Glu Met Val Leu Leu Thr
465                 470                 475                 480

Met Lys Glu Arg Ser Trp Leu Val His Lys Gln Trp Phe Leu Asp Leu
                485                 490                 495

Pro Leu Pro Trp Thr Ser Gly Ala Ser Thr Ser Gln Glu Thr Trp Asn
            500                 505                 510

Arg Gln Asp Leu Leu Val Thr Phe Lys Thr Ala His Ala Lys Lys Gln
        515                 520                 525

Glu Val Val Val Leu Gly Ser Gln Glu Gly Ala Met His Thr Ala Leu
    530                 535                 540

Thr Gly Ala Thr Glu Ile Gln Thr Ser Gly Thr Thr Thr Ile Phe Ala
545                 550                 555                 560

Gly His Leu Lys Cys Arg Leu Lys Met Asp Lys Leu Thr Leu Lys Gly
                565                 570                 575

Met Ser Tyr Val Met Cys Thr Gly Ser Phe Lys Leu Glu Lys Glu Val
            580                 585                 590

Ala Glu Thr Gln His Gly Thr Val Leu Val Gln Val Lys Tyr Glu Gly
        595                 600                 605

Thr Asp Ala Pro Cys Lys Ile Pro Phe Ser Thr Gln Asp Glu Lys Gly
    610                 615                 620

Ala Thr Gln Asn Gly Arg Leu Ile Thr Ala Asn Pro Ile Val Thr Asp
625                 630                 635                 640

Lys Glu Lys Pro Val Asn Ile Glu Ala Glu Pro Pro Phe Gly Glu Ser
                645                 650                 655

Tyr Ile Val Val Gly Ala Gly Glu Lys Ala Leu Lys Leu Ser Trp Phe
            660                 665                 670

Lys Lys Gly Ser Ser Ile Gly Lys Met Phe Glu Ala Thr Ala Arg Gly
        675                 680                 685

Ala Arg Arg Met Ala Ile Leu Gly Asp Thr Ala Trp Asp Phe Gly Ser
    690                 695                 700

Ile Gly Gly Val Phe Thr Ser Met Gly Lys Leu Val His Gln Val Phe
705                 710                 715                 720

Gly Thr Ala Tyr Gly Val Leu Phe Ser Gly Val Ser Trp Thr Met Lys
                725                 730                 735

Ile Gly Ile Gly Ile Leu Leu Thr Trp Leu Gly Leu Asn Ser Arg Asn
            740                 745                 750

Thr Ser Leu Ser Met Met Cys Ile Ala Val Gly Met Val Thr Leu Tyr
        755                 760                 765

Leu Gly Val Met Val Gln Ala Asp Ser Gly Cys Val Ile Asn Trp Lys
    770                 775                 780

Gly Arg Glu Leu Lys Cys Gly Ser Gly Ile Phe Val Thr Asn Glu Val
785                 790                 795                 800

His Thr Trp Thr Glu Gln Tyr Lys Phe Gln Ala Asp Ser Pro Lys Arg
                805                 810                 815

Leu Ser Ala Ala Ile Gly Lys Ala Trp Glu Glu Gly Val Cys Gly Ile
```

```
            820                 825                 830

Arg Ser Ala Thr Arg Leu Glu Asn Ile Met Trp Lys Gln Ile Ser Asn
        835                 840                 845

Glu Leu Asn His Ile Leu Leu Glu Asn Asp Met Lys Phe Thr Val Val
    850                 855                 860

Val Gly Asp Val Ser Gly Ile Leu Ala Gln Gly Lys Lys Met Ile Arg
865                 870                 875                 880

Pro Gln Pro Met Glu His Lys Tyr Ser Trp Lys Ser Trp Gly Lys Ala
                885                 890                 895

Lys Ile Ile Gly Ala Asp Val Gln Asn Thr Thr Phe Ile Ile Asp Gly
            900                 905                 910

Pro Asn Thr Pro Glu Cys Pro Asp Asn Gln Arg Ala Trp Asn Ile Trp
        915                 920                 925

Glu Val Glu Asp Tyr Gly Phe Gly Ile Phe Thr Thr Asn Ile Trp Leu
    930                 935                 940

Lys Leu Arg Asp Ser Tyr Thr Gln Val Cys Asp His Arg Leu Met Ser
945                 950                 955                 960

Ala Ala Ile Lys Asp Ser Lys Ala Val His Ala Asp Met Gly Tyr Trp
                965                 970                 975

Ile Glu Ser Glu Lys Asn Glu Thr Trp Lys Leu Ala Arg Ala Ser Phe
            980                 985                 990

Ile Glu Val Lys Thr Cys Ile Trp  Pro Lys Ser His Thr  Leu Trp Ser
        995                 1000                1005

Asn Gly  Val Leu Glu Ser Glu  Met Ile Ile Pro Lys  Ile Tyr Gly
    1010                1015                1020

Gly Pro  Ile Ser Gln His Asn  Tyr Arg Pro Gly Tyr  Phe Thr Gln
    1025                1030                1035

Thr Ala  Gly Pro Trp His Leu  Gly Lys Leu Glu Leu  Asp Phe Asp
    1040                1045                1050

Phe Cys  Glu Gly Thr Thr Val  Val Val Asp Glu His  Cys Gly Asn
    1055                1060                1065

Arg Gly  Pro Ser Leu Arg Thr  Thr Thr Val Thr Gly  Lys Ile Ile
    1070                1075                1080

His Glu  Trp Cys Cys Arg Ser  Cys Thr Leu Pro Pro  Leu Arg Phe
    1085                1090                1095

Lys Gly  Glu Asp Gly Cys Trp  Tyr Gly Met Glu Ile  Arg Pro Val
    1100                1105                1110

Lys Asp  Lys Glu Glu Asn Leu  Val Lys Ser Met Val  Ser Ala Gly
    1115                1120                1125

Ser Gly  Glu Val Asp Ser Phe  Ser Leu Gly Leu Leu  Cys Ile Ser
    1130                1135                1140

Ile Met  Ile Glu Glu Val Met  Arg Ser Arg Trp Ser  Lys Lys Met
    1145                1150                1155

Leu Met  Thr Gly Thr Leu Ala  Val Phe Leu Leu Leu  Ile Met Gly
    1160                1165                1170

Gln Leu  Thr Trp Ser Asp Leu  Ile Arg Leu Cys Ile  Met Val Gly
    1175                1180                1185

Ala Asn  Ala Ser Asp Lys Met  Gly Met Gly Thr Thr  Tyr Leu Ala
    1190                1195                1200

Leu Met  Ala Thr Phe Lys Met  Arg Pro Met Phe Ala  Val Gly Leu
    1205                1210                1215

Leu Phe  Arg Arg Leu Thr Ser  Arg Glu Val Leu Leu  Leu Thr Ile
    1220                1225                1230
```

```
Gly Leu  Ser Leu Val Ala Ser  Val Glu Leu Pro Ser  Ser Leu Glu
    1235                 1240                 1245

Glu Leu  Gly Asp Gly Leu Ala  Ile Gly Ile Met Met  Leu Lys Leu
    1250                 1255                 1260

Leu Thr  Asp Phe Gln Ser His  Gln Leu Trp Ala Thr  Leu Leu Ser
    1265                 1270                 1275

Leu Thr  Phe Ile Lys Thr Thr  Phe Ser Leu His Tyr  Ala Trp Lys
    1280                 1285                 1290

Thr Met  Ala Met Val Leu Ser  Ile Val Ser Leu Phe  Pro Leu Cys
    1295                 1300                 1305

Leu Ser  Thr Thr Ser Gln Lys  Thr Thr Trp Leu Pro  Val Leu Leu
    1310                 1315                 1320

Gly Ser  Leu Gly Cys Lys Pro  Leu Pro Met Phe Leu  Ile Thr Glu
    1325                 1330                 1335

Asn Lys  Ile Trp Gly Arg Lys  Ser Trp Pro Leu Asn  Glu Gly Ile
    1340                 1345                 1350

Met Ala  Val Gly Ile Val Ser  Ile Leu Leu Ser Ser  Leu Leu Lys
    1355                 1360                 1365

Asn Asp  Val Pro Leu Ala Gly  Pro Leu Ile Ala Gly  Gly Met Leu
    1370                 1375                 1380

Ile Ala  Cys Tyr Val Ile Ser  Gly Ser Ser Ala Asp  Leu Ser Leu
    1385                 1390                 1395

Glu Lys  Ala Ala Glu Val Ser  Trp Glu Glu Glu Ala  Glu His Ser
    1400                 1405                 1410

Gly Ala  Ser His Asn Ile Leu  Val Glu Val Gln Asp  Asp Gly Thr
    1415                 1420                 1425

Met Lys  Ile Lys Asp Glu Glu  Arg Asp Asp Thr Leu  Thr Ile Leu
    1430                 1435                 1440

Leu Lys  Ala Thr Leu Leu Ala  Val Ser Gly Val Tyr  Pro Met Ser
    1445                 1450                 1455

Ile Pro  Ala Thr Leu Phe Val  Trp Tyr Phe Trp Gln  Lys Lys Lys
    1460                 1465                 1470

Gln Arg  Ser Gly Val Leu Trp  Asp Thr Pro Ser Pro  Pro Glu Val
    1475                 1480                 1485

Glu Arg  Ala Val Leu Asp Asp  Gly Ile Tyr Arg Ile  Leu Gln Arg
    1490                 1495                 1500

Gly Leu  Leu Gly Arg Ser Gln  Val Gly Val Gly Val  Phe Gln Glu
    1505                 1510                 1515

Gly Val  Phe His Thr Met Trp  His Val Thr Arg Gly  Ala Val Leu
    1520                 1525                 1530

Met Tyr  Gln Gly Lys Arg Leu  Glu Pro Ser Trp Ala  Ser Val Lys
    1535                 1540                 1545

Lys Asp  Leu Ile Ser Tyr Gly  Gly Gly Trp Arg Phe  Gln Gly Ser
    1550                 1555                 1560

Trp Asn  Thr Gly Glu Glu Val  Gln Val Ile Ala Val  Glu Pro Gly
    1565                 1570                 1575

Lys Asn  Pro Lys Asn Val Gln  Thr Thr Pro Gly Thr  Phe Lys Thr
    1580                 1585                 1590

Pro Glu  Gly Glu Val Gly Ala  Ile Ala Leu Asp Phe  Lys Pro Gly
    1595                 1600                 1605

Thr Ser  Gly Ser Pro Ile Val  Asn Arg Glu Gly Lys  Ile Val Gly
    1610                 1615                 1620
```

-continued

Leu Tyr Gly Asn Gly Val Val Thr Thr Ser Gly Thr Tyr Val Ser
1625 1630 1635

Ala Ile Ala Gln Ala Lys Ala Ser Gln Glu Gly Pro Leu Pro Glu
1640 1645 1650

Ile Glu Asp Glu Val Phe Arg Lys Arg Asn Leu Thr Ile Met Asp
1655 1660 1665

Leu His Pro Gly Ser Gly Lys Thr Arg Arg Tyr Leu Pro Ala Ile
1670 1675 1680

Val Arg Glu Ala Ile Lys Arg Lys Leu Arg Thr Leu Ile Leu Ala
1685 1690 1695

Pro Thr Arg Val Val Ala Ser Glu Met Ala Glu Ala Leu Lys Gly
1700 1705 1710

Val Pro Ile Arg Tyr Gln Thr Thr Ala Val Lys Ser Glu His Thr
1715 1720 1725

Gly Lys Glu Ile Val Asp Leu Met Cys His Ala Thr Phe Thr Met
1730 1735 1740

Arg Leu Leu Ser Pro Val Arg Val Pro Asn Tyr Asn Met Ile Ile
1745 1750 1755

Met Asp Glu Ala His Phe Thr Asp Pro Ala Ser Ile Ala Ala Arg
1760 1765 1770

Gly Tyr Ile Ser Thr Arg Val Gly Met Gly Glu Ala Ala Ala Ile
1775 1780 1785

Phe Met Thr Ala Thr Pro Pro Gly Ser Val Glu Ala Phe Pro Gln
1790 1795 1800

Ser Asn Ala Ile Ile Gln Asp Glu Glu Arg Asp Ile Pro Glu Arg
1805 1810 1815

Ser Trp Asn Ser Gly Tyr Asp Trp Ile Thr Asp Phe Pro Gly Lys
1820 1825 1830

Thr Val Trp Phe Val Pro Ser Ile Lys Ser Gly Asn Asp Ile Ala
1835 1840 1845

Asn Cys Leu Arg Lys Asn Gly Lys Arg Val Ile Gln Leu Ser Arg
1850 1855 1860

Lys Thr Phe Asp Thr Glu Tyr Gln Lys Thr Lys Asn Asn Asp Trp
1865 1870 1875

Asp Tyr Val Val Thr Thr Asp Ile Ser Glu Met Gly Ala Asn Phe
1880 1885 1890

Arg Ala Asp Arg Val Ile Asp Pro Arg Arg Cys Leu Lys Pro Val
1895 1900 1905

Ile Leu Lys Asp Gly Pro Glu Arg Val Ile Leu Ala Gly Pro Met
1910 1915 1920

Pro Val Thr Val Ala Ser Ala Ala Gln Arg Arg Gly Arg Ile Gly
1925 1930 1935

Arg Asn Gln Asn Lys Glu Gly Asp Gln Tyr Ile Tyr Met Gly Gln
1940 1945 1950

Pro Leu Asn Asn Asp Glu Asp His Ala His Trp Thr Glu Ala Lys
1955 1960 1965

Met Leu Leu Asp Asn Ile Asn Thr Pro Glu Gly Ile Ile Pro Ala
1970 1975 1980

Leu Tyr Glu Pro Glu Arg Glu Lys Ser Ala Ala Ile Asp Gly Glu
1985 1990 1995

Tyr Arg Leu Arg Gly Glu Ala Arg Lys Thr Phe Val Glu Leu Met
2000 2005 2010

Arg Arg Gly Asp Leu Pro Val Trp Leu Ser Tyr Lys Val Ala Ser

-continued

```
    2015                2020                2025

Glu Gly  Phe Gln Tyr Ser Asp  Arg Arg Trp Cys Phe  Asp Gly Glu
    2030                2035                2040

Arg Asn  Asn Gln Val Leu Glu  Glu Asn Met Asp Val  Glu Ile Trp
    2045                2050                2055

Thr Lys  Glu Gly Glu Arg Lys  Lys Leu Arg Pro Arg  Trp Leu Asp
    2060                2065                2070

Ala Arg  Thr Tyr Ser Asp Pro  Leu Ala Leu Arg Glu  Phe Lys Glu
    2075                2080                2085

Phe Ala  Ala Gly Arg Arg Ser  Val Ser Gly Asp Leu  Ile Leu Glu
    2090                2095                2100

Ile Gly  Lys Leu Pro Gln His  Leu Thr Gln Arg Ala  Gln Asn Ala
    2105                2110                2115

Leu Asp  Asn Leu Val Met Leu  His Asn Ser Glu Gln  Gly Gly Lys
    2120                2125                2130

Ala Tyr  Arg His Ala Met Glu  Glu Leu Pro Asp Thr  Ile Glu Thr
    2135                2140                2145

Leu Met  Leu Leu Ala Leu Ile  Ala Val Leu Thr Gly  Gly Val Thr
    2150                2155                2160

Leu Phe  Phe Leu Ser Gly Arg  Gly Leu Gly Lys Thr  Ser Ile Gly
    2165                2170                2175

Leu Leu  Cys Val Met Ala Ser  Ser Ala Leu Leu Trp  Met Ala Ser
    2180                2185                2190

Val Glu  Pro His Trp Ile Ala  Ala Ser Ile Ile Leu  Glu Phe Phe
    2195                2200                2205

Leu Met  Val Leu Leu Ile Pro  Glu Pro Asp Arg Gln  Arg Thr Pro
    2210                2215                2220

Gln Asp  Asn Gln Leu Ala Tyr  Val Val Ile Gly Leu  Leu Phe Met
    2225                2230                2235

Ile Leu  Thr Val Ala Ala Asn  Glu Met Gly Leu Leu  Glu Thr Thr
    2240                2245                2250

Lys Lys  Asp Leu Gly Ile Gly  His Val Ala Ala Glu  Asn His His
    2255                2260                2265

His Ala  Thr Met Leu Asp Val  Asp Leu His Pro Ala  Ser Ala Trp
    2270                2275                2280

Thr Leu  Tyr Ala Val Ala Thr  Thr Ile Ile Thr Pro  Met Met Arg
    2285                2290                2295

His Thr  Ile Glu Asn Thr Thr  Ala Asn Ile Ser Leu  Thr Ala Ile
    2300                2305                2310

Ala Asn  Gln Ala Ala Ile Leu  Met Gly Leu Asp Lys  Gly Trp Pro
    2315                2320                2325

Ile Ser  Lys Met Asp Ile Gly  Val Pro Leu Leu Ala  Leu Gly Cys
    2330                2335                2340

Tyr Ser  Gln Val Asn Pro Leu  Thr Leu Ile Ala Ala  Val Leu Met
    2345                2350                2355

Leu Val  Ala His Tyr Ala Ile  Ile Gly Pro Gly Leu  Gln Ala Lys
    2360                2365                2370

Ala Thr  Arg Glu Ala Gln Lys  Arg Thr Ala Ala Gly  Ile Met Lys
    2375                2380                2385

Asn Pro  Thr Val Asp Gly Ile  Val Ala Ile Asp Leu  Asp Pro Val
    2390                2395                2400

Val Tyr  Asp Ala Lys Phe Glu  Lys Gln Leu Gly Gln  Ile Met Leu
    2405                2410                2415
```

```
Leu Ile Leu Cys Thr Ser Gln Ile Leu Leu Met Arg Thr Thr Trp
    2420                2425                2430

Ala Leu Cys Glu Ser Ile Thr Leu Ala Thr Gly Pro Leu Thr Thr
    2435                2440                2445

Leu Trp Glu Gly Ser Pro Gly Lys Phe Trp Asn Thr Thr Ile Ala
    2450                2455                2460

Val Ser Met Ala Asn Ile Phe Arg Gly Ser Tyr Leu Ala Gly Ala
    2465                2470                2475

Gly Leu Ala Phe Ser Leu Met Lys Ser Leu Gly Gly Gly Arg Arg
    2480                2485                2490

Gly Thr Gly Ala Gln Gly Glu Thr Leu Gly Glu Lys Trp Lys Arg
    2495                2500                2505

Gln Leu Asn Gln Leu Ser Lys Ser Glu Phe Asn Thr Tyr Lys Arg
    2510                2515                2520

Ser Gly Ile Met Glu Val Asp Arg Ser Glu Ala Lys Glu Gly Leu
    2525                2530                2535

Lys Arg Gly Glu Thr Thr Lys His Ala Val Ser Arg Gly Thr Ala
    2540                2545                2550

Lys Leu Arg Trp Phe Val Glu Arg Asn Leu Val Lys Pro Glu Gly
    2555                2560                2565

Lys Val Ile Asp Leu Gly Cys Gly Arg Gly Gly Trp Ser Tyr Tyr
    2570                2575                2580

Cys Ala Gly Leu Lys Lys Val Thr Glu Val Lys Gly Tyr Thr Lys
    2585                2590                2595

Gly Gly Pro Gly His Glu Glu Pro Ile Pro Met Ala Thr Tyr Gly
    2600                2605                2610

Trp Asn Leu Val Lys Leu His Ser Gly Lys Asp Val Phe Phe Ile
    2615                2620                2625

Pro Pro Glu Lys Cys Asp Thr Leu Leu Cys Asp Ile Gly Glu Ser
    2630                2635                2640

Ser Pro Asn Pro Thr Ile Glu Glu Gly Arg Thr Leu Arg Val Leu
    2645                2650                2655

Lys Met Val Glu Pro Trp Leu Arg Gly Asn Gln Phe Cys Ile Lys
    2660                2665                2670

Ile Leu Asn Pro Tyr Met Pro Ser Val Val Glu Thr Leu Glu Gln
    2675                2680                2685

Met Gln Arg Lys His Gly Gly Met Leu Val Arg Asn Pro Leu Ser
    2690                2695                2700

Arg Asn Ser Thr His Glu Met Tyr Trp Val Ser Cys Gly Thr Gly
    2705                2710                2715

Asn Ile Val Ser Ala Val Asn Met Thr Ser Arg Met Leu Leu Asn
    2720                2725                2730

Arg Phe Thr Met Ala His Arg Lys Pro Thr Tyr Glu Arg Asp Val
    2735                2740                2745

Asp Leu Gly Ala Gly Thr Arg His Val Ala Val Glu Pro Glu Val
    2750                2755                2760

Ala Asn Leu Asp Ile Ile Gly Gln Arg Ile Glu Asn Ile Lys Asn
    2765                2770                2775

Glu His Lys Ser Thr Trp His Tyr Asp Glu Asp Asn Pro Tyr Lys
    2780                2785                2790

Thr Trp Ala Tyr His Gly Ser Tyr Glu Val Lys Pro Ser Gly Ser
    2795                2800                2805
```

```
Ala Ser  Ser Met Val Asn Gly  Val Val Arg Leu Leu  Thr Lys Pro
    2810                 2815                 2820

Trp Asp  Val Ile Pro Met Val  Thr Gln Ile Ala Met  Thr Asp Thr
    2825                 2830                 2835

Thr Pro  Phe Gly Gln Gln Arg  Val Phe Lys Glu Lys  Val Asp Thr
    2840                 2845                 2850

Arg Thr  Pro Lys Ala Lys Arg  Gly Thr Ala Gln Ile  Met Glu Val
    2855                 2860                 2865

Thr Ala  Arg Trp Leu Trp Gly  Phe Leu Ser Arg Asn  Lys Lys Pro
    2870                 2875                 2880

Arg Ile  Cys Thr Arg Glu Glu  Phe Thr Arg Lys Val  Arg Ser Asn
    2885                 2890                 2895

Ala Ala  Ile Gly Ala Val Phe  Val Asp Glu Asn Gln  Trp Asn Ser
    2900                 2905                 2910

Ala Lys  Glu Ala Val Glu Asp  Glu Arg Phe Trp Glu  Leu Val His
    2915                 2920                 2925

Arg Glu  Arg Glu Leu His Lys  Gln Gly Lys Cys Ala  Thr Cys Val
    2930                 2935                 2940

Tyr Asn  Met Met Gly Lys Arg  Glu Lys Lys Leu Gly  Glu Phe Gly
    2945                 2950                 2955

Lys Ala  Lys Gly Ser Arg Ala  Ile Trp Tyr Met Trp  Leu Gly Ala
    2960                 2965                 2970

Arg Phe  Leu Glu Phe Glu Ala  Leu Gly Phe Met Asn  Glu Asp His
    2975                 2980                 2985

Trp Phe  Ser Arg Glu Asn Ser  Leu Ser Gly Val Glu  Gly Glu Gly
    2990                 2995                 3000

Leu His  Lys Leu Gly Tyr Ile  Leu Arg Asp Ile Ser  Arg Ile Pro
    3005                 3010                 3015

Gly Gly  Asn Met Tyr Ala Asp  Asp Thr Ala Gly Trp  Asp Thr Arg
    3020                 3025                 3030

Ile Thr  Glu Asp Asp Leu Gln  Asn Glu Ala Lys Ile  Thr Asp Ile
    3035                 3040                 3045

Met Glu  Pro Glu His Ala Leu  Leu Ala Thr Ser Ile  Phe Lys Leu
    3050                 3055                 3060

Thr Tyr  Gln Asn Lys Val Val  Arg Val Gln Arg Pro  Ala Lys Asn
    3065                 3070                 3075

Gly Thr  Val Met Asp Val Ile  Ser Arg Arg Asp Gln  Arg Gly Ser
    3080                 3085                 3090

Gly Gln  Val Gly Thr Tyr Gly  Leu Asn Thr Phe Thr  Asn Met Glu
    3095                 3100                 3105

Ala Gln  Leu Ile Arg Gln Met  Glu Ser Glu Gly Ile  Phe Leu Pro
    3110                 3115                 3120

Ser Glu  Leu Glu Thr Pro Asn  Leu Ala Gly Arg Val  Leu Asp Trp
    3125                 3130                 3135

Leu Glu  Lys Tyr Gly Val Glu  Arg Leu Lys Arg Met  Ala Ile Ser
    3140                 3145                 3150

Gly Asp  Asp Cys Val Val Lys  Pro Ile Asp Asp Arg  Phe Ala Thr
    3155                 3160                 3165

Ala Leu  Thr Ala Leu Asn Asp  Met Gly Lys Val Arg  Lys Asp Ile
    3170                 3175                 3180

Pro Gln  Trp Glu Pro Ser Lys  Gly Trp Asn Asp Trp  Gln Gln Val
    3185                 3190                 3195

Pro Phe  Cys Ser His His Phe  His Gln Leu Ile Met  Lys Asp Gly
```

```
    3200                3205                3210

Arg Glu  Ile Val Val Pro Cys  Arg Asn Gln Asp Glu  Leu Val Gly
    3215                3220                3225

Arg Ala  Arg Val Ser Gln Gly  Ala Gly Trp Ser Leu  Arg Glu Thr
    3230                3235                3240

Ala Cys  Leu Gly Lys Ser Tyr  Ala Gln Met Trp Gln  Leu Met Tyr
    3245                3250                3255

Phe His  Arg Arg Asp Leu Arg  Leu Ala Ala Asn Ala  Ile Cys Ser
    3260                3265                3270

Ala Val  Pro Val Asp Trp Val  Pro Thr Ser Arg Thr  Thr Trp Ser
    3275                3280                3285

Ile His  Ala His His Gln Trp  Met Thr Thr Glu Asp  Met Leu Ser
    3290                3295                3300

Val Trp  Asn Arg Val Trp Ile  Glu Glu Asn Pro Trp  Met Glu Asp
    3305                3310                3315

Lys Thr  His Val Ser Ser Trp  Glu Glu Val Pro Tyr  Leu Gly Lys
    3320                3325                3330

Arg Glu  Asp Gln Trp Cys Gly  Ser Leu Ile Gly Leu  Thr Ala Arg
    3335                3340                3345

Ala Thr  Trp Ala Thr Asn Ile  Gln Val Ala Ile Asn  Gln Val Arg
    3350                3355                3360

Arg Leu  Ile Gly Asn Glu Asn  Tyr Leu Asp Tyr Met  Thr Ser Met
    3365                3370                3375

Lys Arg  Phe Lys Asn Glu Ser  Asp Pro Glu Gly Ala  Leu Trp
    3380                3385                3390
```

<210> SEQ ID NO 11
<211> LENGTH: 10723
<212> TYPE: DNA
<213> ORGANISM: dengue virus

<400> SEQUENCE: 11

```
agttgttagt ctacgtggac cgacaaagac agattctttg agggagctaa gctcaacgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggatggcgt gaacatgtgt    540

accctcatgg ccatggacct tggtgaattg tgtgaagaca caatcacgta caagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgggaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatt    900

ttcatcttac tgacagctgt cactccttca atgacaatgc gttgcatagg aatgtcaaat    960

agagactttg tggaaggggt ttcaggagga agctgggttg acatagtctt agaacatgga   1020
```

agctgtgtga cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaagggag gcattgtgac ctgtgctatg ttcagatgca aaaagaacat ggaaggaaaa 1320
gttgtgcaac cagaaaactt ggaatacacc attgtgataa cacctcactc aggggaagag 1380
catgcagtcg gaaatgacac aggaaaacat ggcaaggaaa tcaaaataac accacagagt 1440
tccatcacag aagcagaatt gacaggttat ggcactgtca caatggagtg ctctccaaga 1500
acgggcctcg acttcaatga gatggtgttg ctgcagatgg aaaataaagc ttggctggtg 1560
cacaggcaat ggttcctaga cctgccgtta ccatggttgc ccggagcgga cacacaaggg 1620
tcaaattgga tacagaaaga gacattggtc actttcaaaa atccccatgc gaagaaacag 1680
gatgttgttg ttttaggatc ccaagaaggg gccatgcaca cagcacttac aggggccaca 1740
gaaatccaaa tgtcatcagg aaacttactc ttcacaggac atctcaagtg caggctgaga 1800
atggacaagc tacagctcaa aggaatgtca tactctatgt gcacaggaaa gtttaaagtt 1860
gtgaaggaaa tagcagaaac acaacatgga acaatagtta tcagagtgca atatgaaggg 1920
gacggctctc catgcaagat cccttttgag ataatggatt tggaaaaaag acatgtctta 1980
ggtcgcctga ttacagtcaa cccaattgtg acagaaaaag atagcccagt caacatagaa 2040
gcagaacctc cattcggaga cagctacatc atcataggag tagagccggg acaactgaag 2100
ctcaactggt ttaagaaagg aagttctatc ggccaaatgt ttgagacaac aatgaggggg 2160
gcgaagagaa tggccatttt aggtgacaca gcctgggatt ttggatcctt gggaggagtg 2220
tttacatcta taggaaaggc tctccaccaa gtctttggag caatctatgg agctgccttc 2280
agtggggttt catggactat gaaaatcctc ataggagtca ttatcacatg gataggaatg 2340
aattcacgca gcacctcact gtctgtgaca ctagtattgg tgggaattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagagggc 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggctaaa attgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagctt 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360

-continued cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840
gagttgactg atgcgttagc cttaggcatg atggtcctca aaatggtgag aaatatggaa 3900
aagtatcaat tggcagtgac tatcatggct atcttgtgcg tcccaaacgc agtgatatta 3960
caaaacgcat ggaaagtgag ttgcacaata ttggcagtgg tgtccgtttc cccactgctc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggccga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aacaggattg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctga gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgttcg tggaattccg gacatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct ttttattctt gatgagcgga 6600
aggggcatag ggaagatgac cctgggaatg tgctgcataa tcacggctag catcctccta 6660
tggtacgcac aaatacagcc acactggata gcagcttcaa taatactgga gttttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100

```
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag ctggagtaaa ctatgcagcc tgtagctcca cctgagaagg  10440
tgtaaaaaat ccgggaggcc acaaaccatg gaagctgtac gcatggcgta gtggactagc  10500
```

```
ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723


<210> SEQ ID NO 12
<211> LENGTH: 3391
<212> TYPE: PRT
<213> ORGANISM: dengue virus

<400> SEQUENCE: 12

Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335
```

-continued

```
Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750
```

```
Thr Ser Leu Ser Val Thr Leu Val Leu Val Gly Ile Val Thr Leu Tyr
        755                 760                 765

Leu Gly Val Met Val Gln Ala Asp Ser Gly Cys Val Val Ser Trp Lys
    770                 775                 780

Asn Lys Glu Leu Lys Cys Gly Ser Gly Ile Phe Ile Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Pro
        835                 840                 845

Glu Leu Asn His Ile Leu Ser Glu Asn Glu Val Lys Leu Thr Ile Met
    850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Thr Trp Gly Lys Ala
                885                 890                 895

Lys Met Leu Ser Thr Glu Ser His Asn Gln Thr Phe Leu Ile Asp Gly
            900                 905                 910

Pro Glu Thr Ala Glu Cys Pro Asn Thr Asn Arg Ala Trp Asn Ser Leu
        915                 920                 925

Glu Val Glu Asp Tyr Gly Phe Gly Val Phe Thr Thr Asn Ile Trp Leu
    930                 935                 940

Lys Leu Lys Glu Lys Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Asn Cys His Trp  Pro Lys Ser His Thr  Leu Trp Ser
        995                 1000                1005

Asn Gly  Val Leu Glu Ser Glu  Met Ile Ile Pro Lys  Asn Leu Ala
    1010                 1015                 1020

Gly Pro  Val Ser Gln His Asn  Tyr Arg Pro Gly Tyr  His Thr Gln
    1025                 1030                 1035

Ile Thr  Gly Pro Trp His Leu  Gly Lys Leu Glu Met  Asp Phe Asp
    1040                 1045                 1050

Phe Cys  Asp Gly Thr Thr Val  Val Val Thr Glu Asp  Cys Gly Asn
    1055                 1060                 1065

Arg Gly  Pro Ser Leu Arg Thr  Thr Thr Ala Ser Gly  Lys Leu Ile
    1070                 1075                 1080

Thr Glu  Trp Cys Cys Arg Ser  Cys Thr Leu Pro Pro  Leu Arg Tyr
    1085                 1090                 1095

Arg Gly  Glu Asp Gly Cys Trp  Tyr Gly Met Glu Ile  Arg Pro Leu
    1100                 1105                 1110

Lys Glu  Lys Glu Glu Asn Leu  Val Asn Ser Leu Val  Thr Ala Gly
    1115                 1120                 1125

His Gly  Gln Val Asp Asn Phe  Ser Leu Gly Val Leu  Gly Met Ala
    1130                 1135                 1140

Leu Phe  Leu Glu Glu Met Leu  Arg Thr Arg Val Gly  Thr Lys His
    1145                 1150                 1155

Ala Ile  Leu Leu Val Ala Val  Ser Phe Val Thr Leu  Ile Thr Gly
```

```
    1160                1165                1170

Asn Met  Ser Phe Arg Asp Leu  Gly Arg Val Met Val  Met Val Gly
    1175                1180                1185

Ala Thr  Met Thr Asp Asp Ile  Gly Met Gly Val Thr  Tyr Leu Ala
    1190                1195                1200

Leu Leu  Ala Ala Phe Lys Val  Arg Pro Thr Phe Ala  Ala Gly Leu
    1205                1210                1215

Leu Leu  Arg Lys Leu Thr Ser  Lys Glu Leu Met Met  Thr Thr Ile
    1220                1225                1230

Gly Ile  Val Leu Leu Ser Gln  Ser Thr Ile Pro Glu  Thr Ile Leu
    1235                1240                1245

Glu Leu  Thr Asp Ala Leu Ala  Leu Gly Met Met Val  Leu Lys Met
    1250                1255                1260

Val Arg  Asn Met Glu Lys Tyr  Gln Leu Ala Val Thr  Ile Met Ala
    1265                1270                1275

Ile Leu  Cys Val Pro Asn Ala  Val Ile Leu Gln Asn  Ala Trp Lys
    1280                1285                1290

Val Ser  Cys Thr Ile Leu Ala  Val Val Ser Val Ser  Pro Leu Leu
    1295                1300                1305

Leu Thr  Ser Ser Gln Gln Lys  Thr Asp Trp Ile Pro  Leu Ala Leu
    1310                1315                1320

Thr Ile  Lys Gly Leu Asn Pro  Thr Ala Ile Phe Leu  Thr Thr Leu
    1325                1330                1335

Ser Arg  Thr Ser Lys Lys Arg  Ser Trp Pro Leu Asn  Glu Ala Ile
    1340                1345                1350

Met Ala  Val Gly Met Val Ser  Ile Leu Ala Ser Ser  Leu Leu Lys
    1355                1360                1365

Asn Asp  Ile Pro Met Thr Gly  Pro Leu Val Ala Gly  Gly Leu Leu
    1370                1375                1380

Thr Val  Cys Tyr Val Leu Thr  Gly Arg Ser Ala Asp  Leu Glu Leu
    1385                1390                1395

Glu Arg  Ala Ala Asp Val Lys  Trp Glu Asp Gln Ala  Glu Ile Ser
    1400                1405                1410

Gly Ser  Ser Pro Ile Leu Ser  Ile Thr Ile Ser Glu  Asp Gly Ser
    1415                1420                1425

Met Ser  Ile Lys Asn Glu Glu  Glu Glu Gln Thr Leu  Thr Ile Leu
    1430                1435                1440

Ile Arg  Thr Gly Leu Leu Val  Ile Ser Gly Leu Phe  Pro Val Ser
    1445                1450                1455

Ile Pro  Ile Thr Ala Ala Ala  Trp Tyr Leu Trp Glu  Val Lys Lys
    1460                1465                1470

Gln Arg  Ala Gly Val Leu Trp  Asp Val Pro Ser Pro  Pro Pro Met
    1475                1480                1485

Gly Lys  Ala Glu Leu Glu Asp  Gly Ala Tyr Arg Ile  Lys Gln Lys
    1490                1495                1500

Gly Ile  Leu Gly Tyr Ser Gln  Ile Gly Ala Gly Val  Tyr Lys Glu
    1505                1510                1515

Gly Thr  Phe His Thr Met Trp  His Val Thr Arg Gly  Ala Val Leu
    1520                1525                1530

Met His  Lys Gly Lys Arg Ile  Glu Pro Ser Trp Ala  Asp Val Lys
    1535                1540                1545

Lys Asp  Leu Ile Ser Tyr Gly  Gly Gly Trp Lys Leu  Glu Gly Glu
    1550                1555                1560
```

```
Trp Lys  Glu Gly Glu Glu Val  Gln Val Leu Ala Leu  Glu Pro Gly
    1565                 1570                 1575

Lys Asn  Pro Arg Ala Val Gln  Thr Lys Pro Gly Leu  Phe Lys Thr
    1580                 1585                 1590

Asn Ala  Gly Thr Ile Gly Ala  Val Ser Leu Asp Phe  Ser Pro Gly
    1595                 1600                 1605

Thr Ser  Gly Ser Pro Ile Ile  Asp Lys Lys Gly Lys  Val Val Gly
    1610                 1615                 1620

Leu Tyr  Gly Asn Gly Val Val  Thr Arg Ser Gly Ala  Tyr Val Ser
    1625                 1630                 1635

Ala Ile  Ala Gln Thr Glu Lys  Ser Ile Glu Asp Asn  Pro Glu Ile
    1640                 1645                 1650

Glu Asp  Asp Ile Phe Arg Lys  Arg Arg Leu Thr Ile  Met Asp Leu
    1655                 1660                 1665

His Pro  Gly Ala Gly Lys Thr  Lys Arg Tyr Leu Pro  Ala Ile Val
    1670                 1675                 1680

Arg Glu  Ala Ile Lys Arg Gly  Leu Arg Thr Leu Ile  Leu Ala Pro
    1685                 1690                 1695

Thr Arg  Val Val Ala Ala Glu  Met Glu Glu Ala Leu  Arg Gly Leu
    1700                 1705                 1710

Pro Ile  Arg Tyr Gln Thr Pro  Ala Ile Arg Ala Glu  His Thr Gly
    1715                 1720                 1725

Arg Glu  Ile Val Asp Leu Met  Cys His Ala Thr Phe  Thr Met Arg
    1730                 1735                 1740

Leu Leu  Ser Pro Val Arg Val  Pro Asn Tyr Asn Leu  Ile Ile Met
    1745                 1750                 1755

Asp Glu  Ala His Phe Thr Asp  Pro Ala Ser Ile Ala  Ala Arg Gly
    1760                 1765                 1770

Tyr Ile  Ser Thr Arg Val Glu  Met Gly Glu Ala Ala  Gly Ile Phe
    1775                 1780                 1785

Met Thr  Ala Thr Pro Pro Gly  Ser Arg Asp Pro Phe  Pro Gln Ser
    1790                 1795                 1800

Asn Ala  Pro Ile Ile Asp Glu  Glu Arg Glu Ile Pro  Glu Arg Ser
    1805                 1810                 1815

Trp Asn  Ser Gly His Glu Trp  Val Thr Asp Phe Lys  Gly Lys Thr
    1820                 1825                 1830

Val Trp  Phe Val Pro Ser Ile  Lys Ala Gly Asn Asp  Ile Ala Ala
    1835                 1840                 1845

Cys Leu  Arg Lys Asn Gly Lys  Lys Val Ile Gln Leu  Ser Arg Lys
    1850                 1855                 1860

Thr Phe  Asp Ser Glu Tyr Val  Lys Thr Arg Thr Asn  Asp Trp Asp
    1865                 1870                 1875

Phe Val  Val Thr Thr Asp Ile  Ser Glu Met Gly Ala  Asn Phe Lys
    1880                 1885                 1890

Ala Glu  Arg Val Ile Asp Pro  Arg Arg Cys Met Lys  Pro Val Ile
    1895                 1900                 1905

Leu Thr  Asp Gly Glu Glu Arg  Val Ile Leu Ala Gly  Pro Met Pro
    1910                 1915                 1920

Val Thr  His Ser Ser Ala Ala  Gln Arg Arg Gly Arg  Ile Gly Arg
    1925                 1930                 1935

Asn Pro  Lys Asn Glu Asn Asp  Gln Tyr Ile Tyr Met  Gly Glu Pro
    1940                 1945                 1950
```

```
Leu Glu  Asn Asp Glu Asp Cys  Ala His Trp Lys Glu  Ala Lys Met
    1955                 1960                 1965

Leu Leu  Asp Asn Ile Asn Thr  Pro Glu Gly Ile Ile  Pro Ser Met
    1970                 1975                 1980

Phe Glu  Pro Glu Arg Glu Lys  Val Asp Ala Ile Asp  Gly Glu Tyr
    1985                 1990                 1995

Arg Leu  Arg Gly Glu Ala Arg  Lys Thr Phe Val Asp  Leu Met Arg
    2000                 2005                 2010

Arg Gly  Asp Leu Pro Val Trp  Leu Ala Tyr Arg Val  Ala Ala Glu
    2015                 2020                 2025

Gly Ile  Asn Tyr Ala Asp Arg  Arg Trp Cys Phe Asp  Gly Val Lys
    2030                 2035                 2040

Asn Asn  Gln Ile Leu Glu Glu  Asn Val Glu Val Glu  Ile Trp Thr
    2045                 2050                 2055

Lys Glu  Gly Glu Arg Lys Lys  Leu Lys Pro Arg Trp  Leu Asp Ala
    2060                 2065                 2070

Arg Ile  Tyr Ser Asp Pro Leu  Ala Leu Lys Glu Phe  Lys Glu Phe
    2075                 2080                 2085

Ala Ala  Gly Arg Lys Ser Leu  Thr Leu Asn Leu Ile  Thr Glu Met
    2090                 2095                 2100

Gly Arg  Leu Pro Thr Phe Met  Thr Gln Lys Ala Arg  Asp Ala Leu
    2105                 2110                 2115

Asp Asn  Leu Ala Val Leu His  Thr Ala Glu Ala Gly  Gly Arg Ala
    2120                 2125                 2130

Tyr Asn  His Ala Leu Ser Glu  Leu Pro Glu Thr Leu  Glu Thr Leu
    2135                 2140                 2145

Leu Leu  Leu Thr Leu Leu Ala  Thr Val Thr Gly Gly  Ile Phe Leu
    2150                 2155                 2160

Phe Leu  Met Ser Gly Arg Gly  Ile Gly Lys Met Thr  Leu Gly Met
    2165                 2170                 2175

Cys Cys  Ile Ile Thr Ala Ser  Ile Leu Leu Trp Tyr  Ala Gln Ile
    2180                 2185                 2190

Gln Pro  His Trp Ile Ala Ala  Ser Ile Ile Leu Glu  Phe Phe Leu
    2195                 2200                 2205

Ile Val  Leu Leu Ile Pro Glu  Pro Glu Lys Gln Arg  Thr Pro Gln
    2210                 2215                 2220

Asp Asn  Gln Leu Thr Tyr Val  Val Ile Ala Ile Leu  Thr Val Val
    2225                 2230                 2235

Ala Ala  Thr Met Ala Asn Glu  Met Gly Phe Leu Glu  Lys Thr Lys
    2240                 2245                 2250

Lys Asp  Leu Gly Leu Gly Ser  Ile Ala Thr Gln Gln  Pro Glu Ser
    2255                 2260                 2265

Asn Ile  Leu Asp Ile Asp Leu  Arg Pro Ala Ser Ala  Trp Thr Leu
    2270                 2275                 2280

Tyr Ala  Val Ala Thr Thr Phe  Val Thr Pro Met Leu  Arg His Ser
    2285                 2290                 2295

Ile Glu  Asn Ser Ser Val Asn  Val Ser Leu Thr Ala  Ile Ala Asn
    2300                 2305                 2310

Gln Ala  Thr Val Leu Met Gly  Leu Gly Lys Gly Trp  Pro Leu Ser
    2315                 2320                 2325

Lys Met  Asp Ile Gly Val Pro  Leu Leu Ala Ile Gly  Cys Tyr Ser
    2330                 2335                 2340

Gln Val  Asn Pro Ile Thr Leu  Thr Ala Ala Leu Phe  Leu Leu Val
```

-continued

```
    2345                2350                2355

Ala His  Tyr Ala Ile Ile Gly  Pro Gly Leu Gln Ala  Lys Ala Thr
    2360                2365                2370

Arg Glu  Ala Gln Lys Arg Ala  Ala Ala Gly Ile Met  Lys Asn Pro
    2375                2380                2385

Thr Val  Asp Gly Ile Thr Val  Ile Asp Leu Asp Pro  Ile Pro Tyr
    2390                2395                2400

Asp Pro  Lys Phe Glu Lys Gln  Leu Gly Gln Val Met  Leu Leu Val
    2405                2410                2415

Leu Cys  Val Thr Gln Val Leu  Met Met Arg Thr Thr  Trp Ala Leu
    2420                2425                2430

Cys Glu  Ala Leu Thr Leu Ala  Thr Gly Pro Ile Ser  Thr Leu Trp
    2435                2440                2445

Glu Gly  Asn Pro Gly Arg Phe  Trp Asn Thr Thr Ile  Ala Val Ser
    2450                2455                2460

Met Ala  Asn Ile Phe Arg Gly  Ser Tyr Leu Ala Gly  Ala Gly Leu
    2465                2470                2475

Leu Phe  Ser Ile Met Lys Asn  Thr Thr Asn Thr Arg  Arg Gly Thr
    2480                2485                2490

Gly Asn  Ile Gly Glu Thr Leu  Gly Glu Lys Trp Lys  Ser Arg Leu
    2495                2500                2505

Asn Ala  Leu Gly Lys Ser Glu  Phe Gln Ile Tyr Lys  Lys Ser Gly
    2510                2515                2520

Ile Gln  Glu Val Asp Arg Thr  Leu Ala Lys Glu Gly  Ile Lys Arg
    2525                2530                2535

Gly Glu  Thr Asp His His Ala  Val Ser Arg Gly Ser  Ala Lys Leu
    2540                2545                2550

Arg Trp  Phe Val Glu Arg Asn  Met Val Thr Pro Glu  Gly Lys Val
    2555                2560                2565

Val Asp  Leu Gly Cys Gly Arg  Gly Gly Trp Ser Tyr  Tyr Cys Gly
    2570                2575                2580

Gly Leu  Lys Asn Val Arg Glu  Val Lys Gly Leu Thr  Lys Gly Gly
    2585                2590                2595

Pro Gly  His Glu Glu Pro Ile  Pro Met Ser Thr Tyr  Gly Trp Asn
    2600                2605                2610

Leu Val  Arg Leu Gln Ser Gly  Val Asp Val Phe Phe  Ile Pro Pro
    2615                2620                2625

Glu Lys  Cys Asp Thr Leu Leu  Cys Asp Ile Gly Glu  Ser Ser Pro
    2630                2635                2640

Asn Pro  Thr Val Glu Ala Gly  Arg Thr Leu Arg Val  Leu Asn Leu
    2645                2650                2655

Val Glu  Asn Trp Leu Asn Asn  Asn Thr Gln Phe Cys  Ile Lys Val
    2660                2665                2670

Leu Asn  Pro Tyr Met Pro Ser  Val Ile Glu Lys Met  Glu Ala Leu
    2675                2680                2685

Gln Arg  Lys Tyr Gly Gly Ala  Leu Val Arg Asn Pro  Leu Ser Arg
    2690                2695                2700

Asn Ser  Thr His Glu Met Tyr  Trp Val Ser Asn Ala  Ser Gly Asn
    2705                2710                2715

Ile Val  Ser Ser Val Asn Met  Ile Ser Arg Met Leu  Ile Asn Arg
    2720                2725                2730

Phe Thr  Met Arg Tyr Lys Lys  Ala Thr Tyr Glu Pro  Asp Val Asp
    2735                2740                2745
```

```
Leu Gly  Ser Gly Thr Arg Asn  Ile Gly Ile Glu Ser  Glu Ile Pro
    2750                 2755                 2760

Asn Leu  Asp Ile Ile Gly Lys  Arg Ile Glu Lys Ile  Lys Gln Glu
    2765                 2770                 2775

His Glu  Thr Ser Trp His Tyr  Asp Gln Asp His Pro  Tyr Lys Thr
    2780                 2785                 2790

Trp Ala  Tyr His Gly Ser Tyr  Glu Thr Lys Gln Thr  Gly Ser Ala
    2795                 2800                 2805

Ser Ser  Met Val Asn Gly Val  Val Arg Leu Leu Thr  Lys Pro Trp
    2810                 2815                 2820

Asp Val  Val Pro Met Val Thr  Gln Met Ala Met Thr  Asp Thr Thr
    2825                 2830                 2835

Pro Phe  Gly Gln Gln Arg Val  Phe Lys Glu Lys Val  Asp Thr Arg
    2840                 2845                 2850

Thr Gln  Glu Pro Lys Glu Gly  Thr Lys Lys Leu Met  Lys Ile Thr
    2855                 2860                 2865

Ala Glu  Trp Leu Trp Lys Glu  Leu Gly Lys Lys Lys  Thr Pro Arg
    2870                 2875                 2880

Met Cys  Thr Arg Glu Glu Phe  Thr Arg Lys Val Arg  Ser Asn Ala
    2885                 2890                 2895

Ala Leu  Gly Ala Ile Phe Thr  Asp Glu Asn Lys Trp  Lys Ser Ala
    2900                 2905                 2910

Arg Glu  Ala Val Glu Asp Ser  Arg Phe Trp Glu Leu  Val Asp Lys
    2915                 2920                 2925

Glu Arg  Asn Leu His Leu Glu  Gly Lys Cys Glu Thr  Cys Val Tyr
    2930                 2935                 2940

Asn Met  Met Gly Lys Arg Glu  Lys Lys Leu Gly Glu  Phe Gly Lys
    2945                 2950                 2955

Ala Lys  Gly Ser Arg Ala Ile  Trp Tyr Met Trp Leu  Gly Ala Arg
    2960                 2965                 2970

Phe Leu  Glu Phe Glu Ala Leu  Gly Phe Leu Asn Glu  Asp His Trp
    2975                 2980                 2985

Phe Ser  Arg Glu Asn Ser Leu  Ser Gly Val Glu Gly  Glu Gly Leu
    2990                 2995                 3000

His Lys  Leu Gly Tyr Ile Leu  Arg Asp Val Ser Lys  Lys Glu Gly
    3005                 3010                 3015

Gly Ala  Met Tyr Ala Asp Asp  Thr Ala Gly Trp Asp  Thr Arg Ile
    3020                 3025                 3030

Thr Leu  Glu Asp Leu Lys Asn  Glu Glu Met Val Thr  Asn His Met
    3035                 3040                 3045

Glu Gly  Glu His Lys Lys Leu  Ala Glu Ala Ile Phe  Lys Leu Thr
    3050                 3055                 3060

Tyr Gln  Asn Lys Val Val Arg  Val Gln Arg Pro Thr  Pro Arg Gly
    3065                 3070                 3075

Thr Val  Met Asp Ile Ile Ser  Arg Arg Asp Gln Arg  Gly Ser Gly
    3080                 3085                 3090

Gln Val  Gly Thr Tyr Gly Leu  Asn Thr Phe Thr Asn  Met Glu Ala
    3095                 3100                 3105

Gln Leu  Ile Arg Gln Met Glu  Gly Glu Gly Val Phe  Lys Ser Ile
    3110                 3115                 3120

Gln His  Leu Thr Ile Thr Glu  Glu Ile Ala Val Gln  Asn Trp Leu
    3125                 3130                 3135
```

```
Ala Arg  Val Gly Arg Glu Arg  Leu Ser Arg Met Ala  Ile Ser Gly
    3140                 3145                 3150

Asp Asp  Cys Val Val Lys Pro  Leu Asp Asp Arg Phe  Ala Ser Ala
    3155                 3160                 3165

Leu Thr  Ala Leu Asn Asp Met  Gly Lys Ile Arg Lys  Asp Ile Gln
    3170                 3175                 3180

Gln Trp  Glu Pro Ser Arg Gly  Trp Asn Asp Trp Thr  Gln Val Pro
    3185                 3190                 3195

Phe Cys  Ser His His Phe His  Glu Leu Ile Met Lys  Asp Gly Arg
    3200                 3205                 3210

Val Leu  Val Val Pro Cys Arg  Asn Gln Asp Glu Leu  Ile Gly Arg
    3215                 3220                 3225

Ala Arg  Ile Ser Gln Gly Ala  Gly Trp Ser Leu Arg  Glu Thr Ala
    3230                 3235                 3240

Cys Leu  Gly Lys Ser Tyr Ala  Gln Met Trp Ser Leu  Met Tyr Phe
    3245                 3250                 3255

His Arg  Arg Asp Leu Arg Leu  Ala Ala Asn Ala Ile  Cys Ser Ala
    3260                 3265                 3270

Val Pro  Ser His Trp Val Pro  Thr Ser Arg Thr Thr  Trp Ser Ile
    3275                 3280                 3285

His Ala  Lys His Glu Trp Met  Thr Thr Glu Asp Met  Leu Thr Val
    3290                 3295                 3300

Trp Asn  Arg Val Trp Ile Gln  Glu Asn Pro Trp Met  Glu Asp Lys
    3305                 3310                 3315

Thr Pro  Val Glu Ser Trp Glu  Glu Ile Pro Tyr Leu  Gly Lys Arg
    3320                 3325                 3330

Glu Asp  Gln Trp Cys Gly Ser  Leu Ile Gly Leu Thr  Ser Arg Ala
    3335                 3340                 3345

Thr Trp  Ala Lys Asn Ile Gln  Ala Ala Ile Asn Gln  Val Arg Ser
    3350                 3355                 3360

Leu Ile  Gly Asn Glu Glu Tyr  Thr Asp Tyr Met Pro  Ser Met Lys
    3365                 3370                 3375

Arg Phe  Arg Arg Glu Glu Glu  Glu Ala Gly Val Leu  Trp
    3380                 3385                 3390
```

<210> SEQ ID NO 13
<211> LENGTH: 10696
<212> TYPE: DNA
<213> ORGANISM: dengue virus

<400> SEQUENCE: 13

```
agttgttagt ctacgtggac cgacaagaac agtttcgact cggaagcttg cttaacgtag     60

tgctgacagt tttttattag agagcagatc tctgatgaac aaccaacgga aaaagacggg    120

aaaaccgtct atcaatatgc tgaaacgcgt gagaaaccgt gtgtcaactg gatcacagtt    180

ggcgaagaga ttctcaagag gattgctgaa cggccaagga ccaatgaaat tggttatggc    240

atttatagct ttcctcagat ttctagccat tccaccgaca gcaggagtct tggctagatg    300

gggtaccttt aagaagtcgg gggctattaa ggtcttaaaa ggcttcaaga aggagatctc    360

aaacatgctg agcattatca acaaacggaa aaagacatcg ctctgtctca tgatgatgtt    420

accagcaaca cttgctttcc acttaacttc acgagatgga gagccgcgca tgattgtggg    480

gaagaatgaa agaggaaaat ccctactttt caagacagcc tctggaatca acatgtgcac    540

actcatagcc atggatctgg gagagatgtg tgatgacacg gtcacttaca aatgccccca    600
```

-continued

```
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggccctt aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
caagggaagc ttggtgacat gcgcgaaatt tcaatgttta gaatcaatag agggaaaagt   1320
ggtgcaacat gagaacctca aatacaccgt catcatcaca gtgcacacag gagaccaaca   1380
ccaggtggga aatgaaacgc agggagtcac ggctgagata acaccccagg catcaaccgc   1440
tgaagtcatt ttacctgaat atggaaccct cgggctagaa tgctcaccac ggacaggttt   1500
ggatttcaat gaaatgatct cattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740
aacctcagga ggcacaagta tctttgcggg gcacttaaaa tgtagactca agatggacaa   1800
attggaactc aaggggatga gctatgcaat gtgcttgagt agctttgtgt tgaagaaaga   1860
agtctccgaa acgcagcatg ggacaatact cattaaggtt gagtacaaag gggaagatgc   1920
accctgcaag attcctttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggcc actgccagag gtgcaaggcg   2160
catggccatc ttgggagaca cagcctggga ctttggatca gtgggtggtg ttttgaattc   2220
attagggaaa atggtccacc aaatatttgg gagtgcttac acagccctat ttggtggagt   2280
ctcctggatg atgaaaattg gaataggtgt cctcttaacc tggatagggt tgaactcaaa   2340
aaatacttct atgtcatttt catgcatcgc gataggaatc attacactct atctgggagc   2400
cgtggtgcaa gctgacatgg ggtgtgtcat aaactggaaa ggcaaagaac tcaaatgtgg   2460
aagtggaatt ttcgtcacta atgaggtcca cacctggaca gagcaataca aatttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
```

cgacatgggc tattggatag aaagccaaaa gaatgggagt tggaagctag aaaaagcatc 3060
cttcatagag gtgaaaacct gcacatggcc aaaatcacac actctctgga gcaatggtgt 3120
gctagagagt gacatgatta tcccaaagag tctagctggt cccatttcgc aacacaacca 3180
caggcccggg taccacaccc aaacggcagg accctggcac ttaggaaaat tggagctgga 3240
cttcaactat tgtgaaggaa caacagttgt catctcagaa aactgtggga caagaggccc 3300
atcattgaga acaacaacgg tgtcagggaa gttgatacac gaatggtgct gccgctcgtg 3360
cacacttcct cccctacgat acatgggaga agacggctgc tggtatggca tggaaatcag 3420
acccattaat gagaaagaag agaatatggt aaagtctcta gcctcagcag ggagtggaaa 3480
ggtggacaac ttcacaatgg gtgtcttgtg tttggcaatc ctctttgaag aggtgatgag 3540
aggaaaattt gggaaaaaac acatgattgc aggggttctc ttcacgtttg tgctcctcct 3600
ctcagggcaa ataacatgga gagacatggc gcacacactc ataatgattg ggtccaacgc 3660
ctctgacaga atggggatgg gcgtcactta cctagctcta attgcaacat ttaaaattca 3720
gccattcctg gctttgggat tcttcctgag gaaactgaca tctagagaaa atttattgct 3780
gggagttggg ttggccatgg cagcaacgtt acgactgcca gaggacattg aacagatggc 3840
gaatggaatt gctttggggc tcatggctct taaactgata acacaatttg aaacatacca 3900
actatggacg gcattagttt ccctaacgtg ttcaaataca attttcacgt tgactgttgc 3960
ctggagaaca gccactctga ttttagccgg aatttcgctt ttgccagtgt gccagtcttc 4020
gagcatgagg aaaacagatt ggctcccaat gactgtggca gctatgggag ctcaacccct 4080
accacttttt attttcagtc tgaaagatac actcaaaagg agaagctggc cactgaatga 4140
gggggtgatg gcagttggac ttgtgagcat tctagctagt tctctcctta ggaatgatgt 4200
gcctatggct ggaccattag tggctggggg cttgctgata gcgtgctacg tcataactgg 4260
cacgtcagca gacctcactg tagaaaaagc agcagatgta acatgggagg aagaggccga 4320
gcaaacagga gtgtcccaca atttaatggt cacagttgat gatgatggaa caatgagaat 4380
aaaagatgac gagactgaga acatcttaac agtgctttta aaaacagcac tactaatagt 4440
atcaggcatc tttccatact ccatacccgc aacactgttg gtctggcata cttggcaaaa 4500
gcaaacccaa agatccggcg tcctatggga cgtacccagc cccccagaga cacagaaagc 4560
ggaactggaa gaaggggtct ataggatcaa acagcaagga atttttggga aaacccaagt 4620
gggggttgga gtacagaaag aaggagtttt ccacaccatg tggcatgtca caagaggggc 4680
agtgttgaca cacaatggga aaagactgga accaaactgg gctagcgtga aaaaagatct 4740
gatttcatac ggaggaggat ggagattgag tgcacaatgg caaaaggggg aggaggtgca 4800
ggttattgcc gtagagcctg ggaagaaccc aaagaacttt caaaccatgc caggcatttt 4860
tcagacaaca acaggggaaa taggagcaat tgcactggat ttcaagcctg gaacttcagg 4920
atctcccatc ataaacagag agggaaaggt agtgggactg tatggcaatg gagtggttac 4980
aaagaatgga ggctatgtca gtggaatagc gcaaacaaat gcagaaccag atggaccgac 5040
accagagttg gaagaagaga tgttcaaaaa gcgaaatcta accataatgg atctccatcc 5100
tgggtcagga aagacgcgga aatatcttcc agctattgtt agagaggcaa tcaagagacg 5160
cttaaggact ctaattttgg caccaacaag ggtagttgca gctgagatgg aagaagcatt 5220
gaaagggctc ccaataaggt atcaaacaac tgcaacaaaa tctgaacaca caggaagaga 5280
gattgttgat ctaatgtgtc acgcaacgtt cacaatgcgc ttgctgtcac cagtcagggt 5340

-continued tccaaactac aacttgataa taatggatga ggcccatttc acagacccag ccagtatagc 5400
ggctagaggg tacatatcaa ctcgtgtagg aatgggagag gcagccgcaa ttttcatgac 5460
agcaacaccc cctggaacag ctgatgcctt tcctcagagc aacgctccaa ttcaagatga 5520
agagagagac ataccggaac gctcatggaa ttcaggcaat gaatggatta ctgactttgt 5580
tgggaagaca gtgtggtttg tccctagcat caaagccgga aatgacatag caaactgctt 5640
gcggaaaaat ggaaaaaagg ttattcaact cagcaggaag acctttgaca cagaatatca 5700
aaagaccaaa ctgaatgatt gggactttgt ggtgacaaca gacatttcag aaatgggagc 5760
caatttcaaa gcagatagag tgatcgaccc aagaagatgt ctcaagccgg tgattttgac 5820
agatggaccc gagcgggtga tcctggctgg accaatgcca gtcaccgtag cgagcgctgc 5880
gcaaaggaga gggagagttg gcaggaaccc acaaaaagaa aatgaccagt acatattcat 5940
gggccagcct ctcaacaatg atgaagacca tgctcactgg acagaagcaa aaatgctgct 6000
ggacaacatc aacacaccag aagggattat accagctctc tttgaaccag aaagggagaa 6060
gtcagccgcc atagacggcg aataccgcct gaagggtgag tccaggaaga ctttcgtgga 6120
actcatgagg aggggtgacc tcccagtttg gctagcccat aaagtagcat cagaagggat 6180
caaatataca gatagaaaat ggtgctttga tggagaacgt aataatcaaa ttttagagga 6240
gaatatggat gtggaaatct ggacaaagga aggagaaaag aaaaaactga gacctaggtg 6300
gcttgatgcc cgcacttatt cagatccttt agcactcaaa gaattcaagg attttgcagc 6360
tggcagaaag tcaatcgccc ttgatcttgt gacagaaata ggaagagtgc cttcacactt 6420
agcccacaga acgagaaacg ccctggataa tttggtgatg ctgcacacgt cagaacatgg 6480
cggtagggcc tacaggcatg cagtggagga actaccagaa acgatggaaa cactcttact 6540
cctgggactg atgatcttgt taacaggtgg agcaatgctc ttcttgatat caggtaaagg 6600
gattggaaag acttcaatag gactcatttg tgtaattgct tccagcggca tgttatggat 6660
ggctgatgtc ccactccaat ggatcgcatc ggctatagtc ctggagtttt ttatgatggt 6720
gttgctcata ccagaaccag aaaagcagag aactccccaa gacaaccaac tcgcatatgt 6780
cgtgataggc atacttacat tggctgcaat agtagcggcc aatgaaatgg gactgttgga 6840
aactacaaag agagatttag gaatgtctaa agaaccaggt gttgtttctc caaccagcta 6900
tttggatgtg gacttgcacc cagcatcagc ctggacattg tacgccgtgg ccacaacagt 6960
aataacacca atgttgagac acaccataga gaattccaca gcaaatgtgt ctctggcagc 7020
catagctaac caggcagtgg tcctgatggg tttagacaaa ggatggccga tatcgaaaat 7080
ggacttgggc gtaccactat tggcactggg ttgctattca caagtgaacc cactaactct 7140
tgcagcggca gtacttttgc tagtcacaca ttatgcaatt ataggtccag gattgcaggc 7200
aaaagccacc cgtgaagctc agaaaaggac agctgctgga ataatgaaga atccaacggt 7260
ggatggaata atgacaatag acctagatcc tgtaatatat gattcaaaat ttgaaaagca 7320
actaggacag gtcatgctcc tggttctgtg tgcagtccaa cttttattga tgagaacatc 7380
atgggccttg tgtgaagttc taaccctagc cacaggacca ataacaacac tctgggaagg 7440
atcacctggg aagttctgga acaccacgat agctgtttcc atggcgaaca tctttagagg 7500
gagctattta gcaggagctg ggcttgcttt ttctatcatg aaatcagttg gaacaggaaa 7560
gagaggaaca gggtcacaag gtgaaacctt aggagaaaag tggaaaaaga aattaaatca 7620
gttatcccgg aaagagtttg acctttacaa gaaatccgga atcaccgaag tggatagaac 7680
agaagccaaa gaagggttaa aaagaggaga aataacacac catgccgtgt ccagaggcag 7740
cgcaaaactt caatggttcg tggagagaaa catggtcatt cctgaaggaa gagtcataga 7800
cctaggctgt ggaagaggag gctggtcata ttactgtgca ggactgaaaa aagttacaga 7860
agtgcgagga tacacaaaag gcggcccagg acacgaagaa ccagtaccta tgtctacata 7920
cggatggaac atagtcaagt taatgagtgg aaaggatgtt ttttatctgc cacctgaaaa 7980
gtgtgatacc ctattgtgtg acattggaga atcttcacca agcccaacag tggaagaaag 8040
cagaaccata agagttttga agatggttga accatggcta aagaacaacc agttttgcat 8100
taaagtattg aacccataca tgccaactgt gattgagcac ttagaaagac tacaaaggaa 8160
acatggagga atgcttgtga gaaatccact ctcacgaaac tccacgcacg aaatgtattg 8220
gatatccaat ggtacaggca atatcgtctc ttcagtcaac atggtatcca gattgctact 8280
gaacagattc acaatgacac acaggagacc caccatagag aaagatgtgg atctaggagc 8340
aggaacccga catgtcaatg cggaaccaga aacacccaac atggatgtca ttggggaaag 8400
aataaaaagg atcaaagagg agcatagttc aacatggcac tatgatgatg aaaatcctta 8460
caaaacgtgg gcttaccatg gatcctatga agtaaaagcc acaggctcag cctcctccat 8520
gataaatgga gtcgtgaaac tcctcacaaa accatgggat gtggtgccca tggtgacaca 8580
gatggcaatg acagatacaa ctccattcgg ccagcaaaga gtttttaaag agaaagtgga 8640
caccaggaca cctaggccca tgccaggaac aagaaaggtt atggagatca cagcggagtg 8700
gctttggagg accctgggaa ggaacaaaag acccagatta tgcacaaggg aggaattcac 8760
aaagaaggtc agaaccaacg cagctatggg cgctgtcttc acagaagaga accaatggga 8820
cagtgcgaga gctgctgttg aggacgaaga attttggaaa cttgtggaca gagaacgtga 8880
actccacaaa ctgggcaagt gtggaagctg cgtttacaac atgatgggca agagagagaa 8940
aaaacttgga gagtttggta aagcaaaagg cagtagggct atatggtaca tgtggttggg 9000
agccaggtac cttgagttcg aggcgctcgg attcctcaat gaagaccact ggttctcgcg 9060
tgaaaactct tacagtggag tagaaggaga aggactgcac aagctgggat acatcttgag 9120
agatatttcc aagataccog gaggagccat gtatgctgat gacacagccg gttgggacac 9180
aagaataaca gaagatgacc tgcacaatga ggaaaaaatc acacagcaga tggaccctga 9240
acacaggcag ctagcgaacg ctatattcaa gctcacatac caaaacaaag tggtcaaagt 9300
ccaacgacca actccaaagg gcacggtaat ggacatcata tctaggaaag accaaagagg 9360
cagtggacag gtgggaactt atggtctgaa cacattcacc aacatggaag cccagctaat 9420
cagacaaatg gaaggagaag gcgtgttgtc aaaggcagac ctcgagaacc cccatccgct 9480
agagaagaaa attacacaat ggttggaaac taaaggagtg gaaaggttaa aaagaatggc 9540
catcagcggg gatgattgcg ttgtgaaacc aatcgacgac agattcgcca atgccctgct 9600
tgccctgaac gatatgggaa aggttagaaa ggacatacct caatggcagc catcaaaggg 9660
atggcatgat tggcaacagg tccccttctg ctcccaccac tttcatgaat tgatcatgaa 9720
agatggaaga aagttggtag ttccctgcag accccaggac gaactaatag gaagagcgag 9780
aatctcccaa ggagcaggat ggagccttag agaaactgca tgtctaggga aagcctacgc 9840
tcaaatgtgg gctctcatgt attttcacag aagagatctt agactagcat ccaacgccat 9900
atgttcagca gtaccagtcc actgggtccc cacgagcaga acgacatggt ctattcatgc 9960
tcaccatcag tggatgacta cagaagacat gcttactgtc tggaacaggg tgtggataga 10020
ggacaatcca tggatggaag acaaaactcc agtcacaacg tgggaagatg ttccatatct 10080

-continued

```
agggaagaga gaagaccaat ggtgcggatc actcataggt ctcacttcca gagcaacctg  10140

ggcccagaac atactcacag caatccaaca ggtgagaagc ctcataggca atgaagagtt  10200

tctggactac atgccttcga tgaagagatt caggaaggag gaggagtcag agggagccat  10260

ttggtaaaag caggaggtaa actgtcaggc cacattaagc cacagtacgg aagaagctgt  10320

gcagcctgtg agccccgtcc aaggacgtta aaagaagaag tcaggcccaa aagccacggt  10380

ttgagcaaac cgtgctgcct gtagctccgt cgtggggacg taaagcctgg gaggctgcaa  10440

accgtggaag ctgtacgcac ggtgtagcag actagtggtt agaggagacc cctcccatga  10500

cacaacgcag cagcggggcc cgagcactga gggaagctgt acctccttgc aaaggactag  10560

aggttagagg agaccccccg caaacaaaaa cagcatattg acgctgggag agaccagaga  10620

tcctgctgtc tcctcagcat cattccaggc acagaacgcc agaaaatgga atggtgctgt  10680

tgaatcaaca ggttct                                                  10696
```

<210> SEQ ID NO 14
<211> LENGTH: 3390
<212> TYPE: PRT
<213> ORGANISM: dengue virus

<400> SEQUENCE: 14

```
Met Asn Asn Gln Arg Lys Lys Thr Gly Lys Pro Ser Ile Asn Met Leu
1               5                   10                  15

Lys Arg Val Arg Asn Arg Val Ser Thr Gly Ser Gln Leu Ala Lys Arg
            20                  25                  30

Phe Ser Arg Gly Leu Leu Asn Gly Gln Gly Pro Met Lys Leu Val Met
        35                  40                  45

Ala Phe Ile Ala Phe Leu Arg Phe Leu Ala Ile Pro Pro Thr Ala Gly
    50                  55                  60

Val Leu Ala Arg Trp Gly Thr Phe Lys Lys Ser Gly Ala Ile Lys Val
65                  70                  75                  80

Leu Lys Gly Phe Lys Lys Glu Ile Ser Asn Met Leu Ser Ile Ile Asn
                85                  90                  95

Lys Arg Lys Lys Thr Ser Leu Cys Leu Met Met Met Leu Pro Ala Thr
            100                 105                 110

Leu Ala Phe His Leu Thr Ser Arg Asp Gly Glu Pro Arg Met Ile Val
        115                 120                 125

Gly Lys Asn Glu Arg Gly Lys Ser Leu Leu Phe Lys Thr Ala Ser Gly
    130                 135                 140

Ile Asn Met Cys Thr Leu Ile Ala Met Asp Leu Gly Glu Met Cys Asp
145                 150                 155                 160

Asp Thr Val Thr Tyr Lys Cys Pro His Ile Thr Glu Val Glu Pro Glu
                165                 170                 175

Asp Ile Asp Cys Trp Cys Asn Leu Thr Ser Thr Trp Val Thr Tyr Gly
            180                 185                 190

Thr Cys Asn Gln Ala Gly Glu His Arg Arg Asp Lys Arg Ser Val Ala
        195                 200                 205

Leu Ala Pro His Val Gly Met Gly Leu Asp Thr Arg Thr Gln Thr Trp
    210                 215                 220

Met Ser Ala Glu Gly Ala Trp Arg Gln Val Glu Lys Val Glu Thr Trp
225                 230                 235                 240

Ala Leu Arg His Pro Gly Phe Thr Ile Leu Ala Leu Phe Leu Ala His
                245                 250                 255

Tyr Ile Gly Thr Ser Leu Thr Gln Lys Val Val Ile Phe Ile Leu Leu
```

-continued

```
            260                 265                 270

Met Leu Val Thr Pro Ser Met Thr Met Arg Cys Val Gly Val Gly Asn
        275                 280                 285

Arg Asp Phe Val Glu Gly Leu Ser Gly Ala Thr Trp Val Asp Val Val
    290                 295                 300

Leu Glu His Gly Gly Cys Val Thr Thr Met Ala Lys Asn Lys Pro Thr
305                 310                 315                 320

Leu Asp Ile Glu Leu Gln Lys Thr Glu Ala Thr Gln Leu Ala Thr Leu
                325                 330                 335

Arg Lys Leu Cys Ile Glu Gly Lys Ile Thr Asn Ile Thr Thr Asp Ser
            340                 345                 350

Arg Cys Pro Thr Gln Gly Glu Ala Ile Leu Pro Glu Glu Gln Asp Gln
        355                 360                 365

Asn Tyr Val Cys Lys His Thr Tyr Val Asp Arg Gly Trp Gly Asn Gly
    370                 375                 380

Cys Gly Leu Phe Gly Lys Gly Ser Leu Val Thr Cys Ala Lys Phe Gln
385                 390                 395                 400

Cys Leu Glu Ser Ile Glu Gly Lys Val Val Gln His Glu Asn Leu Lys
                405                 410                 415

Tyr Thr Val Ile Ile Thr Val His Thr Gly Asp Gln His Gln Val Gly
            420                 425                 430

Asn Glu Thr Gln Gly Val Thr Ala Glu Ile Thr Pro Gln Ala Ser Thr
        435                 440                 445

Ala Glu Val Ile Leu Pro Glu Tyr Gly Thr Leu Gly Leu Glu Cys Ser
    450                 455                 460

Pro Arg Thr Gly Leu Asp Phe Asn Glu Met Ile Ser Leu Thr Met Lys
465                 470                 475                 480

Asn Lys Ala Trp Met Val His Arg Gln Trp Phe Phe Asp Leu Pro Leu
                485                 490                 495

Pro Trp Thr Ser Gly Ala Thr Ala Glu Thr Pro Thr Trp Asn Arg Lys
            500                 505                 510

Glu Leu Leu Val Thr Phe Lys Asn Ala His Ala Lys Lys Gln Glu Val
        515                 520                 525

Val Val Leu Gly Ser Gln Glu Gly Ala Met His Thr Ala Leu Thr Gly
    530                 535                 540

Ala Thr Glu Ile Gln Thr Ser Gly Gly Thr Ser Ile Phe Ala Gly His
545                 550                 555                 560

Leu Lys Cys Arg Leu Lys Met Asp Lys Leu Glu Leu Lys Gly Met Ser
                565                 570                 575

Tyr Ala Met Cys Leu Ser Ser Phe Val Leu Lys Lys Glu Val Ser Glu
            580                 585                 590

Thr Gln His Gly Thr Ile Leu Ile Lys Val Glu Tyr Lys Gly Glu Asp
        595                 600                 605

Ala Pro Cys Lys Ile Pro Phe Ser Thr Glu Asp Gly Gln Gly Lys Ala
    610                 615                 620

His Asn Gly Arg Leu Ile Thr Ala Asn Pro Val Val Thr Lys Lys Glu
625                 630                 635                 640

Glu Pro Val Asn Ile Glu Ala Glu Pro Pro Phe Gly Glu Ser Asn Ile
                645                 650                 655

Val Ile Gly Ile Gly Asp Lys Ala Leu Lys Ile Asn Trp Tyr Lys Lys
            660                 665                 670

Gly Ser Ser Ile Gly Lys Met Phe Glu Ala Thr Ala Arg Gly Ala Arg
        675                 680                 685
```

```
Arg Met Ala Ile Leu Gly Asp Thr Ala Trp Asp Phe Gly Ser Val Gly
    690                 695                 700

Gly Val Leu Asn Ser Leu Gly Lys Met Val His Gln Ile Phe Gly Ser
705                 710                 715                 720

Ala Tyr Thr Ala Leu Phe Gly Gly Val Ser Trp Met Met Lys Ile Gly
                725                 730                 735

Ile Gly Val Leu Leu Thr Trp Ile Gly Leu Asn Ser Lys Asn Thr Ser
            740                 745                 750

Met Ser Phe Ser Cys Ile Ala Ile Gly Ile Ile Thr Leu Tyr Leu Gly
        755                 760                 765

Ala Val Val Gln Ala Asp Met Gly Cys Val Ile Asn Trp Lys Gly Lys
    770                 775                 780

Glu Leu Lys Cys Gly Ser Gly Ile Phe Val Thr Asn Glu Val His Thr
785                 790                 795                 800

Trp Thr Glu Gln Tyr Lys Phe Gln Ala Asp Ser Pro Lys Arg Leu Ala
                805                 810                 815

Thr Ala Ile Ala Gly Ala Trp Glu Asn Gly Val Cys Gly Ile Arg Ser
            820                 825                 830

Thr Thr Arg Met Glu Asn Leu Leu Trp Lys Gln Ile Ala Asn Glu Leu
        835                 840                 845

Asn Tyr Ile Leu Trp Glu Asn Asn Ile Lys Leu Thr Val Val Val Gly
    850                 855                 860

Asp Ile Thr Gly Val Leu Glu Gln Gly Lys Arg Thr Leu Thr Pro Gln
865                 870                 875                 880

Pro Met Glu Leu Lys Tyr Ser Trp Lys Thr Trp Gly Lys Ala Lys Ile
                885                 890                 895

Val Thr Ala Glu Thr Gln Asn Ser Ser Phe Ile Ile Asp Gly Pro Ser
            900                 905                 910

Thr Pro Glu Cys Pro Ser Ala Ser Arg Ala Trp Asn Val Trp Glu Val
        915                 920                 925

Glu Asp Tyr Gly Phe Gly Val Phe Thr Thr Asn Ile Trp Leu Lys Leu
    930                 935                 940

Arg Glu Val Tyr Thr Gln Leu Cys Asp His Arg Leu Met Ser Ala Ala
945                 950                 955                 960

Val Lys Asp Glu Arg Ala Val His Ala Asp Met Gly Tyr Trp Ile Glu
                965                 970                 975

Ser Gln Lys Asn Gly Ser Trp Lys Leu Glu Lys Ala Ser Phe Ile Glu
            980                 985                 990

Val Lys Thr Cys Thr Trp Pro Lys  Ser His Thr Leu Trp  Ser Asn Gly
        995                 1000                1005

Val Leu  Glu Ser Asp Met Ile  Ile Pro Lys Ser Leu  Ala Gly Pro
    1010                1015                1020

Ile Ser  Gln His Asn His Arg  Pro Gly Tyr His Thr  Gln Thr Ala
    1025                1030                1035

Gly Pro  Trp His Leu Gly Lys  Leu Glu Leu Asp Phe  Asn Tyr Cys
    1040                1045                1050

Glu Gly  Thr Thr Val Val Ile  Ser Glu Asn Cys Gly  Thr Arg Gly
    1055                1060                1065

Pro Ser  Leu Arg Thr Thr Thr  Val Ser Gly Lys Leu  Ile His Glu
    1070                1075                1080

Trp Cys  Cys Arg Ser Cys Thr  Leu Pro Pro Leu Arg  Tyr Met Gly
    1085                1090                1095
```

```
Glu Asp  Gly Cys Trp Tyr Gly  Met Glu Ile Arg Pro  Ile Asn Glu
    1100                 1105                 1110

Lys Glu  Glu Asn Met Val Lys  Ser Leu Ala Ser Ala  Gly Ser Gly
    1115                 1120                 1125

Lys Val  Asp Asn Phe Thr Met  Gly Val Leu Cys Leu  Ala Ile Leu
    1130                 1135                 1140

Phe Glu  Glu Val Met Arg Gly  Lys Phe Gly Lys Lys  His Met Ile
    1145                 1150                 1155

Ala Gly  Val Leu Phe Thr Phe  Val Leu Leu Leu Ser  Gly Gln Ile
    1160                 1165                 1170

Thr Trp  Arg Asp Met Ala His  Thr Leu Ile Met Ile  Gly Ser Asn
    1175                 1180                 1185

Ala Ser  Asp Arg Met Gly Met  Gly Val Thr Tyr Leu  Ala Leu Ile
    1190                 1195                 1200

Ala Thr  Phe Lys Ile Gln Pro  Phe Leu Ala Leu Gly  Phe Phe Leu
    1205                 1210                 1215

Arg Lys  Leu Thr Ser Arg Glu  Asn Leu Leu Leu Gly  Val Gly Leu
    1220                 1225                 1230

Ala Met  Ala Ala Thr Leu Arg  Leu Pro Glu Asp Ile  Glu Gln Met
    1235                 1240                 1245

Ala Asn  Gly Ile Ala Leu Gly  Leu Met Ala Leu Lys  Leu Ile Thr
    1250                 1255                 1260

Gln Phe  Glu Thr Tyr Gln Leu  Trp Thr Ala Leu Val  Ser Leu Thr
    1265                 1270                 1275

Cys Ser  Asn Thr Ile Phe Thr  Leu Thr Val Ala Trp  Arg Thr Ala
    1280                 1285                 1290

Thr Leu  Ile Leu Ala Gly Ile  Ser Leu Leu Pro Val  Cys Gln Ser
    1295                 1300                 1305

Ser Ser  Met Arg Lys Thr Asp  Trp Leu Pro Met Thr  Val Ala Ala
    1310                 1315                 1320

Met Gly  Ala Gln Pro Leu Pro  Leu Phe Ile Phe Ser  Leu Lys Asp
    1325                 1330                 1335

Thr Leu  Lys Arg Arg Ser Trp  Pro Leu Asn Glu Gly  Val Met Ala
    1340                 1345                 1350

Val Gly  Leu Val Ser Ile Leu  Ala Ser Ser Leu Leu  Arg Asn Asp
    1355                 1360                 1365

Val Pro  Met Ala Gly Pro Leu  Val Ala Gly Gly Leu  Leu Ile Ala
    1370                 1375                 1380

Cys Tyr  Val Ile Thr Gly Thr  Ser Ala Asp Leu Thr  Val Glu Lys
    1385                 1390                 1395

Ala Ala  Asp Val Thr Trp Glu  Glu Glu Ala Glu Gln  Thr Gly Val
    1400                 1405                 1410

Ser His  Asn Leu Met Val Thr  Val Asp Asp Asp Gly  Thr Met Arg
    1415                 1420                 1425

Ile Lys  Asp Asp Glu Thr Glu  Asn Ile Leu Thr Val  Leu Leu Lys
    1430                 1435                 1440

Thr Ala  Leu Leu Ile Val Ser  Gly Ile Phe Pro Tyr  Ser Ile Pro
    1445                 1450                 1455

Ala Thr  Leu Leu Val Trp His  Thr Trp Gln Lys Gln  Thr Gln Arg
    1460                 1465                 1470

Ser Gly  Val Leu Trp Asp Val  Pro Ser Pro Pro Glu  Thr Gln Lys
    1475                 1480                 1485

Ala Glu  Leu Glu Glu Gly Val  Tyr Arg Ile Lys Gln  Gln Gly Ile
```

-continued

```
    1490                1495                1500

Phe Gly  Lys Thr Gln Val Gly  Val Gly Val Gln Lys  Glu Gly Val
    1505                1510                1515

Phe His  Thr Met Trp His Val  Thr Arg Gly Ala Val  Leu Thr His
    1520                1525                1530

Asn Gly  Lys Arg Leu Glu Pro  Asn Trp Ala Ser Val  Lys Lys Asp
    1535                1540                1545

Leu Ile  Ser Tyr Gly Gly Gly  Trp Arg Leu Ser Ala  Gln Trp Gln
    1550                1555                1560

Lys Gly  Glu Glu Val Gln Val  Ile Ala Val Glu Pro  Gly Lys Asn
    1565                1570                1575

Pro Lys  Asn Phe Gln Thr Met  Pro Gly Ile Phe Gln  Thr Thr Thr
    1580                1585                1590

Gly Glu  Ile Gly Ala Ile Ala  Leu Asp Phe Lys Pro  Gly Thr Ser
    1595                1600                1605

Gly Ser  Pro Ile Ile Asn Arg  Glu Gly Lys Val Val  Gly Leu Tyr
    1610                1615                1620

Gly Asn  Gly Val Val Thr Lys  Asn Gly Gly Tyr Val  Ser Gly Ile
    1625                1630                1635

Ala Gln  Thr Asn Ala Glu Pro  Asp Gly Pro Thr Pro  Glu Leu Glu
    1640                1645                1650

Glu Glu  Met Phe Lys Lys Arg  Asn Leu Thr Ile Met  Asp Leu His
    1655                1660                1665

Pro Gly  Ser Gly Lys Thr Arg  Lys Tyr Leu Pro Ala  Ile Val Arg
    1670                1675                1680

Glu Ala  Ile Lys Arg Arg Leu  Arg Thr Leu Ile Leu  Ala Pro Thr
    1685                1690                1695

Arg Val  Val Ala Ala Glu Met  Glu Glu Ala Leu Lys  Gly Leu Pro
    1700                1705                1710

Ile Arg  Tyr Gln Thr Thr Ala  Thr Lys Ser Glu His  Thr Gly Arg
    1715                1720                1725

Glu Ile  Val Asp Leu Met Cys  His Ala Thr Phe Thr  Met Arg Leu
    1730                1735                1740

Leu Ser  Pro Val Arg Val Pro  Asn Tyr Asn Leu Ile  Ile Met Asp
    1745                1750                1755

Glu Ala  His Phe Thr Asp Pro  Ala Ser Ile Ala Ala  Arg Gly Tyr
    1760                1765                1770

Ile Ser  Thr Arg Val Gly Met  Gly Glu Ala Ala Ala  Ile Phe Met
    1775                1780                1785

Thr Ala  Thr Pro Pro Gly Thr  Ala Asp Ala Phe Pro  Gln Ser Asn
    1790                1795                1800

Ala Pro  Ile Gln Asp Glu Glu  Arg Asp Ile Pro Glu  Arg Ser Trp
    1805                1810                1815

Asn Ser  Gly Asn Glu Trp Ile  Thr Asp Phe Val Gly  Lys Thr Val
    1820                1825                1830

Trp Phe  Val Pro Ser Ile Lys  Ala Gly Asn Asp Ile  Ala Asn Cys
    1835                1840                1845

Leu Arg  Lys Asn Gly Lys Lys  Val Ile Gln Leu Ser  Arg Lys Thr
    1850                1855                1860

Phe Asp  Thr Glu Tyr Gln Lys  Thr Lys Leu Asn Asp  Trp Asp Phe
    1865                1870                1875

Val Val  Thr Thr Asp Ile Ser  Glu Met Gly Ala Asn  Phe Lys Ala
    1880                1885                1890
```

Asp Arg Val Ile Asp Pro Arg Arg Cys Leu Lys Pro Val Ile Leu
1895 1900 1905

Thr Asp Gly Pro Glu Arg Val Ile Leu Ala Gly Pro Met Pro Val
1910 1915 1920

Thr Val Ala Ser Ala Ala Gln Arg Arg Gly Arg Val Gly Arg Asn
1925 1930 1935

Pro Gln Lys Glu Asn Asp Gln Tyr Ile Phe Met Gly Gln Pro Leu
1940 1945 1950

Asn Asn Asp Glu Asp His Ala His Trp Thr Glu Ala Lys Met Leu
1955 1960 1965

Leu Asp Asn Ile Asn Thr Pro Glu Gly Ile Ile Pro Ala Leu Phe
1970 1975 1980

Glu Pro Glu Arg Glu Lys Ser Ala Ala Ile Asp Gly Glu Tyr Arg
1985 1990 1995

Leu Lys Gly Glu Ser Arg Lys Thr Phe Val Glu Leu Met Arg Arg
2000 2005 2010

Gly Asp Leu Pro Val Trp Leu Ala His Lys Val Ala Ser Glu Gly
2015 2020 2025

Ile Lys Tyr Thr Asp Arg Lys Trp Cys Phe Asp Gly Glu Arg Asn
2030 2035 2040

Asn Gln Ile Leu Glu Glu Asn Met Asp Val Glu Ile Trp Thr Lys
2045 2050 2055

Glu Gly Glu Lys Lys Lys Leu Arg Pro Arg Trp Leu Asp Ala Arg
2060 2065 2070

Thr Tyr Ser Asp Pro Leu Ala Leu Lys Glu Phe Lys Asp Phe Ala
2075 2080 2085

Ala Gly Arg Lys Ser Ile Ala Leu Asp Leu Val Thr Glu Ile Gly
2090 2095 2100

Arg Val Pro Ser His Leu Ala His Arg Thr Arg Asn Ala Leu Asp
2105 2110 2115

Asn Leu Val Met Leu His Thr Ser Glu His Gly Gly Arg Ala Tyr
2120 2125 2130

Arg His Ala Val Glu Glu Leu Pro Glu Thr Met Glu Thr Leu Leu
2135 2140 2145

Leu Leu Gly Leu Met Ile Leu Leu Thr Gly Gly Ala Met Leu Phe
2150 2155 2160

Leu Ile Ser Gly Lys Gly Ile Gly Lys Thr Ser Ile Gly Leu Ile
2165 2170 2175

Cys Val Ile Ala Ser Ser Gly Met Leu Trp Met Ala Asp Val Pro
2180 2185 2190

Leu Gln Trp Ile Ala Ser Ala Ile Val Leu Glu Phe Phe Met Met
2195 2200 2205

Val Leu Leu Ile Pro Glu Pro Glu Lys Gln Arg Thr Pro Gln Asp
2210 2215 2220

Asn Gln Leu Ala Tyr Val Val Ile Gly Ile Leu Thr Leu Ala Ala
2225 2230 2235

Ile Val Ala Ala Asn Glu Met Gly Leu Leu Glu Thr Thr Lys Arg
2240 2245 2250

Asp Leu Gly Met Ser Lys Glu Pro Gly Val Val Ser Pro Thr Ser
2255 2260 2265

Tyr Leu Asp Val Asp Leu His Pro Ala Ser Ala Trp Thr Leu Tyr
2270 2275 2280

```
Ala Val  Ala Thr Thr Val Ile  Thr Pro Met Leu Arg  His Thr Ile
    2285                 2290                 2295

Glu Asn  Ser Thr Ala Asn Val  Ser Leu Ala Ala Ile  Ala Asn Gln
    2300                 2305                 2310

Ala Val  Val Leu Met Gly Leu  Asp Lys Gly Trp Pro  Ile Ser Lys
    2315                 2320                 2325

Met Asp  Leu Gly Val Pro Leu  Leu Ala Leu Gly Cys  Tyr Ser Gln
    2330                 2335                 2340

Val Asn  Pro Leu Thr Leu Ala  Ala Ala Val Leu Leu  Leu Val Thr
    2345                 2350                 2355

His Tyr  Ala Ile Ile Gly Pro  Gly Leu Gln Ala Lys  Ala Thr Arg
    2360                 2365                 2370

Glu Ala  Gln Lys Arg Thr Ala  Ala Gly Ile Met Lys  Asn Pro Thr
    2375                 2380                 2385

Val Asp  Gly Ile Met Thr Ile  Asp Leu Asp Pro Val  Ile Tyr Asp
    2390                 2395                 2400

Ser Lys  Phe Glu Lys Gln Leu  Gly Gln Val Met Leu  Leu Val Leu
    2405                 2410                 2415

Cys Ala  Val Gln Leu Leu Leu  Met Arg Thr Ser Trp  Ala Leu Cys
    2420                 2425                 2430

Glu Val  Leu Thr Leu Ala Thr  Gly Pro Ile Thr Thr  Leu Trp Glu
    2435                 2440                 2445

Gly Ser  Pro Gly Lys Phe Trp  Asn Thr Thr Ile Ala  Val Ser Met
    2450                 2455                 2460

Ala Asn  Ile Phe Arg Gly Ser  Tyr Leu Ala Gly Ala  Gly Leu Ala
    2465                 2470                 2475

Phe Ser  Ile Met Lys Ser Val  Gly Thr Gly Lys Arg  Gly Thr Gly
    2480                 2485                 2490

Ser Gln  Gly Glu Thr Leu Gly  Glu Lys Trp Lys Lys  Lys Leu Asn
    2495                 2500                 2505

Gln Leu  Ser Arg Lys Glu Phe  Asp Leu Tyr Lys Lys  Ser Gly Ile
    2510                 2515                 2520

Thr Glu  Val Asp Arg Thr Glu  Ala Lys Glu Gly Leu  Lys Arg Gly
    2525                 2530                 2535

Glu Ile  Thr His His Ala Val  Ser Arg Gly Ser Ala  Lys Leu Gln
    2540                 2545                 2550

Trp Phe  Val Glu Arg Asn Met  Val Ile Pro Glu Gly  Arg Val Ile
    2555                 2560                 2565

Asp Leu  Gly Cys Gly Arg Gly  Gly Trp Ser Tyr Tyr  Cys Ala Gly
    2570                 2575                 2580

Leu Lys  Lys Val Thr Glu Val  Arg Gly Tyr Thr Lys  Gly Gly Pro
    2585                 2590                 2595

Gly His  Glu Glu Pro Val Pro  Met Ser Thr Tyr Gly  Trp Asn Ile
    2600                 2605                 2610

Val Lys  Leu Met Ser Gly Lys  Asp Val Phe Tyr Leu  Pro Pro Glu
    2615                 2620                 2625

Lys Cys  Asp Thr Leu Leu Cys  Asp Ile Gly Glu Ser  Ser Pro Ser
    2630                 2635                 2640

Pro Thr  Val Glu Glu Ser Arg  Thr Ile Arg Val Leu  Lys Met Val
    2645                 2650                 2655

Glu Pro  Trp Leu Lys Asn Asn  Gln Phe Cys Ile Lys  Val Leu Asn
    2660                 2665                 2670

Pro Tyr  Met Pro Thr Val Ile  Glu His Leu Glu Arg  Leu Gln Arg
```

```
    2675                2680                2685

Lys His Gly Gly Met Leu Val Arg Asn Pro Leu Ser Arg Asn Ser
    2690                2695                2700

Thr His Glu Met Tyr Trp Ile Ser Asn Gly Thr Gly Asn Ile Val
    2705                2710                2715

Ser Ser Val Asn Met Val Ser Arg Leu Leu Leu Asn Arg Phe Thr
    2720                2725                2730

Met Thr His Arg Arg Pro Thr Ile Glu Lys Asp Val Asp Leu Gly
    2735                2740                2745

Ala Gly Thr Arg His Val Asn Ala Glu Pro Glu Thr Pro Asn Met
    2750                2755                2760

Asp Val Ile Gly Glu Arg Ile Lys Arg Ile Lys Glu Glu His Ser
    2765                2770                2775

Ser Thr Trp His Tyr Asp Asp Glu Asn Pro Tyr Lys Thr Trp Ala
    2780                2785                2790

Tyr His Gly Ser Tyr Glu Val Lys Ala Thr Gly Ser Ala Ser Ser
    2795                2800                2805

Met Ile Asn Gly Val Val Lys Leu Leu Thr Lys Pro Trp Asp Val
    2810                2815                2820

Val Pro Met Val Thr Gln Met Ala Met Thr Asp Thr Thr Pro Phe
    2825                2830                2835

Gly Gln Gln Arg Val Phe Lys Glu Lys Val Asp Thr Arg Thr Pro
    2840                2845                2850

Arg Pro Met Pro Gly Thr Arg Lys Val Met Glu Ile Thr Ala Glu
    2855                2860                2865

Trp Leu Trp Arg Thr Leu Gly Arg Asn Lys Arg Pro Arg Leu Cys
    2870                2875                2880

Thr Arg Glu Glu Phe Thr Lys Lys Val Arg Thr Asn Ala Ala Met
    2885                2890                2895

Gly Ala Val Phe Thr Glu Glu Asn Gln Trp Asp Ser Ala Arg Ala
    2900                2905                2910

Ala Val Glu Asp Glu Glu Phe Trp Lys Leu Val Asp Arg Glu Arg
    2915                2920                2925

Glu Leu His Lys Leu Gly Lys Cys Gly Ser Cys Val Tyr Asn Met
    2930                2935                2940

Met Gly Lys Arg Glu Lys Lys Leu Gly Glu Phe Gly Lys Ala Lys
    2945                2950                2955

Gly Ser Arg Ala Ile Trp Tyr Met Trp Leu Gly Ala Arg Tyr Leu
    2960                2965                2970

Glu Phe Glu Ala Leu Gly Phe Leu Asn Glu Asp His Trp Phe Ser
    2975                2980                2985

Arg Glu Asn Ser Tyr Ser Gly Val Glu Gly Glu Gly Leu His Lys
    2990                2995                3000

Leu Gly Tyr Ile Leu Arg Asp Ile Ser Lys Ile Pro Gly Gly Ala
    3005                3010                3015

Met Tyr Ala Asp Asp Thr Ala Gly Trp Asp Thr Arg Ile Thr Glu
    3020                3025                3030

Asp Asp Leu His Asn Glu Glu Lys Ile Thr Gln Gln Met Asp Pro
    3035                3040                3045

Glu His Arg Gln Leu Ala Asn Ala Ile Phe Lys Leu Thr Tyr Gln
    3050                3055                3060

Asn Lys Val Val Lys Val Gln Arg Pro Thr Pro Lys Gly Thr Val
    3065                3070                3075
```

```
Met Asp  Ile Ile Ser Arg Lys  Asp Gln Arg Gly Ser  Gly Gln Val
    3080                 3085                 3090

Gly Thr  Tyr Gly Leu Asn Thr  Phe Thr Asn Met Glu  Ala Gln Leu
    3095                 3100                 3105

Ile Arg  Gln Met Glu Gly Glu  Gly Val Leu Ser Lys  Ala Asp Leu
    3110                 3115                 3120

Glu Asn  Pro His Pro Leu Glu  Lys Lys Ile Thr Gln  Trp Leu Glu
    3125                 3130                 3135

Thr Lys  Gly Val Glu Arg Leu  Lys Arg Met Ala Ile  Ser Gly Asp
    3140                 3145                 3150

Asp Cys  Val Val Lys Pro Ile  Asp Asp Arg Phe Ala  Asn Ala Leu
    3155                 3160                 3165

Leu Ala  Leu Asn Asp Met Gly  Lys Val Arg Lys Asp  Ile Pro Gln
    3170                 3175                 3180

Trp Gln  Pro Ser Lys Gly Trp  His Asp Trp Gln Gln  Val Pro Phe
    3185                 3190                 3195

Cys Ser  His His Phe His Glu  Leu Ile Met Lys Asp  Gly Arg Lys
    3200                 3205                 3210

Leu Val  Val Pro Cys Arg Pro  Gln Asp Glu Leu Ile  Gly Arg Ala
    3215                 3220                 3225

Arg Ile  Ser Gln Gly Ala Gly  Trp Ser Leu Arg Glu  Thr Ala Cys
    3230                 3235                 3240

Leu Gly  Lys Ala Tyr Ala Gln  Met Trp Ala Leu Met  Tyr Phe His
    3245                 3250                 3255

Arg Arg  Asp Leu Arg Leu Ala  Ser Asn Ala Ile Cys  Ser Ala Val
    3260                 3265                 3270

Pro Val  His Trp Val Pro Thr  Ser Arg Thr Thr Trp  Ser Ile His
    3275                 3280                 3285

Ala His  His Gln Trp Met Thr  Thr Glu Asp Met Leu  Thr Val Trp
    3290                 3295                 3300

Asn Arg  Val Trp Ile Glu Asp  Asn Pro Trp Met Glu  Asp Lys Thr
    3305                 3310                 3315

Pro Val  Thr Thr Trp Glu Asp  Val Pro Tyr Leu Gly  Lys Arg Glu
    3320                 3325                 3330

Asp Gln  Trp Cys Gly Ser Leu  Ile Gly Leu Thr Ser  Arg Ala Thr
    3335                 3340                 3345

Trp Ala  Gln Asn Ile Leu Thr  Ala Ile Gln Gln Val  Arg Ser Leu
    3350                 3355                 3360

Ile Gly  Asn Glu Glu Phe Leu  Asp Tyr Met Pro Ser  Met Lys Arg
    3365                 3370                 3375

Phe Arg  Lys Glu Glu Glu Ser  Glu Gly Ala Ile Trp
    3380                 3385                 3390
```

<210> SEQ ID NO 15
<211> LENGTH: 10648
<212> TYPE: DNA
<213> ORGANISM: dengue virus

<400> SEQUENCE: 15

```
agttgttagt ctgtgtggac cgacaaggac agttccaaat cggaagcttg cttaacacag     60

ttctaacagt ttgtttgaat agagagcaga tctctggaaa aatgaaccaa cgaaaaaagg    120

tggttagacc acctttcaat atgctgaaac gcgagagaaa ccgcgtatca acccctcaag    180

ggttggtgaa gagattctca accggacttt tttctgggaa aggaccctta cggatggtgc    240
```

-continued

```
tagcattcat cacgtttttg cgagtccttt ccatcccacc aacagcaggg attctgaaaa    300
gatggggaca gttgaagaaa aataaggcca tcaggatact gattggattc aggaaggaga    360
taggccgcat gctgaacatc ttgaacggga gaaaaaggtc aacgataaca ttgctgtgct    420
tgattcccac cgtaatggcg tttcacttgt caacaagaga tggcgaaccc ctcatgatag    480
tggcaaaaca tgaaaggggg agacctctct tgtttaagac aacagagggg atcaacaaat    540
gcactctcat tgccatggac ttgggtgaaa tgtgtgagga cactgtcacg tataaatgcc    600
ccttactggt caataccgaa cctgaagaca ttgattgctg gtgcaatctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgccccat cctacggaat gcgatgcgta ggagtaggaa    960
acagagactt tgtggaagga gtctcaggtg gagcatgggt cgatctggtg ctagaacatg   1020
gaggatgcgt cacaaccatg gcccagggaa aaccaacctt ggattttgaa ctgactaaga   1080
caacagccaa ggaagtggct ctgttaagaa cctattgcat tgaagcctca atatcaaaca   1140
taaccacggc aacaagatgt ccaacgcaag gagagcctta tctaaaagag gaacaagacc   1200
aacagtacat ttgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccacgata actcccaggt   1440
caccatcggt ggaagtcaaa ttgccggact atggagaact aacactcgat tgtgaaccca   1500
ggtctggaat tgactttaat gagatgattc tgatgaaaat gaaaaagaaa acatggcttg   1560
tgcataagca atggtttttg gatctacctc taccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatctcaag tgcaaagtcc   1800
gtatggagaa attgagaatc aagggaatgt catacacgat gtgttcagga aagttctcaa   1860
ttgacaaaga gatggcagaa acacagcatg ggacaacagt ggtgaaagtc aagtatgaag   1920
gtgctggagc tccgtgtaaa gtccccatag agataagaga tgtgaacaag gaaaaagtgg   1980
ttgggcgtat catctcatcc accccttttgg ctgagaatac caacagtgca accaacatag   2040
agttagaacc cccctttggg gacagctaca tagtgatagg tgttggaaac agtgcattaa   2100
cactccattg gttcaggaaa gggagttcca ttggcaagat gtttgagtcc acatacagag   2160
gtgcaaaacg aatggccatt ctaggtgaaa cagcttggga ttttggttcc gttggtggac   2220
tgttcacatc attgggaaag gctgtgcacc aggtttttgg aagtgtgtat acaaccatgt   2280
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
```

-continued

```
gggtctgtgg aattagatca accacgaggc tggaaaatgt catgtggaag caaataacca   2640
acgagctaaa ttatgttctc tgggaaggag gacatgacct cactgtagtg gctggggatg   2700
tgaagggggt gttgaccaaa ggcaagagag cactcacacc cccagtgaat gatctgaaat   2760
attcatggaa gacatgggga aaagcaaaaa tcttcacccc agaagcaaga aatagcacat   2820
ttttaataga cggaccagac acctccgaat gccccaatga acgaagagca tggaactttc   2880
ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
ctgtgcatgc tgacatgggt tattggatag agagctcaaa aaaccagacc tggcagatag   3060
agaaagcatc tcttattgaa gtgaaaacat gtctgtggcc caagacccac acattgtgga   3120
gcaatggagt gctggaaagc cagatgctca ttccaaaatc atatgcgggc cctttttcac   3180
agcacaatta ccgccagggc tatgccacgc aaaccgtggg cccatggcac ttaggcaaat   3240
tagagataga ctttggagaa tgccccggaa caacagtcgc aattcaggag gattgtgacc   3300
atagaggccc atctttgagg accaccactg catctggaaa actagtcacg caatggtgct   3360
gccgctcctg cacgatgcct cccttaaggt tcttgggaga agatgggtgc tggtatggga   3420
tggagattag gcccttgagt gaaaaagaag agaacatggt caaatcacag gtaacggccg   3480
gacagggcac atcagaaact tttctatgg gtctgttgtg cctgaccttg tttgtggaag   3540
aatgcttgag gagaagagtc actaggaaac acatgatatt ggttgtggtg atcactcttt   3600
gtgccatcat cctaggaggc ctcacatgga tggacttact acgagccctc atcatgttgg   3660
gggacactat gtctggtaga ataggaggac agatccacct agccatcatg gcagtgttca   3720
agatgtcacc aggatacgtg ctgggtgtgt ttttaaggaa actcacttca agagagacag   3780
cactaatggt aataggaatg gccatgacaa cggtgctttc aattccacat gaccttatgg   3840
aactcattga tggaatatca ctggggctaa ttttgctaaa aatagtgaca cattttgaca   3900
acacccaagt gggaacctta gccctttcct tgaccttcat aagatcaaca atgccattgg   3960
tcatggcttg gaggaccatt atggctgtgt tgtttgtggt cacactcatt cctttgtgca   4020
ggacaagctg tcttcaaaaa cagtctcatt gggtagaaat aacagcactc atcctaggag   4080
cccaagctct gccagtgtac ctaatgactc ttatgaaagg agcctcaaga agatcttggc   4140
ctcttaacga gggcataatg gctgtgggtt tggttagtct cttaggaagc gctcttttaa   4200
agaatgatgt ccctttagct ggcccaatgg tggcaggagg cttacttctg gcggcttacg   4260
tgatgagtgg tagctcagca gatctgtcac tagagaaggc cgccaatgtg cagtgggatg   4320
aaatggcaga cataacaggc tcaagcccaa tcatagaagt gaagcaggat gaagatggct   4380
ctttctccat acgggacgtc gaggaaacca atatgataac ccttttggtg aaactggcac   4440
tgataacagt gtcaggtctc tacccccttgg caattccagt cacaatgacc ttatggtaca   4500
tgtggcaagt gaaaacacaa agatcaggag ccctgtggga cgtcccctca cccgctgcca   4560
ctcaaaaagc cgcactgtct gaaggagtgt acaggatcat gcaaagaggg ttatttggga   4620
aaactcaggt tggagtaggg atacacatgg aaggtgtatt tcacacaatg tggcatgtaa   4680
caagaggatc agtgatctgc catgagactg ggagattgga gccatcttgg gctgacgtca   4740
ggaatgacat gatatcatac ggtgggggat ggagacttgg agacaaatgg gacaaagaag   4800
aagatgttca ggtcctcgcc atagaaccag gaaaaaatcc taaacatgtc caaacgaaac   4860
ccggcctttt caagacccta actggagaaa ttggagcagt aacattagat ttcaaacccg   4920
gaacgtctgg ttctcccatc atcaacagga aaggaaaagt catcggactc tatggaaatg   4980
```

gagtagttac caaatcaggt gattacgtca gtgccataac gcaagccgaa agaattggag 5040
agccagatta tgaagtggat gaggacattt ttcgaaagaa aagattaact ataatggact 5100
tacaccccgg agctggaaag acaaaaagaa ttcttccatc aatagtgaga gaagccttaa 5160
aaaggaggct gcgaaccttg attttggctc ccacgagagt ggtggcggcc gagatggaag 5220
aggccctacg tggactgcca atccgttatc agaccccagc tgtgaaatca gaacacacag 5280
gaagagagat tgtagacctc atgtgtcatg caaccttcac aacaagactt ttgtcatcaa 5340
ccagagttcc aaattacaac ctcatagtga tggatgaagc acatttcacc gatccttcta 5400
gtgtcgcggc tagaggatac atctcgacca gggtggaaat gggagaggca gcagccatct 5460
tcatgaccgc aacccctccc ggagcgacag atccctttcc ccagagcaac agcccaatag 5520
aagacatcga gagggaaatt ccggaaaggt catggaacac agggttcgac tggataacag 5580
actaccaagg gaaaactgtg tggtttgttc ccagcataaa agctggaaat gacattgcaa 5640
attgtttgag aaagtcggga aagaaagtta tccagttgag taggaaaacc tttgatacag 5700
agtatccaaa aacgaaactc acggactggg attttgtggt cactacagac atatctgaaa 5760
tgggggccaa ttttagagct gggagagtga tagaccctag gagatgcctc aagccagtta 5820
tcctaacaga tgggccagag agagtcattt tagcaggtcc tattccagtg actccagcaa 5880
gcgctgctca gagaagaggg cgaataggaa ggaacccagc acaagaagac gaccaatacg 5940
ttttctccgg agacccacta aaaaatgatg aagatcatgc ccactggaca gaagcaaaga 6000
tgctgcttga caatatctac accccagaag ggatcattcc aacattgttt ggtccggaaa 6060
gggaaaaaac ccaagccatt gatggagagt ttcgcctcag aggggaacaa aggaagactt 6120
ttgtggaatt aatgaggaga ggagaccttc cggtgtggct gagctataag gtagcttctg 6180
ctggcatttc ttacaaagat cgggaatggt gcttcacagg ggaaaggaat aaccaaattt 6240
tagaagaaaa catggaggtt gaaatttgga ctagagaggg agaaaagaaa aagctaaggc 6300
caagatggtt agatgcacgt gtatacgctg accccatggc tttgaaggat tttaaggagt 6360
ttgctagtgg aaggaagagc ataactctcg acatcctaac agagattgcc agtttgccaa 6420
cttacctttc ctctagggcc aagctcgccc ttgataacat agtcatgctc cacacaacag 6480
aaagaggagg gagggcctac caacacgccc tgaacgaact cccggagtca ctggaaacac 6540
ttatgcttgt agctttacta ggtgctatga cagcaggtat cttcctgttt ttcatgcaag 6600
ggaaaggaat agggaaattg tcaatgggtt tgataaccat tgcggtggct agtggcttgc 6660
tctgggtagc agaaattcaa ccccagtgga tagcggcctc aatcatacta gagtttttc 6720
tcatggtact gttgataccg gaaccagaaa aacaaaggac cccacaagac aatcaattga 6780
tctacgtcat attgaccatt ctcaccatta ttggtctcat agcagccaac gagatggggc 6840
tgattgaaaa aacaaaaacg gattttgggt tttaccaggt aaaaacagaa accaccatcc 6900
tcgatgtgga cttgagacca gcttcagcat ggacgctcta tgcagtagcc accacaattc 6960
tgactcccat gctgagacac accatagaaa acacgtcggc caacctatct ctagcagcca 7020
ttgccaacca ggcggccgtc ctaatggggc ttggaaaagg atggccgctc cacagaatgg 7080
acctcggtgt gccgctgtta gcaatgggat gctattctca agtgaaccca acaactttga 7140
cagcatcctt agtcatgctt ttagtccatt atgcaataat aggtccagga ttgcaggcaa 7200
aagccacaag agaggcccag aaaaggacag ctgctgggat catgaaaaac cccacggtgg 7260
acgggataac agtaatagat ctagaaccaa tatcctatga cccaaaattt gaaaagcaat 7320

-continued

```
tagggcaggt catgctactc gtcttgtgtg ctggacaact actcttgatg agaacaacat   7380
gggctttctg tgaagtcttg actttggcca caggaccaat cttgaccttg tgggagggca   7440
acccgggaag gttttggaac acgaccatag ccgtatccac cgccaacatt ttcaggggaa   7500
gttacctggc gggagctgga ctggcttttt cactcataaa gaatgtacaa acccctagga   7560
ggggaactgg gaccacagga gagacactgg gagagaagtg gaagagacag ctaaactcat   7620
tagacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taacccctac atgccaacag tcatagaaga gctggagaaa ctgcagagaa   8160
aacatggtgg gaaccttgtc agatgcccgc tgtccaggaa ctccacccat gagatgtatt   8220
gggtgtcagg agcgtcggga aacattgtga gctctgtgaa cacaacatca aagatgttgt   8280
tgaacaggtt cacaacaagg cataggaaac ccacttatga gaaggacgta gatcttgggg   8340
caggaacgag aagtgtctcc actgaaacag aaaaaccaga catgacaatt attgggagaa   8400
ggcttcagcg attgcaagag gagcacaaag aaacctggca ttatgatcag gaaaacccat   8460
acagaacctg ggcgtatcat ggaagctatg aagctccttc gacaggctct gcatcctcca   8520
tggtgaacgg ggtagtaaaa ctgctaacaa aaccttggga tgtggttcca atggtgaccc   8580
agttagccat gacagacaca acccctttttg ggcaacaaag agtgttcaaa gagaaggtgg   8640
ataccagaac accacaacca aaacccggta cacgaatggt tatgaccacg acagccaatt   8700
ggctgtgggc cctccttggg aagaagaaaa atcccagact gtgcacaagg gaagagttca   8760
tctcaaaagt tagatcaaac gcagccatag gcgcagtctt tcaggaagaa cagggatgga   8820
catcagccag tgaagctgtg aatgacagcc ggtttttggga actggttgac aaagaaaggg   8880
ccctacacca ggaagggaaa tgtgaatcgt gtgtctacaa catgatggga aaacgtgaga   8940
aaaagttagg agagtttggc agagccaagg gaagccgagc aatctggtac atgtggctgg   9000
gagcgcggtt tctggaattt gaagccctgg gtttttttgaa tgaagatcac tggtttggca   9060
gagaaaattc atggagtgga gtggaagggg aaggtctgca cagattggga tatatcctgg   9120
aggagataga caagaaggat ggagacctaa tgtatgctga tgacacagca ggctgggaca   9180
caagaatcac tgaggatgac cttcaaaatg aagaactgat cacggaacag atggcccccc   9240
accacaagat cctagccaaa gccattttca aactaaccta tcaaaacaaa gtggtgaaag   9300
tcctcagacc cacaccgaga ggagcggtga tggatatcat atccaggaaa gaccaaagag   9360
gtagtggaca agttggaaca tatggtttga acacattcac caacatggaa gttcaactca   9420
tccgccaaat ggaagctgaa ggagtcatca cacaagatga catgcagaac ccaaaagggt   9480
tgaaagaaag agttgagaaa tggctgaaag agtgtggtgt cgacaggtta aagaggatgg   9540
caatcagtgg agacgattgc gtggtgaagc ccctggatga gaggtttggc acttccctcc   9600
tcttcttgaa cgacatggga aaggtgagga aagacattcc gcagtgggaa ccatctaagg   9660
gatggaaaaa ctggcaagag gttccttttt gctcccacca ctttcacaag atcttcatga   9720
```

```
aggatggccg ctcactagtt gttccatgta gaaaccagga tgaactgata gggagagcca    9780
gaatctcgca gggggctgga tggagcttaa gagaaacagc ctgcctgggc aaagcttacg    9840
cccagatgtg gtcgctcatg tacttccaca gaagggatct gcgtttagcc tccatggcca    9900
tatgctcagc agttccaacg gaatggtttc caacaagcag aacaacatgg tcaatccacg    9960
ctcatcatca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcacacg gccataaccc aggtcagaaa cctgatcgga aaagaggaat   10200
acgtggatta catgccagta atgaaaagat acagcgctcc ttcagagagt gaaggagttc   10260
tgtaattacc aacaacaaac accaaaggct attgaagtca ggccacttgt gccacggctt   10320
gagcaaaccg tgctgcctgt agctccgcca ataatgggag gcgtgaaatc cctagggagg   10380
ccatgcgcca cggaagctgt acgcgtggca tattggacta gcggttagag gagacccctc   10440
ccatcactga caaaacgcag caaaaggggg cccgaagcca ggaggaagct gtactcctgg   10500
tggaaggact agaggttaga ggagaccccc ccaacacaaa aacagcatat tgacgctggg   10560
aaagaccaga gatcctgctg tctctgcaac atcaatccag gcacagagcg ccgcaagatg   10620
gattggtgtt gttgatccaa caggttct                                      10648
```

<210> SEQ ID NO 16
<211> LENGTH: 3387
<212> TYPE: PRT
<213> ORGANISM: dengue virus

<400> SEQUENCE: 16

```
Met Asn Gln Arg Lys Lys Val Val Arg Pro Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Arg Ile Leu
65                  70                  75                  80

Ile Gly Phe Arg Lys Glu Ile Gly Arg Met Leu Asn Ile Leu Asn Gly
                85                  90                  95

Arg Lys Arg Ser Thr Ile Thr Leu Leu Cys Leu Ile Pro Thr Val Met
            100                 105                 110

Ala Phe His Leu Ser Thr Arg Asp Gly Glu Pro Leu Met Ile Val Ala
        115                 120                 125

Lys His Glu Arg Gly Arg Pro Leu Leu Phe Lys Thr Thr Glu Gly Ile
    130                 135                 140

Asn Lys Cys Thr Leu Ile Ala Met Asp Leu Gly Glu Met Cys Glu Asp
145                 150                 155                 160

Thr Val Thr Tyr Lys Cys Pro Leu Leu Val Asn Thr Glu Pro Glu Asp
                165                 170                 175

Ile Asp Cys Trp Cys Asn Leu Thr Ser Thr Trp Val Met Tyr Gly Thr
            180                 185                 190

Cys Thr Gln Ser Gly Glu Arg Arg Arg Glu Lys Arg Ser Val Ala Leu
        195                 200                 205
```

```
Thr Pro His Ser Gly Met Gly Leu Glu Thr Arg Ala Glu Thr Trp Met
    210                 215                 220

Ser Ser Glu Gly Ala Trp Lys His Ala Gln Arg Val Glu Ser Trp Ile
225                 230                 235                 240

Leu Arg Asn Pro Gly Phe Ala Leu Leu Ala Gly Phe Met Ala Tyr Met
                245                 250                 255

Ile Gly Gln Thr Gly Ile Gln Arg Thr Val Phe Phe Val Leu Met Met
            260                 265                 270

Leu Val Ala Pro Ser Tyr Gly Met Arg Cys Val Gly Val Gly Asn Arg
        275                 280                 285

Asp Phe Val Glu Gly Val Ser Gly Gly Ala Trp Val Asp Leu Val Leu
    290                 295                 300

Glu His Gly Gly Cys Val Thr Thr Met Ala Gln Gly Lys Pro Thr Leu
305                 310                 315                 320

Asp Phe Glu Leu Thr Lys Thr Thr Ala Lys Glu Val Ala Leu Leu Arg
                325                 330                 335

Thr Tyr Cys Ile Glu Ala Ser Ile Ser Asn Ile Thr Thr Ala Thr Arg
            340                 345                 350

Cys Pro Thr Gln Gly Glu Pro Tyr Leu Lys Glu Glu Gln Asp Gln Gln
        355                 360                 365

Tyr Ile Cys Arg Arg Asp Val Val Asp Arg Gly Trp Gly Asn Gly Cys
    370                 375                 380

Gly Leu Phe Gly Lys Gly Gly Val Val Thr Cys Ala Lys Phe Ser Cys
385                 390                 395                 400

Ser Gly Lys Ile Thr Gly Asn Leu Val Gln Ile Glu Asn Leu Glu Tyr
                405                 410                 415

Thr Val Val Val Thr Val His Asn Gly Asp Thr His Ala Val Gly Asn
            420                 425                 430

Asp Thr Ser Asn His Gly Val Thr Ala Thr Ile Thr Pro Arg Ser Pro
        435                 440                 445

Ser Val Glu Val Lys Leu Pro Asp Tyr Gly Glu Leu Thr Leu Asp Cys
    450                 455                 460

Glu Pro Arg Ser Gly Ile Asp Phe Asn Glu Met Ile Leu Met Lys Met
465                 470                 475                 480

Lys Lys Lys Thr Trp Leu Val His Lys Gln Trp Phe Leu Asp Leu Pro
                485                 490                 495

Leu Pro Trp Thr Ala Gly Ala Asp Thr Ser Glu Val His Trp Asn Tyr
            500                 505                 510

Lys Glu Arg Met Val Thr Phe Lys Val Pro His Ala Lys Arg Gln Asp
        515                 520                 525

Val Thr Val Leu Gly Ser Gln Glu Gly Ala Met His Ser Ala Leu Ala
    530                 535                 540

Gly Ala Thr Glu Val Asp Ser Gly Asp Gly Asn His Met Phe Ala Gly
545                 550                 555                 560

His Leu Lys Cys Lys Val Arg Met Glu Lys Leu Arg Ile Lys Gly Met
                565                 570                 575

Ser Tyr Thr Met Cys Ser Gly Lys Phe Ser Ile Asp Lys Glu Met Ala
            580                 585                 590

Glu Thr Gln His Gly Thr Thr Val Val Lys Val Lys Tyr Glu Gly Ala
        595                 600                 605

Gly Ala Pro Cys Lys Val Pro Ile Glu Ile Arg Asp Val Asn Lys Glu
    610                 615                 620
```

```
Lys Val Val Gly Arg Ile Ile Ser Ser Thr Pro Leu Ala Glu Asn Thr
625                 630                 635                 640

Asn Ser Ala Thr Asn Ile Glu Leu Glu Pro Pro Phe Gly Asp Ser Tyr
                645                 650                 655

Ile Val Ile Gly Val Gly Asn Ser Ala Leu Thr Leu His Trp Phe Arg
            660                 665                 670

Lys Gly Ser Ser Ile Gly Lys Met Phe Glu Ser Thr Tyr Arg Gly Ala
        675                 680                 685

Lys Arg Met Ala Ile Leu Gly Glu Thr Ala Trp Asp Phe Gly Ser Val
    690                 695                 700

Gly Gly Leu Phe Thr Ser Leu Gly Lys Ala Val His Gln Val Phe Gly
705                 710                 715                 720

Ser Val Tyr Thr Thr Met Phe Gly Gly Val Ser Trp Met Ile Arg Ile
                725                 730                 735

Leu Ile Gly Phe Leu Val Leu Trp Ile Gly Thr Asn Ser Arg Asn Thr
            740                 745                 750

Ser Met Ala Met Thr Cys Ile Ala Val Gly Gly Ile Thr Leu Phe Leu
        755                 760                 765

Gly Phe Thr Val Gln Ala Asp Met Gly Cys Val Val Ser Trp Ser Gly
    770                 775                 780

Lys Glu Leu Lys Cys Gly Ser Gly Ile Phe Val Val Asp Asn Val His
785                 790                 795                 800

Thr Trp Thr Glu Gln Tyr Lys Phe Gln Pro Glu Ser Pro Ala Arg Leu
                805                 810                 815

Ala Ser Ala Ile Leu Asn Ala His Lys Asp Gly Val Cys Gly Ile Arg
            820                 825                 830

Ser Thr Thr Arg Leu Glu Asn Val Met Trp Lys Gln Ile Thr Asn Glu
        835                 840                 845

Leu Asn Tyr Val Leu Trp Glu Gly Gly His Asp Leu Thr Val Val Ala
    850                 855                 860

Gly Asp Val Lys Gly Val Leu Thr Lys Gly Lys Arg Ala Leu Thr Pro
865                 870                 875                 880

Pro Val Asn Asp Leu Lys Tyr Ser Trp Lys Thr Trp Gly Lys Ala Lys
                885                 890                 895

Ile Phe Thr Pro Glu Ala Arg Asn Ser Thr Phe Leu Ile Asp Gly Pro
            900                 905                 910

Asp Thr Ser Glu Cys Pro Asn Glu Arg Arg Ala Trp Asn Phe Leu Glu
        915                 920                 925

Val Glu Asp Tyr Gly Phe Gly Met Phe Thr Thr Asn Ile Trp Met Lys
    930                 935                 940

Phe Arg Glu Gly Ser Ser Glu Val Cys Asp His Arg Leu Met Ser Ala
945                 950                 955                 960

Ala Ile Lys Asp Gln Lys Ala Val His Ala Asp Met Gly Tyr Trp Ile
                965                 970                 975

Glu Ser Ser Lys Asn Gln Thr Trp Gln Ile Glu Lys Ala Ser Leu Ile
            980                 985                 990

Glu Val Lys Thr Cys Leu Trp Pro  Lys Thr His Thr Leu  Trp Ser Asn
        995                 1000                 1005

Gly Val  Leu Glu Ser Gln Met  Leu Ile Pro Lys Ser  Tyr Ala Gly
    1010                 1015                 1020

Pro Phe  Ser Gln His Asn Tyr  Arg Gln Gly Tyr Ala  Thr Gln Thr
    1025                 1030                 1035

Val Gly  Pro Trp His Leu Gly  Lys Leu Glu Ile Asp  Phe Gly Glu
```

```
    1040                 1045                 1050

Cys Pro  Gly Thr Thr Val Ala  Ile Gln Glu Asp Cys  Asp His Arg
    1055                 1060                 1065

Gly Pro  Ser Leu Arg Thr Thr  Thr Ala Ser Gly Lys  Leu Val Thr
    1070                 1075                 1080

Gln Trp  Cys Cys Arg Ser Cys  Thr Met Pro Pro Leu  Arg Phe Leu
    1085                 1090                 1095

Gly Glu  Asp Gly Cys Trp Tyr  Gly Met Glu Ile Arg  Pro Leu Ser
    1100                 1105                 1110

Glu Lys  Glu Glu Asn Met Val  Lys Ser Gln Val Thr  Ala Gly Gln
    1115                 1120                 1125

Gly Thr  Ser Glu Thr Phe Ser  Met Gly Leu Leu Cys  Leu Thr Leu
    1130                 1135                 1140

Phe Val  Glu Glu Cys Leu Arg  Arg Arg Val Thr Arg  Lys His Met
    1145                 1150                 1155

Ile Leu  Val Val Val Ile Thr  Leu Cys Ala Ile Ile  Leu Gly Gly
    1160                 1165                 1170

Leu Thr  Trp Met Asp Leu Leu  Arg Ala Leu Ile Met  Leu Gly Asp
    1175                 1180                 1185

Thr Met  Ser Gly Arg Ile Gly  Gly Gln Ile His Leu  Ala Ile Met
    1190                 1195                 1200

Ala Val  Phe Lys Met Ser Pro  Gly Tyr Val Leu Gly  Val Phe Leu
    1205                 1210                 1215

Arg Lys  Leu Thr Ser Arg Glu  Thr Ala Leu Met Val  Ile Gly Met
    1220                 1225                 1230

Ala Met  Thr Thr Val Leu Ser  Ile Pro His Asp Leu  Met Glu Leu
    1235                 1240                 1245

Ile Asp  Gly Ile Ser Leu Gly  Leu Ile Leu Leu Lys  Ile Val Thr
    1250                 1255                 1260

His Phe  Asp Asn Thr Gln Val  Gly Thr Leu Ala Leu  Ser Leu Thr
    1265                 1270                 1275

Phe Ile  Arg Ser Thr Met Pro  Leu Val Met Ala Trp  Arg Thr Ile
    1280                 1285                 1290

Met Ala  Val Leu Phe Val Val  Thr Leu Ile Pro Leu  Cys Arg Thr
    1295                 1300                 1305

Ser Cys  Leu Gln Lys Gln Ser  His Trp Val Glu Ile  Thr Ala Leu
    1310                 1315                 1320

Ile Leu  Gly Ala Gln Ala Leu  Pro Val Tyr Leu Met  Thr Leu Met
    1325                 1330                 1335

Lys Gly  Ala Ser Arg Arg Ser  Trp Pro Leu Asn Glu  Gly Ile Met
    1340                 1345                 1350

Ala Val  Gly Leu Val Ser Leu  Leu Gly Ser Ala Leu  Leu Lys Asn
    1355                 1360                 1365

Asp Val  Pro Leu Ala Gly Pro  Met Val Ala Gly Gly  Leu Leu Leu
    1370                 1375                 1380

Ala Ala  Tyr Val Met Ser Gly  Ser Ser Ala Asp Leu  Ser Leu Glu
    1385                 1390                 1395

Lys Ala  Ala Asn Val Gln Trp  Asp Glu Met Ala Asp  Ile Thr Gly
    1400                 1405                 1410

Ser Ser  Pro Ile Ile Glu Val  Lys Gln Asp Glu Asp  Gly Ser Phe
    1415                 1420                 1425

Ser Ile  Arg Asp Val Glu Glu  Thr Asn Met Ile Thr  Leu Leu Val
    1430                 1435                 1440
```

```
Lys Leu  Ala Leu Ile Thr Val  Ser Gly Leu Tyr Pro  Leu Ala Ile
    1445                 1450                 1455

Pro Val  Thr Met Thr Leu Trp  Tyr Met Trp Gln Val  Lys Thr Gln
    1460                 1465                 1470

Arg Ser  Gly Ala Leu Trp Asp  Val Pro Ser Pro Ala  Ala Thr Gln
    1475                 1480                 1485

Lys Ala  Ala Leu Ser Glu Gly  Val Tyr Arg Ile Met  Gln Arg Gly
    1490                 1495                 1500

Leu Phe  Gly Lys Thr Gln Val  Gly Val Gly Ile His  Met Glu Gly
    1505                 1510                 1515

Val Phe  His Thr Met Trp His  Val Thr Arg Gly Ser  Val Ile Cys
    1520                 1525                 1530

His Glu  Thr Gly Arg Leu Glu  Pro Ser Trp Ala Asp  Val Arg Asn
    1535                 1540                 1545

Asp Met  Ile Ser Tyr Gly Gly  Gly Trp Arg Leu Gly  Asp Lys Trp
    1550                 1555                 1560

Asp Lys  Glu Glu Asp Val Gln  Val Leu Ala Ile Glu  Pro Gly Lys
    1565                 1570                 1575

Asn Pro  Lys His Val Gln Thr  Lys Pro Gly Leu Phe  Lys Thr Leu
    1580                 1585                 1590

Thr Gly  Glu Ile Gly Ala Val  Thr Leu Asp Phe Lys  Pro Gly Thr
    1595                 1600                 1605

Ser Gly  Ser Pro Ile Ile Asn  Arg Lys Gly Lys Val  Ile Gly Leu
    1610                 1615                 1620

Tyr Gly  Asn Gly Val Val Thr  Lys Ser Gly Asp Tyr  Val Ser Ala
    1625                 1630                 1635

Ile Thr  Gln Ala Glu Arg Ile  Gly Glu Pro Asp Tyr  Glu Val Asp
    1640                 1645                 1650

Glu Asp  Ile Phe Arg Lys Lys  Arg Leu Thr Ile Met  Asp Leu His
    1655                 1660                 1665

Pro Gly  Ala Gly Lys Thr Lys  Arg Ile Leu Pro Ser  Ile Val Arg
    1670                 1675                 1680

Glu Ala  Leu Lys Arg Arg Leu  Arg Thr Leu Ile Leu  Ala Pro Thr
    1685                 1690                 1695

Arg Val  Val Ala Ala Glu Met  Glu Glu Ala Leu Arg  Gly Leu Pro
    1700                 1705                 1710

Ile Arg  Tyr Gln Thr Pro Ala  Val Lys Ser Glu His  Thr Gly Arg
    1715                 1720                 1725

Glu Ile  Val Asp Leu Met Cys  His Ala Thr Phe Thr  Thr Arg Leu
    1730                 1735                 1740

Leu Ser  Ser Thr Arg Val Pro  Asn Tyr Asn Leu Ile  Val Met Asp
    1745                 1750                 1755

Glu Ala  His Phe Thr Asp Pro  Ser Ser Val Ala Ala  Arg Gly Tyr
    1760                 1765                 1770

Ile Ser  Thr Arg Val Glu Met  Gly Glu Ala Ala Ala  Ile Phe Met
    1775                 1780                 1785

Thr Ala  Thr Pro Pro Gly Ala  Thr Asp Pro Phe Pro  Gln Ser Asn
    1790                 1795                 1800

Ser Pro  Ile Glu Asp Ile Glu  Arg Glu Ile Pro Glu  Arg Ser Trp
    1805                 1810                 1815

Asn Thr  Gly Phe Asp Trp Ile  Thr Asp Tyr Gln Gly  Lys Thr Val
    1820                 1825                 1830
```

```
Trp Phe  Val Pro Ser Ile Lys  Ala Gly Asn Asp Ile  Ala Asn Cys
    1835                 1840                 1845

Leu Arg  Lys Ser Gly Lys Lys  Val Ile Gln Leu Ser  Arg Lys Thr
    1850                 1855                 1860

Phe Asp  Thr Glu Tyr Pro Lys  Thr Lys Leu Thr Asp  Trp Asp Phe
    1865                 1870                 1875

Val Val  Thr Thr Asp Ile Ser  Glu Met Gly Ala Asn  Phe Arg Ala
    1880                 1885                 1890

Gly Arg  Val Ile Asp Pro Arg  Arg Cys Leu Lys Pro  Val Ile Leu
    1895                 1900                 1905

Thr Asp  Gly Pro Glu Arg Val  Ile Leu Ala Gly Pro  Ile Pro Val
    1910                 1915                 1920

Thr Pro  Ala Ser Ala Ala Gln  Arg Arg Gly Arg Ile  Gly Arg Asn
    1925                 1930                 1935

Pro Ala  Gln Glu Asp Asp Gln  Tyr Val Phe Ser Gly  Asp Pro Leu
    1940                 1945                 1950

Lys Asn  Asp Glu Asp His Ala  His Trp Thr Glu Ala  Lys Met Leu
    1955                 1960                 1965

Leu Asp  Asn Ile Tyr Thr Pro  Glu Gly Ile Ile Pro  Thr Leu Phe
    1970                 1975                 1980

Gly Pro  Glu Arg Glu Lys Thr  Gln Ala Ile Asp Gly  Glu Phe Arg
    1985                 1990                 1995

Leu Arg  Gly Glu Gln Arg Lys  Thr Phe Val Glu Leu  Met Arg Arg
    2000                 2005                 2010

Gly Asp  Leu Pro Val Trp Leu  Ser Tyr Lys Val Ala  Ser Ala Gly
    2015                 2020                 2025

Ile Ser  Tyr Lys Asp Arg Glu  Trp Cys Phe Thr Gly  Glu Arg Asn
    2030                 2035                 2040

Asn Gln  Ile Leu Glu Glu Asn  Met Glu Val Glu Ile  Trp Thr Arg
    2045                 2050                 2055

Glu Gly  Glu Lys Lys Lys Leu  Arg Pro Arg Trp Leu  Asp Ala Arg
    2060                 2065                 2070

Val Tyr  Ala Asp Pro Met Ala  Leu Lys Asp Phe Lys  Glu Phe Ala
    2075                 2080                 2085

Ser Gly  Arg Lys Ser Ile Thr  Leu Asp Ile Leu Thr  Glu Ile Ala
    2090                 2095                 2100

Ser Leu  Pro Thr Tyr Leu Ser  Ser Arg Ala Lys Leu  Ala Leu Asp
    2105                 2110                 2115

Asn Ile  Val Met Leu His Thr  Thr Glu Arg Gly Gly  Arg Ala Tyr
    2120                 2125                 2130

Gln His  Ala Leu Asn Glu Leu  Pro Glu Ser Leu Glu  Thr Leu Met
    2135                 2140                 2145

Leu Val  Ala Leu Leu Gly Ala  Met Thr Ala Gly Ile  Phe Leu Phe
    2150                 2155                 2160

Phe Met  Gln Gly Lys Gly Ile  Gly Lys Leu Ser Met  Gly Leu Ile
    2165                 2170                 2175

Thr Ile  Ala Val Ala Ser Gly  Leu Leu Trp Val Ala  Glu Ile Gln
    2180                 2185                 2190

Pro Gln  Trp Ile Ala Ala Ser  Ile Ile Leu Glu Phe  Phe Leu Met
    2195                 2200                 2205

Val Leu  Leu Ile Pro Glu Pro  Glu Lys Gln Arg Thr  Pro Gln Asp
    2210                 2215                 2220
```

```
Asn Gln  Leu Ile Tyr Val Ile  Leu Thr Ile Leu Thr  Ile Ile Gly
    2225                 2230                 2235

Leu Ile  Ala Ala Asn Glu Met  Gly Leu Ile Glu Lys  Thr Lys Thr
    2240                 2245                 2250

Asp Phe  Gly Phe Tyr Gln Val  Lys Thr Glu Thr Thr  Ile Leu Asp
    2255                 2260                 2265

Val Asp  Leu Arg Pro Ala Ser  Ala Trp Thr Leu Tyr  Ala Val Ala
    2270                 2275                 2280

Thr Thr  Ile Leu Thr Pro Met  Leu Arg His Thr Ile  Glu Asn Thr
    2285                 2290                 2295

Ser Ala  Asn Leu Ser Leu Ala  Ala Ile Ala Asn Gln  Ala Ala Val
    2300                 2305                 2310

Leu Met  Gly Leu Gly Lys Gly  Trp Pro Leu His Arg  Met Asp Leu
    2315                 2320                 2325

Gly Val  Pro Leu Leu Ala Met  Gly Cys Tyr Ser Gln  Val Asn Pro
    2330                 2335                 2340

Thr Thr  Leu Thr Ala Ser Leu  Val Met Leu Leu Val  His Tyr Ala
    2345                 2350                 2355

Ile Ile  Gly Pro Gly Leu Gln  Ala Lys Ala Thr Arg  Glu Ala Gln
    2360                 2365                 2370

Lys Arg  Thr Ala Ala Gly Ile  Met Lys Asn Pro Thr  Val Asp Gly
    2375                 2380                 2385

Ile Thr  Val Ile Asp Leu Glu  Pro Ile Ser Tyr Asp  Pro Lys Phe
    2390                 2395                 2400

Glu Lys  Gln Leu Gly Gln Val  Met Leu Leu Val Leu  Cys Ala Gly
    2405                 2410                 2415

Gln Leu  Leu Leu Met Arg Thr  Thr Trp Ala Phe Cys  Glu Val Leu
    2420                 2425                 2430

Thr Leu  Ala Thr Gly Pro Ile  Leu Thr Leu Trp Glu  Gly Asn Pro
    2435                 2440                 2445

Gly Arg  Phe Trp Asn Thr Thr  Ile Ala Val Ser Thr  Ala Asn Ile
    2450                 2455                 2460

Phe Arg  Gly Ser Tyr Leu Ala  Gly Ala Gly Leu Ala  Phe Ser Leu
    2465                 2470                 2475

Ile Lys  Asn Val Gln Thr Pro  Arg Arg Gly Thr Gly  Thr Thr Gly
    2480                 2485                 2490

Glu Thr  Leu Gly Glu Lys Trp  Lys Arg Gln Leu Asn  Ser Leu Asp
    2495                 2500                 2505

Arg Lys  Glu Phe Glu Glu Tyr  Lys Arg Ser Gly Ile  Leu Glu Val
    2510                 2515                 2520

Asp Arg  Thr Glu Ala Lys Ser  Ala Leu Lys Asp Gly  Ser Lys Ile
    2525                 2530                 2535

Lys His  Ala Val Ser Arg Gly  Ser Ser Lys Ile Arg  Trp Ile Val
    2540                 2545                 2550

Glu Arg  Gly Met Val Lys Pro  Lys Gly Lys Val Val  Asp Leu Gly
    2555                 2560                 2565

Cys Gly  Arg Gly Gly Trp Ser  Tyr Tyr Met Ala Thr  Leu Lys Asn
    2570                 2575                 2580

Val Thr  Glu Val Lys Gly Tyr  Thr Lys Gly Gly Pro  Gly His Glu
    2585                 2590                 2595

Glu Pro  Ile Pro Met Ala Thr  Tyr Gly Trp Asn Leu  Val Lys Leu
    2600                 2605                 2610
```

His Ser Gly Val Asp Val Phe Tyr Lys Pro Thr Glu Gln Val Asp
2615 2620 2625

Thr Leu Leu Cys Asp Ile Gly Glu Ser Ser Ser Asn Pro Thr Ile
2630 2635 2640

Glu Glu Gly Arg Thr Leu Arg Val Leu Lys Met Val Glu Pro Trp
2645 2650 2655

Leu Ser Ser Lys Pro Glu Phe Cys Ile Lys Val Leu Asn Pro Tyr
2660 2665 2670

Met Pro Thr Val Ile Glu Glu Leu Glu Lys Leu Gln Arg Lys His
2675 2680 2685

Gly Gly Asn Leu Val Arg Cys Pro Leu Ser Arg Asn Ser Thr His
2690 2695 2700

Glu Met Tyr Trp Val Ser Gly Ala Ser Gly Asn Ile Val Ser Ser
2705 2710 2715

Val Asn Thr Thr Ser Lys Met Leu Leu Asn Arg Phe Thr Thr Arg
2720 2725 2730

His Arg Lys Pro Thr Tyr Glu Lys Asp Val Asp Leu Gly Ala Gly
2735 2740 2745

Thr Arg Ser Val Ser Thr Glu Thr Glu Lys Pro Asp Met Thr Ile
2750 2755 2760

Ile Gly Arg Arg Leu Gln Arg Leu Gln Glu Glu His Lys Glu Thr
2765 2770 2775

Trp His Tyr Asp Gln Glu Asn Pro Tyr Arg Thr Trp Ala Tyr His
2780 2785 2790

Gly Ser Tyr Glu Ala Pro Ser Thr Gly Ser Ala Ser Ser Met Val
2795 2800 2805

Asn Gly Val Val Lys Leu Leu Thr Lys Pro Trp Asp Val Val Pro
2810 2815 2820

Met Val Thr Gln Leu Ala Met Thr Asp Thr Thr Pro Phe Gly Gln
2825 2830 2835

Gln Arg Val Phe Lys Glu Lys Val Asp Thr Arg Thr Pro Gln Pro
2840 2845 2850

Lys Pro Gly Thr Arg Met Val Met Thr Thr Thr Ala Asn Trp Leu
2855 2860 2865

Trp Ala Leu Leu Gly Lys Lys Lys Asn Pro Arg Leu Cys Thr Arg
2870 2875 2880

Glu Glu Phe Ile Ser Lys Val Arg Ser Asn Ala Ala Ile Gly Ala
2885 2890 2895

Val Phe Gln Glu Glu Gln Gly Trp Thr Ser Ala Ser Glu Ala Val
2900 2905 2910

Asn Asp Ser Arg Phe Trp Glu Leu Val Asp Lys Glu Arg Ala Leu
2915 2920 2925

His Gln Glu Gly Lys Cys Glu Ser Cys Val Tyr Asn Met Met Gly
2930 2935 2940

Lys Arg Glu Lys Lys Leu Gly Glu Phe Gly Arg Ala Lys Gly Ser
2945 2950 2955

Arg Ala Ile Trp Tyr Met Trp Leu Gly Ala Arg Phe Leu Glu Phe
2960 2965 2970

Glu Ala Leu Gly Phe Leu Asn Glu Asp His Trp Phe Gly Arg Glu
2975 2980 2985

Asn Ser Trp Ser Gly Val Glu Gly Glu Gly Leu His Arg Leu Gly
2990 2995 3000

```
Tyr Ile  Leu Glu Glu Ile Asp  Lys Lys Asp Gly Asp  Leu Met Tyr
    3005                 3010                 3015

Ala Asp  Asp Thr Ala Gly Trp  Asp Thr Arg Ile Thr  Glu Asp Asp
    3020                 3025                 3030

Leu Gln  Asn Glu Glu Leu Ile  Thr Glu Gln Met Ala  Pro His His
    3035                 3040                 3045

Lys Ile  Leu Ala Lys Ala Ile  Phe Lys Leu Thr Tyr  Gln Asn Lys
    3050                 3055                 3060

Val Val  Lys Val Leu Arg Pro  Thr Pro Arg Gly Ala  Val Met Asp
    3065                 3070                 3075

Ile Ile  Ser Arg Lys Asp Gln  Arg Gly Ser Gly Gln  Val Gly Thr
    3080                 3085                 3090

Tyr Gly  Leu Asn Thr Phe Thr  Asn Met Glu Val Gln  Leu Ile Arg
    3095                 3100                 3105

Gln Met  Glu Ala Glu Gly Val  Ile Thr Gln Asp Asp  Met Gln Asn
    3110                 3115                 3120

Pro Lys  Gly Leu Lys Glu Arg  Val Glu Lys Trp Leu  Lys Glu Cys
    3125                 3130                 3135

Gly Val  Asp Arg Leu Lys Arg  Met Ala Ile Ser Gly  Asp Asp Cys
    3140                 3145                 3150

Val Val  Lys Pro Leu Asp Glu  Arg Phe Gly Thr Ser  Leu Leu Phe
    3155                 3160                 3165

Leu Asn  Asp Met Gly Lys Val  Arg Lys Asp Ile Pro  Gln Trp Glu
    3170                 3175                 3180

Pro Ser  Lys Gly Trp Lys Asn  Trp Gln Glu Val Pro  Phe Cys Ser
    3185                 3190                 3195

His His  Phe His Lys Ile Phe  Met Lys Asp Gly Arg  Ser Leu Val
    3200                 3205                 3210

Val Pro  Cys Arg Asn Gln Asp  Glu Leu Ile Gly Arg  Ala Arg Ile
    3215                 3220                 3225

Ser Gln  Gly Ala Gly Trp Ser  Leu Arg Glu Thr Ala  Cys Leu Gly
    3230                 3235                 3240

Lys Ala  Tyr Ala Gln Met Trp  Ser Leu Met Tyr Phe  His Arg Arg
    3245                 3250                 3255

Asp Leu  Arg Leu Ala Ser Met  Ala Ile Cys Ser Ala  Val Pro Thr
    3260                 3265                 3270

Glu Trp  Phe Pro Thr Ser Arg  Thr Thr Trp Ser Ile  His Ala His
    3275                 3280                 3285

His Gln  Trp Met Thr Thr Glu  Asp Met Leu Lys Val  Trp Asn Arg
    3290                 3295                 3300

Val Trp  Ile Glu Asp Asn Pro  Asn Met Thr Asp Lys  Thr Pro Val
    3305                 3310                 3315

His Ser  Trp Glu Asp Ile Pro  Tyr Leu Gly Lys Arg  Glu Asp Leu
    3320                 3325                 3330

Trp Cys  Gly Ser Leu Ile Gly  Leu Ser Ser Arg Ala  Thr Trp Ala
    3335                 3340                 3345

Lys Asn  Ile His Thr Ala Ile  Thr Gln Val Arg Asn  Leu Ile Gly
    3350                 3355                 3360

Lys Glu  Glu Tyr Val Asp Tyr  Met Pro Val Met Lys  Arg Tyr Ser
    3365                 3370                 3375

Ala Pro  Ser Glu Ser Glu Gly  Val Leu
    3380                 3385
```